(12) United States Patent
Monsan et al.

(10) Patent No.: US 7,524,645 B2
(45) Date of Patent: Apr. 28, 2009

(54) FULLY ACTIVE ALTERNANSUCRASES PARTIALLY DELETED IN ITS CARBOXY-TERMINAL AND AMINO-TERMINAL DOMAINS AND MUTANTS THEREOF

(75) Inventors: Pierre Monsan, Mondonville (FR); Magali Remaud-Simeon, Ramonville Saint Agne (FR); Gilles Joucla, Marsal (FR)

(73) Assignee: Centre National de la Recherche Scientifique (CNRS), Paris (FR)

( * ) Notice: Subject to any disclaimer, the term of this patent is extended or adjusted under 35 U.S.C. 154(b) by 0 days.

(21) Appl. No.: 11/011,702

(22) Filed: Dec. 14, 2004

(65) Prior Publication Data

US 2006/0127328 A1      Jun. 15, 2006

(51) Int. Cl.
*C12P 21/06* (2006.01)
*C12N 9/24* (2006.01)
*C12N 15/00* (2006.01)
(52) U.S. Cl. .................... 435/69.1; 435/200; 435/320.1
(58) Field of Classification Search ................ 435/211, 435/69.1
See application file for complete search history.

(56) References Cited

U.S. PATENT DOCUMENTS 6,570,065 B1 * 5/2003 Kossmann et al. .......... 800/284

OTHER PUBLICATIONS

Lopez-Munguia et al., Production and purification of Leuconostoc mesenteroides NRRL B-1355 alternansucrase. Annals of the New York Academy of Sciences. 1990, vol. 613: 717-722. (Abstract only).*
Leathers et al., Alrenansucrase mutants of Leuconostoc mesenteroides strain NRRL B-21138. J. Indust. Microbiol. Biotechnol., 1997. vol. 18: 278-283.*
Arguello-Morales et al., Sequence analysis of the gene encoding alternansucrase, a sucrose glucosyltransferase from Leuconostoc mesenteroides NRRL B-1335. FEMS Micro. Lett., 2000 vol. 182: 81-85.*
Whisstock et al., Prediction of protein function from sequence and structure. Quarterly Reviews of Biophysics, 36(3): 307-340.*
Guo et a., Proetin tolerance to random amino acid change. PNAS., 2004, vol. 101(25): 9205-9210.*

* cited by examiner

*Primary Examiner*—Richard G. Hutson
*Assistant Examiner*—Ganapathirama Raghu
(74) *Attorney, Agent, or Firm*—Kusner & Jaffe

(57) ABSTRACT

Nucleic acid sequences of truncated or mutated alternansucrases, vectors containing these nucleic acids sequences, host cells transformed with the nucleic acid sequences encoding truncated or mutated alternansucrases are provided. Furthermore, a process to recombinantly alternansucrase with a high level of expression, while retaining the enzymatic activity is described.

1 Claim, 21 Drawing Sheets

```
AAGAGAGTATGTTCTTCTCTTACCTATTTTTATTTGTAATTCCTATTATTTAATTTTGCATGACAATATTA        71

ATAGCGTGTTACGATTCTACTATTTAATGTTAATAAAATTAATAAATATGGTATTATCTTATATGGGTGATA       143

M   K   Q   Q   E      5
GATGCACCAAATACTGTATCATGTCTGGTCACATGAAAGGGAGAATAATTA ATG AAA CAA CAA GAA         209

T   V   T   R   K   K   L   Y   K   S   G   K   V   W   V   A   A   A         23
ACA GTT ACC CGT AAA AAA CTT TAT AAA TCC GGT AAG GTT TGG GTT GCA GCA GCT         263

T   A   F   A   V   L   G   V   S   T   V   T   T   V   H   A   D   T         41
ACT GCA TTT GCG GTA TTG GGG GTT TCA ACT GTA ACA ACA GTC CAT GCG GAT ACA         317

N   S   N   V   A   V   K   Q   I   N   N   T   G   T   N   D   S   G         59
AAT TCG AAT GTC GCT GTT AAG CAA ATA AAT AAT ACA GGA ACC AAT GAT TCT GGC         371

E   K   K   V   P   V   P   S   T   N   N   D   S   L   K   Q   G   T         77
GAA AAA AAG GTA CCG GTT CCA TCA ACT AAT AAT GAT AGT TTG AAG CAA GGA ACA         425

D   G   F   W   Y   D   S   D   G   N   R   V   D   Q   K   T   N   Q         95
GAT GGT TTT TGG TAT GAT TCA GAC GGC AAT CGT GTC GAT CAG AAG ACC AAT CAG         479

I   L   L   T   A   E   Q   L   K   K   N   N   E   K   N   L   S   V        113
ATT CTG CTT ACT GCG GAA CAA CTT AAA AAA AAT AAC GAA AAA AAT TTA TCA GTA         533

I   S   D   D   T   S   K   K   D   D   E   N   I   S   K   Q   T   K        131
ATC AGT GAT GAT ACA TCA AAA AAA GAT GAT GAA AAT ATT TCT AAG CAG ACC AAA         587

I   A   N   Q   Q   T   V   D   T   A   K   G   L   T   T   S   N   L        149
ATT GCT AAT CAA CAA ACA GTA GAT ACT GCT AAA GGC CTG ACT ACC AGT AAT TTA         641

S   D   P   I   T   G   G   H   Y   E   N   H   N   G   Y   F   V   Y        167
TCT GAT CCC ATC ACT GGG GGT CAC TAT GAA AAT CAC AAT GGC TAC TTT GTT TAT         695

I   D   A   S   G   K   Q   V   T   G   L   Q   N   I   D   G   N   L        185
ATA GAT GCT TCA GGA AAA CAA GTA ACA GGT TTG CAA AAT ATT GAT GGT AAT TTA         749

Q   Y   F   D   D   N   G   Y   Q   V   K   G   S   F   R   D   V   N        203
CAA TAT TTT GAT GAC AAT GGA TAT CAA GTC AAG GGA TCC TTC CGA GAT GTC AAC         803

G   K   H   I   Y   F   D   S   V   T   G   K   A   S   S   N   V   D        221
GGC AAG CAT ATC TAT TTT GAT TCA GTA ACA GGG AAA GCT AGT TCA AAT GTT GAT         857

I   V   N   G   K   A   Q   G   Y   D   A   Q   G   N   Q   L   K   K        239
ATT GTT AAC GGT AAA GCT CAA GGA TAT GAT GCG CAA GGC AAC CAA TTA AAG AAA         911

S   Y   V   A   D   S   S   G   Q   T   Y   Y   F   D   G   N   G   Q        257
AGT TAT GTC GCC GAT AGT TCT GGG CAA ACT TAC TAT TTT GAT GGT AAT GGC CAA         965

P   L   I   G   L   Q   T   I   D   G   N   L   Q   Y   F   N   Q   Q        275
CCG TTA ATC GGC TTG CAA ACA ATT GAT GGG AAC CTA CAA TAT TTT AAC CAA CAA        1019

G   V   Q   I   K   G   G   F   Q   D   V   N   N   K   R   I   Y   F        293
GGG GTT CAA ATA AAG GGT GGT TTC CAA GAT GTT AAC AAT AAA CGT ATT TAT TTT        1073

A   P   N   T   G   N   A   V   A   N   T   E   I   I   N   G   K   L        311
GCA CCA AAC ACA GGT AAT GCC GTT GCC AAT ACT GAA ATA ATT AAC GGT AAA TTA        1127

Q   G   R   D   A   N   G   N   Q   V   K   N   A   F   S   K   D   V        329
CAG GGG CGT GAC GCA AAT GGT AAC CAG GTA AAG AAT GCA TTT AGT AAA GAT GTT        1181

A   G   N   T   F   Y   F   D   A   N   G   V   M   L   T   G   L   Q        347
GCA GGA AAT ACA TTT TAT TTT GAC GCA AAC GGT GTG ATG TTA ACA GGG TTG CAA        1235
```

FIGURE 1A

```
  T   I   S   G   K   T   Y   Y   L   D   E   Q   G   H   L   R   K   N     365
 ACT ATT TCA GGA AAG ACA TAT TAT CTT GAT GAA CAA GGA CAC CTG AGA AAA AAT    1289

Y   A   G   T   F   N   N   Q   F   M   Y   F   D   A   D   T   G   A     383
 TAC GCG GGA ACA TTC AAT AAT CAG TTT ATG TAC TTC GAT GCT GAT ACA GGT GCG    1343

G   K   T   A   I   E   Y   Q   F   D   Q   G   L   V   S   Q   S   N     401
 GGT AAA ACA GCG ATT GAA TAT CAA TTT GAT CAA GGA TTG GTA TCA CAA AGT AAT    1397

E   N   T   P   H   N   A   A   K   S   Y   D   K   S   S   F   E   N     419
 GAA AAT ACT CCT CAC AAT GCC GCA AAG TCT TAT GAT AAA AGT AGT TTT GAA AAT    1451

V   D   G   Y   L   T   A   D   T   W   Y   R   P   T   D   I   L   K     437
 GTT GAT GGT TAC TTA ACA GCA GAT ACA TGG TAT CGT CCA ACC GAT ATT TTA AAA    1505

N   G   D   T   W   T   A   S   T   E   T   D   M   R   P   L   L   M     455
 AAT GGA GAT ACT TGG ACG GCA TCT ACC GAA ACT GAT ATG CGT CCG CTT TTA ATG    1559

T   W   W   P   D   K   Q   T   Q   A   N   Y   L   N   F   M   S   S     473
 ACA TGG TGG CCT GAC AAA CAA ACA CAA GCA AAT TAC TTG AAT TTT ATG TCT AGT    1613

K   G   L   G   I   T   T   T   Y   T   A   A   T   S   Q   K   T   L     491
 AAA GGA CTT GGT ATA ACG ACC ACT TAT ACA GCA GCT ACG TCA CAA AAA ACA CTA    1667

N   D   A   A   F   V   I   Q   T   A   I   E   Q   Q   I   S   L   K     509
 AAT GAC GCA GCC TTT GTT ATT CAA ACA GCA ATT GAA CAA CAA ATA TCT TTG AAA    1721

K   S   T   E   W   L   R   D   A   I   D   S   F   V   K   T   Q   A     527
 AAA AGT ACT GAG TGG TTA CGT GAT GCA ATT GAT AGT TTT GTG AAG ACG CAA GCT    1775

N   W   N   K   Q   T   E   D   E   A   F   D   G   L   Q   W   L   Q     545
 AAT TGG AAT AAG CAA ACA GAA GAT GAA GCT TTC GAT GGT TTG CAG TGG CTT CAA    1829

G   G   F   L   A   Y   Q   D   D   S   H   R   T   P   N   T   D   S     563
 GGG GGA TTC CTA GCT TAT CAA GAT GAT TCA CAT CGG ACG CCG AAT ACT GAT TCA    1883

G   N   N   R   K   L   G   R   Q   P   I   N   I   D   G   S   K   D     581
 GGA AAT AAC AGA AAA CTA GGA CGT CAA CCA ATT AAT ATC GAT GGT TCG AAA GAT    1937

T   T   D   G   K   G   S   E   F   L   L   A   N   D   I   D   N   S     599
 ACA ACT GAT GGT AAA GGC TCT GAA TTC TTA TTA GCT AAC GAT ATT GAC AAC TCA    1991

N   P   I   V   Q   A   E   Q   L   N   W   L   H   Y   L   M   N   F     617
 AAT CCG ATT GTT CAA GCT GAG CAA TTA AAC TGG CTA CAC TAT TTA ATG AAT TTT    2045

G   S   I   T   G   N   N   D   N   A   N   F   D   G   I   R   V   D     635
 GGT AGT ATT ACA GGT AAT AAT GAC AAT GCG AAT TTT GAT GGC ATT CGT GTA GAT    2099

A   V   D   N   V   D   A   D   L   L   K   I   A   G   D   Y   F   K     653
 GCT GTT GAT AAT GTT GAT GCT GAT TTA CTA AAA ATA GCT GGC GAT TAT TTT AAA    2153

A   L   Y   G   T   D   K   S   D   A   N   A   N   K   H   L   S   I     671
 GCT CTA TAT GGT ACA GAT AAA AGC GAC GCC AAT GCC AAT AAG CAT TTG TCT ATT    2207

L   E   D   W   N   G   K   D   P   Q   Y   V   N   Q   Q   G   N   A     689
 TTA GAA GAC TGG AAC GGT AAA GAT CCT CAG TAT GTT AAT CAA CAG GGC AAT GCG    2261

Q   L   T   M   D   Y   T   V   T   S   Q   F   G   N   S   L   T   H     707
 CAA TTA ACA ATG GAT TAC ACA GTT ACT TCA CAG TTT GGC AAT TCT CTA ACA CAT    2315

G   A   N   N   R   S   N   M   W   Y   F   L   D   T   G   Y   Y   L     725
 GGC GCC AAC AAC AGG AGT AAC ATG TGG TAT TTC TTA GAT ACT GGC TAT TAT CTT    2369

N   G   D   L   N   K   K   I   V   D   K   N   R   P   N   S   G   T     743
 AAT GGA GAT CTT AAT AAG AAG ATA GTA GAT AAG AAC CGT CCA AAT TCT GGC ACT    2423

```
                                                                                    2477
TTG GTT AAC AGA ATT GCT AAT TCA GGT GAT ACA AAA GTT ATT CCA AAT TAT AGT

F   V   R   A   H   D   Y   D   A   Q   D   P   I   R   K   A   M   I    779
TTT GTT AGA GCA CAT GAT TAC GAT GCT CAA GAT CCA ATT AGA AAA GCC ATG ATT   2531

D   H   G   I   I   K   N   M   Q   D   T   F   T   F   D   Q   L   A    797
GAT CAT GGT ATT ATT AAA AAC ATG CAG GAT ACT TTC ACT TTT GAC CAA CTG GCT   2585

Q   G   M   E   F   Y   Y   K   D   Q   E   N   P   S   G   F   K   K    815
CAG GGA ATG GAA TTC TAC TAT AAA GAT CAA GAG AAT CCG TCT GGT TTC AAA AAG   2639

Y   N   D   Y   N   L   P   S   A   Y   A   M   L   L   T   N   K   D    833
TAT AAC GAT TAT AAC TTA CCT AGT GCT TAT GCA ATG TTG TTG ACT AAT AAG GAT   2693

T   V   P   R   V   Y   Y   G   D   M   Y   L   E   G   G   Q   Y   M    851
ACT GTA CCT CGT GTC TAT TAT GGA GAT ATG TAC CTC GAA GGC GGG CAA TAT ATG   2747

E   K   G   T   I   Y   N   P   V   I   S   A   L   L   K   A   R   I    869
GAA AAA GGG ACG ATT TAC AAT CCT GTC ATT TCA GCG TTG CTC AAA GCT AGA ATA   2801

K   Y   V   S   G   G   Q   T   M   A   T   D   S   S   G   K   D   L    887
AAA TAT GTT TCT GGT GGG CAA ACA ATG GCT ACC GAT AGT TCT GGA AAA GAC CTT   2855

K   D   G   E   T   D   L   L   T   S   V   R   F   G   K   G   I   M    905
AAA GAT GGC GAA ACT GAT TTG TTA ACA AGT GTT CGA TTT GGT AAA GGA ATT ATG   2909

T   S   D   Q   T   T   T   Q   D   N   S   Q   D   Y   K   N   Q   G    923
ACA TCA GAT CAA ACC ACA ACA CAA GAC AAT AGC CAA GAT TAT AAA AAT CAA GGC   2963

I   G   V   I   V   G   N   N   P   D   L   K   L   N   N   D   K   T    941
ATC GGT GTC ATT GTT GGT AAT AAC CCT GAC CTT AAG TTG AAC AAT GAT AAG ACC   3017

I   T   L   H   M   G   K   A   H   K   N   Q   L   Y   R   A   L   V    959
ATT ACC TTG CAT ATG GGA AAG GCG CAT AAG AAT CAA CTT TAC CGT GCC TTA GTA   3071

L   S   N   D   S   G   I   D   V   Y   D   S   D   D   K   A   P   T    977
TTA TCA AAT GAC TCA GGA ATT GAT GTT TAT GAT AGT GAT GAT AAA GCA CCA ACT   3125

L   R   T   N   D   N   G   D   L   I   F   H   K   T   N   T   F   V    995
TTG AGA ACA AAT GAC AAC GGT GAC TTG ATT TTC CAT AAG ACA AAT ACG TTT GTG   3179

K   Q   D   G   T   I   I   N   Y   E   M   K   G   S   L   N   A   L   1013
AAG CAA GAT GGA ACT ATT ATA AAT TAC GAA ATG AAG GGA TCA TTA AAT GCT TTA   3233

I   S   G   Y   L   G   V   W   V   P   V   G   A   S   D   S   Q   D   1031
ATT TCA GGT TAT TTA GGT GTC TGG GTG CCA GTT GGA GCT AGT GAT TCA CAA GAT   3287

A   R   T   V   A   T   E   S   S   S   S   N   D   G   S   V   F   H   1049
GCT CGT ACA GTG GCA ACT GAG TCA TCA TCA AGT AAT GAT GGT TCT GTA TTC CAT   3341

S   N   A   A   L   D   S   N   V   I   Y   E   G   F   S   N   F   Q   1067
TCA AAT GCT GCA TTA GAT TCT AAT GTT ATA TAT GAA GGC TTT TCA AAC TTT CAA   3395

A   M   P   T   S   P   E   Q   S   T   N   V   V   I   A   T   K   A   1085
GCG ATG CCG ACT TCT CCT GAG CAA AGT ACA AAT GTT GTT ATT GCA ACA AAG GCT   3449

N   L   F   K   E   L   G   I   T   S   F   E   L   A   P   Q   Y   R   1103
AAC TTA TTT AAA GAA TTA GGT ATT ACT AGT TTT GAG TTA GCA CCT CAA TAT AGG   3503

S   S   G   D   T   N   Y   G   G   M   S   F   L   D   S   F   L   N   1121
TCT AGT GGT GAC ACT AAT TAC GGT GGC ATG TCA TTC TTA GAT TCT TTC TTA AAT   3557

N   G   Y   A   F   T   D   R   Y   D   L   G   F   N   K   A   D   G   1139
AAT GGT TAT GCA TTT ACC GAT AGA TAT GAT TTA GGC TTT AAC AAA GCA GAC GGG   3611

N   P   N   P   T   K   Y   G   T   D   Q   D   L   R   N   A   I   E   1157
AAT CCT AAC CCA ACA AAG TAT GGA ACA GAT CAA GAT TTA CGT AAT GCA ATA GAG   3665
```

FIGURE 1C

```
  A   L   H   K   N   G   M   Q   A   I   A   D   W   V   P   D   Q   I    1175
GCA TTA CAC AAA AAC GGC ATG CAG GCT ATA GCT GAT TGG GTT CCT GAC CAA ATA    3719

Y   A   L   P   G   K   E   V   V   T   A   T   R   V   D   E   R   G    1193
TAT GCT TTA CCA GGA AAG GAA GTT GTT ACC GCT ACT AGA GTA GAC GAA CGG GGA    3773

N   Q   L   K   D   T   D   F   V   N   L   L   Y   V   A   N   T   K    1211
AAT CAA CTA AAA GAC ACA GAT TTT GTC AAC TTA CTC TAT GTT GCT AAT ACT AAA    3827

S   S   G   V   D   Y   Q   A   K   Y   G   G   E   F   L   D   K   L    1229
AGT AGT GGT GTG GAT TAT CAG GCA AAG TAT GGC GGC GAA TTT TTA GAT AAA TTA    3881

R   E   E   Y   P   S   L   F   K   Q   N   Q   V   S   T   G   Q   P    1247
AGA GAA GAG TAC CCA TCG TTA TTC AAA CAG AAC CAA GTA TCG ACA GGT CAG CCA    3935

I   D   A   S   T   K   I   K   Q   W   S   A   K   Y   M   N   G   T    1265
ATT GAT GCT TCT ACA AAA ATT AAG CAA TGG TCA GCT AAA TAT ATG AAT GGG ACC    3989

N   I   L   H   R   G   A   Y   Y   V   L   K   D   W   A   T   N   Q    1283
AAT ATT TTA CAT CGA GGT GCT TAT TAT GTT TTG AAA GAC TGG GCT ACT AAC CAG    4043

Y   F   N   I   A   K   T   N   E   V   F   L   P   L   Q   L   Q   N    1301
TAT TTT AAC ATT GCA AAA ACG AAT GAA GTA TTT TTG CCA CTA CAG TTG CAG AAT    4097

K   D   A   Q   T   G   F   I   S   D   A   S   G   V   K   Y   Y   S    1319
AAA GAT GCG CAA ACT GGT TTC ATT AGT GAT GCC TCC GGT GTA AAA TAT TAC TCA    4151

I   S   G   Y   Q   A   K   D   T   F   I   E   D   G   N   G   N   W    1337
ATT AGT GGT TAT CAA GCA AAA GAT ACT TTT ATT GAA GAT GGT AAT GGG AAT TGG    4205

Y   Y   F   D   K   D   G   Y   M   V   R   S   Q   Q   G   E   N   P    1355
TAT TAC TTT GAT AAA GAT GGT TAC ATG GTG CGT TCG CAG CAA GGA GAA AAT CCT    4259

I   R   T   V   E   T   S   V   N   T   R   N   G   N   Y   Y   F   M    1373
ATA AGA ACA GTC GAA ACT AGT GTC AAC ACA CGA AAC GGT AAT TAT TAC TTT ATG    4313

P   N   G   V   E   L   R   K   G   F   G   T   D   N   S   G   N   V    1391
CCA AAT GGT GTC GAG TTG CGC AAA GGC TTT GGA ACG GAT AAT AGT GGT AAT GTC    4367

Y   Y   F   D   D   Q   G   K   M   V   R   D   K   Y   I   N   D   D    1409
TAT TAT TTT GAT GAT CAA GGT AAG ATG GTG AGA GAT AAA TAC ATT AAC GAT GAT    4421

A   N   N   F   Y   H   L   N   V   D   G   T   M   S   R   G   L   F    1427
GCT AAT AAT TTT TAT CAC TTA AAT GTT GAT GGG ACT ATG TCT CGA GGA CTA TTT    4475

K   F   D   S   D   T   L   Q   Y   F   A   S   N   G   V   Q   I   K    1445
AAA TTT GAT TCT GAT ACT CTA CAG TAT TTT GCT AGT AAT GGT GTC CAA ATA AAA    4529

D   S   Y   A   K   D   S   K   G   N   K   Y   Y   F   D   S   A   T    1463
GAT AGT TAT GCG AAG GAT AGT AAA GGC AAT AAA TAT TAT TTT GAC TCA GCT ACA    4583

G   N   N   D   T   G   K   A   Q   T   W   D   G   N   G   Y   Y   I    1481
GGA AAT AAC GAT ACT GGG AAA GCC CAA ACT TGG GAT GGT AAT GGC TAC TAT ATT    4637

T   I   D   S   D   A   N   N   T   I   G   V   N   T   D   Y   T   A    1499
ACT ATT GAT TCT GAT GCG AAC AAT ACA ATT GGG GTT AAC ACA GAC TAC ACT GCC    4691

Y   I   T   S   S   L   R   E   D   G   L   F   A   N   A   P   Y   G    1517
TAC ATC ACT AGC TCG CTG CGC GAA GAT GGC TTA TTT GCT AAC GCA CCT TAC GGT    4745

V   V   T   K   D   Q   N   G   N   D   L   K   W   Q   Y   I   N   H    1535
GTT GTA ACA AAA GAC CAA AAT GGT AAC GAT CTT AAG TGG CAG TAT ATT AAC CAT    4799

T   K   Q   Y   E   G   Q   Q   V   Q   V   T   R   Q   Y   T   D   S    1553
ACG AAA CAG TAC GAA GGG CAA CAA GTG CAA GTC ACG CGT CAA TAC ACA GAC AGT    4853

K   G   V   S   W   N   L   I   T   F   A   G   G   D   L   Q   G   Q    1571
AAG GGA GTC AGC TGG AAC TTA ATT ACC TTT GCT GGT GGT GAT TTA CAA GGA CAA    4907
```

FIGURE 1D

```
  R   L   W   V   D   S   R   A   L   T   M   T   P   F   K   T   M   N    1589
AGG CTT TGG GTG GAT AGT CGT GCG TTA ACT ATG ACA CCA TTT AAA ACG ATG AAC    4961

Q   I   S   F   I   S   Y   A   N   R   N   D   G   L   F   L   N   A    1607
CAA ATA AGC TTC ATT AGT TAT GCT AAC CGC AAT GAT GGG TTG TTT TTG AAT GCG    5015

P   Y   Q   V   K   G   Y   Q   L   A   G   M   S   N   Q   Y   K   G    1625
CCA TAC CAA GTC AAG GGG TAT CAA TTA GCT GGG ATG TCC AAC CAA TAC AAG GGC    5069

Q   Q   V   T   I   A   G   V   A   N   V   S   G   K   D   W   S   L    1643
CAA CAA GTG ACC ATT GCT GGG GTG GCG AAC GTT TCT GGA AAA GAC TGG AGT CTG    5123

I   S   F   N   G   T   Q   Y   W   I   D   S   Q   A   L   N   T   N    1661
ATT AGT TTT AAT GGG ACA CAG TAC TGG ATT GAT AGT CAG GCA TTG AAT ACC AAT    5177

F   T   H   D   M   N   Q   K   V   F   V   N   T   T   S   N   L   D    1679
TTC ACA CAT GAC ATG AAC CAA AAG GTC TTT GTC AAT ACA ACT AGT AAT CTT GAT    5231

G   L   F   L   N   A   P   Y   R   Q   P   G   Y   K   L   A   G   L    1697
GGG TTA TTC TTA AAT GCG CCA TAC CGT CAA CCG GGT TAT AAG TTA GCC GGT TTG    5285

A   K   N   Y   N   N   Q   T   V   T   V   S   Q   Q   Y   F   D   D    1715
GCT AAA AAT TAC AAC AAC CAA ACG GTT ACT GTT AGT CAA CAG TAC TTT GAT GAT    5339

Q   G   T   V   W   S   Q   V   V   L   G   G   Q   T   V   W   V   D    1733
CAA GGC ACG GTC TGG AGT CAG GTT GTC CTT GGG GGT CAG ACG GTC TGG GTT GAT    5393

N   H   A   L   A   Q   M   Q   V   S   D   T   D   Q   Q   L   Y   V    1751
AAC CAT GCA TTG GCA CAG ATG CAA GTT AGT GAT ACA GAC CAA CAG CTC TAT GTG    5447

N   S   N   G   R   N   D   G   L   F   L   N   A   P   Y   R   G   Q    1769
AAT AGC AAT GGT CGG AAT GAT GGG TTA TTC TTG AAT GCG CCA TAT CGT GGT CAA    5501

G   S   Q   L   I   G   M   T   A   D   Y   N   G   Q   H   V   Q   V    1787
GGG TCA CAA CTG ATA GGC ATG ACG GCA GAT TAT AAT GGG CAA CAT GTA CAA GTG    5555

T   K   Q   G   Q   D   A   Y   G   A   Q   W   R   L   I   T   L   N    1805
ACC AAG CAA GGG CAA GAT GCC TAT GGT GCA CAA TGG CGT CTT ATT ACG CTA AAT    5609

N   Q   Q   V   W   V   D   S   R   A   L   S   T   T   I   M   Q   A    1823
AAT CAA CAG GTC TGG GTT GAT AGT CGC GCT TTG AGC ACA ACA ATC ATG CAA GCC    5663

M   N   D   N   M   Y   V   N   S   S   Q   R   T   D   G   L   W   L    1841
ATG AAT GAT AAT ATG TAT GTA AAT AGC AGC CAA CGG ACA GAT GGC TTG TGG TTA    5717

N   A   P   Y   T   M   S   G   A   K   W   A   G   D   T   R   S   A    1859
AAC GCA CCT TAT ACG ATG AGT GGG GCT AAA TGG GCT GGT GAT ACA CGT TCA GCT    5771

N   G   R   Y   V   H   I   S   K   A   Y   S   N   E   V   G   N   T    1877
AAT GGG CGC TAT GTC CAT ATT TCA AAA GCT TAT TCA AAC GAA GTC GGC AAT ACA    5825

Y   Y   L   T   N   L   N   G   Q   S   T   W   I   D   K   R   A   F    1895
TAT TAC TTG ACG AAT TTG AAT GGT CAA AGC ACA TGG ATT GAC AAG CGG GCG TTT    5879

T   V   T   F   D   Q   V   V   A   L   N   A   T   I   V   A   R   Q    1913
ACT GTG ACC TTC GAT CAG GTG GTG GCA TTA AAT GCA ACG ATT GTG GCA CGC CAA    5933

R   P   D   G   M   F   K   T   A   P   Y   G   E   A   G   A   Q   F    1931
CGA CCA GAT GGG ATG TTT AAG ACA GCA CCA TAT GGT GAA GCG GGG GCG CAG TTT    5987

V   D   Y   V   T   N   Y   N   Q   Q   T   V   P   V   T   K   Q   H    1949
GTC GAT TAT GTG ACA AAC TAT AAC CAG CAA ACC GTG CCA GTA ACA AAG CAA CAT    6041

S   D   A   Q   G   N   Q   W   Y   L   A   T   V   N   G   T   Q   Y    1967
TCA GAT GCT CAG GGG AAT CAA TGG TAC TTA GCG ACA GTG AAT GGG ACA CAA TAC    6095

```
                TGG ATT GAT CAA CGG TCA TTT TCA CCA GTA GTA ACG AAG GTG GTT GAT TAT CAA      6149

A   K   I   V   P   R   T   T   R   D   G   V   F   S   G   A   P   Y              2003
      GCT AAG ATT GTG CCA CGG ACA ACA CGT GAT GGT GTG TTT AGT GGC GCA CCC TAT              6203

G   E   V   N   A   K   L   V   N   M   A   T   A   Y   Q   N   Q   V              2021
      GGG GAA GTG AAT GCT AAG CTA GTT AAC ATG GCA ACT GCG TAT CAA AAT CAA GTT              6257

V   H   A   T   G   E   Y   T   N   A   S   G   I   T   W   S   Q   F              2039
      GTC CAT GCG ACA GGG GAA TAT ACG AAT GCT TCA GGG ATC ACA TGG AGT CAG TTC              6311

A   L   S   G   Q   E   D   K   L   W   I   D   K   R   A   L   Q   A              2057
      GCG TTA AGC GGG CAA GAA GAC AAG CTA TGG ATT GAT AAG CGT GCT TTG CAA GCT              6365

*   G   K   D   S   T   K   E   G   N   I   I   S   G   W   C   Y   P              2075
      TAA GGG AAG GAT TCG ACA AAG GAG GGT AAC ATT ATC AGC GGA TGG TGT TAT CCT              6419

P   F   L   Y   S   V   F   P   K   *   L   R   Q   F   H   D   K   S              2093
      CCT TTC CTG TAC TCA GTA TTT CCC AAA TAA TTG AGA CAG TTT CAT GAC AAA TCA              6473

T   K   L   V   S   M   P   R   L   W   G   K   L   L   L                          2108
      ACA AAA CTA GTG TCA ATG CCT CGG TTA TGG GGT AAA CTA CTA TTA G                        6519
```

|  | | β4 | | β5 | | β7 |
|---|---|---|---|---|---|---|
| AS | 281 | DILRMDAVAFIWKQ | 323 | VFFKSEAIVHPD | 385 | WVNYVRSHDDIGWTFA |
| GTF-A | 1019 | DSVRVDAPDNIDAD | 1056 | HINILEDWNHAD | 1125 | NYSFVRAHDNNSQDQI |
| DSR-E1 | 522 | DGYRVDAVDNVDAD | 560 | HISILEDWDNND | 630 | NYAFIRAHDSEVQTVI |
| DSR-E2 | 2212 | DSIRIDAVDFIHND | 2250 | HISLVEAGLDAG | 2321 | NYSIIHAHDKGVQEKV |
| GTF-I | 448 | DSIRVDAVDNVDAD | 486 | HVSIVEAWSDND | 556 | SYSFARAHDSEVQDLI |
| GTF-C | 472 | DSIRVDAVDNVDAD | 495 | HLSILEAWSYND | 580 | SYSFIRAHDSEVQDLI |
| GTF-L | 501 | DGVRVDAVDNVNAD | 539 | HLSILEAWSHND | 609 | NYAFVRAHDSEVQSII |
| GTF-D | 460 | DGVRVDAVDNVNAD | 498 | HLSILEAWSDND | 576 | NYIFIRAHDSEVQTVI |
| DSR-S | 546 | DGIRVDAVDNVDAD | 584 | HLSILEDWSHND | 654 | NYSFVRAHDSEVQTVI |
| DSR-C | 497 | DGIRVDAVDNVDAD | 535 | HLSILEDWSHND | 605 | NYSFVRAHDSEVQTVI |
| ASR | 630 | DGIRVDAVDNVDAD | 668 | HLSILEDWNGKD | 759 | NYSFVRAHDYDAQDPI |

FIGURE 8

|  | ASR C-del bis | YDA768SEV | DSR-S |
|---|---|---|---|
|  | Yield (%) [a] | | |
| Panose | 28 | 29 | 17 |
| OA4 | 22 | 46 | - |
| OD4 | 3 | 10 | 30 |
| OA5 | 24 | 5 | - |
| OA6 | 5 | - | - |
| OD5 | - | 8 | 24 |
| OA7 | 6 | - | - |
| OA8 | 2 | - | - |
| OD6 | - | 1 | 11 | ic acid bacteria (*Streptococci, Leuconos-*

SEQUENCE LISTING

```
<160> NUMBER OF SEQ ID NOS: 92

<210> SEQ ID NO 1
<211> LENGTH: 6519
<212> TYPE: DNA
<213> ORGANISM: Artificial Sequence
<220> FEATURE:
<223> OTHER INFORMATION: Gene - Nucleotide sequence of alternansucrase -
      Full Sequence
```

<400> SEQUENCE: 1

```
aagagagtat gttcttctct tacctatttt tatttgtaat tcctattatt taattttgca      60
tgacaatatt aatagcgtgt tacgattcta ctatttaatg ttaataaaat taataaatat     120
ggtattatct tatatgggtg atagatgcac caaatactgt atcatgtctg gtcacatgaa     180
agggagaata attaatgaaa caacaagaaa cagttacccg taaaaaactt tataaatccg     240
gtaaggtttg ggttgcagca gctactgcat ttgcggtatt gggggtttca actgtaacaa     300
cagtccatgc ggatacaaat tcgaatgtcg ctgttaagca ataaataat acaggaacca      360
atgattctgg cgaaaaaaag gtaccggttc catcaactaa taatgatagt ttgaagcaag     420
gaacagatgg tttttggtat gattcagacg gcaatcgtgt cgatcagaag accaatcaga     480
ttctgcttac tgcggaacaa cttaaaaaaa ataacgaaaa aaatttatca gtaatcagtg     540
atgatacatc aaaaaaagat gatgaaaata tttctaagca gaccaaaatt gctaatcaac     600
aaacagtaga tactgctaaa ggcctgacta ccagtaattt atctgatccc atcactgggg     660
gtcactatga aaatcacaat ggctactttg tttatataga tgcttcagga aaacaagtaa     720
caggtttgca aaatattgat ggtaatttac aatattttga tgacaatgga tatcaagtca     780
agggatcctt ccgagatgtc aacggcaagc atatctattt tgattcagta acagggaaag     840
ctagttcaaa tgttgatatt gttaacggta aagctcaagg atatgatgcg caaggcaacc     900
aattaaagaa aagttatgtc gccgatagtt ctgggcaaac ttactatttt gatggtaatg     960
gccaaccgtt aatcggcttg caaacaattg atgggaacct acaatatttt aaccaacaag    1020
gggttcaaat aaagggtggt ttccaagatg ttaacaataa acgtatttat tttgcaccaa    1080
acacaggtaa tgccgttgcc aatactgaaa taattaacgg taaattacag gggcgtgacg    1140
caaatggtaa ccaggtaaag aatgcattta gtaaagatgt tgcaggaaat acattttatt    1200
ttgacgcaaa cggtgtgatg ttaacagggt tgcaaactat ttcaggaaag acatattatc    1260
ttgatgaaca aggacacctg agaaaaaatt acgcgggaac attcaataat cagtttatgt    1320
acttcgatgc tgatacaggt gcgggtaaaa cagcgattga atatcaattt gatcaaggat    1380
tggtatcaca aagtaatgaa aatactcctc acaatgccgc aaagtcttat gataaaagta    1440
gttttgaaaa tgttgatggt tacttaacag cagatacatg gtatcgtcca accgatattt    1500
taaaaaatgg agatacttgg acggcatcta ccgaaactga tatgcgtccg cttttaatga    1560
catggtggcc tgacaaacaa acacaagcaa attacttgaa ttttatgtct agtaaaggac    1620
ttggtataac gaccacttat acagcagcta cgtcacaaaa aacactaaat gacgcagcct    1680
ttgttattca aacagcaatt gaacaacaaa tatctttgaa aaaaagtact gagtggttac    1740
gtgatgcaat tgatagtttt gtgaagacgc aagctaattg gaataagcaa acagaagatg    1800
aagctttcga tggtttgcag tggcttcaag ggggattcct agcttatcaa gatgattcac    1860
atcggacgcc gaatactgat tcaggaaata acagaaaact aggacgtcaa ccaattaata    1920
tcgatggttc gaaagataca actgatggta aaggctctga attcttatta gctaacgata    1980
ttgacaactc aaatccgatt gttcaagctg agcaattaaa ctggctacac tatttaatga    2040
attttggtag tattacaggt aataatgaca atgcgaattt tgatggcatt cgtgtagatg    2100
ctgttgataa tgttgatgct gatttactaa aaatagctgg cgattatttt aaagctctat    2160
atggtacaga taaaagcgac gccaatgcca ataagcattt gtctatttta gaagactgga    2220
acggtaaaga tcctcagtat gttaatcaac agggcaatgc gcaattaaca atggattaca    2280
cagttacttc acagtttggc aattctctaa cacatggcgc caacaacagg agtaacatgt    2340
```

```
ggtatttctt agatactggc tattatctta atggagatct taataagaag atagtagata    2400
agaaccgtcc aaattctggc actttggtta acagaattgc taattcaggt gatacaaaag    2460
ttattccaaa ttatagtttt gttagagcac atgattacga tgctcaagat ccaattagaa    2520
aagccatgat tgatcatggt attattaaaa acatgcagga tactttcact tttgaccaac    2580
tggctcaggg aatggaattc tactataaag atcaagagaa tccgtctggt ttcaaaaagt    2640
ataacgatta taacttacct agtgcttatg caatgttgtt gactaataag gatactgtac    2700
ctcgtgtcta ttatggagat atgtacctcg aaggcgggca atatatggaa aaagggacga    2760
tttacaatcc tgtcatttca gcgttgctca aagctagaat aaaatatgtt tctggtgggc    2820
aaacaatggc taccgatagt tctggaaaag accttaaaga tggcgaaact gatttgttaa    2880
caagtgttcg atttggtaaa ggaattatga catcagatca aaccacaaca caagacaata    2940
gccaagatta taaaaatcaa ggcatcggtg tcattgttgg taataaccct gaccttaagt    3000
tgaacaatga taagaccatt accttgcata tgggaaaggc gcataagaat caactttacc    3060
gtgccttagt attatcaaat gactcaggaa ttgatgttta tgatagtgat gataaagcac    3120
caactttgag aacaaatgac aacggtgact tgattttcca taagacaaat acgtttgtga    3180
agcaagatgg aactattata aattacgaaa tgaagggatc attaaatgct ttaatttcag    3240
gttatttagg tgtctgggtg ccagttggag ctagtgattc acaagatgct cgtacagtgg    3300
caactgagtc atcatcaagt aatgatggtt ctgtattcca ttcaaatgct gcattagatt    3360
ctaatgttat atatgaaggc ttttcaaact ttcaagcgat gccgacttct cctgagcaaa    3420
gtacaaatgt tgttattgca acaaaggcta acttatttaa agaattaggt attactagtt    3480
ttgagttagc acctcaatat aggtctagtg gtgacactaa ttcggtggc atgtcattct    3540 tagattcttt cttaaataat ggttatgcat ttaccgatag atatgattta ggctttaaca    3600
aagcagacgg gaatcctaac ccaacaaagt atggaacaga tcaagattta cgtaatgcaa    3660
tagaggcatt acacaaaaac ggcatgcagg ctatagctga ttgggttcct gaccaaatat    3720 atgcttacc aggaaaggaa gttgttaccg ctactagagt agacgaacgg ggaaatcaac    3780
taaaagacac agattttgtc aacttactct atgttgctaa tactaaaagt agtggtgtgg    3840
attatcaggc aaagtatggc ggcgaatttt tagataaatt aagagaagag tacccatcgt    3900
tattcaaaca gaaccaagta tcgacaggtc agccaattga tgcttctaca aaaattaagc    3960
aatggtcagc taaatatatg aatgggacca atattttaca tcgaggtgct tattatgttt    4020
tgaaagactg ggctactaac cagtatttta acattgcaaa acgaatgaa gtattttgc    4080 cactacagtt gcagaataaa gatgcgcaaa ctggtttcat tagtgatgcc tccggtgtaa    4140
aatattactc aattagtggt tatcaagcaa aagatacttt tattgaagat ggtaatggga    4200
attggtatta ctttgataaa gatggttaca tggtgcgttc gcagcaagga gaaaatccta    4260
taagaacagt cgaaactagt gtcaacacac gaaacggtaa ttattacttt atgccaaatg    4320
gtgtcgagtt gcgcaaaggc tttggaacgg ataatagtgg taatgtctat tattttgatg    4380
atcaaggtaa gatggtgaga gataaataca ttaacgatga tgctaataat ttttatcact    4440
taaatgttga tgggactatg tctcgaggac tatttaaatt tgattctgat actctacagt    4500
attttgctag taatggtgtc caaataaaag atagttatgc gaaggatagt aaaggcaata    4560
aatattattt tgactcagct acaggaaata acgatactgg gaaagcccaa acttgggatg    4620
gtaatggcta ctatattact attgattctg atgcgaacaa tacaattggg gttaacacag    4680
actacactgc ctacatcact agctcgctgc gcgaagatgg cttatttgct aacgcacctt    4740
```

| | |
|---|---|
| acggtgttgt aacaaaagac caaaatggta acgatcttaa gtggcagtat attaaccata | 4800 |
| cgaaacagta cgaagggcaa caagtgcaag tcacgcgtca atacacagac agtaagggag | 4860 |
| tcagctggaa cttaattacc tttgctggtg gtgatttaca aggacaaagg ctttgggtgg | 4920 |
| atagtcgtgc gttaactatg acaccattta aaacgatgaa ccaataagc ttcattagtt | 4980 |
| atgctaaccg caatgatggg ttgttttga atgcgccata ccaagtcaag gggtatcaat | 5040 |
| tagctgggat gtccaaccaa tacaagggcc aacaagtgac cattgctggg gtggcgaacg | 5100 |
| tttctggaaa agactggagt ctgattagtt ttaatgggac acagtactgg attgatagtc | 5160 |
| aggcattgaa taccaatttc acacatgaca tgaaccaaaa ggtctttgtc aatacaacta | 5220 |
| gtaatcttga tgggttattc ttaaatgcgc cataccgtca accgggttat aagttagccg | 5280 |
| gtttggctaa aaattacaac aaccaaacgg ttactgttag tcaacagtac tttgatgatc | 5340 |
| aaggcacggt ctggagtcag gttgtccttg ggggtcagac ggtctgggtt gataaccatg | 5400 |
| cattggcaca gatgcaagtt agtgatacag accaacagct ctatgtgaat agcaatggtc | 5460 |
| ggaatgatgg gttattcttg aatgcgccat atcgtggtca agggtcacaa ctgataggca | 5520 |
| tgacggcaga ttataatggg caacatgtac aagtgaccaa gcaagggcaa gatgcctatg | 5580 |
| gtgcacaatg gcgtcttatt acgctaaata atcaacaggt ctgggttgat agtcgcgctt | 5640 |
| tgagcacaac aatcatgcaa gccatgaatg ataaatgta tgtaaatagc agccaacgga | 5700 |
| cagatggctt gtggttaaac gcaccttata cgatgagtgg ggctaaatgg gctggtgata | 5760 |
| cacgttcagc taatgggcgc tatgtccata tttcaaaagc ttattcaaac gaagtcggca | 5820 |
| atacatatta cttgacgaat ttgaatggtc aaagcacatg gattgacaag cgggcgttta | 5880 |
| ctgtgacctt cgatcaggtg gtggcattaa atgcaacgat tgtggcacgc caacgaccag | 5940 |
| atgggatgtt taagacagca ccatatggtg aagcgggggc gcagtttgtc gattatgtga | 6000 |
| caaactataa ccagcaaacc gtgccagtaa caaagcaaca ttcagatgct cagggggaatc | 6060 |
| aatggtactt agcgacagtg aatgggacac aatactggat tgatcaacgg tcattttcac | 6120 |
| cagtagtaac gaaggtggtt gattatcaag ctaagattgt gccacggaca acacgtgatg | 6180 |
| gtgtgtttag tggcgcaccc tatggggaag tgaatgctaa gctagttaac atggcaactg | 6240 |
| cgtatcaaaa tcaagttgtc catgcgacag gggaatatac gaatgcttca gggatcacat | 6300 |
| ggagtcagtt cgcgttaagc gggcaagaag acaagctatg gattgataag cgtgctttgc | 6360 |
| aagcttaagg gaaggattcg acaaaggagg gtaacattat cagcggatgg tgttatcctc | 6420 |
| ctttcctgta ctcagtattt cccaaataat tgagacagtt tcatgacaaa tcaacaaaac | 6480 |
| tagtgtcaat gcctcggtta tggggtaaac tactattag | 6519 |

<210> SEQ ID NO 2
<211> LENGTH: 4047
<212> TYPE: DNA
<213> ORGANISM: Artificial Sequence
<220> FEATURE:
<223> OTHER INFORMATION: Gene - Nucleotide sequence of Truncated
      alternansucrase - Full Sequence

<400> SEQUENCE: 2

| | |
|---|---|
| atgaaacaac aagaaacagt tacccgtaaa aaactttata aatccggtaa ggtttgggtt | 60 |
| gcagcagcta ctgcatttgc ggtattgggg gtttcaactg taacaacagt ccatgcggat | 120 |
| acaaattcga atgtcgctgt taagcaaata aataatacag gaaccaatga ttctggcgaa | 180 |
| aaaaaggtac cggttccatc aactaataat gatagtttga agcaaggaac agatggtttt | 240 |

-continued

```
tggtatgatt cagacggcaa tcgtgtcgat cagaagacca atcagattct gcttactgcg    300
gaacaactta aaaaaaataa cgaaaaaaat ttatcagtaa tcagtgatga tacatcaaaa    360
aaagatgatg aaaatatttc taagcagacc aaaattgcta atcaacaaac agtagatact    420
gctaaaggcc tgactaccag taatttatct gatcccatca ctgggggtca ctatgaaaat    480
cacaatggct actttgttta tatagatgct tcaggaaaac aagtaacagg tttgcaaaat    540
attgatggta atttacaata ttttgatgac aatggatatc aagtcaaggg atccttccga    600
gatgtcaacg gcaagcatat ctattttgat tcagtaacag ggaaagctag ttcaaatgtt    660
gatattgtta acggtaaagc tcaaggatat gatgcgcaag caaccaatt aaagaaaagt     720
tatgtcgccg atagttctgg gcaaacttac tattttgatg gtaatggcca accgttaatc    780
ggcttgcaaa caattgatgg gaacctacaa tattttaacc aacaagggt tcaaataaag     840
ggtggtttcc aagatgttaa caataaacgt atttatttg caccaaacac aggtaatgcc     900
gttgccaata ctgaaataat taacggtaaa ttacaggggc gtgacgcaaa tggtaaccag    960
gtaaagaatg catttagtaa agatgttgca ggaaatacat tttattttga cgcaaacggt   1020
gtgatgttaa cagggttgca aactatttca ggaaagacat attatcttga tgaacaagga   1080
cacctgagaa aaaattacgc gggaacattc aataatcagt ttatgtactt cgatgctgat   1140
acaggtgcgg gtaaaacagc gattgaatat caatttgatc aaggattggt atcacaaagt   1200
aatgaaaata ctcctcacaa tgccgcaaag tcttatgata aaagtagttt tgaaaatgtt   1260
gatggttact aacagcagaa tacatggtat cgtccaaccg atattttaaa aaatggagat   1320
acttggacgg catctaccga aactgatatg cgtccgcttt aatgacatg gtggcctgac    1380
aaacaaacac aagcaaatta cttgaatttt atgtctagta aaggacttgg tataacgacc   1440
acttatacag cagctacgtc acaaaaaaca ctaaatgacg cagcctttgt tattcaaaca   1500
gcaattgaac aacaaatatc tttgaaaaaa agtactgagt ggttacgtga tgcaattgat   1560
agttttgtga agacgcaagc taattggaat aagcaaacag aagatgaagc tttcgatggt   1620
ttgcagtggc ttcaaggggg attcctagct tatcaagatg attcacatcg gacgccgaat   1680
actgattcag gaaataacag aaaactagga cgtcaaccaa ttaatatcga tggttcgaaa   1740
gatacaactg atggtaaagg ctctgaattc ttattagcta acgatattga caactcaaat   1800
ccgattgttc aagctgagca attaaactgg ctacactatt aatgaatttt tggtagtatt   1860
acaggtaata atgacaatgc gaattttgat ggcattcgtg tagatgctgt tgataatgtt   1920
gatgctgatt tactaaaaat agctggcgat tattttaaag ctctatatgg tacagataaa   1980
agcgacgcca atgccaataa gcatttgtct attttagaag actggaacgg taaagatcct   2040
cagtatgtta atcaacaggg caatgcgcaa ttaacaatgg attacacagt tacttcacag   2100
tttggcaatt ctctaacaca tggcgccaac aacaggagta acatgtggta tttcttagat   2160
actggctatt atcttaatgg agatcttaat aagaagatag tagataagaa ccgtccaaat   2220
tctggcactt tggttaacag aattgctaat tcaggtgata caaaagttat tccaaattat   2280
agttttgtta gagcacatga ttacgatgct caagatccaa ttagaaaagc catgattgat   2340
catggtatta ttaaaaacat gcaggatact ttcactttg accaactggc tcagggaatg    2400
gaattctact ataagatca agagaatccg tctggtttca aaaagtataa cgattataac    2460
ttacctagtg cttatgcaat gttgttgact aataaggata ctgtacctcg tgtctattat   2520
ggagatatgt acctcgaagg cgggcaatat atggaaaaag gacgattta caatcctgtc    2580
atttcagcgt tgctcaaagc tagaataaaa tatgtttctg gtgggcaaac aatggctacc   2640
```

```
gatagttctg gaaaagacct taaagatggc gaaactgatt tgttaacaag tgttcgattt   2700
ggtaaaggaa ttatgacatc agatcaaacc acaacacaag acaatagcca agattataaa   2760
aatcaaggca tcggtgtcat tgttggtaat aaccctgacc ttaagttgaa caatgataag   2820
accattacct tgcatatggg aaaggcgcat aagaatcaac tttaccgtgc cttagtatta   2880
tcaaatgact caggaattga tgtttatgat agtgatgata agcaccaac tttgagaaca    2940 aatgacaacg gtgacttgat tttccataag acaaatacgt tgtgaagca agatggaact    3000 attataaatt acgaaatgaa gggatcatta aatgctttaa tttcaggtta tttaggtgtc   3060
tgggtgccag ttggagctag tgattcacaa gatgctcgta cagtggcaac tgagtcatca   3120
tcaagtaatg atggttctgt attccattca aatgctgcat tagattctaa tgttatatat   3180
gaaggctttt caaactttca agcgatgccg acttctcctg agcaaagtac aaatgttgtt   3240
attgcaacaa aggctaactt atttaaagaa ttaggtatta ctagttttga gttagcacct   3300
caatataggt ctagtggtga cactaattac ggtggcatgt cattcttaga ttctttctta   3360
aataatggtt atgcatttac cgatagatat gatttaggct ttaacaaagc agacgggaat   3420
cctaacccaa caaagtatgg aacagatcaa gatttacgta atgcaataga ggcattacac   3480
aaaaacggca tgcaggctat agctgattgg gttcctgacc aaatatatgc tttaccagga   3540
aaggaagttg ttaccgctac tagagtagac gaacggggaa atcaactaaa agacacagat   3600
tttgtcaact tactctatgt tgctaatact aaaagtagtg gtgtggatta tcaggcaaag   3660
tatggcggcg aatttttaga taaattaaga gaagagtacc catcgttatt caaacagaac   3720
caagtatcga caggtcagcc aattgatgct tctacaaaaa ttaagcaatg gtcagctaaa   3780
tatatgaatg gaccaatat tttacatcga ggtgcttatt atgttttgaa agactgggct    3840
actaaccagt attttaacat tgcaaaaacg aatgaagtat ttttgccact acagttgcag   3900
aataaagatg cgcaaactgg tttcattagt gatgcctccg gtgtaaaata ttactcaatt   3960
agtggttatc aagcaaaaga tacttttatt gaagatggta atgggaattg gtattacttt   4020
gataaagatg gttacatggt gcgttcg                                      4047
```

<210> SEQ ID NO 3
<211> LENGTH: 4275
<212> TYPE: DNA
<213> ORGANISM: Artificial Sequence
<220> FEATURE:
<223> OTHER INFORMATION: Gene - Nucleotide sequence of Truncated
      alternansucrase - Full Sequence

<400> SEQUENCE: 3

```
atgaaacaac aagaaacagt tacccgtaaa aaactttata atccggtaa ggtttgggtt     60 gcagcagcta ctgcatttgc ggtattgggg gtttcaactg taacaacagt ccatgcggat   120
acaaattcga atgtcgctgt taagcaaata aataatacag gaaccaatga ttctggcgaa   180
aaaaaggtac cggttccatc aactaataat gatagtttga agcaaggaac agatggtttt   240
tggtatgatt cagacggcaa tcgtgtcgat cagaagacca atcagattct gcttactgcg   300
gaacaactta aaaaaataa cgaaaaaat ttatcgtaa tcagtgatga tacatcaaaa     360
aaagatgatg aaaatatttc taagcagacc aaaattgcta atcaacaaac agtagatact   420
gctaaaggcc tgactaccag taatttatct gatcccatca ctggggtca ctatgaaaat    480 cacaatggct acttttgttta tatagatgct tcaggaaaac aagtaacagg tttgcaaaat   540
attgatggta attttacaata ttttgatgac aatggatatc aagtcaaggg atccttccga   600
```

```
gatgtcaacg gcaagcatat ctattttgat tcagtaacag ggaaagctag ttcaaatgtt    660
gatattgtta acggtaaagc tcaaggatat gatgcgcaag gcaaccaatt aaagaaaagt    720
tatgtcgccg atagttctgg gcaaacttac tattttgatg gtaatggcca accgttaatc    780
ggcttgcaaa caattgatgg gaacctacaa tattttaacc aacaaggggt tcaaataaag    840
ggtggtttcc aagatgttaa caataaacgt atttattttg caccaaacac aggtaatgcc    900
gttgccaata ctgaaataat taacggtaaa ttacaggggc gtgacgcaaa tggtaaccag    960
gtaaagaatg catttagtaa agatgttgca ggaaatacat tttattttga cgcaaacggt   1020
gtgatgttaa cagggttgca aactatttca ggaaagacat tattcttga tgaacaagga   1080 cacctgagaa aaaattacgc gggaacattc aataatcagt ttatgtactt cgatgctgat   1140
acaggtgcgg gtaaaacagc gattgaatat caatttgatc aaggattggt atcacaaagt   1200
aatgaaaata ctcctcacaa tgccgcaaag tcttatgata aaagtagttt tgaaaatgtt   1260
gatggttact aacagcaga tacatggtat cgtccaaccg atattttaaa aaatggagat   1320
acttggacgg catctaccga aactgatatg cgtccgcttt taatgacatg gtggcctgac   1380
aaacaaacac aagcaaatta cttgaatttt atgtctagta aaggacttgg tataacgacc   1440
acttatacag cagctacgtc acaaaaaaca ctaaatgacg cagcctttgt tattcaaaca   1500
gcaattgaac aacaaatatc tttgaaaaaa agtactgagt ggttacgtga tgcaattgat   1560
agttttgtga agacgcaagc taattggaat aagcaaacag aagatgaagc tttcgatggt   1620
ttgcagtggc ttcaagggg attcctagct tatcaagatg attcacatcg gacgccgaat   1680
actgattcag gaaataacag aaaactagga cgtcaaccaa ttaatatcga tggttcgaaa   1740
gatacaactg atggtaaagg ctctgaattc ttattagcta acgatattga caactcaaat   1800
ccgattgttc aagctgagca attaaactgg ctacactatt taatgaattt tggtagtatt   1860
acaggtaata atgacaatgc gaattttgat ggcattcgtg tagatgctgt tgataatgtt   1920
gatgctgatt tactaaaaat agctggcgat tattttaaag ctctatatgg tacagataaa   1980
agcgacgcca atgccaataa gcatttgtct atttttagaag actggaacgg taaagatcct   2040
cagtatgtta atcaacaggg caatgcgcaa ttaacaatgg attacacagt tacttcacag   2100
tttggcaatt ctctaacaca tggcgccaac aacaggagta acatgtggta tttcttagat   2160
actggctatt atcttaatgg agatcttaat aagaagatag tagataagaa ccgtccaaat   2220
tctggcactt tggttaacag aattgctaat tcaggtgata caaagttat tccaaattat   2280 agttttgtta gagcacatga ttcgatgct caagatccaa ttagaaaagc catgattgat   2340
catggtatta ttaaaaacat gcaggatact ttcactttg accaactggc tcagggaatg   2400
gaattctact ataaagatca agagaatccg tctggtttca aaaagtataa cgattataac   2460
ttacctagtg cttatgcaat gttgttgact aataaggata ctgtacctcg tgtctattat   2520
ggagatatgt acctcgaagg cgggcaatat atggaaaaag gacgattta caatcctgtc   2580 atttcagcgt tgctcaaagc tagaataaaa tatgtttctg gtgggcaaac aatggctacc   2640
gatagttctg gaaaagacct taagatggc gaaactgatt tgttaacaag tgttcgattt   2700
ggtaaaggaa ttatgacatc agatcaaacc acaacacaag acaatagcca agattataaa   2760
aatcaaggca tcggtgtcat tgttggtaat aaccctgacc ttaagttgaa caatgataag   2820
accattacct tgcatatggg aaaggcgcat aagaatcaac tttaccgtgc cttagtatta   2880
tcaaatgact caggaattga tgtttatgat agtgatgata agcaccaac tttgagaaca   2940 aatgacaacg gtgacttgat tttccataag acaaatacgt ttgtgaagca agatggaact   3000
```

```
attataaaatt acgaaatgaa gggatcatta aatgctttaa tttcaggtta tttaggtgtc    3060
tgggtgccag ttggagctag tgattcacaa gatgctcgta cagtggcaac tgagtcatca    3120
tcaagtaatg atggttctgt attccattca aatgctgcat tagattctaa tgttatatat    3180
gaaggctttt caaactttca agcgatgccg acttctcctg agcaaagtac aaatgttgtt    3240
attgcaacaa aggctaactt atttaaagaa ttaggtatta ctagttttga gttagcaccct   3300 caatataggt ctagtggtga cactaattac ggtggcatgt cattcttaga ttctttctta    3360
aataatggtt atgcatttac cgatagatat gatttaggct ttaacaaagc agacgggaat    3420
cctaacccaa caaagtatgg aacagatcaa gatttacgta atgcaataga ggcattacac    3480
aaaaacggca tgcaggctat agctgattgg gttcctgacc aaatatatgc tttaccagga    3540
aaggaagttg ttaccgctac tagagtagac gaacggggaa atcaactaaa agacacagat    3600
tttgtcaact tactctatgt tgctaatact aaaagtagtg gtgtggatta tcaggcaaag    3660 tatgcggcg aattttttaga taaattaaga gaagagtacc catcgttatt caaacagaac    3720
caagtatcga caggtcagcc aattgatgct tctacaaaaa ttaagcaatg gtcagctaaa    3780
tatatgaatg ggaccaatat tttacatcga ggtgcttatt atgttttgaa agactgggct    3840
actaaccagt attttaacat tgcaaaaacg aatgaagtat ttttgccact acagttgcag    3900
aataaagatg cgcaaactgg tttcattagt gatgcctccg gtgtaaaata ttactcaatt    3960
agtggttatc aagcaaaaga tactttttatt gaagatggta atgggaattg gtattacttt    4020
gataaagatg gttacatggt gcgttcgcag caaggagaaa atcctataag aacagtcgaa    4080
actagtgtca acacacgaaa cggtaattat tacttttatgc caaatggtgt cgagttgcgc    4140
aaaggctttg gaacggataa tagtggtaat gtctattatt ttgatgatca aggtaagatg    4200
gtgagagata aatacattaa cgatgatgct aataattttt atcacttaaa tgttgatggg    4260
actatgtctc gagga                                                     4275
```

<210> SEQ ID NO 4
<211> LENGTH: 3252
<212> TYPE: DNA
<213> ORGANISM: Artificial Sequence
<220> FEATURE:
<223> OTHER INFORMATION: Gene - Nucleotide sequence of Truncated alternansucrase - Full Sequence

<400> SEQUENCE: 4

```
atgttaacag ggttgcaaac tatttcagga aagacatatt atcttgatga acaaggacac      60
ctgagaaaaa attacgcggg aacattcaat aatcagttta tgtacttcga tgctgataca    120
ggtgcgggta aaacagcgat tgaatatcaa tttgatcaag gattggtatc acaaagtaat    180
gaaaatactc ctcacaatgc cgcaaagtct tatgataaaa gtagttttga aatgttgat     240 ggttacttaa cagcagatac atggtatcgt ccaaccgata ttttaaaaaa tggagatact    300
tggacggcat ctaccgaaac tgatatgcgt ccgcttttaa tgcatggtg gcctgacaaa    360 caaacacaag caaattactt gaattttatg tctagtaaag gacttggtat aacgaccact    420
tatacagcag ctacgtcaca aaaaacacta atgacgcag cctttgttat tcaaacagca    480
attgaacaac aaatatcttt gaaaaaaagt actgagtggt tacgtgatgc aattgatagt    540
tttgtgaaga cgcaagctaa ttggaataag caaacagaag atgaagcttt cgatggtttg    600
cagtggcttc aagggggatt cctagctat caagatgatt cacatcggac gccgaatact    660
gattcaggaa ataacagaaa actaggacgt caaccaatta atatcgatgg ttcgaaagat    720
```

```
acaactgatg gtaaaggctc tgaattctta ttagctaacg atattgacaa ctcaaatccg    780
attgttcaag ctgagcaatt aaactggcta cactatttaa tgaattttgg tagtattaca    840
ggtaataatg acaatgcgaa ttttgatggc attcgtgtag atgctgttga taatgttgat    900
gctgatttac taaaaatagc tggcgattat tttaaagctc tatatggtac agataaaagc    960
gacgccaatg ccaataagca tttgtctatt ttagaagact ggaacggtaa agatcctcag   1020
tatgttaatc aacagggcaa tgcgcaatta acaatggatt acacagttac ttcacagttt   1080
ggcaattctc taacacatgg cgccaacaac aggagtaaca tgtggtattt cttagatact   1140
ggctattatc ttaatggaga tcttaataag aagatagtag ataagaaccg tccaaattct   1200
ggcactttgg ttaacagaat tgctaattca ggtgatacaa agttattcc aaattatagt    1260 tttgttagag cacatgatta cgatgctcaa gatccaatta gaaaagccat gattgatcat   1320
ggtattatta aaaacatgca ggatactttc acttttgacc aactggctca gggaatggaa   1380
ttctactata aagatcaaga gaatccgtct ggtttcaaaa agtataacga ttataactta   1440
cctagtgctt atgcaatgtt gttgactaat aaggatactg taccctcgtgt ctattatgga   1500 gatatgtacc tcgaaggcgg gcaatatatg gaaaaaggga cgatttacaa tcctgtcatt   1560
tcagcgttgc tcaaagctag aataaaatat gtttctggtg ggcaaacaat ggctaccgat   1620
agttctggaa aagaccttaa agatggcgaa actgatttgt taacaagtgt tcgatttggt   1680 aaggaatta tgacatcaga tcaaaccaca acacaagaca atagccaaga ttataaaaat    1740
caaggcatcg gtgtcattgt tggtaataac cctgacctta agttgaacaa tgataagacc   1800
attaccttgc atatgggaaa ggcgcataag aatcaacttt accgtgcctt agtattatca   1860
aatgactcag gaattgatgt ttatgatagt gatgataaag caccaacttt gagaacaaat   1920
gacaacggtg acttgatttt ccataagaca aatacgtttg tgaagcaaga tggaactatt   1980
ataaattacg aaatgaaggg atcattaaat gctttaattt caggttattt aggtgtctgg   2040
gtgccagttg gagctagtga ttcacaagat gctcgtacag tggcaactga gtcatcatca   2100
agtaatgatg gttctgtatt ccattccaaat gctgcattag attctaatgt tatatatgaa   2160
ggcttttcaa actttcaagc gatgccgact tctcctgagc aaagtacaaa tgttgttatt   2220
gcaacaaagg ctaacttatt taaagaatta ggtattacta gttttgagtt agcacctcaa   2280
tataggtcta gtggtgacac taattacggt ggcatgtcat tcttagattc tttcttaaat   2340
aatggttatg catttaccga tagatatgat ttaggcttta acaaagcaga cgggaatcct   2400
aacccaacaa gtatggaac agatcaagat ttacgtaatg caatagaggc attacacaaa   2460
aacggcatgc aggctatagc tgattgggtt cctgaccaaa tatatgcttt accaggaaag   2520
gaagttgtta ccgctactag agtagacgaa cggggaaatc aactaaaaga cacagatttt   2580
gtcaacttac tctatgttgc taatactaaa agtagtggtg tggattatca ggcaaagtat   2640
ggcggcgaat tttagataa attaagagaa gagtacccat cgttattcaa acagaaccaa   2700
gtatcgacag gtcagccaat tgatgcttct acaaaaatta agcaatggtc agctaaatat   2760
atgaatggga ccaatatttt acatcgaggt gcttattatg ttttgaaaga ctgggctact   2820
aaccagtatt ttaacattgc aaaaacgaat gaagtatttt tgccactaca gttgcagaat   2880
aaagatgcgc aaactggttt cattagtgat gcctccggtg taaaatatta ctcaattagt   2940
ggttatcaag caaagatac ttttattgaa gatggtaatg ggaattggta ttactttgat    3000
aaagatggtt acatggtgcg ttcgcagcaa ggagaaaatc ctataagaac agtcgaaact   3060
agtgtcaaca cacgaaacgg taattattac tttatgccaa atggtgtcga gttgcgcaaa   3120
```

```
ggctttggaa cggataatag tggtaatgtc tattattttg atgatcaagg taagatggtg    3180
agagataaat acattaacga tgatgctaat aatttttatc acttaaatgt tgatgggact    3240
atgtctcgag ga                                                        3252

<210> SEQ ID NO 5
<211> LENGTH: 3252
<212> TYPE: DNA
<213> ORGANISM: Artificial Sequence
<220> FEATURE:
<223> OTHER INFORMATION: Nucleotide sequence of Truncated
      alternansucrase
<220> FEATURE:
<221> NAME/KEY: Gene
<222> LOCATION: (1003)..(1005)
<223> OTHER INFORMATION: n TGT modified to AGT

<400> SEQUENCE: 5
atgttaacag gttgcaaac tatttcagga aagacatatt atcttgatga acaaggacac      60
ctgagaaaaa attacgcggg aacattcaat aatcagttta tgtacttcga tgctgataca    120
ggtgcgggta aaacagcgat tgaatatcaa tttgatcaag gattggtatc acaaagtaat    180
gaaaatactc ctcacaatgc cgcaaagtct tatgataaaa gtagttttga aaatgttgat    240
ggttacttaa cagcagatac atggtatcgt ccaaccgata ttttaaaaaa tggagatact    300
tggacggcat ctaccgaaac tgatatgcgt ccgcttttaa tgcatggtg gcctgacaaa    360 caaacacaag caaattactt gaattttatg tctagtaaag gacttggtat aacgaccact    420
tatacagcag ctacgtcaca aaaaacacta atgacgcag cctttgttat tcaaacagca    480
attgaacaac aaatatcttt gaaaaaaagt actgagtggt tacgtgatgc aattgatagt    540
tttgtgaaga cgcaagctaa ttggaataag caaacagaag atgaagcttt cgatggtttg    600
cagtggcttc aagggggatt cctagcttat caagatgatt cacatcggac gccgaatact    660
gattcaggaa ataacagaaa actaggacgt caaccaatta atatcgatgg ttcgaaagat    720
acaactgatg gtaaaggctc tgaattctta ttagctaacg atattgacaa ctcaaatccg    780
attgttcaag ctgagcaatt aaactggcta cactatttaa tgaattttgg tagtattaca    840
ggtaataatg acaatgcgaa ttttgatggc attcgtgtag atgctgttga taatgttgat    900
gctgatttac taaaaatagc tggcgattat tttaaagctc tatatggtac agataaaagc    960
gacgccaatg ccaataagca tttgtctatt ttagaagact ggagtggtaa agatcctcag    1020
tatgttaatc aacagggcaa tgcgcaatta acaatggatt acacagttac ttcacagttt    1080
ggcaattctc taacacatgg cgccaacaac aggagtaaca tgtggtattt cttagatact    1140
ggctattatc ttaatggaga tcttaataag aagatagtag ataagaaccg tccaaattct    1200
ggcactttgg ttaacagaat tgctaattca ggtgatacaa aagttattcc aaattatagt    1260
tttgttagag cacatgatta cgatgctcaa gatccaatta aaaagccat gattgatcat    1320 ggtattatta aaaacatgca ggatactttc acttttgacc aactggctca gggaatggaa    1380
ttctactata agatcaaga gaatccgtct ggtttcaaaa agtataacga ttataactta    1440
cctagtgctt atgcaatgtt gttgactaat aaggatactg tacctcgtgt ctattatgga    1500
gatatgtacc tcgaaggcgg gcaatatatg gaaaagggga cgatttacaa tcctgtcatt    1560
tcagcgttgc tcaaagctag aataaaatat gttctggtg gcaaacaat ggctaccgat    1620 agttctggaa aagaccttaa agatggcgaa actgatttgt taacaagtgt tcgatttggt    1680
aaaggaatta tgacatcaga tcaaaccaca acacaagaca atagccaaga ttataaaaat    1740
```

```
caaggcatcg gtgtcattgt tggtaataac cctgacctta agttgaacaa tgataagacc    1800
attaccttgc atatgggaaa ggcgcataag aatcaacttt accgtgcctt agtattatca    1860
aatgactcag gaattgatgt ttatgatagt gatgataaag caccaacttt gagaacaaat    1920
gacaacggtg acttgatttt ccataagaca aatacgtttg tgaagcaaga tggaactatt    1980
ataaattacg aaatgaaggg atcattaaat gctttaattt caggttattt aggtgtctgg    2040
gtgccagttg gagctagtga ttcacaagat gctcgtacag tggcaactga gtcatcatca    2100
agtaatgatg ttctgtatt ccattcaaat gctgcattag attctaatgt tatatatgaa     2160
ggcttttcaa actttcaagc gatgccgact tctcctgagc aaagtacaaa tgttgttatt    2220
gcaacaaagg ctaacttatt taaagaatta ggtattacta gttttgagtt agcacctcaa    2280
tataggtcta gtggtgacac taattacggt ggcatgtcat tcttagattc tttcttaaat    2340
aatggttatg catttaccga tagatatgat ttaggcttta acaaagcaga cgggaatcct    2400
aacccaacaa gtatggaac agatcaagat ttacgtaatg caatagaggc attacacaaa     2460
aacggcatgc aggctatagc tgattgggtt cctgaccaaa tatatgcttt accaggaaag    2520
gaagttgtta ccgctactag agtagacgaa cggggaaatc aactaaaaga cacagatttt    2580
gtcaacttac tctatgttgc taatactaaa agtagtggtg tggattatca ggcaaagtat    2640
ggcggcgaat tttagataa attaagagaa gagtacccat cgttattcaa acagaaccaa     2700
gtatcgacag gtcagccaat tgatgcttct acaaaaatta gcaatggtc agctaaatat     2760 atgaatggga ccaatatttt acatcgaggt gcttattatg ttttgaaaga ctgggctact    2820
aaccagtatt ttaacattgc aaaaacgaat gaagtatttt tgccactaca gttgcagaat    2880
aaagatgcgc aaactggttt cattagtgat gcctccggtg taaaatatta ctcaattagt    2940
ggttatcaag caaaagatac ttttattgaa gatggtaatg ggaattggta ttactttgat    3000
aaagatggtt acatggtgcg ttcgcagcaa ggagaaaatc ctataagaac agtcgaaact    3060
agtgtcaaca cacgaaacgg taattattac tttatgccaa atggtgtcga gttgcgcaaa    3120
ggctttggaa cggataatag tggtaatgtc tattattttg atgatcaagg taagatggtg    3180
agagataaat acattaacga tgatgctaat aatttttatc acttaaatgt tgatgggact    3240
atgtctcgag ga                                                        3252
```

<210> SEQ ID NO 6
<211> LENGTH: 3252
<212> TYPE: DNA
<213> ORGANISM: Artificial Sequence
<220> FEATURE:
<223> OTHER INFORMATION: Nucleotide sequence of Truncated
      alternansucrase
<220> FEATURE:
<221> NAME/KEY: Gene
<222> LOCATION: (1003)..(1005)
<223> OTHER INFORMATION: n TGT modified to AGC

<400> SEQUENCE: 6

```
atgttaacag ggttgcaaac tatttcagga aagacatatt atcttgatga acaaggacac      60
ctgagaaaaa attacgcggg aacattcaat aatcagttta tgtacttcga tgctgataca     120
ggtgcgggta aacagcgat tgaatatcaa tttgatcaag gattggtatc acaaagtaat      180
gaaaatactc ctcacaatgc cgcaaagtct tatgataaaa gtagttttga aaatgttgat    240
ggttacttaa cagcagatac atggtatcgt ccaaccgata ttttaaaaaa tggagatact    300
tggacggcat ctaccgaaac tgatatgcgt ccgcttttaa tgacatggtg gcctgacaaa    360
```

```
caaacacaag caaattactt gaattttatg tctagtaaag gacttggtat aacgaccact    420
tatacagcag ctacgtcaca aaaaacacta aatgacgcag cctttgttat tcaaacagca    480
attgaacaac aaatatcttt gaaaaaaagt actgagtggt tacgtgatgc aattgatagt    540
tttgtgaaga cgcaagctaa ttggaataag caaacagaag atgaagcttt cgatggtttg    600
cagtggcttc aaggggatt cctagcttat caagatgatt cacatcggac gccgaatact    660
gattcaggaa ataacagaaa actaggacgt caaccaatta atatcgatgg ttcgaaagat    720
acaactgatg gtaaaggctc tgaattctta ttagctaacg atattgacaa ctcaaatccg    780
attgttcaag ctgagcaatt aaactggcta cactatttaa tgaattttgg tagtattaca    840
ggtaataatg acaatgcgaa ttttgatggc attcgtgtag atgctgttga taatgttgat    900
gctgatttac taaaaatagc tggcgattat tttaaagctc tatatggtac agataaaagc    960
gacgccaatg ccaataagca tttgtctatt ttagaagact ggagcggtaa agatcctcag   1020
tatgttaatc aacagggcaa tgcgcaatta acaatggatt acacagttac ttcacagttt   1080
ggcaattctc taacacatgg cgccaacaac aggagtaaca tgtggtattt cttagatact   1140
ggctattatc ttaatggaga tcttaataag aagatagtag ataagaaccg tccaaattct   1200
ggcactttgg ttaacagaat tgctaattca ggtgatacaa aagttattcc aaattatagt   1260
tttgttagag cacatgatta cgatgctcaa gatccaatta gaaaagccat gattgatcat   1320
ggtattatta aaaacatgca ggatactttc acttttgacc aactggctca gggaatggaa   1380
ttctactata aagatcaaga gaatccgtct ggtttcaaaa agtataacga ttataactta   1440
cctagtgctt atgcaatgtt gttgactaat aaggatactg tacctcgtgt ctattatgga   1500
gatatgtacc tcgaaggcgg gcaatatatg gaaaaaggga cgatttacaa tcctgtcatt   1560
tcagcgttgc tcaaagctag aataaaaatat gtttctggtg ggcaaacaat ggctaccgat   1620
agttctggaa aagaccttaa agatggcgaa actgatttgt taacaagtgt tcgatttggt   1680
aaaggaatta tgacatcaga tcaaaccaca acacaagaca atagccaaga ttataaaaat   1740
caaggcatcg gtgtcattgt tggtaataac cctgacctta agttgaacaa tgataagacc   1800
attaccttgc atatgggaaa ggcgcataag aatcaacttt accgtgcctt agtattatca   1860
aatgactcag gaattgatgt ttatgatagt gatgataaag caccaacttt gagaacaaat   1920
gacaacggtg acttgatttt ccataagaca aatacgtttg tgaagcaaga tggaactatt   1980
ataaattacg aaatgaaggg atcattaaat gctttaattt caggttattt aggtgtctgg   2040
gtgccagttg gagctagtga ttcacaagat gctcgtacag tggcaactga gtcatcatca   2100
agtaatgatg gttctgtatt ccattcaaat gctgcattag attctaatgt tatatatgaa   2160
ggcttttcaa actttcaagc gatgccgact tctcctgagc aaagtacaaa tgttgttatt   2220
gcaacaaagg ctaacttatt taaagaatta ggtattacta gttttgagtt agcacctcaa   2280
tataggtcta gtggtgacac taattacggt ggcatgtcat tcttagattc tttcttaaat   2340
aatggttatg catttaccga tagatatgat ttaggcttta caaagcaga cgggaatcct   2400 aacccaacaa agtatggaac agatcaagat ttacgtaatg caatagaggc attacacaaa   2460
aacggcatgc aggctatagc tgattgggtt cctgaccaaa tatatgcttt accaggaaag   2520
gaagttgtta ccgctactag agtagacgaa cgggaaatc aactaaaaga cacagatttt   2580
gtcaacttac tctatgttgc taatactaaa agtagtggtg tggattatca ggcaaagtat   2640
ggcggcgaat tttagataa attaagagaa gagtacccat cgttattcaa acagaaccaa   2700
gtatcgacag gtcagccaat tgatgcttct acaaaaatta agcaatggtc agctaaatat   2760
```

-continued

| | |
|---|---|
| atgaatggga ccaatatttt acatcgaggt gcttattatg ttttgaaaga ctgggctact | 2820 |
| aaccagtatt ttaacattgc aaaaacgaat gaagtatttt tgccactaca gttgcagaat | 2880 |
| aaagatgcgc aaactggttt cattagtgat gcctccggtg taaaatatta ctcaattagt | 2940 |
| ggttatcaag caaaagatac ttttattgaa gatggtaatg ggaattggta ttactttgat | 3000 |
| aaagatggtt acatggtgcg ttcgcagcaa ggagaaaatc ctataagaac agtcgaaact | 3060 |
| agtgtcaaca cacgaaacgg taattattac tttatgccaa atggtgtcga gttgcgcaaa | 3120 |
| ggctttggaa cggataatag tggtaatgtc tattattttg atgatcaagg taagatggtg | 3180 |
| agagataaat acattaacga tgatgctaat aatttttatc acttaaatgt tgatgggact | 3240 |
| atgtctcgag ga | 3252 |

<210> SEQ ID NO 7
<211> LENGTH: 3252
<212> TYPE: DNA
<213> ORGANISM: Artificial Sequence
<220> FEATURE:
<223> OTHER INFORMATION: Nucleotide sequence of Truncated
      alternansucrase
<220> FEATURE:
<221> NAME/KEY: Gene
<222> LOCATION: (1003)..(1005)
<223> OTHER INFORMATION: n TGT modified to TCT

<400> SEQUENCE: 7

| | |
|---|---|
| atgttaacag gttgcaaac tatttcagga aagacatatt atcttgatga acaaggacac | 60 |
| ctgagaaaaa attacgcggg aacattcaat aatcagttta tgtacttcga tgctgataca | 120 |
| ggtgcgggta aaacagcgat tgaatatcaa tttgatcaag gattggtatc acaaagtaat | 180 |
| gaaaatactc ctcacaatgc cgcaaagtct tatgataaaa gtagttttga aaatgttgat | 240 |
| ggttacttaa cagcagatac atggtatcgt ccaaccgata ttttaaaaaa tggagatact | 300 |
| tggacggcat ctaccgaaac tgtatatgcgt ccgcttttaa tgacatggtg gcctgacaaa | 360 |
| caaacacaag caaattactt gaattttatg tctagtaaag gacttggtat aacgaccact | 420 |
| tatacagcag ctacgtcaca aaaaacacta atgacgcag cctttgttat tcaaacagca | 480 |
| attgaacaac aaatatcttt gaaaaaagt actgagtggt tacgtgatgc aattgatagt | 540 |
| tttgtgaaga cgcaagctaa ttggaataag caaacagaag atgaagcttt cgatggtttg | 600 |
| cagtggcttc aagggggatt cctagcttat caagatgatt cacatcggac gccgaatact | 660 |
| gattcaggaa ataacagaaa actaggacgt caaccaatta tatcgatgg ttcgaaagat | 720 |
| acaactgatg gtaaaggctc tgaattctta ttagctaacg atattgacaa ctcaaatccg | 780 |
| attgttcaag ctgagcaatt aaactggcta cactatttaa tgaattttgg tagtattaca | 840 |
| ggtaataatg acaatgcgaa ttttgatggc attcgtgtag atgctgttga taatgttgat | 900 |
| gctgatttac taaaaatagc tggcgattat tttaaagctc tatatggtac agataaaagc | 960 |
| gacgccaatg ccaataagca tttgtctatt ttagaagact ggtctggtaa agatcctcag | 1020 |
| tatgttaatc aacagggcaa tgcgcaatta caatggatt acacagttac ttcacagttt | 1080 |
| ggcaattctc taacacatgg cgccaacaac aggagtaaca tgtggtattt cttagatact | 1140 |
| ggctattatc ttaatggaga tcttaataag aagatagtag ataagaaccg tccaaattct | 1200 |
| ggcacttttgg ttaacagaat tgctaattca ggtgatacaa aagttattcc aaattatagt | 1260 |
| tttgttagag cacatgatta cgatgctcaa gatccaatta gaaaagccat gattgatcat | 1320 |
| ggtattatta aaaacatgca ggatactttc acttttgacc aactggctca gggaatggaa | 1380 |

```
ttctactata aagatcaaga gaatccgtct ggtttcaaaa agtataacga ttataactta    1440
cctagtgctt atgcaatgtt gttgactaat aaggatactg tacctcgtgt ctattatgga    1500
gatatgtacc tcgaaggcgg gcaatatatg gaaaaaggga cgatttacaa tcctgtcatt    1560
tcagcgttgc tcaaagctag aataaaatat gtttctggtg ggcaaacaat ggctaccgat    1620
agttctggaa aagaccttaa agatggcgaa actgatttgt taacaagtgt tcgatttggt    1680
aaaggaatta tgacatcaga tcaaaccaca acacaagaca atagccaaga ttataaaaat    1740
caaggcatcg gtgtcattgt tggtaataac cctgacctta agttgaacaa tgataagacc    1800
attaccttgc atatgggaaa ggcgcataag aatcaacttt accgtgcctt agtattatca    1860
aatgactcag gaattgatgt ttatgatagt gatgataaag caccaacttt gagaacaaat    1920
gacaacggtg acttgatttt ccataagaca aatacgtttg tgaagcaaga tggaactatt    1980
ataaattacg aaatgaaggg atcattaaat gctttaattt caggttattt aggtgtctgg    2040
gtgccagttg gagctagtga ttcacaagat gctcgtacag tggcaactga gtcatcatca    2100
agtaatgatg gttctgtatt ccattcaaat gctgcattag attctaatgt tatatatgaa    2160
ggcttttcaa actttcaagc gatgccgact tctcctgagc aaagtacaaa tgttgttatt    2220
gcaacaaagg ctaacttatt taagaattag gtattacta gttttgagtt agcacctcaa    2280
tataggtcta gtggtgacac taattacggt ggcatgtcat tcttagattc tttcttaaat    2340
aatggttatg catttaccga tagatatgat ttaggcttta acaaagcaga cgggaatcct    2400
aacccaacaa gtatggaac agatcaagat ttacgtaatg caatagaggc attacacaaa    2460
aacggcatgc aggctatagc tgattgggtt cctgaccaaa tatatgcttt accaggaaag    2520
gaagttgtta ccgctactag agtagacgaa cggggaaatc aactaaaaga cacagatttt    2580
gtcaacttac tctatgttgc taatactaaa agtagtggtg tggattatca ggcaaagtat    2640
ggcggcgaat ttttagataa attaagagaa gagtacccat cgttattcaa acagaaccaa    2700
gtatcgacag gtcagccaat tgatgcttct acaaaaatta agcaatggtc agctaaatat    2760
atgaatggga ccaatatttt acatcgaggt gcttattatg ttttgaaaga ctgggctact    2820
aaccagtatt ttaacattgc aaaaacgaat gaagtatttt tgccactaca gttgcagaat    2880
aaagatgcgc aaactggttt cattagtgat gcctccggtg taaaatatta ctcaattagt    2940
ggttatcaag caaaagatac ttttattgaa gatggtaatg ggaattggta ttactttgat    3000
aaagatggtt acatggtgcg ttcgcagcaa ggagaaaatc ctataagaac agtcgaaact    3060
agtgtcaaca cacgaaacgg taattattac tttatgccaa atggtgtcga gttgcgcaaa    3120
ggctttggaa cggataatag tggtaatgtc tattattttg atgatcaagg taagatggtg    3180
agagataaat acattaacga tgatgctaat aatttttatc acttaaatgt tgatgggact    3240
atgtctcgag ga                                                        3252
```

<210> SEQ ID NO 8
<211> LENGTH: 3252
<212> TYPE: DNA
<213> ORGANISM: Artificial Sequence
<220> FEATURE:
<223> OTHER INFORMATION: Nucleotide sequence of Truncated
      alternansucrase
<220> FEATURE:
<221> NAME/KEY: Gene
<222> LOCATION: (1003)..(1005)
<223> OTHER INFORMATION: n TGT modified to TCC

```
<400> SEQUENCE: 8
atgttaacag ggttgcaaac tatttcagga aagacatatt atcttgatga acaaggacac      60
ctgagaaaaa attacgcggg aacattcaat aatcagttta tgtacttcga tgctgataca     120
ggtgcgggta aacagcgat tgaatatcaa tttgatcaag gattggtatc acaaagtaat      180
gaaaatactc ctcacaatgc cgcaaagtct tatgataaaa gtagttttga aaatgttgat     240
ggttacttaa cagcagatac atggtatcgt ccaaccgata ttttaaaaaa tggagatact     300
tggacggcat ctaccgaaac tgatatgcgt ccgcttttaa tgacatggtg gcctgacaaa     360
caaacacaag caaattactt gaattttatg tctagtaaag acttggtat aacgaccact     420 tatacagcag ctacgtcaca aaaaacacta atgacgcag cctttgttat tcaaacagca      480
attgaacaac aaatatcttt gaaaaaaagt actgagtggt tacgtgatgc aattgatagt     540
tttgtgaaga cgcaagctaa ttggaataag caaacagaag atgaagcttt cgatggtttg     600
cagtggcttc aaggggatt cctagcttat caagatgatt cacatcggac gccgaatact      660
gattcaggaa ataacagaaa actaggacgt caaccaatta atatcgatgg ttcgaaagat     720
acaactgatg gtaaaggctc tgaattctta ttagctaacg atattgacaa ctcaaatccg     780
attgttcaag ctgagcaatt aaactggcta cactatttaa tgaattttgg tagtattaca     840
ggtaataatg acaatgcgaa ttttgatggc attcgtgtag atgctgttga taatgttgat     900
gctgatttac taaaaatagc tggcgattat tttaaagctc tatatggtac agataaaagc     960
gacgccaatg ccaataagca tttgtctatt ttagaagact ggtccggtaa agatcctcag    1020
tatgttaatc aacagggcaa tgcgcaatta acaatggatt cacagttac ttcacagttt     1080 ggcaattctc taacacatgg cgccaacaac aggagtaaca tgtggtattt cttagatact    1140
ggctattatc ttaatggaga tcttaataag aagatagtag ataagaaccg tccaaattct    1200
ggcactttgg ttaacagaat tgctaattca ggtgatacaa aagttattcc aaattatagt    1260
tttgttagag cacatgatta cgatgctcaa gatccaatta gaaaagccat gattgatcat    1320
ggtattatta aaaacatgca ggatacttc acttttgacc aactggctca gggaatggaa     1380
ttctactata aagatcaaga gaatccgtct ggtttcaaaa agtataacga ttataactta    1440
cctagtgctt atgcaatgtt gttgactaat aaggatactg tacctcgtgt ctattatgga    1500
gatatgtacc tcgaaggcgg gcaatatatg gaaaaaggga cgatttacaa tcctgtcatt    1560
tcagcgttgc tcaaagctag aataaaatat gtttctggtg gcaaacaat ggctaccgat     1620 agttctggaa aagaccttaa agatggcgaa actgatttgt taacaagtgt tcgatttggt    1680
aaaggaatta tgcatcaga tcaaaccaca acacaagaca atagccaaga ttataaaaat     1740
caaggcatcg gtgtcattgt tggtaataac cctgacctta gttgaacaa tgataagacc     1800 attaccttgc atatgggaaa ggcgcataag aatcaacttt accgtgcctt agtattatca    1860
aatgactcag gaattgatgt ttatgatagt gatgataaag caccaacttt gagaacaaat    1920
gacaacggtg acttgatttt ccataagaca aatacgtttg tgaagcaaga tggaactatt    1980
ataaattacg aaatgaaggg atcattaaat gctttaattt caggttattt aggtgtctgg    2040
gtgccagttg gagctagtga ttcacaagat gctcgtacag tggcaactga gtcatcatca    2100
agtaatgatg gttctgtatt ccattcaaat gctgcattag attctaatgt tatatatgaa    2160
ggcttttcaa actttcaagc gatgccgact tctcctgagc aaagtacaaa tgttgttatt    2220
gcaacaaagg ctaacttatt taagaatta ggtattacta gttttgagtt agcacctcaa     2280
tataggtcta gtggtgacac taattacggt ggcatgtcat tcttagattc tttcttaaat    2340
```

-continued

```
aatggttatg catttaccga tagatatgat ttaggctttta acaaagcaga cgggaatcct      2400
aacccaacaa agtatggaac agatcaagat ttacgtaatg caatagaggc attacacaaa      2460
aacggcatgc aggctatagc tgattgggtt cctgaccaaa tatatgcttt accaggaaag      2520
gaagttgtta ccgctactag agtagacgaa cggggaaatc aactaaaaga cacagatttt      2580
gtcaacttac tctatgttgc taatactaaa agtagtggtg tggattatca ggcaaagtat      2640
ggcggcgaat ttttagataa attaagagaa gagtacccat cgttattcaa acagaaccaa      2700
gtatcgacag gtcagccaat tgatgcttct acaaaaatta gcaatggtc agctaaatat       2760 atgaatggga ccaatatttt acatcgaggt gcttattatg ttttgaaaga ctgggctact      2820
aaccagtatt ttaacattgc aaaaacgaat gaagtatttt tgccactaca gttgcagaat      2880
aaagatgcgc aaactggttt cattagtgat gcctccggtg taaaatatta ctcaattagt      2940
ggttatcaag caaaagatac ttttattgaa gatggtaatg ggaattggta ttactttgat      3000
aaagatggtt acatggtgcg ttcgcagcaa ggagaaaatc ctataagaac agtcgaaact      3060
agtgtcaaca cacgaaacgg taattattac tttatgccaa atggtgtcga gttgcgcaaa      3120
ggctttggaa cggataatag tggtaatgtc tattattttg atgatcaagg taagatggtg      3180
agagataaat acattaacga tgatgctaat aatttttatc acttaaatgt tgatgggact      3240
atgtctcgag ga                                                          3252
```

<210> SEQ ID NO 9
<211> LENGTH: 3252
<212> TYPE: DNA
<213> ORGANISM: Artificial Sequence
<220> FEATURE:
<223> OTHER INFORMATION: Nucleotide sequence of Truncated
      alternansucrase
<220> FEATURE:
<221> NAME/KEY: Gene
<222> LOCATION: (1003)..(1005)
<223> OTHER INFORMATION: n TGT modified to TCA

<400> SEQUENCE: 9

```
atgttaacag ggttgcaaac tatttcagga aagacatatt atcttgatga acaaggacac       60
ctgagaaaaa attacgcggg aacattcaat aatcagttta tgtacttcga tgctgataca      120
ggtgcgggta aaacagcgat tgaatatcaa tttgatcaag gattggtatc acaaagtaat      180
gaaaatactc ctcacaatgc cgcaaagtct tatgataaaa gtagttttga aaatgttgat      240
ggttacttaa cagcagatac atggtatcgt ccaaccgata ttttaaaaaa tggagatact      300
tggacggcat ctaccgaaac tgatatgcgt ccgctttaa tgacatggtg gcctgacaaa       360
caaacacaag caaattactt gaattttatg tctagtaaag gacttggtat aacgaccact      420
tatacagcag ctacgtcaca aaaaacacta aatgacgcag cctttgttat tcaaacagca      480
attgaacaac aaatatcttt gaaaaaaagt actgagtggt tacgtgatgc aattgatagt      540
tttgtgaaga cgcaagctaa ttggaataag caaacagaag atgaagcttt cgatggtttg      600
cagtggcttc aaggggggatt cctagcttat caagatgatt cacatcggac gccgaatact      660
gattcaggaa ataacagaaa actaggacgt caaccaatta atatcgatgg ttcgaaagat      720
acaactgatg gtaaaggctc tgaattctta ttagctaacg atattgacaa ctcaaatccg      780
attgttcaag ctgagcaatt aaactggcta cactatttaa tgaattttgg tagtattaca      840
ggtaataatg acaatgcgaa ttttgatggc attcgtgtag atgctgttga taatgttgat      900
gctgatttac taaaaatagc tggcgattat tttaaagctc tatatggtac agataaaagc      960
```

```
gacgccaatg ccaataagca tttgtctatt ttagaagact ggtcaggtaa agatcctcag    1020
tatgttaatc aacagggcaa tgcgcaatta acaatggatt acacagttac ttcacagttt    1080
ggcaattctc taacacatgg cgccaacaac aggagtaaca tgtggtattt cttagatact    1140
ggctattatc ttaatggaga tcttaataag aagatagtag ataagaaccg tccaaattct    1200
ggcactttgg ttaacagaat tgctaattca ggtgatacaa agttattcc aaattatagt     1260 tttgttagag cacatgatta cgatgctcaa gatccaatta gaaaagccat gattgatcat    1320
ggtattatta aaaacatgca ggatactttc acttttgacc aactggctca gggaatggaa    1380
ttctactata aagatcaaga gaatccgtct ggtttcaaaa agtataacga ttataactta    1440
cctagtgctt atgcaatgtt gttgactaat aaggatactg tacctcgtgt ctattatgga    1500
gatatgtacc tcgaaggcgg gcaatatatg gaaaaaggga cgatttacaa tcctgtcatt    1560
tcagcgttgc tcaaagctag aataaaatat gtttctggtg gcaaacaat ggctaccgat     1620 agttctggaa aagaccttaa agatggcgaa actgatttgt taacaagtgt tcgatttggt    1680
aaaggaatta tgacatcaga tcaaaccaca acacaagaca atagccaaga ttataaaaat    1740
caaggcatcg gtgtcattgt tggtaataac cctgacctta agttgaacaa tgataagacc    1800 attccttgc atatgggaaa ggcgcataag aatcaacttt accgtgcctt agtattatca     1860
aatgactcag gaattgatgt ttatgatagt gatgataaag caccaacttt gagaacaaat    1920
gacaacggtg acttgatttt ccataagaca aatacgtttg tgaagcaaga tggaactatt    1980
ataaattacg aaatgaaggg atcattaaat gctttaattt caggttattt aggtgtctgg    2040
gtgccagttg gagctagtga ttcacaagat gctcgtacag tggcaactga gtcatcatca    2100
agtaatgatg ttctgtatt ccattcaaat gctgcattag attctaatgt tatatatgaa     2160
ggcttttcaa actttcaagc gatgccgact tctcctgagc aaagtacaaa tgttgttatt    2220
gcaacaaagg ctaacttatt taagaatta ggtattacta gttttgagtt agcacctcaa     2280
tataggtcta gtggtgacac taattacggt ggcatgtcat tcttagattc tttcttaaat    2340
aatggttatg catttaccga tagatatgat ttaggcttta acaaagcaga cgggaatcct    2400
aacccaacaa gtatggaac agatcaagat ttacgtaatg caatagaggc attacacaaa     2460
aacggcatgc aggctatagc tgattgggtt cctgaccaaa tatatgcttt accaggaaag    2520
gaagttgtta ccgctactag agtagacgaa cggggaaatc aactaaaaga cacagatttt    2580
gtcaacttac tctatgttgc taatactaaa agtagtggtg tggattatca ggcaaagtat    2640
ggcggcgaat ttttagataa attaagagaa gagtacccat cgttattcaa acagaaccaa    2700
gtatcgacag gtcagccaat tgatgcttct acaaaaatta gcaatggtc agctaaatat     2760 atgaatggga ccaatatttt acatcgaggt gcttattatg ttttgaaaga ctgggctact    2820
aaccagtatt ttaacattgc aaaaacgaat gaagtatttt tgccactaca gttgcagaat    2880
aaagatgcgc aaactggttt cattagtgat gcctccggtg taaaatatta ctcaattagt    2940
ggttatcaag caaagatac ttttattgaa gatggtaatg ggaattggta ttactttgat      3000
aaagatggtt acatggtgcg ttcgcagcaa ggagaaaatc ctataagaac agtcgaaact    3060
agtgtcaaca cacgaaacgg taattattac tttatgccaa atggtgtcga gttgcgcaaa    3120
ggctttggaa cggataatag tggtaatgtc tattattttg atgatcaagg taagatggtg    3180
agagataaat acattaacga tgatgctaat aattttatc acttaaatgt tgatgggact     3240
atgtctcgag ga                                                       3252
```

<210> SEQ ID NO 10
<211> LENGTH: 3252
<212> TYPE: DNA
<213> ORGANISM: Artificial Sequence
<220> FEATURE:
<223> OTHER INFORMATION: Nucleotide sequence of Truncated
      alternansucrase
<220> FEATURE:
<221> NAME/KEY: Gene
<222> LOCATION: (1003)..(1005)
<223> OTHER INFORMATION: n TGT modified to TCG

<400> SEQUENCE: 10

| | | | | | |
|---|---|---|---|---|---|
| atgttaacag | ggttgcaaac | tatttcagga | aagacatatt | atcttgatga | acaaggacac | 60 |
| ctgagaaaaa | attacgcggg | aacattcaat | aatcagttta | tgtacttcga | tgctgataca | 120 |
| ggtgcgggta | aaacagcgat | tgaatatcaa | tttgatcaag | gattggtatc | acaaagtaat | 180 |
| gaaaatactc | ctcacaatgc | cgcaaagtct | tatgataaaa | gtagttttga | aaatgttgat | 240 |
| ggttacttaa | cagcagatac | atggtatcgt | ccaaccgata | ttttaaaaaa | tggagatact | 300 |
| tggacggcat | ctaccgaaac | tgatatgcgt | ccgcttttaa | tgacatggtg | gcctgacaaa | 360 |
| caaacacaag | caaattactt | gaattttatg | tctagtaaag | gacttggtat | aacgaccact | 420 |
| tatacagcag | ctacgtcaca | aaaaacacta | aatgacgcag | cctttgttat | tcaaacagca | 480 |
| attgaacaac | aaatatcttt | gaaaaaaagt | actgagtggt | tacgtgatgc | aattgatagt | 540 |
| tttgtgaaga | cgcaagctaa | ttggaataag | caaacagaag | atgaagcttt | cgatggtttg | 600 |
| cagtggcttc | aagggggatt | cctagcttat | caagatgatt | cacatcggac | gccgaatact | 660 |
| gattcaggaa | ataacagaaa | actaggacgt | caaccaatta | atatcgatgg | ttcgaaagat | 720 |
| acaactgatg | gtaaaggctc | tgaattctta | ttagctaacg | atattgacaa | ctcaaatccg | 780 |
| attgttcaag | ctgagcaatt | aaactggcta | cactatttaa | tgaattttgg | tagtattaca | 840 |
| ggtaataatg | acaatgcgaa | ttttgatggc | attcgtgtag | atgctgttga | taatgttgat | 900 |
| gctgatttac | taaaaatagc | tggcgattat | tttaaagctc | tatatggtac | agataaaagc | 960 |
| gacgccaatg | ccaataagca | tttgtctatt | ttagaagact | ggtcgggtaa | agatcctcag | 1020 |
| tatgttaatc | aacagggcaa | tgcgcaatta | acaatggatt | acacagttac | ttcacagttt | 1080 |
| ggcaattctc | taacacatgg | cgccaacaac | aggagtaaca | tgtggtattt | cttagatact | 1140 |
| ggctattatc | ttaatggaga | tcttaataag | aagatagtag | ataagaaccg | tccaaattct | 1200 |
| ggcactttgg | ttaacagaat | tgctaattca | ggtgatacaa | aagttattcc | aaattatagt | 1260 |
| tttgttagag | cacatgatta | cgatgctcaa | gatccaatta | gaaaagccat | gattgatcat | 1320 |
| ggtattatta | aaaacatgca | ggatactttc | acttttgacc | aactggctca | gggaatggaa | 1380 |
| ttctactata | aagatcaaga | gaatccgtct | ggtttcaaaa | agtataacga | ttataactta | 1440 |
| cctagtgctt | atgcaatgtt | gttgactaat | aaggatactg | tacctcgtgt | ctattatgga | 1500 |
| gatatgtacc | tcgaaggcgg | gcaatatatg | gaaaaaggga | cgatttacaa | tcctgtcatt | 1560 |
| tcagcgttgc | tcaaagctag | aataaaatat | gtttctggtg | gcaaacaat | ggctaccgat | 1620 |
| agttctggaa | aagaccttaa | agatggcgaa | actgatttgt | taacaagtgt | tcgatttggt | 1680 |
| aaaggaatta | tgcatcaga | tcaaaccaca | acacaagaca | atagccaaga | ttataaaaat | 1740 |
| caaggcatcg | tgtcattgt | tggtaataac | cctgacctta | gttgaacaa | tgataagacc | 1800 |
| attccttgc | atatgggaaa | ggcgcataag | aatcaacttt | accgtgcctt | agtattatca | 1860 |
| aatgactcag | gaattgatgt | ttatgatagt | gatgataaag | caccaacttt | gagaacaaat | 1920 |
| gacaacggtg | acttgatttt | ccataagaca | aatacgtttg | tgaagcaaga | tggaactatt | 1980 |

-continued

```
ataaattacg aaatgaaggg atcattaaat gctttaatttt caggttatttt aggtgtctgg    2040 gtgccagttg gagctagtga ttcacaagat gctcgtacag tggcaactga gtcatcatca     2100
agtaatgatg gttctgtatt ccattcaaat gctgcattag attctaatgt tatatatgaa     2160
ggcttttcaa actttcaagc gatgccgact tctcctgagc aaagtacaaa tgttgttatt     2220
gcaacaaagg ctaacttatt taaagaatta ggtattacta gttttgagtt agcacctcaa     2280
tataggtcta gtggtgacac taattacggt ggcatgtcat tcttagattc tttcttaaat     2340
aatggttatg catttaccga tagatatgat ttaggcttta acaaagcaga cgggaatcct     2400
aacccaacaa agtatggaac agatcaagat ttacgtaatg caatagaggc attacacaaa     2460
aacggcatgc aggctatagc tgattgggtt cctgaccaaa tatatgcttt accaggaaag     2520
gaagttgtta ccgctactag agtagacgaa cggggaaatc aactaaaaga cacagattt      2580 gtcaacttac tctatgttgc taatactaaa agtagtggtg tggattatca ggcaaagtat     2640
ggcggcgaat ttttagataa attaagagaa gagtacccat cgttattcaa acagaaccaa     2700
gtatcgacag gtcagccaat tgatgcttct acaaaaatta gcaatggtc agctaaatat      2760 atgaatggga ccaatatttt acatcgaggt gcttattatg ttttgaaaga ctgggctact    2820
aaccagtatt ttaacattgc aaaaacgaat gaagtatttt tgccactaca gttgcagaat     2880
aaagatgcgc aaactggttt cattagtgat gcctccggtg taaaatatta ctcaattagt     2940
ggttatcaag caaagatac ttttattgaa gatggtaatg ggaattggta ttactttgat      3000
aaagatggtt acatggtgcg ttcgcagcaa ggagaaaatc ctataagaac agtcgaaact     3060
agtgtcaaca cacgaaacgg taattattac tttatgccaa atggtgtcga gttgcgcaaa    3120
ggctttggaa cggataatag tggtaatgtc tattattttg atgatcaagg taagatggtg     3180
agagataaat acattaacga tgatgctaat aatttttatc acttaaatgt tgatgggact     3240
atgtctcgag ga                                                        3252
```

<210> SEQ ID NO 11
<211> LENGTH: 3252
<212> TYPE: DNA
<213> ORGANISM: Artificial Sequence
<220> FEATURE:
<223> OTHER INFORMATION: Nucleotide sequence of Truncated
      alternansucrase
<220> FEATURE:
<221> NAME/KEY: Gene
<222> LOCATION: (1009)..(1011)
<223> OTHER INFORMATION: n AAA modified to AAT

<400> SEQUENCE: 11

```
atgttaacag ggttgcaaac tatttcagga aagacatatt atcttgatga acaaggacac       60
ctgagaaaaa attacgcggg aacattcaat aatcagttta tgtacttcga tgctgataca      120
ggtgcgggta aaacagcgat tgaatatcaa tttgatcaag gattggtatc acaaagtaat      180
gaaaatactc ctcacaatgc cgcaaagtct tatgataaaa gtagttttga aaatgttgat      240
ggttacttaa cagcagatac atggtatcgt ccaaccgata ttttaaaaaa tggagatact      300
tggacggcat ctaccgaaac tgatatgcgt ccgcttttaa tgcatggtg gcctgacaaa      360 caaacacaag caaattactt gaatttttatg tctagtaaag gacttggtat aacgaccact     420
tatacagcag ctacgtcaca aaaaacacta aatgacgcag cctttgttat tcaaacagca    480
attgaacaac aaatatcttt gaaaaaaagt actgagtggt tacgtgatgc aattgatagt     540
tttgtgaaga cgcaagctaa ttggaataag caaacagaag atgaagcttt cgatggtttg      600
```

-continued

```
cagtggcttc aagggggatt cctagcttat caagatgatt cacatcggac gccgaatact      660
gattcaggaa ataacagaaa actaggacgt caaccaatta atatcgatgg ttcgaaagat      720
acaactgatg gtaaaggctc tgaattctta ttagctaacg atattgacaa ctcaaatccg      780
attgttcaag ctgagcaatt aaactggcta cactatttaa tgaattttgg tagtattaca      840
ggtaataatg acaatgcgaa ttttgatggc attcgtgtag atgctgttga taatgttgat      900
gctgatttac taaaaatagc tggcgattat tttaaagctc tatatggtac agataaaagc      960
gacgccaatg ccataagca tttgtctatt ttagaagact ggaacggtaa tgatcctcag     1020
tatgttaatc aacagggcaa tgcgcaatta acaatggatt acacagttac ttcacagttt     1080
ggcaattctc taacacatgg cgccaacaac aggagtaaca tgtggtattt cttagatact     1140
ggctattatc ttaatggaga tcttaataag aagatagtag ataagaaccg tccaaattct     1200
ggcactttgg ttaacagaat tgctaattca ggtgatacaa agttattcc aaattatagt     1260 tttgttagag cacatgatta cgatgctcaa gatccaatta gaaagccat gattgatcat     1320 ggtattatta aaaacatgca ggatactttc acttttgacc aactggctca gggaatggaa     1380
ttctactata aagatcaaga gaatccgtct ggtttcaaaa agtataacga ttataactta     1440
cctagtgctt atgcaatgtt gttgactaat aaggatactg tacctcgtgt ctattatgga     1500
gatatgtacc tcgaaggcgg gcaatatatg gaaaaaggga cgatttacaa tcctgtcatt     1560
tcagcgttgc tcaaagctag aataaaatat gtttctggtg ggcaaacaat ggctaccgat     1620
agttctggaa aagaccttaa agatggcgaa actgatttgt taacaagtgt tcgatttggt     1680
aaaggaatta tgacatcaga tcaaaccaca acacaagaca atagccaaga ttataaaat     1740 caaggcatcg gtgtcattgt tggtaataac cctgaccttá agttgaacaa tgataagacc     1800 attccttgc atatgggaaa ggcgcataag aatcaacttt accgtgcctt agtattatca     1860
aatgactcag gaattgatgt ttatgatagt gatgataaag caccaacttt gagaacaaat     1920
gacaacggtg acttgatttt ccataagaca aatacgtttg tgaagcaaga tggaactatt     1980
ataaattacg aaatgaaggg atcattaaat gctttaattt caggttattt aggtgtctgg     2040
gtgccagttg gagctagtga ttcacaagat gctcgtacag tggcaactga gtcatcatca     2100
agtaatgatg gttctgtatt ccattcaaat gctgcattag attctaatgt tatatatgaa     2160 ggctttttcaa actttcaagc gatgccgact tctcctgagc aaagtacaaa tgttgttatt     2220
gcaacaaagg ctaacttatt taaagaatta ggtattacta gttttgagtt agcacctcaa     2280
tataggtcta gtggtgacac taattaccgt ggcatgtcat tcttagattc tttcttaaat     2340
aatggttatg catttaccga tagatatgat ttaggcttta acaaagcaga cgggaatcct     2400
aacccaacaa agtatggaac agatcaagat ttacgtaatg caatagaggc attacacaaa     2460
aacggcatgc aggctatagc tgattgggtt cctgaccaaa tatatgcttt accaggaaag     2520
gaagttgtta ccgctactag agtagacgaa cggggaaatc aactaaaaga cacagatttt     2580
gtcaacttac tctatgttgc taatactaaa agtagtggtg tggattatca ggcaaagtat     2640
ggcggcgaat ttttagataa attaagagaa gagtacccat cgttattcaa acagaaccaa     2700
gtatcgacag gtcagccaat tgatgcttct acaaaaatta agcaatggtc agctaaatat     2760
atgaatggga ccaatatttt acatcgaggt gcttattatg ttttgaaaga ctgggctact     2820
aaccagtatt ttaacattgc aaaaacgaat gaagtatttt tgccactaca gttgcagaat     2880
aaagatgcgc aaactggttt cattagtgat gcctccggtg taaaatatta ctcaattagt     2940
ggttatcaag caaaagatac ttttattgaa gatggtaatg ggaattggta ttactttgat     3000
```

```
aaagatggtt acatggtgcg ttcgcagcaa ggagaaaatc ctataagaac agtcgaaact    3060
agtgtcaaca cacgaaacgg taattattac tttatgccaa atggtgtcga gttgcgcaaa    3120
ggctttggaa cggataatag tggtaatgtc tattattttg atgatcaagg taagatggtg    3180
agagataaat acattaacga tgatgctaat aatttttatc acttaaatgt tgatgggact    3240
atgtctcgag ga                                                        3252
```

<210> SEQ ID NO 12
<211> LENGTH: 3252
<212> TYPE: DNA
<213> ORGANISM: Artificial Sequence
<220> FEATURE:
<223> OTHER INFORMATION: Nucleotide sequence of Truncated
      alternansucrase
<220> FEATURE:
<221> NAME/KEY: Gene
<222> LOCATION: (1009)..(1011)
<223> OTHER INFORMATION: n AAA modified to AAC

<400> SEQUENCE: 12

```
atgttaacag ggttgcaaac tatttcagga aagacatatt atcttgatga acaaggacac      60
ctgagaaaaa attacgcggg aacattcaat aatcagttta tgtacttcga tgctgataca    120
ggtgcgggta aaacagcgat tgaatatcaa tttgatcaag gattggtatc acaaagtaat    180
gaaaatactc ctcacaatgc cgcaaagtct tatgataaaa gtagttttga aaatgttgat    240
ggttacttaa cagcagatac atggtatcgt ccaaccgata ttttaaaaaa tggagatact    300
tggacggcat ctaccgaaac tgtatatgcgt ccgcttttaa tgcatggtg gcctgacaaa    360 caaacacaag caaattactt gaattttatg tctagtaaag gacttggtat aacgaccact    420
tatacagcag ctacgtcaca aaaaacacta atgacgcag cctttgttat tcaaacagca    480
attgaacaac aaatatcttt gaaaaaaagt actgagtggt tacgtgatgc aattgatagt    540
tttgtgaaga cgcaagctaa ttggaataag caaacagaag atgaagcttt cgatggtttg    600
cagtggcttc aaggggggatt cctagcttat caagatgatt cacatcggac gccgaatact    660
gattcaggaa ataacagaaa actaggacgt caaccaatta atatcgatgg ttcgaaagat    720
acaactgatg gtaaaggctc tgaattctta ttagctaacg atattgacaa ctcaaatccg    780
attgttcaag ctgagcaatt aaactggcta cactattaa tgaattttgg tagtattaca    840
ggtaataatg acaatgcgaa ttttgatggc attcgtgtag atgctgttga taatgttgat    900
gctgatttac taaaaatagc tggcgattat tttaaagctc tatatggtac agataaaagc    960
gacgccaatg ccaataagca tttgtctatt ttagaagact ggaacggtaa cgatcctcag   1020
tatgttaatc aacagggcaa tgcgcaatta acaatggatt acacagttac ttcacagttt   1080
ggcaattctc taacacatgg cgccaacaac aggagtaaca tgtggtattt cttagatact   1140
ggctattatc ttaatggaga tcttaataag aagatagtag ataagaaccg tccaaaattct  1200 ggcactttgg ttaacagaat tgctaattca ggtgatacaa aagttattcc aaattatagt   1260
tttgttagag cacatgatta cgatgctcaa gatccaatta gaaaagccat gattgatcat   1320
ggtattatta aaaacatgca ggatactttc acttttgacc aactggctca gggaatggaa   1380
ttctactata aagatcaaga gaatccgtct ggtttcaaaa agtataacga ttataactta   1440
cctagtgctt atgcaatgtt gttgactaat aaggatactg tacctcgtgt ctattatgga   1500
gatatgtacc tcgaaggcgg gcaatatatg gaaaaaggga cgatttacaa tcctgtcatt   1560
tcagcgttgc tcaaagctag aataaaaata gtttctggtg ggcaaacaat ggctaccgat   1620
```

```
agttctggaa aagaccttaa agatggcgaa actgatttgt taacaagtgt tcgatttggt    1680
aaaggaatta tgacatcaga tcaaaccaca acacaagaca atagccaaga ttataaaaat    1740
caaggcatcg gtgtcattgt tggtaataac cctgaccttta agttgaacaa tgataagacc    1800
attaccttgc atatgggaaa ggcgcataag aatcaacttt accgtgcctt agtattatca    1860
aatgactcag gaattgatgt ttatgatagt gatgataaag caccaacttt gagaacaaat    1920
gacaacggtg acttgatttt ccataagaca atacgtttg tgaagcaaga tggaactatt    1980
ataaattacg aaatgaaggg atcattaaat gctttaattt caggttattt aggtgtctgg    2040
gtgccagttg gagctagtga ttcacaagat gctcgtacag tggcaactga gtcatcatca    2100
agtaatgatg gttctgtatt ccattcaaat gctgcattag attctaatgt tatatatgaa    2160
ggcttttcaa actttcaagc gatgccgact tctcctgagc aaagtacaaa tgttgttatt    2220
gcaacaaagg ctaacttatt taaagaatta ggtattacta gttttgagtt agcacctcaa    2280
tataggtcta gtggtgacac taattacggt ggcatgtcat tcttagattc tttcttaaat    2340
aatggttatg catttaccga tagatatgat ttaggctttta acaaagcaga cgggaatcct    2400
aacccaacaa gtatggaac agatcaagat ttacgtaatg caatagaggc attacacaaa    2460
aacggcatgc aggctatagc tgattgggtt cctgaccaaa tatatgcttt accaggaaag    2520
gaagttgtta ccgctactag agtagacgaa cggggaaatc aactaaaaga cacagatttt    2580
gtcaacttac tctatgttgc taatactaaa agtagtggtg tggattatca ggcaaagtat    2640
ggcggcgaat ttttagataa attaagagaa gagtacccat cgttattcaa acagaaccaa    2700
gtatcgacag gtcagccaat tgatgcttct acaaaaatta gcaatggtc agctaaatat    2760
atgaatggga ccaatatttt acatcgaggt gcttattatg ttttgaaaga ctgggctact    2820
aaccagtatt ttaacattgc aaaaacgaat gaagtatttt tgccactaca gttgcagaat    2880
aaagatgcgc aaactggttt cattagtgat gcctccggtg taaaatatta ctcaattagt    2940
ggttatcaag caaagatac ttttattgaa gatggtaatg ggaattggta ttactttgat    3000
aaagatggtt acatggtgcg ttcgcagcaa ggagaaaatc ctataagaac agtcgaaact    3060
agtgtcaaca cacgaaacgg taattattac tttatgccaa atggtgtcga gttgcgcaaa    3120
ggctttggaa cggataatag tggtaatgtc tattattttg atgatcaagg taagatggtg    3180
agagataaat acattaacga tgatgctaat aatttttatc acttaaatgt tgatgggact    3240
atgtctcgag ga                                                         3252

<210> SEQ ID NO 13
<211> LENGTH: 3252
<212> TYPE: DNA
<213> ORGANISM: Artificial Sequence
<220> FEATURE:
<223> OTHER INFORMATION: Nucleotide sequence of Truncated
      alternansucrase
<220> FEATURE:
<221> NAME/KEY: Gene
<222> LOCATION: (1279)..(1281)
<223> OTHER INFORMATION: n TAC modified to AGT

<400> SEQUENCE: 13
atgttaacag ggttgcaaac tatttcagga aagacatatt atcttgatga acaaggacac      60
ctgagaaaaa attacgcggg aacattcaat aatcagttta tgtacttcga tgctgataca     120
ggtgcgggta aacagcgat tgaatatcaa tttgatcaag gattggtatc acaaagtaat     180
gaaaatactc ctcacaatgc cgcaaagtct tatgataaaa gtagttttga aaatgttgat     240
```

```
ggttacttaa cagcagatac atggtatcgt ccaaccgata ttttaaaaaa tggagatact    300
tggacggcat ctaccgaaac tgatatgcgt ccgcttttaa tgacatggtg gcctgacaaa    360
caaacacaag caaattactt gaatttatg tctagtaaag gacttggtat aacgaccact     420
tatacagcag ctacgtcaca aaaaacacta aatgacgcag cctttgttat tcaaacagca    480
attgaacaac aaatatcttt gaaaaaaagt actgagtggt tacgtgatgc aattgatagt    540
tttgtgaaga cgcaagctaa ttggaataag caaacagaag atgaagcttt cgatggtttg    600
cagtggcttc aagggggatt cctagcttat caagatgatt cacatcggac gccgaatact    660
gattcaggaa ataacagaaa actaggacgt caaccaatta atatcgatgg ttcgaaagat    720
acaactgatg gtaaaggctc tgaattctta ttagctaacg atattgacaa ctcaaatccg    780
attgttcaag ctgagcaatt aaactggcta cactatttaa tgaattttgg tagtattaca    840
ggtaataatg acaatgcgaa ttttgatggc attcgtgtag atgctgttga taatgttgat    900
gctgatttac taaaaatagc tggcgattat tttaaagctc tatatggtac agataaaagc    960
gacgccaatg ccaataagca tttgtctatt ttagaagact ggaacggtaa agatcctcag   1020
tatgttaatc aacagggcaa tgcgcaatta acaatggatt acacagttac ttcacagttt   1080
ggcaattctc taacacatgg cgccaacaac aggagtaaca tgtggtattt cttagatact   1140
ggctattatc ttaatggaga tcttaataag aagatagtag ataagaaccg tccaaattct   1200
ggcactttgg ttaacagaat tgctaattca ggtgatacaa aagttattcc aaattatagt   1260
tttgttagag cacatgatag tgatgctcaa gatccaatta gaaaagccat gattgatcat   1320
ggtattatta aaaacatgca ggatactttc acttttgacc aactggctca gggaatggaa   1380
ttctactata aagatcaaga gaatccgtct ggtttcaaaa agtataacga ttataactta   1440
cctagtgctt atgcaatgtt gttgactaat aaggatactg tacctcgtgt ctattatgga   1500
gatatgtacc tcgaaggcgg gcaatatatg gaaaagggga cgatttacaa tcctgtcatt   1560
tcagcgttgc tcaaagctag aataaaaatat gtttctggtg ggcaaacaat ggctaccgat   1620
agttctggaa aagaccttaa agatggcgaa actgatttgt taacaagtgt tcgatttggt   1680
aaaggaatta tgacatcaga tcaaaccaca acacaagaca atagccaaga ttataaaaat   1740
caaggcatcg gtgtcattgt tggtaataac cctgacctta agttgaacaa tgataagacc   1800
attaccttgc atatgggaaa ggcgcataag aatcaacttt accgtgcctt agtattatca   1860
aatgactcag gaattgatgt ttatgatagt gatgataaag caccaacttt gagaacaaat   1920
gacaacggtg acttgatttt ccataagaca aatacgtttg tgaagcaaga tggaactatt   1980
ataaattacg aaatgaaggg atcattaaat gctttaattt caggttattt aggtgtctgg   2040
gtgccagttg gagctagtga ttcacaagat gctcgtacag tggcaactga gtcatcatca   2100
agtaatgatg gttctgtatt ccattcaaat gctgcattag attctaatgt tatatatgaa   2160
ggcttttcaa acttcaagc gatgccgact ctcctgagc aaagtacaaa tgttgttatt    2220
gcaacaaagg ctaacttatt taaagaatta ggtattacta gttttgagtt agcacctcaa   2280
tataggtcta gtggtgacac taattacggt ggcatgtcat tcttagattc tttcttaaat   2340
aatggttatg catttaccga tagatatgat ttaggcttta caaagcaga cgggaatcct    2400
aacccaacaa gtatggaac agatcaagat ttacgtaatg caatagaggc attacacaaa    2460
aacggcatgc aggctatagc tgattgggtt cctgaccaaa tatatgcttt accaggaaag   2520
gaagttgtta ccgctactag agtagacgaa cggggaaatc aactaaaaga cacagatttt   2580
gtcaacttac tctatgttgc taatactaaa agtagtggtg tggattatca ggcaaagtat   2640
```

```
ggcggcgaat ttttagataa attaagagaa gagtacccat cgttattcaa acagaaccaa    2700
gtatcgacag gtcagccaat tgatgcttct acaaaaatta agcaatggtc agctaaatat    2760
atgaatggga ccaatatttt acatcgaggt gcttattatg ttttgaaaga ctgggctact    2820
aaccagtatt ttaacattgc aaaaacgaat gaagtatttt tgccactaca gttgcagaat    2880
aaagatgcgc aaactggttt cattagtgat gcctccggtg taaaatatta ctcaattagt    2940
ggttatcaag caaaagatac ttttattgaa gatggtaatg ggaattggta ttactttgat    3000
aaagatggtt acatggtgcg ttcgcagcaa ggagaaaatc ctataagaac agtcgaaact    3060
agtgtcaaca cacgaaacgg taattattac tttatgccaa atggtgtcga gttgcgcaaa    3120
ggctttggaa cggataatag tggtaatgtc tattattttg atgatcaagg taagatggtg    3180
agagataaat acattaacga tgatgctaat aatttttatc acttaaatgt tgatgggact    3240
atgtctcgag ga                                                       3252

<210> SEQ ID NO 14
<211> LENGTH: 3252
<212> TYPE: DNA
<213> ORGANISM: Artificial Sequence
<220> FEATURE:
<223> OTHER INFORMATION: Nucleotide sequence of Truncated
      alternansucrase
<220> FEATURE:
<221> NAME/KEY: Gene
<222> LOCATION: (1279)..(1281)
<223> OTHER INFORMATION: n TAC modified to AGC

<400> SEQUENCE: 14
atgttaacag ggttgcaaac tatttcagga aagacatatt atcttgatga acaaggacac      60
ctgagaaaaa attacgcggg aacattcaat aatcagttta tgtacttcga tgctgataca     120
ggtgcgggta aaacagcgat tgaatatcaa tttgatcaag gattggtatc acaaagtaat     180
gaaaatactc ctcacaatgc cgcaaagtct tatgataaaa gtagttttga aaatgttgat     240
ggttacttaa cagcagatac atggtatcgt ccaaccgata ttttaaaaaa tggagatact     300
tggacggcat ctaccgaaac tgatatgcgt ccgcttttaa tgacatggtg gcctgacaaa     360
caaacacaag caaattactt gaattttatg tctagtaaag gacttggtat aacgaccact     420
tatacagcag ctacgtcaca aaaaacacta atgacgcag cctttgttat tcaaacagca     480
attgaacaac aaatatcttt gaaaaaaagt actgagtggt tacgtgatgc aattgatagt     540
tttgtgaaga cgcaagctaa ttggaataag caaacagaag atgaagcttt cgatggtttg     600
cagtggcttc aagggggatt cctagcttat caagatgatt cacatcggac gccgaatact     660
gattcaggaa ataacagaaa actaggacgt caaccaatta atatcgatgg ttcgaaagat     720
acaactgatg gtaaaggctc tgaattctta ttagctaacg atattgacaa ctcaaatccg     780
attgttcaag ctgagcaatt aaactggcta cactatttaa tgaatttttgg tagtattaca     840 ggtaataatg acaatgcgaa ttttgatggc attcgtgtag atgctgttga taatgttgat     900
gctgatttac taaaaatagc tggcgattat tttaaagctc tatatggtac agataaaagc     960
gacgccaatg ccaataagca tttgtctatt ttagaagact ggaacggtaa agatcctcag    1020
tatgttaatc aacagggcaa tgcgcaatta acaatggatt acacagttac ttcacagttt    1080
ggcaattctc taacacatgg cgccaacaac aggagtaaca tgtggtattt cttagatact    1140
ggctattatc ttaatggaga tcttaataag aagatagtag ataagaaccg tccaaattct    1200
ggcactttgg ttaacagaat tgctaattca ggtgatacaa aagttattcc aaattatagt    1260
```

```
tttgttagag cacatgatag cgatgctcaa gatccaatta gaaaagccat gattgatcat    1320
ggtattatta aaaacatgca ggatactttc acttttgacc aactggctca gggaatggaa    1380
ttctactata aagatcaaga gaatccgtct ggtttcaaaa agtataacga ttataactta    1440
cctagtgctt atgcaatgtt gttgactaat aaggatactg tacctcgtgt ctattatgga    1500
gatatgtacc tcgaaggcgg gcaatatatg gaaaaaggga cgatttacaa tcctgtcatt    1560
tcagcgttgc tcaaagctag aataaaatat gtttctggtg gcaaacaat ggctaccgat     1620
agttctggaa aagaccttaa agatggcgaa actgatttgt taacaagtgt tcgatttggt    1680
aaaggaatta tgacatcaga tcaaaccaca acacaagaca atagccaaga ttataaaaat    1740
caaggcatcg gtgtcattgt tggtaataac cctgaccta agttgaacaa tgataagacc     1800
attaccttgc atatgggaaa ggcgcataag aatcaacttt accgtgcctt agtattatca    1860
aatgactcag gaattgatgt ttatgatagt gatgataaag caccaacttt gagaacaaat    1920
gacaacggtg acttgatttt ccataagaca aatacgtttg tgaagcaaga tggaactatt    1980
ataaattacg aaatgaaggg atcattaaat gctttaattt caggttattt aggtgtctgg    2040
gtgccagttg gagctagtga ttcacaagat gctcgtacag tggcaactga gtcatcatca    2100
agtaatgatg gttctgtatt ccattcaaat gctgcattag attctaatgt tatatatgaa    2160
ggcttttcaa actttcaagc gatgccgact tctcctgagc aaagtacaaa tgttgttatt    2220
gcaacaaagg ctaacttatt taagaattag gtattacta gttttgagtt agcacctcaa     2280
tataggtcta gtggtgacac taattacggt ggcatgtcat tcttagattc tttcttaaat    2340
aatggttatg catttaccga tagatatgat ttaggctta acaaagcaga cgggaatcct     2400
aacccaacaa gtatggaac agatcaagat ttacgtaatg caatagaggc attacacaaa     2460
aacggcatgc aggctatagc tgattgggtt cctgaccaaa tatatgcttt accaggaaag    2520
gaagttgtta ccgctactag agtagacgaa cggggaaatc aactaaaaga cacagatttt    2580
gtcaacttac tctatgttgc taatactaaa agtagtggtg tggattatca ggcaaagtat    2640
ggcggcgaat ttttagataa attaagagaa gagtacccat cgttattcaa acagaaccaa    2700
gtatcgacag gtcagccaat tgatgcttct acaaaaatta agcaatggtc agctaaatat    2760
atgaatggga ccaatatttt acatcgaggt gcttattatg ttttgaaaga ctgggctact    2820
aaccagtatt ttaacattgc aaaaacgaat gaagtatttt tgccactaca gttgcagaat    2880
aaagatgcgc aaactggttt cattagtgat gcctccggtg taaaatatta ctcaattagt    2940
ggttatcaag caaagatac ttttattgaa gatggtaatg ggaattggta ttactttgat     3000
aaagatggtt acatggtgcg ttcgcagcaa ggagaaaatc ctataagaac agtcgaaact    3060
agtgtcaaca cacgaaacgg taattattac tttatgccaa atggtgtcga gttgcgcaaa    3120
ggctttggaa cggataatag tggtaatgtc tattattttg atgatcaagg taagatggtg    3180
agagataaat acattaacga tgatgctaat aattttatc acttaaatgt tgatgggact     3240
atgtctcgag ga                                                        3252
```

<210> SEQ ID NO 15
<211> LENGTH: 3252
<212> TYPE: DNA
<213> ORGANISM: Artificial Sequence
<220> FEATURE:
<223> OTHER INFORMATION: Nucleotide sequence of Truncated
      alternansucrase

```
<220> FEATURE:
<221> NAME/KEY: Gene
<222> LOCATION: (1279)..(1281)
<223> OTHER INFORMATION: n TAC modified to TCT

<400> SEQUENCE: 15
atgttaacag ggttgcaaac tatttcagga aagacatatt atcttgatga acaaggacac      60
ctgagaaaaa attacgcggg aacattcaat aatcagttta tgtacttcga tgctgataca     120
ggtgcgggta aacagcgat tgaatatcaa tttgatcaag gattggtatc acaaagtaat      180
gaaaatactc ctcacaatgc cgcaaagtct tatgataaaa gtagttttga aaatgttgat     240
ggttacttaa cagcagatac atggtatcgt ccaaccgata ttttaaaaaa tggagatact     300
tggacggcat ctaccgaaac tgatatgcgt ccgcttttaa tgacatggtg gcctgacaaa     360
caaacacaag caaattactt gaatttatg tctagtaaag gacttggtat aacgaccact      420
tatacagcag ctacgtcaca aaaaacacta atgacgcag cctttgttat tcaaacagca      480
attgaacaac aaatatcttt gaaaaaagt actgagtggt tacgtgatgc aattgatagt      540
tttgtgaaga cgcaagctaa ttggaataag caaacagaag atgaagcttt cgatggtttg     600
cagtggcttc aaggggggatt cctagcttat caagatgatt cacatcggac gccgaatact    660
gattcaggaa ataacagaaa actaggacgt caaccaatta atatcgatgg ttcgaaagat     720
acaactgatg gtaaaggctc tgaattctta ttagctaacg atattgacaa ctcaaatccg     780
attgttcaag ctgagcaatt aaactggcta cactatttaa tgaattttgg tagtattaca     840
ggtaataatg acaatgcgaa ttttgatggc attcgtgtag atgctgttga taatgttgat     900
gctgatttac taaaaatagc tggcgattat tttaaagctc tatatggtac agataaaagc     960
gacgccaatg ccaataagca tttgtctatt ttagaagact ggaacggtaa agatcctcag    1020
tatgttaatc aacagggcaa tgcgcaatta caatggatt acacagttac ttcacagttt     1080
ggcaattctc taacacatgg cgccaacaac aggagtaaca tgtggtattt cttagatact    1140
ggctattatc ttaatggaga tcttaataag aagatagtag ataagaaccg tccaaattct    1200
ggcactttgg ttaacagaat tgctaattca ggtgatacaa aagttattcc aaattatagt    1260
tttgttagag cacatgattc tgatgctcaa gatccaatta gaaaagccat gattgatcat    1320
ggtattatta aaaacatgca ggatactttc acttttgacc aactggctca gggaatggaa    1380
ttctactata agatcaaga gaatccgtct ggtttcaaaa agtataacga ttataactta     1440
cctagtgctt atgcaatgtt gttgactaat aaggatactg tacctcgtgt ctattatgga    1500
gatatgtacc tcgaaggcgg gcaatatatg gaaaaaggga cgatttacaa tcctgtcatt    1560
tcagcgttgc tcaaagctag aataaaatat gtttctggtg gcaaacaat ggctaccgat     1620
agttctggaa aagaccttaa agatggcgaa actgatttgt taacaagtgt tcgatttggt    1680
aaaggaatta tgcatcaga tcaaaccaca acacaagaca atagccaaga ttataaaaat     1740
caaggcatcg gtgtcattgt tggtaataac cctgacctta gttgaacaa tgataagacc     1800
attaccttgc atatgggaaa ggcgcataag aatcaacttt accgtgcctt agtattatca    1860
aatgactcag gaattgatgt ttatgatagt gatgataaag caccaacttt gagaacaaat    1920
gacaacggtg acttgatttt ccataagaca aatacgtttg tgaagcaaga tggaactatt    1980
ataaattacg aaatgaaggg atcattaaat gctttaattt caggttattt aggtgtctgg    2040
gtgccagttg gagctagtga ttcacaagat gctcgtacag tggcaactga gtcatcatca    2100
agtaatgatg gttctgtatt ccattcaaat gctgcattag attctaatgt tatatatgaa    2160
```

-continued

```
ggcttttcaa actttcaagc gatgccgact tctcctgagc aaagtacaaa tgttgttatt      2220
gcaacaaagg ctaacttatt taaagaatta ggtattacta gttttgagtt agcacctcaa      2280
tataggtcta gtggtgacac taattacggt ggcatgtcat tcttagattc tttcttaaat      2340
aatggttatg catttaccga tagatatgat ttaggcttta acaaagcaga cgggaatcct      2400
aacccaacaa gtatggaac agatcaagat ttacgtaatg caatagaggc attacacaaa       2460
aacggcatgc aggctatagc tgattgggtt cctgaccaaa tatatgcttt accaggaaag      2520
gaagttgtta ccgctactag agtagacgaa cggggaaatc aactaaaaga cacagatttt      2580
gtcaacttac tctatgttgc taatactaaa agtagtggtg tggattatca ggcaaagtat      2640
ggcggcgaat ttttagataa attaagagaa gagtacccat cgttattcaa acagaaccaa      2700
gtatcgacag gtcagccaat tgatgcttct acaaaaatta gcaatggtc agctaaatat       2760 atgaatggga ccaatatttt acatcgaggt gcttattatg ttttgaaaga ctgggctact      2820
aaccagtatt ttaacattgc aaaaacgaat gaagtatttt tgccactaca gttgcagaat      2880
aaagatgcgc aaactggttt cattagtgat gcctccggtg taaaatatta ctcaattagt      2940
ggttatcaag caaagatac ttttattgaa gatggtaatg ggaattggta ttactttgat       3000
aaagatggtt acatggtgcg ttcgcagcaa ggagaaaatc ctataagaac agtcgaaact      3060
agtgtcaaca cacgaaacgg taattattac tttatgccaa atggtgtcga gttgcgcaaa      3120
ggctttggaa cggataatag tggtaatgtc tattattttg atgatcaagg taagatggtg      3180
agagataaat acattaacga tgatgctaat aattttatc acttaaatgt tgatgggact       3240
atgtctcgag ga                                                          3252
```

<210> SEQ ID NO 16
<211> LENGTH: 3252
<212> TYPE: DNA
<213> ORGANISM: Artificial Sequence
<220> FEATURE:
<223> OTHER INFORMATION: Nucleotide sequence of Truncated
      alternansucrase
<220> FEATURE:
<221> NAME/KEY: Gene
<222> LOCATION: (1279)..(1281)
<223> OTHER INFORMATION: n TAC modified to TCC

<400> SEQUENCE: 16

```
atgttaacag ggttgcaaac tatttcagga aagacatatt atcttgatga acaaggacac        60
ctgagaaaaa attacgcggg aacattcaat aatcagttta tgtacttcga tgctgataca       120
ggtgcgggta aaacagcgat tgaatatcaa tttgatcaag gattggtatc acaaagtaat       180
gaaaatactc ctcacaatgc cgcaaagtct tatgataaaa gtagttttga aaatgttgat       240
ggttacttaa cagcagatac atggtatcgt ccaaccgata ttttaaaaaa tggagatact       300
tggacggcat ctaccgaaac tgatatgcgt ccgcttttaa tgcatggtg gcctgacaaa        360 caaacacaag caaattactt gaatttatg tctagtaaag gacttggtat aacgaccact       420
tatacagcag ctacgtcaca aaaaacacta atgacgcag cctttgttat tcaaacagca       480
attgaacaac aaatatcttt gaaaaaaagt actgagtggt tacgtgatgc aattgatagt      540
tttgtgaaga cgcaagctaa ttggaataag caaacagaag atgaagcttt cgatggtttg      600
cagtggcttc aaggggggatt cctagcttat caagatgatt cacatcggac gccgaatact     660
gattcaggaa ataacagaaa actaggacgt caaccaatta tatcgatgg ttcgaaagat       720 acaactgatg gtaaaggctc tgaattctta ttagctaacg atattgacaa ctcaaatccg      780
```

```
attgttcaag ctgagcaatt aaactggcta cactatttaa tgaattttgg tagtattaca    840
ggtaataatg acaatgcgaa ttttgatggc attcgtgtag atgctgttga taatgttgat    900
gctgatttac taaaaatagc tggcgattat tttaaagctc tatatggtac agataaaagc    960
gacgccaatg ccaataagca tttgtctatt ttagaagact ggaacggtaa agatcctcag   1020
tatgttaatc aacagggcaa tgcgcaatta acaatggatt acacagttac ttcacagttt   1080
ggcaattctc taacacatgg cgccaacaac aggagtaaca tgtggtattt cttagatact   1140
ggctattatc ttaatggaga tcttaataag aagatagtag ataagaaccg tccaaattct   1200
ggcactttgg ttaacagaat tgctaattca ggtgatacaa agttattcc aaattatagt    1260 tttgttagag cacatgattc cgatgctcaa gatccaatta gaaaagccat gattgatcat   1320
ggtattatta aaaacatgca ggtactttc acttttgacc aactggctca gggaatggaa    1380
ttctactata agatcaaga gaatccgtct ggtttcaaaa agtataacga ttataactta    1440
cctagtgctt atgcaatgtt gttgactaat aaggatactg tacctcgtgt ctattatgga   1500
gatatgtacc tcgaaggcgg gcaatatatg gaaaaaggga cgatttacaa tcctgtcatt   1560
tcagcgttgc tcaaagctag aataaaatat gtttctggtg gcaaacaat ggctaccgat    1620 agttctggaa aagaccttaa agatggcgaa actgatttgt taacaagtgt tcgatttggt   1680
aaaggaatta tgacatcaga tcaaaccaca acacaagaca atagccaaga ttataaaaat   1740
caaggcatcg gtgtcattgt tggtaataac cctgacctta agttgaacaa tgataagacc   1800
attaccttgc atatgggaaa ggcgcataag aatcaacttt accgtgcctt agtattatca   1860
aatgactcag gaattgatgt ttatgatagt gatgataaag caccaacttt gagaacaaat   1920
gacaacggtg acttgatttt ccataagaca aatacgtttg tgaagcaaga tggaactatt   1980
ataaattacg aaatgaaggg atcattaaat gctttaattt caggttattt aggtgtctgg   2040
gtgccagttg gagctagtga ttcacaagat gctcgtacag tggcaactga gtcatcatca   2100
agtaatgatg gttctgtatt ccattcaaat gctgcattag attctaatgt tatatatgaa   2160
ggcttttcaa actttcaagc gatgccgact tctcctgagc aaagtacaaa tgttgttatt   2220
gcaacaaagg ctaacttatt taagaatta ggtattacta gttttgagtt agcacctcaa    2280
tataggtcta gtggtgacac taattacggt ggcatgtcat tcttagattc tttcttaaat   2340
aatggttatg catttaccga tagatatgat ttaggctta acaaagcaga cgggaatcct    2400
aacccaacaa agtatggaac agatcaagat ttacgtaatg caatagaggc attacacaaa   2460
aacggcatgc aggctatagc tgattgggtt cctgaccaaa tatatgcttt accaggaaag   2520
gaagttgtta ccgctactag agtagacgaa cggggaaatc aactaaaaga cacagatttt   2580
gtcaacttac tctatgttgc taatactaaa agtagtggtg tggattatca ggcaaagtat   2640
ggcggcgaat ttttagataa attaagagaa gagtacccat cgttattcaa acagaaccaa   2700
gtatcgacag gtcagccaat tgatgcttct acaaaaatta gcaatggtc agctaaatat    2760 atgaatggga ccaatatttt acatcgaggt gcttattatg ttttgaaaga ctgggctact   2820
aaccagtatt ttaacattgc aaaaacgaat gaagtatttt tgccactaca gttgcagaat   2880
aaagatgcgc aaactggttt cattagtgat gcctccggtg taaaatatta ctcaattagt   2940
ggttatcaag caaagatac ttttattgaa gatggtaatg ggaattggta ttactttgat    3000
aaagatggtt acatggtgcg ttcgcagcaa ggagaaaatc ctataagaac agtcgaaact   3060
agtgtcaaca cacgaaacgg taattattac tttatgccaa atggtgtcga gttgcgcaaa   3120
ggctttggaa cggataatag tggtaatgtc tattatttg atgatcaagg taagatggtg    3180
```

```
agagataaat acattaacga tgatgctaat aattttatc acttaaatgt tgatgggact    3240
atgtctcgag ga                                                      3252
```

<210> SEQ ID NO 17
<211> LENGTH: 3252
<212> TYPE: DNA
<213> ORGANISM: Artificial Sequence
<220> FEATURE:
<223> OTHER INFORMATION: Nucleotide sequence of Truncated
      alternansucrase
<220> FEATURE:
<221> NAME/KEY: Gene
<222> LOCATION: (1279)..(1281)
<223> OTHER INFORMATION: n TAC modified to TCA

<400> SEQUENCE: 17

```
atgttaacag ggttgcaaac tatttcagga agacatatt atcttgatga acaaggacac      60
ctgagaaaaa attacgcggg aacattcaat aatcagttta tgtacttcga tgctgataca    120
ggtgcgggta aacagcgat tgaatatcaa tttgatcaag gattggtatc acaaagtaat     180
gaaaatactc ctcacaatgc cgcaaagtct tatgataaaa gtagttttga aaatgttgat    240
ggttacttaa cagcagatac atggtatcgt ccaaccgata ttttaaaaaa tggagatact    300
tggacggcat ctaccgaaac tgatatgcgt ccgcttttaa tgacatggtg gcctgacaaa    360
caaacacaag caaattactt gaattttatg tctagtaaag gacttggtat aacgaccact    420
tatacagcag ctacgtcaca aaaaacacta aatgacgcag cctttgttat tcaaacagca    480
attgaacaac aaatatcttt gaaaaaaagt actgagtggt tacgtgatgc aattgatagt    540
tttgtgaaga cgcaagctaa ttggaataag caaacagaag atgaagcttt cgatggtttg    600
cagtggcttc aaggggggatt cctagcttat caagatgatt cacatcggac gccgaatact    660
gattcaggaa ataacagaaa actaggacgt caaccaatta atatcgatgg ttcgaaagat    720
acaactgatg gtaaaggctc tgaattctta ttagctaacg atattgacaa ctcaaatccg    780
attgttcaag ctgagcaatt aaactggcta cactatttaa tgaattttgg tagtattaca    840
ggtaataatg acaatgcgaa ttttgatggc attcgtgtag atgctgttga taatgttgat    900
gctgatttac taaaaatagc tggcgattat tttaaagctc tatatggtac agataaaagc    960
gacgccaatg ccaataagca tttgtctatt ttagaagact ggaacggtaa agatcctcag   1020
tatgttaatc aacagggcaa tgcgcaatta acaatggatt acacagttac ttcacagttt   1080
ggcaattctc taacacatgg cgccaacaac aggagtaaca tgtggtatttt cttagatact   1140
ggctattatc ttaatggaga tcttaataag aagatagtag ataagaaccg tccaaattct   1200
ggcactttgg ttaacagaat tgctaattca ggtgatacaa aagttattcc aaattatagt   1260
tttgttagag cacatgattc agatgctcaa gatccaatta gaaaagccat gattgatcat   1320
ggtattatta aaacatgca ggatactttc acttttgacc aactggctca gggaatggaa   1380
ttctactata aagatcaaga gaatccgtct ggtttcaaaa agtataacga ttataactta   1440
cctagtgctt atgcaatgtt gttgactaat aaggatactg tacctcgtgt ctattatgga   1500
gatatgtacc tcgaaggcgg gcaatatatg gaaaaaggga cgatttacaa tcctgtcatt   1560
tcagcgttgc tcaaagctag aataaaatat gtttctggtg ggcaaacaat ggctaccgat   1620
agttctggaa aagaccttaa agatggcgaa actgatttgt taacaagtgt tcgatttggt   1680
aaaggaatta tgcatcaga tcaaaccaca acacaagaca atagccaaga ttataaaaat   1740
caaggcatcg gtgtcattgt tggtaataac cctgacctta agttgaacaa tgataagacc   1800
```

```
attaccttgc atatgggaaa ggcgcataag aatcaacttt accgtgcctt agtattatca    1860
aatgactcag gaattgatgt ttatgatagt gatgataaag caccaacttt gagaacaaat    1920
gacaacggtg acttgatttt ccataagaca aatacgtttg tgaagcaaga tggaactatt    1980
ataaattacg aaatgaaggg atcattaaat gctttaattt caggttattt aggtgtctgg    2040
gtgccagttg gagctagtga ttcacaagat gctcgtacag tggcaactga gtcatcatca    2100
agtaatgatg gttctgtatt ccattcaaat gctgcattag attctaatgt tatatatgaa    2160
ggcttttcaa actttcaagc gatgccgact tctcctgagc aaagtacaaa tgttgttatt    2220
gcaacaaagg ctaacttatt taaagaatta ggtattacta gttttgagtt agcacctcaa    2280
tataggtcta gtggtgacac taattacggt ggcatgtcat tcttagattc tttcttaaat    2340
aatggttatg catttaccga tagatatgat ttaggcttta acaaagcaga cgggaatcct    2400
aacccaacaa agtatggaac agatcaagat ttacgtaatg caatagaggc attacacaaa    2460
aacggcatgc aggctatagc tgattgggtt cctgaccaaa tatatgcttt accaggaaag    2520
gaagttgtta ccgctactag agtagacgaa cggggaaatc aactaaaaga cacagatttt    2580
gtcaacttac tctatgttgc taatactaaa agtagtggtg tggattatca ggcaaagtat    2640
ggcggcgaat ttttagataa attaagagaa gagtacccat cgttattcaa acagaaccaa    2700
gtatcgacag gtcagccaat tgatgcttct acaaaaatta agcaatggtc agctaaatat    2760
atgaatggga ccaatatttt catcgaggt gcttattatg ttttgaaaga ctgggctact    2820
aaccagtatt ttaacattgc aaaaacgaat gaagtatttt tgccactaca gttgcagaat    2880
aaagatgcgc aaactggttt cattagtgat gcctccggtg taaaatatta ctcaattagt    2940
ggttatcaag caaagatac ttttattgaa gatggtaatg ggaattggta ttactttgat    3000
aaagatggtt acatggtgcg ttcgcagcaa ggagaaaatc ctataagaac agtcgaaact    3060
agtgtcaaca cacgaaacgg taattattac tttatgccaa atggtgtcga gttgcgcaaa    3120
ggctttggaa cggataatag tggtaatgtc tattattttg atgatcaagg taagatggtg    3180
agagataaat acattaacga tgatgctaat aattttttatc acttaaatgt tgatgggact    3240
atgtctcgag ga                                                       3252

<210> SEQ ID NO 18
<211> LENGTH: 3252
<212> TYPE: DNA
<213> ORGANISM: Artificial Sequence
<220> FEATURE:
<223> OTHER INFORMATION: Nucleotide sequence of Truncated
      alternansucrase
<220> FEATURE:
<221> NAME/KEY: Gene
<222> LOCATION: (1279)..(1281)
<223> OTHER INFORMATION: n TAC modified to TCG

<400> SEQUENCE: 18
atgttaacag ggttgcaaac tatttcagga aagacatatt atcttgatga acaaggacac      60
ctgagaaaaa attacgcggg aacattcaat aatcagttta tgtacttcga tgctgataca     120
ggtgcgggta aaacagcgat tgaatatcaa tttgatcaag gattggtatc acaaagtaat     180
gaaaatactc ctcacaatgc cgcaaagtct tatgataaaa gtagttttga aaatgttgat     240
ggttacttaa cagcagatac atggtatcgt ccaaccgata ttttaaaaaa tggagatact     300
tggacggcat ctaccgaaac tgatatgcgt ccgcttttaa tgcatggtg gcctgacaaa     360 caaacacaag caaattactt gaattttatg tctagtaaag gacttggtat aacgaccact     420
```

-continued

| | | | | |
|---|---|---|---|---|
| tatacagcag | ctacgtcaca | aaaaacacta | aatgacgcag | cctttgttat tcaaacagca | 480 |
| attgaacaac | aaatatcttt | gaaaaaaagt | actgagtggt | tacgtgatgc aattgatagt | 540 |
| tttgtgaaga | cgcaagctaa | ttggaataag | caaacagaag | atgaagcttt cgatggtttg | 600 |
| cagtggcttc | aagggggatt | cctagcttat | caagatgatt | cacatcggac gccgaatact | 660 |
| gattcaggaa | ataacagaaa | actaggacgt | caaccaatta | atatcgatgg ttcgaaagat | 720 |
| acaactgatg | gtaaaggctc | tgaattctta | ttagctaacg | atattgacaa ctcaaatccg | 780 |
| attgttcaag | ctgagcaatt | aaactggcta | cactatttaa | tgaattttgg tagtattaca | 840 |
| ggtaataatg | acaatgcgaa | ttttgatggc | attcgtgtag | atgctgttga taatgttgat | 900 |
| gctgatttac | taaaaatagc | tggcgattat | tttaaagctc | tatatggtac agataaaagc | 960 |
| gacgccaatg | ccaataagca | tttgtctatt | ttagaagact | ggaacggtaa agatcctcag | 1020 |
| tatgttaatc | aacagggcaa | tgcgcaatta | acaatggatt | acacagttac ttcacagttt | 1080 |
| ggcaattctc | taacacatgg | cgccaacaac | aggagtaaca | tgtggtattt cttagatact | 1140 |
| ggctattatc | ttaatggaga | tcttaataag | aagatagtag | ataagaaccg tccaaattct | 1200 |
| ggcactttgg | ttaacagaat | tgctaattca | ggtgatacaa | aagttattcc aaattatagt | 1260 |
| tttgttagag | cacatgattc | ggatgctcaa | gatccaatta | gaaaagccat gattgatcat | 1320 |
| ggtattatta | aaaacatgca | ggatactttc | acttttgacc | aactggctca gggaatggaa | 1380 |
| ttctactata | aagatcaaga | gaatccgtct | ggtttcaaaa | agtataacga ttataactta | 1440 |
| cctagtgctt | atgcaatgtt | gttgactaat | aaggatactg | tacctcgtgt ctattatgga | 1500 |
| gatatgtacc | tcgaaggcgg | gcaatatatg | gaaaaaggga | cgatttacaa tcctgtcatt | 1560 |
| tcagcgttgc | tcaaagctag | aataaaatat | gtttctggtg | ggcaaacaat ggctaccgat | 1620 |
| agttctggaa | aagaccttaa | agatggcgaa | actgatttgt | taacaagtgt tcgatttggt | 1680 |
| aaaggaatta | tgacatcaga | tcaaaccaca | acacaagaca | atagccaaga ttataaaaat | 1740 |
| caaggcatcg | gtgtcattgt | tggtaataac | cctgaccttaa | agttgaacaa tgataagacc | 1800 |
| attaccttgc | atatgggaaa | ggcgcataag | aatcaacttt | accgtgcctt agtattatca | 1860 |
| aatgactcag | gaattgatgt | ttatgatagt | gatgataaag | caccaacttt gagaacaaat | 1920 |
| gacaacggtg | acttgatttt | ccataagaca | aatacgtttg | tgaagcaaga tggaactatt | 1980 |
| ataaattacg | aaatgaaggg | atcattaaat | gctttaattt | caggttattt aggtgtctgg | 2040 |
| gtgccagttg | gagctagtga | ttcacaagat | gctcgtacag | tggcaactga gtcatcatca | 2100 |
| agtaatgatg | gttctgtatt | ccattcaaat | gctgcattag | attctaatgt tatatatgaa | 2160 |
| ggcttttcaa | actttcaagc | gatgccgact | tctcctgagc | aaagtacaaa tgttgttatt | 2220 |
| gcaacaaagg | ctaacttatt | taagaattaa | ggtattacta | gttttgagtt agcacctcaa | 2280 |
| tataggtcta | gtggtgacac | taattacggt | ggcatgtcat | tcttagattc tttcttaaat | 2340 |
| aatggttatg | catttaccga | tagatatgat | ttaggcttta | acaaagcaga cgggaatcct | 2400 |
| aacccaacaa | agtatggaac | agatcaagat | ttacgtaatg | caatagaggc attacacaaa | 2460 |
| aacggcatgc | aggctatagc | tgattgggtt | cctgaccaaa | tatatgcttt accaggaaag | 2520 |
| gaagttgtta | ccgctactag | agtagacgaa | cggggaaatc | aactaaaaga cacagatttt | 2580 |
| gtcaacttac | tctatgttgc | taatactaaa | agtagtggtg | tggattatca ggcaaagtat | 2640 |
| ggcggcgaat | ttttagataa | attaagagaa | gagtacccat | cgttattcaa acagaaccaa | 2700 |
| gtatcgacag | gtcagccaat | tgatgcttct | acaaaaatta | agcaatggtc agctaaatat | 2760 |
| atgaatggga | ccaatatttt | acatcgaggt | gcttattatg | ttttgaaaga ctgggctact | 2820 |

```
aaccagtatt ttaacattgc aaaaacgaat gaagtatttt tgccactaca gttgcagaat    2880
aaagatgcgc aaactggttt cattagtgat gcctccggtg taaaatatta ctcaattagt    2940
ggttatcaag caaagatac  ttttattgaa gatggtaatg ggaattggta ttactttgat    3000
aaagatggtt acatggtgcg ttcgcagcaa ggagaaaatc ctataagaac agtcgaaact    3060
agtgtcaaca cacgaaacgg taattattac tttatgccaa atggtgtcga gttgcgcaaa    3120
ggctttggaa cggataatag tggtaatgtc tattattttg atgatcaagg taagatggtg    3180
agagataaat acattaacga tgatgctaat aattttatc  acttaaatgt tgatgggact    3240
atgtctcgag ga                                                       3252

<210> SEQ ID NO 19
<211> LENGTH: 3252
<212> TYPE: DNA
<213> ORGANISM: Artificial Sequence
<220> FEATURE:
<223> OTHER INFORMATION: Nucleotide sequence of Truncated
      alternansucrase
<220> FEATURE:
<221> NAME/KEY: Gene
<222> LOCATION: (1282)..(1284)
<223> OTHER INFORMATION: n GAT modified to GAA

<400> SEQUENCE: 19
atgttaacag ggttgcaaac tatttcagga aagacatatt atcttgatga acaaggacac      60
ctgagaaaaa attacgcggg aacattcaat aatcagttta tgtacttcga tgctgataca     120
ggtgcgggta aacagcgat  tgaatatcaa tttgatcaag gattggtatc acaaagtaat     180
gaaaatactc ctcacaatgc cgcaaagtct tatgataaaa gtagttttga aaatgttgat     240
ggttacttaa cagcagatac atggtatcgt ccaaccgata ttttaaaaaa tggagatact     300
tggacggcat ctaccgaaac tgatatgcgt ccgcttttaa tgacatggtg gcctgacaaa     360
caaacacaag caaattactt gaattttatg tctagtaaag gacttggtat aacgaccact     420
tatacagcag ctacgtcaca aaaaacacta aatgacgcag cctttgttat tcaaacagca     480
attgaacaac aaatatcttt gaaaaaaagt actgagtggt tacgtgatgc aattgatagt     540
tttgtgaaga cgcaagctaa ttggaataag caaacagaag atgaagcttt cgatggtttg     600
cagtggcttc aaggggggatt cctagcttat caagatgatt cacatcggac gccgaatact     660
gattcaggaa ataacagaaa actaggacgt caaccaatta atatcgatgg ttcgaaagat     720
acaactgatg gtaaaggctc tgaattctta ttagctaacg atattgacaa ctcaaatccg     780
attgttcaag ctgagcaatt aaactggcta cactatttaa tgaattttgg tagtattaca     840
ggtaataatg acaatgcgaa ttttgatggc attcgtgtag atgctgttga taatgttgat     900
gctgatttac taaaaatagc tggcgattat tttaaagctc tatatggtac agataaaagc     960
gacgccaatg ccaataagca tttgtctatt ttagaagact ggaacggtaa agatcctcag    1020
tatgttaatc aacagggcaa tgcgcaatta acaatggatt acacagttac ttcacagttt    1080
ggcaattctc taacacatgg cgccaacaac aggagtaaca tgtggtattt cttagatact    1140
ggctattatc ttaatggaga tcttaataag aagatagtag ataagaaccg tccaaattct    1200
ggcactttgg ttaacagaat tgctaattca ggtgatacaa aagttattcc aaattatagt    1260
tttgttagag cacatgatta cgaagctcaa gatccaatta gaaagccat  gattgatcat    1320 ggtattatta aaaacatgca ggatactttc acttttgacc aactggctca gggaatggaa    1380
ttctactata aagatcaaga gaatccgtct ggtttcaaaa agtataacga ttataactta    1440
```

```
cctagtgctt atgcaatgtt gttgactaat aaggatactg tacctcgtgt ctattatgga    1500
gatatgtacc tcgaaggcgg gcaatatatg gaaaaaggga cgatttacaa tcctgtcatt    1560
tcagcgttgc tcaaagctag aataaaatat gtttctggtg ggcaaacaat ggctaccgat    1620
agttctggaa aagaccttaa agatggcgaa actgatttgt taacaagtgt tcgatttggt    1680
aaaggaatta tgacatcaga tcaaaccaca acacaagaca atagccaaga ttataaaaat    1740
caaggcatcg gtgtcattgt tggtaataac cctgacctta agttgaacaa tgataagacc    1800
attaccttgc atatgggaaa ggcgcataag aatcaacttt accgtgcctt agtattatca    1860
aatgactcag gaattgatgt ttatgatagt gatgataaag caccaacttt gagaacaaat    1920
gacaacggtg acttgatttt ccataagaca aatacgtttg tgaagcaaga tggaactatt    1980
ataaattacg aaatgaaggg atcattaaat gctttaattt caggttattt aggtgtctgg    2040
gtgccagttg gagctagtga ttcacaagat gctcgtacag tggcaactga gtcatcatca    2100
agtaatgatg gttctgtatt ccattccaaat gctgcattag attctaatgt tatatatgaa    2160
ggcttttcaa actttcaagc gatgccgact tctcctgagc aaagtacaaa tgttgttatt    2220
gcaacaaagg ctaacttatt taaagaatta ggtattacta gttttgagtt agcacctcaa    2280
tataggtcta gtggtgacac taattacggt ggcatgtcat tcttagattc tttcttaaat    2340
aatggttatg catttaccga tagatatgat ttaggcttta acaaagcaga cgggaatcct    2400
aacccaacaa gtatggaac agatcaagat ttacgtaatg caatagaggc attacacaaa    2460
aacggcatgc aggctatagc tgattgggtt cctgaccaaa tatatgcttt accaggaaag    2520
gaagttgtta ccgctactag agtagacgaa cggggaaatc aactaaaaga cacagatttt    2580
gtcaacttac tctatgttgc taatactaaa agtagtggtg tggattatca ggcaaagtat    2640
ggcggcgaat ttttagataa attaagagaa gagtacccat cgttattcaa acagaaccaa    2700
gtatcgacag gtcagccaat tgatgcttct acaaaaatta gcaatggtc agctaaatat    2760 atgaatggga ccaatatttt acatcgaggt gcttattatg tttttgaaaga ctgggctact    2820 aaccagtatt ttaacattgc aaaaacgaat gaagtatttt tgccactaca gttgcagaat    2880
aaagatgcgc aaactggttt cattagtgat gcctccggtg taaaatatta ctcaattagt    2940
ggttatcaag caaaagatac ttttattgaa gatggtaatg ggaattggta ttactttgat    3000
aaagatggtt acatggtgcg ttcgcagcaa ggagaaaatc ctataagaac agtcgaaact    3060
agtgtcaaca cacgaaacgg taattattac tttatgccaa atggtgtcga gttgcgcaaa    3120
ggctttggaa cggataatag tggtaatgtc tattattttg atgatcaagg taagatggtg    3180
agagataaat acattaacga tgatgctaat aattttttatc acttaaatgt tgatgggact    3240
atgtctcgag ga                                                       3252

<210> SEQ ID NO 20
<211> LENGTH: 3252
<212> TYPE: DNA
<213> ORGANISM: Artificial Sequence
<220> FEATURE:
<223> OTHER INFORMATION: Nucleotide sequence of Truncated
      alternansucrase
<220> FEATURE:
<221> NAME/KEY: Gene
<222> LOCATION: (1282)..(1284)
<223> OTHER INFORMATION: n GAT modified to GAG
```

<400> SEQUENCE: 20

```
atgttaacag ggttgcaaac tatttcagga aagacatatt atcttgatga acaaggacac    60
ctgagaaaaa attacgcggg aacattcaat aatcagttta tgtacttcga tgctgataca   120
ggtgcgggta aaacagcgat tgaatatcaa tttgatcaag gattggtatc acaaagtaat   180
gaaaatactc ctcacaatgc cgcaaagtct tatgataaaa gtagttttga aaatgttgat   240
ggttacttaa cagcagatac atggtatcgt ccaaccgata ttttaaaaaa tggagatact   300
tggacggcat ctaccgaaac tgatatgcgt ccgcttttaa tgacatggtg gcctgacaaa   360
caaacacaag caaattactt gaattttatg tctagtaaag acttggtat aacgaccact   420
tatacagcag ctacgtcaca aaaaacacta atgacgcag cctttgttat tcaaacagca   480
attgaacaac aaatatcttt gaaaaaaagt actgagtggt tacgtgatgc aattgatagt   540
tttgtgaaga cgcaagctaa ttggaataag caaacagaag atgaagcttt cgatggtttg   600
cagtggcttc aagggggatt cctagcttat caagatgatt cacatcggac gccgaatact   660
gattcaggaa ataacagaaa actaggacgt caaccaatta atatcgatgg ttcgaaagat   720
acaactgatg gtaaaggctc tgaattctta ttagctaacg atattgacaa ctcaaatccg   780
attgttcaag ctgagcaatt aaactggcta cactatttaa tgaattttgg tagtattaca   840
ggtaataatg acaatgcgaa ttttgatggc attcgtgtag atgctgttga taatgttgat   900
gctgatttac taaaaatagc tggcgattat tttaaagctc tatatggtac agataaaagc   960
gacgccaatg ccaataagca tttgtctatt ttagaagact ggaacggtaa agatcctcag  1020
tatgttaatc aacagggcaa tgcgcaatta acaatggatt acacagttac ttcacagttt  1080
ggcaattctc taacacatgg cgccaacaac aggagtaaca tgtggtattt cttagatact  1140
ggctattatc ttaatggaga tcttaataag aagatagtag ataagaaccg tccaaattct  1200
ggcactttgg ttaacagaat tgctaattca ggtgatacaa aagttattcc aaattatagt  1260
tttgttagag cacatgatta cgaggctcaa gatccaatta gaaaagccat gattgatcat  1320
ggtattatta aaaacatgca ggatactttc acttttgacc aactggctca gggaatggaa  1380
ttctactata aagatcaaga gaatccgtct ggtttcaaaa agtataacga ttataactta  1440
cctagtgctt atgcaatgtt gttgactaat aaggatactg tacctcgtgt ctattatgga  1500
gatatgtacc tcgaaggcgg gcaatatatg gaaaaaggga cgatttacaa tcctgtcatt  1560
tcagcgttgc tcaaagctag aataaaatat gtttctggtg gcaaacaat ggctaccgat  1620
agttctggaa aagaccttaa agatggcgaa actgatttgt taacaagtgt tcgatttggt  1680
aaaggaatta tgcatcaga tcaaaccaca acacaagaca atagccaaga ttataaaaat  1740
caaggcatcg gtgtcattgt tggtaataac cctgacctta agttgaacaa tgataagacc  1800
attaccttgc atatgggaaa ggcgcataag aatcaacttt accgtgcctt agtattatca  1860
aatgactcag gaattgatgt ttatgatagt gatgataaag caccaacttt gagaacaaat  1920
gacaacggtg acttgatttt ccataagaca aatacgtttg tgaagcaaga tggaactatt  1980
ataaattacg aaatgaaggg atcattaaat gctttaattt caggttattt aggtgtctgg  2040
gtgccagttg gagctagtga ttcacaagat gctcgtacag tggcaactga gtcatcatca  2100
agtaatgatg gttctgtatt ccattcaaat gctgcattag attctaatgt tatatatgaa  2160
ggcttttcaa actttcaagc gatgccgact tctcctgagc aaagtacaaa tgttgttatt  2220
gcaacaaagg ctaacttatt taagaattta ggtattacta gttttgagtt agcacctcaa  2280
tataggtcta gtggtgacac taattacggt ggcatgtcat tcttagattc tttcttaaat  2340
```

```
aatggttatg catttaccga tagatatgat ttaggcttta acaaagcaga cgggaatcct    2400
aacccaacaa agtatggaac agatcaagat ttacgtaatg caatagaggc attacacaaa    2460
aacggcatgc aggctatagc tgattgggtt cctgaccaaa tatatgcttt accaggaaag    2520
gaagttgtta ccgctactag agtagacgaa cggggaaatc aactaaaaga cacagatttt    2580
gtcaacttac tctatgttgc taatactaaa agtagtggtg tggattatca ggcaaagtat    2640
ggcggcgaat ttttagataa attaagagaa gagtacccat cgttattcaa acagaaccaa    2700
gtatcgacag gtcagccaat tgatgcttct acaaaaatta gcaatggtc agctaaatat     2760 atgaatggga ccaatatttt acatcgaggt gcttattatg ttttgaaaga ctgggctact    2820
aaccagtatt ttaacattgc aaaaacgaat gaagtatttt tgccactaca gttgcagaat    2880
aaagatgcgc aaactggttt cattagtgat gcctccggtg taaaatatta ctcaattagt    2940
ggttatcaag caaaagatac ttttattgaa gatggtaatg ggaattggta ttactttgat    3000
aaagatggtt acatggtgcg ttcgcagcaa ggagaaaatc ctataagaac agtcgaaact    3060
agtgtcaaca cacgaaacgg taattattac tttatgccaa atggtgtcga gttgcgcaaa    3120
ggctttggaa cggataatag tggtaatgtc tattattttg atgatcaagg taagatggtg    3180
agagataaat acattaacga tgatgctaat aattttatc acttaaatgt tgatgggact     3240
atgtctcgag ga                                                       3252

<210> SEQ ID NO 21
<211> LENGTH: 3252
<212> TYPE: DNA
<213> ORGANISM: Artificial Sequence
<220> FEATURE:
<223> OTHER INFORMATION: Nucleotide sequence of Truncated
      alternansucrase
<220> FEATURE:
<221> NAME/KEY: Gene
<222> LOCATION: (1285)..(1287)
<223> OTHER INFORMATION: n GCT modified to GTT

<400> SEQUENCE: 21
atgttaacag ggttgcaaac tatttcagga aagacatatt atcttgatga acaaggacac      60
ctgagaaaaa attacgcggg aacattcaat aatcagttta tgtacttcga tgctgataca     120
ggtgcgggta aaacagcgat tgaatatcaa tttgatcaag gattggtatc acaaagtaat     180
gaaaatactc ctcacaatgc cgcaaagtct tatgataaaa gtagttttga aaatgttgat     240
ggttacttaa cagcagatac atggtatcgt ccaaccgata ttttaaaaaa tggagatact     300
tggacggcat ctaccgaaac tgatatgcgt ccgcttttaa tgacatggtg gcctgacaaa     360
caaacacaag caaattactt gaattttatg tctagtaaag gacttggtat aacgaccact     420
tatacagcag ctacgtcaca aaaaacacta aatgacgcag cctttgttat tcaaacagca     480
attgaacaac aaatatcttt gaaaaaaagt actgagtggt tacgtgatgc aattgatagt     540
tttgtgaaga cgcaagctaa ttggaataag caaacagaag atgaagcttt cgatggtttg     600
cagtggcttc aagggggatt cctagcttat caagatgatt cacatcggac gccgaatact     660
gattcaggaa ataacagaaa actaggacgt caaccaatta atatcgatgg ttcgaaagat     720
acaactgatg gtaaaggctc tgaattctta ttagctaacg atattgacaa ctcaaatccg     780
attgttcaag ctgagcaatt aaactggcta cactatttaa tgaatttttgg tagtattaca    840 ggtaataatg acaatgcgaa ttttgatggc attcgtgtag atgctgttga taatgttgat    900
gctgatttac taaaaatagc tggcgattat tttaaagctc tatatggtac agataaaagc    960
```

```
gacgccaatg ccaataagca tttgtctatt ttagaagact ggaacggtaa agatcctcag    1020
tatgttaatc aacagggcaa tgcgcaatta acaatggatt acacagttac ttcacagttt    1080
ggcaattctc taacacatgg cgccaacaac aggagtaaca tgtggtattt cttagatact    1140
ggctattatc ttaatggaga tcttaataag aagatagtag ataagaaccg tccaaattct    1200
ggcactttgg ttaacagaat tgctaattca ggtgatacaa agttattcc aaattatagt     1260 tttgttagag cacatgatta cgatgttcaa gatccaatta gaaaagccat gattgatcat    1320
ggtattatta aaacatgca ggatactttc acttttgacc aactggctca gggaatggaa     1380
ttctactata aagatcaaga gaatccgtct ggtttcaaaa agtataacga ttataactta    1440
cctagtgctt atgcaatgtt gttgactaat aaggatactg tacctcgtgt ctattatgga    1500
gatatgtacc tcgaaggcgg gcaatatatg gaaaaaggga cgatttacaa tcctgtcatt    1560
tcagcgttgc tcaaagctag aataaaatat gtttctggtg gcaaacaat ggctaccgat     1620 agttctggaa aagaccttaa agatggcgaa actgatttgt taacaagtgt tcgatttggt    1680
aaaggaatta tgacatcaga tcaaaccaca acacaagaca atagccaaga ttataaaaat    1740
caaggcatcg gtgtcattgt tggtaataac cctgacctta agttgaacaa tgataagacc    1800
attaccttgc atatgggaaa ggcgcataag aatcaacttt accgtgcctt agtattatca    1860
aatgactcag gaattgatgt ttatgatagt gatgataaag caccaacttt gagaacaaat    1920
gacaacggtg acttgatttt ccataagaca aatacgtttg tgaagcaaga tggaactatt    1980
ataaattacg aaatgaaggg atcattaaat gctttaattt caggttattt aggtgtctgg    2040
gtgccagttg gagctagtga ttcacaagat gctcgtacag tggcaactga gtcatcatca    2100
agtaatgatg gttctgtatt ccattcaaat gctgcattag attctaatgt tatatatgaa    2160
ggcttttcaa actttcaagc gatgccgact tctcctgagc aaagtacaaa tgttgttatt    2220
gcaacaaagg ctaacttatt taagaattaa ggtattacta gttttgagtt agcacctcaa    2280
tataggtcta gtggtgacac taattacggt ggcatgtcat tcttagattc tttcttaaat    2340
aatggttatg catttaccga tagatatgat ttaggcttta acaaagcaga cgggaatcct    2400
aacccaacaa agtatggaac agatcaagat ttacgtaatg caatagaggc attacacaaa    2460
aacggcatgc aggctatagc tgattgggtt cctgaccaaa tatatgctt accaggaaag     2520 gaagttgtta ccgctactag agtagacgaa cggggaaatc aactaaaaga cacagatttt    2580
gtcaacttac tctatgttgc taatactaaa agtagtggtg tggattatca ggcaaagtat    2640
ggcggcgaat ttttagataa attaagagaa gagtacccat cgttattcaa acagaaccaa    2700
gtatcgacag gtcagccaat tgatgcttct acaaaaatta gcaatggtc agctaaatat     2760 atgaatggga ccaatatttt acatcgaggt gcttattatg ttttgaaaga ctgggctact    2820
aaccagtatt ttaacattgc aaaaacgaat gaagtatttt tgccactaca gttgcagaat    2880
aaagatgcgc aaactggttt cattagtgat gcctccggtg taaaatatta ctcaattagt    2940
ggttatcaag caaagatac ttttattgaa gatggtaatg ggaattggta ttactttgat     3000
aaagatggtt acatggtgcg ttcgcagcaa ggagaaaatc ctataagaac agtcgaaact    3060
agtgtcaaca cacgaaacgg taattattac tttatgccaa atggtgtcga gttgcgcaaa    3120
ggctttggaa cggataatag tggtaatgtc tattattttg atgatcaagg taagatggtg    3180
agagataaat acattaacga tgatgctaat aattttatc acttaaatgt tgatgggact     3240
atgtctcgag ga                                                       3252
```

<210> SEQ ID NO 22
<211> LENGTH: 3252
<212> TYPE: DNA
<213> ORGANISM: Artificial Sequence
<220> FEATURE:
<223> OTHER INFORMATION: Nucleotide sequence of Truncated
      alternansucrase
<220> FEATURE:
<221> NAME/KEY: Gene
<222> LOCATION: (1285)..(1287)
<223> OTHER INFORMATION: n GCT modified to GTC

<400> SEQUENCE: 22

| | | | | | |
|---|---|---|---|---|---|
| atgttaacag | ggttgcaaac | tatttcagga | aagacatatt | atcttgatga | acaaggacac | 60 |
| ctgagaaaaa | attacgcggg | aacattcaat | aatcagttta | tgtacttcga | tgctgataca | 120 |
| ggtgcgggta | aaacagcgat | tgaatatcaa | tttgatcaag | gattggtatc | acaaagtaat | 180 |
| gaaaatactc | ctcacaatgc | cgcaaagtct | tatgataaaa | gtagttttga | aaatgttgat | 240 |
| ggttacttaa | cagcagatac | atggtatcgt | ccaaccgata | ttttaaaaaa | tggagatact | 300 |
| tggacggcat | ctaccgaaac | tgatatgcgt | ccgcttttaa | tgacatggtg | gcctgacaaa | 360 |
| caaacacaag | caaattactt | gaattttatg | tctagtaaag | gacttggtat | aacgaccact | 420 |
| tatacagcag | ctacgtcaca | aaaaacacta | aatgacgcag | cctttgttat | tcaaacagca | 480 |
| attgaacaac | aaatatcttt | gaaaaaaagt | actgagtggt | tacgtgatgc | aattgatagt | 540 |
| tttgtgaaga | cgcaagctaa | ttggaataag | caaacagaag | atgaagcttt | cgatggtttg | 600 |
| cagtggcttc | aagggggatt | cctagcttat | caagatgatt | cacatcggac | gccgaatact | 660 |
| gattcaggaa | ataacagaaa | actaggacgt | caaccaatta | atatcgatgg | ttcgaaagat | 720 |
| acaactgatg | gtaaaggctc | tgaattctta | ttagctaacg | atattgacaa | ctcaaatccg | 780 |
| attgttcaag | ctgagcaatt | aaactggcta | cactatttaa | tgaattttgg | tagtattaca | 840 |
| ggtaataatg | acaatgcgaa | ttttgatggc | attcgtgtag | atgctgttga | taatgttgat | 900 |
| gctgatttac | taaaaatagc | tggcgattat | tttaaagctc | tatatggtac | agataaaagc | 960 |
| gacgccaatg | ccaataagca | tttgtctatt | ttagaagact | ggaacggtaa | agatcctcag | 1020 |
| tatgttaatc | aacagggcaa | tgcgcaatta | acaatggatt | acacagttac | ttcacagttt | 1080 |
| ggcaattctc | taacacatgg | cgccaacaac | aggagtaaca | tgtggtattt | cttagatact | 1140 |
| ggctattatc | ttaatggaga | tcttaataag | aagatagtag | ataagaaccg | tccaaattct | 1200 |
| ggcactttgg | ttaacagaat | tgctaattca | ggtgatacaa | aagttattcc | aaattatagt | 1260 |
| tttgttagag | cacatgatta | cgatgtccaa | gatccaatta | gaaaagccat | gattgatcat | 1320 |
| ggtattatta | aaaacatgca | ggatactttc | acttttgacc | aactggctca | gggaatggaa | 1380 |
| ttctactata | aagatcaaga | gaatccgtct | ggtttcaaaa | agtataacga | ttataactta | 1440 |
| cctagtgctt | atgcaatgtt | gttgactaat | aaggatactg | tacctcgtgt | ctattatgga | 1500 |
| gatatgtacc | tcgaaggcgg | gcaatatatg | gaaaaaggga | cgatttacaa | tcctgtcatt | 1560 |
| tcagcgttgc | tcaaagctag | aataaaatat | gtttctggtg | gcaaacaat | ggctaccgat | 1620 |
| agttctggaa | aagaccttaa | agatggcgaa | actgatttgt | taacaagtgt | tcgatttggt | 1680 |
| aaaggaatta | tgcatcaga | tcaaaccaca | acacaagaca | atagccaaga | ttataaaaat | 1740 |
| caaggcatcg | gtgtcattgt | tggtaataac | cctgacctta | gttgaacaa | tgataagacc | 1800 |
| attccttgc | atatgggaaa | ggcgcataag | aatcaacttt | accgtgcctt | agtattatca | 1860 |
| aatgactcag | gaattgatgt | ttatgatagt | gatgataaag | caccaacttt | gagaacaaat | 1920 |
| gacaacggtg | acttgatttt | ccataagaca | aatacgtttg | tgaagcaaga | tggaactatt | 1980 |

```
ataaattacg aaatgaaggg atcattaaat gctttaatttt caggttatttt aggtgtctgg    2040 gtgccagttg gagctagtga ttcacaagat gctcgtacag tggcaactga gtcatcatca    2100
agtaatgatg gttctgtatt ccattcaaat gctgcattag attctaatgt tatatatgaa    2160
ggcttttcaa actttcaagc gatgccgact tctcctgagc aaagtacaaa tgttgttatt    2220
gcaacaaagg ctaacttatt taaagaatta ggtattacta gttttgagtt agcacctcaa    2280
tataggtcta gtggtgacac taattacggt ggcatgtcat tcttagattc tttcttaaat    2340
aatggttatg catttaccga tagatatgat ttaggcttta acaaagcaga cgggaatcct    2400
aacccaacaa agtatggaac agatcaagat ttacgtaatg caatagaggc attacacaaa    2460
aacggcatgc aggctatagc tgattgggtt cctgaccaaa tatatgcttt accaggaaag    2520
gaagttgtta ccgctactag agtagacgaa cggggaaatc aactaaaaga cacagatttt    2580
gtcaacttac tctatgttgc taatactaaa agtagtggtg tggattatca ggcaaagtat    2640
ggcggcgaat ttttagataa attaagagaa gagtacccat cgttattcaa acagaaccaa    2700
gtatcgacag gtcagccaat tgatgcttct acaaaaatta agcaatggtc agctaaatat    2760
atgaatggga ccaatatttt acatcgaggt gcttattatg ttttgaaaga ctgggctact    2820
aaccagtatt ttaacattgc aaaaacgaat gaagtatttt tgccactaca gttgcagaat    2880
aaagatgcgc aaactggttt cattagtgat gcctccggtg taaaatatta ctcaattagt    2940
ggttatcaag caaagatac ttttattgaa gatggtaatg ggaattggta ttactttgat    3000
aaagatggtt acatggtgcg ttcgcagcaa ggagaaaatc ctataagaac agtcgaaact    3060
agtgtcaaca cacgaaacgg taattattac tttatgccaa atggtgtcga gttgcgcaaa    3120
ggctttggaa cggataatag tggtaatgtc tattattttg atgatcaagg taagatggtg    3180
agagataaat acattaacga tgatgctaat aatttttatc acttaaatgt tgatgggact    3240
atgtctcgag ga                                                         3252

<210> SEQ ID NO 23
<211> LENGTH: 3252
<212> TYPE: DNA
<213> ORGANISM: Artificial Sequence
<220> FEATURE:
<223> OTHER INFORMATION: Nucleotide sequence of Truncated
      alternansucrase
<220> FEATURE:
<221> NAME/KEY: Gene
<222> LOCATION: (1285)..(1287)
<223> OTHER INFORMATION: n GCT modified to GTA

<400> SEQUENCE: 23
atgttaacag ggttgcaaac tatttcagga aagacatatt atcttgatga acaaggacac      60
ctgagaaaaa attacgcggg aacattcaat aatcagttta tgtacttcga tgctgataca    120
ggtgcgggta aaacagcgat tgaatatcaa tttgatcaag gattggtatc acaaagtaat    180
gaaaatactc ctcacaatgc cgcaaagtct tatgataaaa gtagttttga aaatgttgat    240
ggttacttaa cagcagatac atggtatcgt ccaaccgata ttttaaaaaa tggagatact    300
tggacggcat ctaccgaaac tgatatgcgt ccgcttttaa tgcatggtg gcctgacaaa    360 caaacacaag caaattactt gaatttatg tctagtaaag gacttggtat aacgaccact    420
tatacagcag ctacgtcaca aaaaacacta aatgacgcag cctttgttat tcaaacagca    480
attgaacaac aaatatcttt gaaaaaagt actgagtggt tacgtgatgc aattgatagt    540
tttgtgaaga cgcaagctaa ttggaataag caaacagaag atgaagcttt cgatggtttg    600
```

```
cagtggcttc aagggggatt cctagcttat caagatgatt cacatcggac gccgaatact      660
gattcaggaa ataacagaaa actaggacgt caaccaatta atatcgatgg ttcgaaagat      720
acaactgatg gtaaaggctc tgaattctta ttagctaacg atattgacaa ctcaaatccg      780
attgttcaag ctgagcaatt aaactggcta cactatttaa tgaattttgg tagtattaca      840
ggtaataatg acaatgcgaa ttttgatggc attcgtgtag atgctgttga taatgttgat      900
gctgatttac taaaaatagc tggcgattat tttaaagctc tatatggtac agataaaagc      960
gacgccaatg ccataagca tttgtctatt ttagaagact ggaacggtaa agatcctcag     1020
tatgttaatc aacagggcaa tgcgcaatta acaatggatt acacagttac ttcacagttt     1080
ggcaattctc taacacatgg cgccaacaac aggagtaaca tgtggtattt cttagatact     1140
ggctattatc ttaatggaga tcttaataag aagatagtag ataagaaccg tccaaattct     1200
ggcactttgg ttaacagaat tgctaattca ggtgatacaa agttattcc aaattatagt     1260 tttgttagag cacatgatta cgatgtacaa gatccaatta gaaaagccat gattgatcat     1320
ggtattatta aaaacatgca ggatactttc acttttgacc aactggctca gggaatggaa     1380
ttctactata aagatcaaga gaatccgtct ggttttcaaaa agtataacga ttataactta     1440
cctagtgctt atgcaatgtt gttgactaat aaggatactg tacctcgtgt ctattatgga     1500
gatatgtacc tcgaaggcgg gcaatatatg gaaaaaggga cgatttacaa tcctgtcatt     1560
tcagcgttgc tcaaagctag aataaaatat gtttctggtg ggcaaacaat ggctaccgat     1620
agttctggaa aagaccttaa agatggcgaa actgatttgt taacaagtgt tcgatttggt     1680
aaaggaatta tgacatcaga tcaaaccaca acacaagaca atagccaaga ttataaaaat     1740
caaggcatcg gtgtcattgt tggtaataac cctgaccta agttgaacaa tgataagacc     1800
attaccttgc atatgggaaa ggcgcataag aatcaacttt accgtgcctt agtattatca     1860
aatgactcag gaattgatgt ttatgatagt gatgataaag caccaacttt gagaacaaat     1920
gacaacggtg acttgatttt ccataagaca aatacgtttg tgaagcaaga tggaactatt     1980
ataaattacg aaatgaaggg atcattaaat gctttaattt caggttattt aggtgtctgg     2040
gtgccagttg gagctagtga ttcacaagat gctcgtacag tggcaactga gtcatcatca     2100
agtaatgatg gttctgtatt ccattcaaat gctgcattag attctaatgt tatatatgaa     2160
ggcttttcaa actttcaagc gatgccgact tctcctgagc aaagtacaaa tgttgttatt     2220
gcaacaaagg ctaacttatt taagaatta ggtattacta gttttgagtt agcacctcaa     2280
tataggtcta gtggtgacac taattacggt ggcatgtcat tcttagattc tttcttaaat     2340
aatggttatg catttaccga tagatatgat ttaggcttta acaaagcaga cgggaatcct     2400
aacccaacaa agtatggaac agatcaagat ttacgtaatg caatagaggc attacacaaa     2460
aacggcatgc aggctatagc tgattgggtt cctgaccaaa tatatgcttt accaggaaag     2520
gaagttgtta ccgctactag agtagacgaa cggggaaatc aactaaaaga cacagatttt     2580
gtcaacttac tctatgttgc taatactaaa agtagtggtg tggattatca ggcaaagtat     2640
ggcggcgaat ttttagataa attaagagaa gagtacccat cgttattcaa acagaaccaa     2700
gtatcgacag gtcagccaat tgatgcttct acaaaaatta agcaatggtc agctaaatat     2760
atgaatggga ccaatatttt acatcgaggt gcttattatg ttttgaaaga ctgggctact     2820
aaccagtatt ttaacattgc aaaaacgaat gaagtatttt tgccactaca gttgcagaat     2880
aaagatgcgc aaactggttt cattagtgat gcctccggtg taaaatatta ctcaattagt     2940
ggttatcaag caaaagatac ttttattgaa gatggtaatg ggaattggta ttactttgat     3000
```

| aaagatggtt acatggtgcg ttcgcagcaa ggagaaaatc ctataagaac agtcgaaact | 3060 |
| agtgtcaaca cacgaaacgg taattattac tttatgccaa atggtgtcga gttgcgcaaa | 3120 |
| ggctttggaa cggataatag tggtaatgtc tattattttg atgatcaagg taagatggtg | 3180 |
| agagataaat acattaacga tgatgctaat aattttatc acttaaatgt tgatgggact | 3240 |
| atgtctcgag ga | 3252 |

<210> SEQ ID NO 24
<211> LENGTH: 3252
<212> TYPE: DNA
<213> ORGANISM: Artificial Sequence
<220> FEATURE:
<223> OTHER INFORMATION: Nucleotide sequence of Truncated
      alternansucrase
<220> FEATURE:
<221> NAME/KEY: Gene
<222> LOCATION: (1285)..(1287)
<223> OTHER INFORMATION: n GCT modified to GTG

<400> SEQUENCE: 24

| atgttaacag ggttgcaaac tatttcagga aagacatatt atcttgatga acaaggacac | 60 |
| ctgagaaaaa attacgcggg aacattcaat aatcagttta tgtacttcga tgctgataca | 120 |
| ggtgcgggta aaacagcgat tgaatatcaa tttgatcaag gattggtatc acaaagtaat | 180 |
| gaaaatactc ctcacaatgc cgcaaagtct tatgataaaa gtagttttga aaatgttgat | 240 |
| ggttacttaa cagcagatac atggtatcgt ccaaccgata ttttaaaaaa tggagatact | 300 |
| tggacggcat ctaccgaaac tgatatgcgt ccgcttttaa tgcatggtg gcctgacaaa | 360 |
| caaacacaag caaattactt gaattttatg tctagtaaag gacttggtat aacgaccact | 420 |
| tatacagcag ctacgtcaca aaaaacacta atgacgcag cctttgttat tcaaacagca | 480 |
| attgaacaac aaatatcttt gaaaaaaagt actgagtggt tacgtgatgc aattgatagt | 540 |
| tttgtgaaga cgcaagctaa ttggaataag caaacagaag atgaagcttt cgatggtttg | 600 |
| cagtggcttc aaggggatt cctagcttat caagatgatt cacatcggac gccgaatact | 660 |
| gattcaggaa ataacagaaa actaggacgt caaccaatta atatcgatgg ttcgaaagat | 720 |
| acaactgatg gtaaaggctc tgaattctta ttagctaacg atattgacaa ctcaaatccg | 780 |
| attgttcaag ctgagcaatt aaactggcta cactatttaa tgaattttgg tagtattaca | 840 |
| ggtaataatg acaatgcgaa ttttgatggc attcgtgtag atgctgttga taatgttgat | 900 |
| gctgatttac taaaaatagc tggcgattat tttaaagctc tatatggtac agataaaagc | 960 |
| gacgccaatg ccaataagca tttgtctatt ttagaagact ggaacggtaa agatcctcag | 1020 |
| tatgttaatc aacagggcaa tgcgcaatta acaatggatt acacagttac ttcacagttt | 1080 |
| ggcaattctc taacacatgg cgccaacaac aggagtaaca tgtggtattt cttagatact | 1140 |
| ggctattatc ttaatggaga tcttaataag aagatagtag ataagaaccg tccaaattct | 1200 |
| ggcactttgg ttaacagaat tgctaattca ggtgatacaa aagttattcc aaattatagt | 1260 |
| tttgttagag cacatgatta cgatgtgcaa gatccaatta gaaaagccat gattgatcat | 1320 |
| ggtattatta aaacatgca ggatactttc acttttgacc aactggctca gggaatggaa | 1380 |
| ttctactata agatcaaga gaatccgtct ggtttcaaaa agtataacga ttataactta | 1440 |
| cctagtgctt atgcaatgtt gttgactaat aaggatactg tacctcgtgt ctattatgga | 1500 |
| gatatgtacc tcgaaggcgg gcaatatatg gaaaaaggga cgatttacaa tcctgtcatt | 1560 |
| tcagcgttgc tcaaagctag aataaaaat gtttctggtg ggcaaacaat ggctaccgat | 1620 |

```
agttctggaa aagaccttaa agatggcgaa actgatttgt taacaagtgt tcgatttggt      1680
aaaggaatta tgacatcaga tcaaaccaca acacaagaca atagccaaga ttataaaaat      1740
caaggcatcg gtgtcattgt tggtaataac cctgacctta agttgaacaa tgataagacc      1800
attaccttgc atatgggaaa ggcgcataag aatcaacttt accgtgcctt agtattatca      1860
aatgactcag gaattgatgt ttatgatagt gatgataaag caccaacttt gagaacaaat      1920
gacaacggtg acttgatttt ccataagaca atacgtttg tgaagcaaga tggaactatt      1980
ataaattacg aaatgaaggg atcattaaat gctttaattt caggttattt aggtgtctgg      2040
gtgccagttg gagctagtga ttcacaagat gctcgtacag tggcaactga gtcatcatca      2100
agtaatgatg gttctgtatt ccattcaaat gctgcattag attctaatgt tatatatgaa      2160
ggcttttcaa actttcaagc gatgccgact ctcctgagc aaagtacaaa tgttgttatt       2220
gcaacaaagg ctaacttatt taagaatta ggtattacta gttttgagtt agcacctcaa       2280
tataggtcta gtggtgacac taattacggt ggcatgtcat tcttagattc tttcttaaat      2340
aatggttatg catttaccga tagatatgat ttaggcttta acaaagcaga cgggaatcct      2400
aacccaacaa gtatggaac agatcaagat ttacgtaatg caatagaggc attacacaaa       2460
aacggcatgc aggctatagc tgattgggtt cctgaccaaa tatatgcttt accaggaaag      2520
gaagttgtta ccgctactag agtagacgaa cggggaaatc aactaaaaga cacagatttt      2580
gtcaacttac tctatgttgc taatactaaa agtagtggtg tggattatca ggcaaagtat      2640
ggcggcgaat ttttagataa attaagagaa gagtacccat cgttattcaa acagaaccaa      2700
gtatcgacag gtcagccaat tgatgcttct acaaaaatta agcaatggtc agctaaatat      2760
atgaatggga ccaatatttt cacatcgaggt gcttattatg ttttgaaaga ctgggctact      2820
aaccagtatt ttaacattgc aaaaacgaat gaagtatttt tgccactaca gttgcagaat      2880
aaagatgcgc aaactggttt cattagtgat gcctccggtg taaaatatta ctcaattagt      2940
ggttatcaag caaaagatac ttttattgaa gatggtaatg ggaattggta ttactttgat      3000
aaagatggtt acatggtgcg ttcgcagcaa ggagaaaatc ctataagaac agtcgaaact      3060
agtgtcaaca cacgaaacgg taattattac tttatgccaa atggtgtcga gttgcgcaaa      3120
ggctttggaa cggataatag tggtaatgtc tattattttg atgatcaagg taagatggtg      3180
agagataaat acattaacga tgatgctaat aatttttatc acttaaatgt tgatgggact      3240
atgtctcgag ga                                                         3252
```

<210> SEQ ID NO 25
<211> LENGTH: 2057
<212> TYPE: PRT
<213> ORGANISM: Artificial Sequence
<220> FEATURE:
<223> OTHER INFORMATION: Peptide - Alternansucrase amino acid sequence -
      Full length amino acid sequence

<400> SEQUENCE: 25

Met Lys Gln Gln Glu Thr Val Thr Arg Lys Lys Leu Tyr Lys Ser Gly
1               5                   10                  15

Lys Val Trp Val Ala Ala Thr Ala Phe Ala Val Leu Gly Val Ser
            20                  25                  30

Thr Val Thr Thr Val His Ala Asp Thr Asn Ser Asn Val Ala Val Lys
        35                  40                  45

Gln Ile Asn Asn Thr Gly Thr Asn Asp Ser Gly Glu Lys Lys Val Pro
    50                  55                  60

-continued

```
Val Pro Ser Thr Asn Asn Asp Ser Leu Lys Gln Gly Thr Asp Gly Phe
 65                  70                  75                  80

Trp Tyr Asp Ser Asp Gly Asn Arg Val Asp Gln Lys Thr Asn Gln Ile
                 85                  90                  95

Leu Leu Thr Ala Glu Gln Leu Lys Lys Asn Asn Glu Lys Asn Leu Ser
            100                 105                 110

Val Ile Ser Asp Asp Thr Ser Lys Lys Asp Asp Glu Asn Ile Ser Lys
            115                 120                 125

Gln Thr Lys Ile Ala Asn Gln Gln Thr Val Asp Thr Ala Lys Gly Leu
        130                 135                 140

Thr Thr Ser Asn Leu Ser Asp Pro Ile Thr Gly Gly His Tyr Glu Asn
145                 150                 155                 160

His Asn Gly Tyr Phe Val Tyr Ile Asp Ala Ser Gly Lys Gln Val Thr
                165                 170                 175

Gly Leu Gln Asn Ile Asp Gly Asn Leu Gln Tyr Phe Asp Asp Asn Gly
            180                 185                 190

Tyr Gln Val Lys Gly Ser Phe Arg Asp Val Asn Gly Lys His Ile Tyr
        195                 200                 205

Phe Asp Ser Val Thr Gly Lys Ala Ser Ser Asn Val Asp Ile Val Asn
210                 215                 220

Gly Lys Ala Gln Gly Tyr Asp Ala Gln Gly Asn Gln Leu Lys Lys Ser
225                 230                 235                 240

Tyr Val Ala Asp Ser Ser Gly Gln Thr Tyr Tyr Phe Asp Gly Asn Gly
                245                 250                 255

Gln Pro Leu Ile Gly Leu Gln Thr Ile Asp Gly Asn Leu Gln Tyr Phe
            260                 265                 270

Asn Gln Gln Gly Val Gln Ile Lys Gly Phe Gln Asp Val Asn Asn
        275                 280                 285

Lys Arg Ile Tyr Phe Ala Pro Asn Thr Gly Asn Ala Val Ala Asn Thr
290                 295                 300

Glu Ile Ile Asn Gly Lys Leu Gln Gly Arg Asp Ala Asn Gly Asn Gln
305                 310                 315                 320

Val Lys Asn Ala Phe Ser Lys Asp Val Ala Gly Asn Thr Phe Tyr Phe
                325                 330                 335

Asp Ala Asn Gly Val Met Leu Thr Gly Leu Gln Thr Ile Ser Gly Lys
            340                 345                 350

Thr Tyr Tyr Leu Asp Glu Gln Gly His Leu Arg Lys Asn Tyr Ala Gly
        355                 360                 365

Thr Phe Asn Asn Gln Phe Met Tyr Phe Asp Ala Asp Thr Gly Ala Gly
        370                 375                 380

Lys Thr Ala Ile Glu Tyr Gln Phe Asp Gln Gly Leu Val Ser Gln Ser
385                 390                 395                 400

Asn Glu Asn Thr Pro His Asn Ala Ala Lys Ser Tyr Asp Lys Ser Ser
                405                 410                 415

Phe Glu Asn Val Asp Gly Tyr Leu Thr Ala Asp Thr Trp Tyr Arg Pro
            420                 425                 430

Thr Asp Ile Leu Lys Asn Gly Asp Thr Trp Thr Ala Ser Thr Glu Thr
        435                 440                 445

Asp Met Arg Pro Leu Leu Met Thr Trp Trp Pro Asp Lys Gln Thr Gln
        450                 455                 460

Ala Asn Tyr Leu Asn Phe Met Ser Ser Lys Gly Leu Gly Ile Thr Thr
465                 470                 475                 480
```

-continued

```
Thr Tyr Thr Ala Ala Thr Ser Gln Lys Thr Leu Asn Asp Ala Ala Phe
                485                 490                 495

Val Ile Gln Thr Ala Ile Glu Gln Gln Ile Ser Leu Lys Lys Ser Thr
            500                 505                 510

Glu Trp Leu Arg Asp Ala Ile Asp Ser Phe Val Lys Thr Gln Ala Asn
            515                 520                 525

Trp Asn Lys Gln Thr Glu Asp Glu Ala Phe Asp Gly Leu Gln Trp Leu
        530                 535                 540

Gln Gly Gly Phe Leu Ala Tyr Gln Asp Asp Ser His Arg Thr Pro Asn
545                 550                 555                 560

Thr Asp Ser Gly Asn Asn Arg Lys Leu Gly Arg Gln Pro Ile Asn Ile
                565                 570                 575

Asp Gly Ser Lys Asp Thr Thr Asp Gly Lys Gly Ser Glu Phe Leu Leu
            580                 585                 590

Ala Asn Asp Ile Asp Asn Ser Asn Pro Ile Val Gln Ala Glu Gln Leu
        595                 600                 605

Asn Trp Leu His Tyr Leu Met Asn Phe Gly Ser Ile Thr Gly Asn Asn
        610                 615                 620

Asp Asn Ala Asn Phe Asp Gly Ile Arg Val Asp Ala Val Asp Asn Val
625                 630                 635                 640

Asp Ala Asp Leu Leu Lys Ile Ala Gly Asp Tyr Phe Lys Ala Leu Tyr
                645                 650                 655

Gly Thr Asp Lys Ser Asp Ala Asn Ala Asn Lys His Leu Ser Ile Leu
            660                 665                 670

Glu Asp Trp Asn Gly Lys Asp Pro Gln Tyr Val Asn Gln Gly Asn
        675                 680                 685

Ala Gln Leu Thr Met Asp Tyr Thr Val Thr Ser Gln Phe Gly Asn Ser
        690                 695                 700

Leu Thr His Gly Ala Asn Asn Arg Ser Asn Met Trp Tyr Phe Leu Asp
705                 710                 715                 720

Thr Gly Tyr Tyr Leu Asn Gly Asp Leu Asn Lys Ile Val Asp Lys
                725                 730                 735

Asn Arg Pro Asn Ser Gly Thr Leu Val Asn Arg Ile Ala Asn Ser Gly
            740                 745                 750

Asp Thr Lys Val Ile Pro Asn Tyr Ser Phe Val Arg Ala His Asp Tyr
        755                 760                 765

Asp Ala Gln Asp Pro Ile Arg Lys Ala Met Ile Asp His Gly Ile Ile
        770                 775                 780

Lys Asn Met Gln Asp Thr Phe Thr Phe Asp Gln Leu Ala Gln Gly Met
785                 790                 795                 800

Glu Phe Tyr Tyr Lys Asp Gln Glu Asn Pro Ser Gly Phe Lys Lys Tyr
                805                 810                 815

Asn Asp Tyr Asn Leu Pro Ser Ala Tyr Ala Met Leu Leu Thr Asn Lys
            820                 825                 830

Asp Thr Val Pro Arg Val Tyr Tyr Gly Asp Met Tyr Leu Glu Gly Gly
        835                 840                 845

Gln Tyr Met Glu Lys Gly Thr Ile Tyr Asn Pro Val Ile Ser Ala Leu
        850                 855                 860

Leu Lys Ala Arg Ile Lys Tyr Val Ser Gly Gly Gln Thr Met Ala Thr
865                 870                 875                 880

Asp Ser Ser Gly Lys Asp Leu Lys Asp Gly Glu Thr Asp Leu Leu Thr
                885                 890                 895
```

-continued

```
Ser Val Arg Phe Gly Lys Gly Ile Met Thr Ser Asp Gln Thr Thr Thr
            900                 905                 910

Gln Asp Asn Ser Gln Asp Tyr Lys Asn Gln Gly Ile Gly Val Ile Val
            915                 920                 925

Gly Asn Asn Pro Asp Leu Lys Leu Asn Asn Asp Lys Thr Ile Thr Leu
            930                 935                 940

His Met Gly Lys Ala His Lys Asn Gln Leu Tyr Arg Ala Leu Val Leu
945                 950                 955                 960

Ser Asn Asp Ser Gly Ile Asp Val Tyr Asp Ser Asp Lys Ala Pro
                965                 970                 975

Thr Leu Arg Thr Asn Asp Asn Gly Asp Leu Ile Phe His Lys Thr Asn
                980                 985                 990

Thr Phe Val Lys Gln Asp Gly Thr Ile Ile Asn Tyr Glu Met Lys Gly
                995                 1000                1005

Ser Leu Asn Ala Leu Ile Ser Gly Tyr Leu Gly Val Trp Val Pro
    1010                1015                1020

Val Gly Ala Ser Asp Ser Gln Asp Ala Arg Thr Val Ala Thr Glu
    1025                1030                1035

Ser Ser Ser Ser Asn Asp Gly Ser Val Phe His Ser Asn Ala Ala
    1040                1045                1050

Leu Asp Ser Asn Val Ile Tyr Glu Gly Phe Ser Asn Phe Gln Ala
    1055                1060                1065

Met Pro Thr Ser Pro Glu Gln Ser Thr Asn Val Val Ile Ala Thr
    1070                1075                1080

Lys Ala Asn Leu Phe Lys Glu Leu Gly Ile Thr Ser Phe Glu Leu
    1085                1090                1095

Ala Pro Gln Tyr Arg Ser Ser Gly Asp Thr Asn Tyr Gly Gly Met
    1100                1105                1110

Ser Phe Leu Asp Ser Phe Leu Asn Asn Gly Tyr Ala Phe Thr Asp
    1115                1120                1125

Arg Tyr Asp Leu Gly Phe Asn Lys Ala Asp Gly Asn Pro Asn Pro
    1130                1135                1140

Thr Lys Tyr Gly Thr Asp Gln Asp Leu Arg Asn Ala Ile Glu Ala
    1145                1150                1155

Leu His Lys Asn Gly Met Gln Ala Ile Ala Asp Trp Val Pro Asp
    1160                1165                1170

Gln Ile Tyr Ala Leu Pro Gly Lys Glu Val Val Thr Ala Thr Arg
    1175                1180                1185

Val Asp Glu Arg Gly Asn Gln Leu Lys Asp Thr Asp Phe Val Asn
    1190                1195                1200

Leu Leu Tyr Val Ala Asn Thr Lys Ser Ser Gly Val Asp Tyr Gln
    1205                1210                1215

Ala Lys Tyr Gly Gly Glu Phe Leu Asp Lys Leu Arg Glu Glu Tyr
    1220                1225                1230

Pro Ser Leu Phe Lys Gln Asn Gln Val Ser Thr Gly Gln Pro Ile
    1235                1240                1245

Asp Ala Ser Thr Lys Ile Lys Gln Trp Ser Ala Lys Tyr Met Asn
    1250                1255                1260

Gly Thr Asn Ile Leu His Arg Gly Ala Tyr Tyr Val Leu Lys Asp
    1265                1270                1275

Trp Ala Thr Asn Gln Tyr Phe Asn Ile Ala Lys Thr Asn Glu Val
    1280                1285                1290
```

```
Phe Leu Pro Leu Gln Leu Gln Asn Lys Asp Ala Gln Thr Gly Phe
    1295                1300                1305

Ile Ser Asp Ala Ser Gly Val Lys Tyr Tyr Ser Ile Ser Gly Tyr
    1310                1315                1320

Gln Ala Lys Asp Thr Phe Ile Glu Asp Gly Asn Gly Asn Trp Tyr
    1325                1330                1335

Tyr Phe Asp Lys Asp Gly Tyr Met Val Arg Ser Gln Gln Gly Glu
    1340                1345                1350

Asn Pro Ile Arg Thr Val Glu Thr Ser Val Asn Thr Arg Asn Gly
    1355                1360                1365

Asn Tyr Tyr Phe Met Pro Asn Gly Val Glu Leu Arg Lys Gly Phe
    1370                1375                1380

Gly Thr Asp Asn Ser Gly Asn Val Tyr Tyr Phe Asp Asp Gln Gly
    1385                1390                1395

Lys Met Val Arg Asp Lys Tyr Ile Asn Asp Asp Ala Asn Asn Phe
    1400                1405                1410

Tyr His Leu Asn Val Asp Gly Thr Met Ser Arg Gly Leu Phe Lys
    1415                1420                1425

Phe Asp Ser Asp Thr Leu Gln Tyr Phe Ala Ser Asn Gly Val Gln
    1430                1435                1440

Ile Lys Asp Ser Tyr Ala Lys Asp Ser Lys Gly Asn Lys Tyr Tyr
    1445                1450                1455

Phe Asp Ser Ala Thr Gly Asn Asn Asp Thr Gly Lys Ala Gln Thr
    1460                1465                1470

Trp Asp Gly Asn Gly Tyr Tyr Ile Thr Ile Asp Ser Asp Ala Asn
    1475                1480                1485

Asn Thr Ile Gly Val Asn Thr Asp Tyr Thr Ala Tyr Ile Thr Ser
    1490                1495                1500

Ser Leu Arg Glu Asp Gly Leu Phe Ala Asn Ala Pro Tyr Gly Val
    1505                1510                1515

Val Thr Lys Asp Gln Asn Gly Asn Asp Leu Lys Trp Gln Tyr Ile
    1520                1525                1530

Asn His Thr Lys Gln Tyr Glu Gly Gln Gln Val Gln Val Thr Arg
    1535                1540                1545

Gln Tyr Thr Asp Ser Lys Gly Val Ser Trp Asn Leu Ile Thr Phe
    1550                1555                1560

Ala Gly Gly Asp Leu Gln Gly Gln Arg Leu Trp Val Asp Ser Arg
    1565                1570                1575

Ala Leu Thr Met Thr Pro Phe Lys Thr Met Asn Gln Ile Ser Phe
    1580                1585                1590

Ile Ser Tyr Ala Asn Arg Asn Asp Gly Leu Phe Leu Asn Ala Pro
    1595                1600                1605

Tyr Gln Val Lys Gly Tyr Gln Leu Ala Gly Met Ser Asn Gln Tyr
    1610                1615                1620

Lys Gly Gln Gln Val Thr Ile Ala Gly Val Ala Asn Val Ser Gly
    1625                1630                1635

Lys Asp Trp Ser Leu Ile Ser Phe Asn Gly Thr Gln Tyr Trp Ile
    1640                1645                1650

Asp Ser Gln Ala Leu Asn Thr Asn Phe Thr His Asp Met Asn Gln
    1655                1660                1665

Lys Val Phe Val Asn Thr Thr Ser Asn Leu Asp Gly Leu Phe Leu
    1670                1675                1680
```

-continued

```
Asn Ala Pro Tyr Arg Gln Pro Gly Tyr Lys Leu Ala Gly Leu Ala
1685                1690                1695

Lys Asn Tyr Asn Asn Gln Thr Val Thr Val Ser Gln Gln Tyr Phe
1700                1705                1710

Asp Asp Gln Gly Thr Val Trp Ser Gln Val Val Leu Gly Gly Gln
1715                1720                1725

Thr Val Trp Val Asp Asn His Ala Leu Ala Gln Met Gln Val Ser
1730                1735                1740

Asp Thr Asp Gln Gln Leu Tyr Val Asn Ser Asn Gly Arg Asn Asp
1745                1750                1755

Gly Leu Phe Leu Asn Ala Pro Tyr Arg Gly Gln Gly Ser Gln Leu
1760                1765                1770

Ile Gly Met Thr Ala Asp Tyr Asn Gly Gln His Val Gln Val Thr
1775                1780                1785

Lys Gln Gly Gln Asp Ala Tyr Gly Ala Gln Trp Arg Leu Ile Thr
1790                1795                1800

Leu Asn Asn Gln Gln Val Trp Val Asp Ser Arg Ala Leu Ser Thr
1805                1810                1815

Thr Ile Met Gln Ala Met Asn Asp Asn Met Tyr Val Asn Ser Ser
1820                1825                1830

Gln Arg Thr Asp Gly Leu Trp Leu Asn Ala Pro Tyr Thr Met Ser
1835                1840                1845

Gly Ala Lys Trp Ala Gly Asp Thr Arg Ser Ala Asn Gly Arg Tyr
1850                1855                1860

Val His Ile Ser Lys Ala Tyr Ser Asn Glu Val Gly Asn Thr Tyr
1865                1870                1875

Tyr Leu Thr Asn Leu Asn Gly Gln Ser Thr Trp Ile Asp Lys Arg
1880                1885                1890

Ala Phe Thr Val Thr Phe Asp Gln Val Val Ala Leu Asn Ala Thr
1895                1900                1905

Ile Val Ala Arg Gln Arg Pro Asp Gly Met Phe Lys Thr Ala Pro
1910                1915                1920

Tyr Gly Glu Ala Gly Ala Gln Phe Val Asp Tyr Val Thr Asn Tyr
1925                1930                1935

Asn Gln Gln Thr Val Pro Val Thr Lys Gln His Ser Asp Ala Gln
1940                1945                1950

Gly Asn Gln Trp Tyr Leu Ala Thr Val Asn Gly Thr Gln Tyr Trp
1955                1960                1965

Ile Asp Gln Arg Ser Phe Ser Pro Val Val Thr Lys Val Val Asp
1970                1975                1980

Tyr Gln Ala Lys Ile Val Pro Arg Thr Thr Arg Asp Gly Val Phe
1985                1990                1995

Ser Gly Ala Pro Tyr Gly Glu Val Asn Ala Lys Leu Val Asn Met
2000                2005                2010

Ala Thr Ala Tyr Gln Asn Gln Val Val His Ala Thr Gly Glu Tyr
2015                2020                2025

Thr Asn Ala Ser Gly Ile Thr Trp Ser Gln Phe Ala Leu Ser Gly
2030                2035                2040

Gln Glu Asp Lys Leu Trp Ile Asp Lys Arg Ala Leu Gln Ala
2045                2050                2055
```

-continued

```
<210> SEQ ID NO 26
<211> LENGTH: 1349
<212> TYPE: PRT
<213> ORGANISM: Artificial Sequence
<220> FEATURE:
<223> OTHER INFORMATION: Peptide - Truncated alternansucrase amino acid
      sequence - Full length amino acid sequence

<400> SEQUENCE: 26

Met Lys Gln Gln Glu Thr Val Thr Arg Lys Lys Leu Tyr Lys Ser Gly
1               5                   10                  15

Lys Val Trp Val Ala Ala Thr Ala Phe Ala Val Leu Gly Val Ser
            20                  25                  30

Thr Val Thr Thr Val His Ala Asp Thr Asn Ser Asn Val Ala Val Lys
        35                  40                  45

Gln Ile Asn Asn Thr Gly Thr Asn Asp Ser Gly Glu Lys Lys Val Pro
    50                  55                  60

Val Pro Ser Thr Asn Asn Asp Ser Leu Lys Gln Gly Thr Asp Gly Phe
65                  70                  75                  80

Trp Tyr Asp Ser Asp Gly Asn Arg Val Asp Gln Lys Thr Asn Gln Ile
                85                  90                  95

Leu Leu Thr Ala Glu Gln Leu Lys Lys Asn Asn Glu Lys Asn Leu Ser
            100                 105                 110

Val Ile Ser Asp Asp Thr Ser Lys Lys Asp Asp Glu Asn Ile Ser Lys
        115                 120                 125

Gln Thr Lys Ile Ala Asn Gln Gln Thr Val Asp Thr Ala Lys Gly Leu
    130                 135                 140

Thr Thr Ser Asn Leu Ser Asp Pro Ile Thr Gly Gly His Tyr Glu Asn
145                 150                 155                 160

His Asn Gly Tyr Phe Val Tyr Ile Asp Ala Ser Gly Lys Gln Val Thr
                165                 170                 175

Gly Leu Gln Asn Ile Asp Gly Asn Leu Gln Tyr Phe Asp Asp Asn Gly
            180                 185                 190

Tyr Gln Val Lys Gly Ser Phe Arg Asp Val Asn Gly Lys His Ile Tyr
        195                 200                 205

Phe Asp Ser Val Thr Gly Lys Ala Ser Ser Asn Val Asp Ile Val Asn
    210                 215                 220

Gly Lys Ala Gln Gly Tyr Asp Ala Gln Gly Asn Gln Leu Lys Lys Ser
225                 230                 235                 240

Tyr Val Ala Asp Ser Ser Gly Gln Thr Tyr Tyr Phe Asp Gly Asn Gly
                245                 250                 255

Gln Pro Leu Ile Gly Leu Gln Thr Ile Asp Gly Asn Leu Gln Tyr Phe
            260                 265                 270

Asn Gln Gln Gly Val Gln Ile Lys Gly Gly Phe Gln Asp Val Asn Asn
        275                 280                 285

Lys Arg Ile Tyr Phe Ala Pro Asn Thr Gly Asn Ala Val Ala Asn Thr
    290                 295                 300

Glu Ile Ile Asn Gly Lys Leu Gln Gly Arg Asp Ala Asn Gly Asn Gln
305                 310                 315                 320

Val Lys Asn Ala Phe Ser Lys Asp Val Ala Gly Asn Thr Phe Tyr Phe
                325                 330                 335

Asp Ala Asn Gly Val Met Leu Thr Gly Leu Gln Thr Ile Ser Gly Lys
            340                 345                 350

Thr Tyr Tyr Leu Asp Glu Gln Gly His Leu Arg Lys Asn Tyr Ala Gly
        355                 360                 365
```

-continued

```
Thr Phe Asn Asn Gln Phe Met Tyr Phe Asp Ala Asp Thr Gly Ala Gly
    370                 375                 380
Lys Thr Ala Ile Glu Tyr Gln Phe Asp Gln Gly Leu Val Ser Gln Ser
385                 390                 395                 400
Asn Glu Asn Thr Pro His Asn Ala Ala Lys Ser Tyr Asp Lys Ser Ser
                405                 410                 415
Phe Glu Asn Val Asp Gly Tyr Leu Thr Ala Asp Thr Trp Tyr Arg Pro
                420                 425                 430
Thr Asp Ile Leu Lys Asn Gly Asp Thr Trp Thr Ala Ser Thr Glu Thr
                435                 440                 445
Asp Met Arg Pro Leu Leu Met Thr Trp Trp Pro Asp Lys Gln Thr Gln
    450                 455                 460
Ala Asn Tyr Leu Asn Phe Met Ser Ser Lys Gly Leu Gly Ile Thr Thr
465                 470                 475                 480
Thr Tyr Thr Ala Ala Thr Ser Gln Lys Thr Leu Asn Asp Ala Ala Phe
                485                 490                 495
Val Ile Gln Thr Ala Ile Glu Gln Gln Ile Ser Leu Lys Lys Ser Thr
                500                 505                 510
Glu Trp Leu Arg Asp Ala Ile Asp Ser Phe Val Lys Thr Gln Ala Asn
    515                 520                 525
Trp Asn Lys Gln Thr Glu Asp Glu Ala Phe Asp Gly Leu Gln Trp Leu
    530                 535                 540
Gln Gly Gly Phe Leu Ala Tyr Gln Asp Asp Ser His Arg Thr Pro Asn
545                 550                 555                 560
Thr Asp Ser Gly Asn Asn Arg Lys Leu Gly Arg Gln Pro Ile Asn Ile
                565                 570                 575
Asp Gly Ser Lys Asp Thr Thr Asp Gly Lys Gly Ser Glu Phe Leu Leu
                580                 585                 590
Ala Asn Asp Ile Asp Asn Ser Asn Pro Ile Val Gln Ala Glu Gln Leu
    595                 600                 605
Asn Trp Leu His Tyr Leu Met Asn Phe Gly Ser Ile Thr Gly Asn Asn
    610                 615                 620
Asp Asn Ala Asn Phe Asp Gly Ile Arg Val Asp Ala Val Asp Asn Val
625                 630                 635                 640
Asp Ala Asp Leu Leu Lys Ile Ala Gly Asp Tyr Phe Lys Ala Leu Tyr
                645                 650                 655
Gly Thr Asp Lys Ser Asp Ala Asn Ala Asn Lys His Leu Ser Ile Leu
                660                 665                 670
Glu Asp Trp Asn Gly Lys Asp Pro Gln Tyr Val Asn Gln Gln Gly Asn
    675                 680                 685
Ala Gln Leu Thr Met Asp Tyr Thr Val Thr Ser Gln Phe Gly Asn Ser
    690                 695                 700
Leu Thr His Gly Ala Asn Asn Arg Ser Asn Met Trp Tyr Phe Leu Asp
705                 710                 715                 720
Thr Gly Tyr Tyr Leu Asn Gly Asp Leu Asn Lys Ile Val Asp Lys
                725                 730                 735
Asn Arg Pro Asn Ser Gly Thr Leu Val Asn Arg Ile Ala Asn Ser Gly
                740                 745                 750
Asp Thr Lys Val Ile Pro Asn Tyr Ser Phe Val Arg Ala His Asp Tyr
    755                 760                 765
Asp Ala Gln Asp Pro Ile Arg Lys Ala Met Ile Asp His Gly Ile Ile
    770                 775                 780
```

-continued

```
Lys Asn Met Gln Asp Thr Phe Thr Phe Asp Gln Leu Ala Gln Gly Met
785                 790                 795                 800

Glu Phe Tyr Tyr Lys Asp Gln Glu Asn Pro Ser Gly Phe Lys Lys Tyr
                805                 810                 815

Asn Asp Tyr Asn Leu Pro Ser Ala Tyr Ala Met Leu Leu Thr Asn Lys
            820                 825                 830

Asp Thr Val Pro Arg Val Tyr Tyr Gly Asp Met Tyr Leu Glu Gly Gly
        835                 840                 845

Gln Tyr Met Glu Lys Gly Thr Ile Tyr Asn Pro Val Ile Ser Ala Leu
    850                 855                 860

Leu Lys Ala Arg Ile Lys Tyr Val Ser Gly Gln Thr Met Ala Thr
865                 870                 875                 880

Asp Ser Ser Gly Lys Asp Leu Lys Asp Gly Glu Thr Asp Leu Leu Thr
                885                 890                 895

Ser Val Arg Phe Gly Lys Gly Ile Met Thr Ser Asp Gln Thr Thr Thr
                900                 905                 910

Gln Asp Asn Ser Gln Asp Tyr Lys Asn Gln Gly Ile Gly Val Ile Val
            915                 920                 925

Gly Asn Asn Pro Asp Leu Lys Leu Asn Asn Asp Lys Thr Ile Thr Leu
930                 935                 940

His Met Gly Lys Ala His Lys Asn Gln Leu Tyr Arg Ala Leu Val Leu
945                 950                 955                 960

Ser Asn Asp Ser Gly Ile Asp Val Tyr Asp Ser Asp Lys Ala Pro
                965                 970                 975

Thr Leu Arg Thr Asn Asp Asn Gly Asp Leu Ile Phe His Lys Thr Asn
                980                 985                 990

Thr Phe Val Lys Gln Asp Gly Thr Ile Ile Asn Tyr Glu Met Lys Gly
            995                 1000                1005

Ser Leu Asn Ala Leu Ile Ser Gly Tyr Leu Gly Val Trp Val Pro
    1010                1015                1020

Val Gly Ala Ser Asp Ser Gln Asp Ala Arg Thr Val Ala Thr Glu
    1025                1030                1035

Ser Ser Ser Ser Asn Asp Gly Ser Val Phe His Ser Asn Ala Ala
    1040                1045                1050

Leu Asp Ser Asn Val Ile Tyr Glu Gly Phe Ser Asn Phe Gln Ala
    1055                1060                1065

Met Pro Thr Ser Pro Glu Gln Ser Thr Asn Val Val Ile Ala Thr
    1070                1075                1080

Lys Ala Asn Leu Phe Lys Glu Leu Gly Ile Thr Ser Phe Glu Leu
    1085                1090                1095

Ala Pro Gln Tyr Arg Ser Ser Gly Asp Thr Asn Tyr Gly Gly Met
    1100                1105                1110

Ser Phe Leu Asp Ser Phe Leu Asn Asn Gly Tyr Ala Phe Thr Asp
    1115                1120                1125

Arg Tyr Asp Leu Gly Phe Asn Lys Ala Asp Gly Asn Pro Asn Pro
    1130                1135                1140

Thr Lys Tyr Gly Thr Asp Gln Asp Leu Arg Asn Ala Ile Glu Ala
    1145                1150                1155

Leu His Lys Asn Gly Met Gln Ala Ile Ala Asp Trp Val Pro Asp
    1160                1165                1170

Gln Ile Tyr Ala Leu Pro Gly Lys Glu Val Val Thr Ala Thr Arg
    1175                1180                1185
```

```
Val Asp Glu Arg Gly Asn Gln Leu Lys Asp Thr Asp Phe Val Asn
    1190                1195                1200

Leu Leu Tyr Val Ala Asn Thr Lys Ser Ser Gly Val Asp Tyr Gln
        1205                1210                1215

Ala Lys Tyr Gly Gly Glu Phe Leu Asp Lys Leu Arg Glu Glu Tyr
    1220                1225                1230

Pro Ser Leu Phe Lys Gln Asn Gln Val Ser Thr Gly Gln Pro Ile
    1235                1240                1245

Asp Ala Ser Thr Lys Ile Lys Gln Trp Ser Ala Lys Tyr Met Asn
    1250                1255                1260

Gly Thr Asn Ile Leu His Arg Gly Ala Tyr Tyr Val Leu Lys Asp
    1265                1270                1275

Trp Ala Thr Asn Gln Tyr Phe Asn Ile Ala Lys Thr Asn Glu Val
    1280                1285                1290

Phe Leu Pro Leu Gln Leu Gln Asn Lys Asp Ala Gln Thr Gly Phe
    1295                1300                1305

Ile Ser Asp Ala Ser Gly Val Lys Tyr Tyr Ser Ile Ser Gly Tyr
    1310                1315                1320

Gln Ala Lys Asp Thr Phe Ile Glu Asp Gly Asn Gly Asn Trp Tyr
    1325                1330                1335

Tyr Phe Asp Lys Asp Gly Tyr Met Val Arg Ser
    1340                1345
```

<210> SEQ ID NO 27
<211> LENGTH: 1425
<212> TYPE: PRT
<213> ORGANISM: Artificial Sequence
<220> FEATURE:
<223> OTHER INFORMATION: Peptide - Truncated alternansucrase amino acid
      sequence - Full length amino acid sequence

<400> SEQUENCE: 27

```
Met Lys Gln Gln Glu Thr Val Thr Arg Lys Lys Leu Tyr Lys Ser Gly
1               5                   10                  15

Lys Val Trp Val Ala Ala Ala Thr Ala Phe Ala Val Leu Gly Val Ser
            20                  25                  30

Thr Val Thr Thr Val His Ala Asp Thr Asn Ser Asn Val Ala Val Lys
        35                  40                  45

Gln Ile Asn Asn Thr Gly Thr Asn Asp Ser Gly Glu Lys Lys Val Pro
    50                  55                  60

Val Pro Ser Thr Asn Asn Asp Ser Leu Lys Gln Gly Thr Asp Gly Phe
65                  70                  75                  80

Trp Tyr Asp Ser Asp Gly Asn Arg Val Asp Gln Lys Thr Asn Gln Ile
                85                  90                  95

Leu Leu Thr Ala Glu Gln Leu Lys Lys Asn Asn Glu Lys Asn Leu Ser
            100                 105                 110

Val Ile Ser Asp Asp Thr Ser Lys Lys Asp Asp Glu Asn Ile Ser Lys
        115                 120                 125

Gln Thr Lys Ile Ala Asn Gln Gln Thr Val Asp Thr Ala Lys Gly Leu
    130                 135                 140

Thr Thr Ser Asn Leu Ser Asp Pro Ile Thr Gly Gly His Tyr Glu Asn
145                 150                 155                 160

His Asn Gly Tyr Phe Val Tyr Ile Asp Ala Ser Gly Lys Gln Val Thr
                165                 170                 175

Gly Leu Gln Asn Ile Asp Gly Asn Leu Gln Tyr Phe Asp Asp Asn Gly
            180                 185                 190
```

```
Tyr Gln Val Lys Gly Ser Phe Arg Asp Val Asn Gly Lys His Ile Tyr
        195                 200                 205
Phe Asp Ser Val Thr Gly Lys Ala Ser Ser Asn Val Asp Ile Val Asn
        210                 215                 220
Gly Lys Ala Gln Gly Tyr Asp Ala Gln Gly Asn Gln Leu Lys Lys Ser
225                 230                 235                 240
Tyr Val Ala Asp Ser Ser Gly Gln Thr Tyr Tyr Phe Asp Gly Asn Gly
                245                 250                 255
Gln Pro Leu Ile Gly Leu Gln Thr Ile Asp Gly Asn Leu Gln Tyr Phe
            260                 265                 270
Asn Gln Gln Gly Val Gln Ile Lys Gly Gly Phe Gln Asp Val Asn Asn
        275                 280                 285
Lys Arg Ile Tyr Phe Ala Pro Asn Thr Gly Asn Ala Val Ala Asn Thr
290                 295                 300
Glu Ile Ile Asn Gly Lys Leu Gln Gly Arg Asp Ala Asn Gly Asn Gln
305                 310                 315                 320
Val Lys Asn Ala Phe Ser Lys Asp Val Ala Gly Asn Thr Phe Tyr Phe
                325                 330                 335
Asp Ala Asn Gly Val Met Leu Thr Gly Leu Gln Thr Ile Ser Gly Lys
            340                 345                 350
Thr Tyr Tyr Leu Asp Glu Gln Gly His Leu Arg Lys Asn Tyr Ala Gly
        355                 360                 365
Thr Phe Asn Asn Gln Phe Met Tyr Phe Asp Ala Asp Thr Gly Ala Gly
        370                 375                 380
Lys Thr Ala Ile Glu Tyr Gln Phe Asp Gln Gly Leu Val Ser Gln Ser
385                 390                 395                 400
Asn Glu Asn Thr Pro His Asn Ala Ala Lys Ser Tyr Asp Lys Ser Ser
                405                 410                 415
Phe Glu Asn Val Asp Gly Tyr Leu Thr Ala Asp Thr Trp Tyr Arg Pro
            420                 425                 430
Thr Asp Ile Leu Lys Asn Gly Asp Thr Trp Thr Ala Ser Thr Glu Thr
        435                 440                 445
Asp Met Arg Pro Leu Leu Met Thr Trp Trp Pro Asp Lys Gln Thr Gln
        450                 455                 460
Ala Asn Tyr Leu Asn Phe Met Ser Ser Lys Gly Leu Gly Ile Thr Thr
465                 470                 475                 480
Thr Tyr Thr Ala Ala Thr Ser Gln Lys Thr Leu Asn Asp Ala Ala Phe
                485                 490                 495
Val Ile Gln Thr Ala Ile Glu Gln Gln Ile Ser Leu Lys Lys Ser Thr
            500                 505                 510
Glu Trp Leu Arg Asp Ala Ile Asp Ser Phe Val Lys Thr Gln Ala Asn
        515                 520                 525
Trp Asn Lys Gln Thr Glu Asp Glu Ala Phe Asp Gly Leu Gln Trp Leu
        530                 535                 540
Gln Gly Gly Phe Leu Ala Tyr Gln Asp Asp Ser His Arg Thr Pro Asn
545                 550                 555                 560
Thr Asp Ser Gly Asn Asn Arg Lys Leu Gly Arg Gln Pro Ile Asn Ile
                565                 570                 575
Asp Gly Ser Lys Asp Thr Thr Asp Gly Lys Gly Ser Glu Phe Leu Leu
            580                 585                 590
Ala Asn Asp Ile Asp Asn Ser Asn Pro Ile Val Gln Ala Glu Gln Leu
        595                 600                 605
```

-continued

```
Asn Trp Leu His Tyr Leu Met Asn Phe Gly Ser Ile Thr Gly Asn Asn
    610                 615                 620

Asp Asn Ala Asn Phe Asp Gly Ile Arg Val Asp Ala Val Asp Asn Val
625                 630                 635                 640

Asp Ala Asp Leu Leu Lys Ile Ala Gly Asp Tyr Phe Lys Ala Leu Tyr
                645                 650                 655

Gly Thr Asp Lys Ser Asp Ala Asn Ala Asn Lys His Leu Ser Ile Leu
            660                 665                 670

Glu Asp Trp Asn Gly Lys Asp Pro Gln Tyr Val Asn Gln Gln Gly Asn
        675                 680                 685

Ala Gln Leu Thr Met Asp Tyr Thr Val Thr Ser Gln Phe Gly Asn Ser
690                 695                 700

Leu Thr His Gly Ala Asn Asn Arg Ser Asn Met Trp Tyr Phe Leu Asp
705                 710                 715                 720

Thr Gly Tyr Tyr Leu Asn Gly Asp Leu Asn Lys Lys Ile Val Asp Lys
                725                 730                 735

Asn Arg Pro Asn Ser Gly Thr Leu Val Asn Arg Ile Ala Asn Ser Gly
            740                 745                 750

Asp Thr Lys Val Ile Pro Asn Tyr Ser Phe Val Arg Ala His Asp Tyr
        755                 760                 765

Asp Ala Gln Asp Pro Ile Arg Lys Ala Met Ile Asp His Gly Ile Ile
770                 775                 780

Lys Asn Met Gln Asp Thr Phe Thr Phe Asp Gln Leu Ala Gln Gly Met
785                 790                 795                 800

Glu Phe Tyr Tyr Lys Asp Gln Glu Asn Pro Ser Gly Phe Lys Lys Tyr
                805                 810                 815

Asn Asp Tyr Asn Leu Pro Ser Ala Tyr Ala Met Leu Leu Thr Asn Lys
            820                 825                 830

Asp Thr Val Pro Arg Val Tyr Tyr Gly Asp Met Tyr Leu Glu Gly Gly
        835                 840                 845

Gln Tyr Met Glu Lys Gly Thr Ile Tyr Asn Pro Val Ile Ser Ala Leu
850                 855                 860

Leu Lys Ala Arg Ile Lys Tyr Val Ser Gly Gly Gln Thr Met Ala Thr
865                 870                 875                 880

Asp Ser Ser Gly Lys Asp Leu Lys Asp Gly Glu Thr Asp Leu Leu Thr
                885                 890                 895

Ser Val Arg Phe Gly Lys Gly Ile Met Thr Ser Asp Gln Thr Thr Thr
            900                 905                 910

Gln Asp Asn Ser Gln Asp Tyr Lys Asn Gln Gly Ile Gly Val Ile Val
        915                 920                 925

Gly Asn Asn Pro Asp Leu Lys Leu Asn Asn Asp Lys Thr Ile Thr Leu
930                 935                 940

His Met Gly Lys Ala His Lys Asn Gln Leu Tyr Arg Ala Leu Val Leu
945                 950                 955                 960

Ser Asn Asp Ser Gly Ile Asp Val Tyr Asp Ser Asp Lys Ala Pro
                965                 970                 975

Thr Leu Arg Thr Asn Asp Asn Gly Asp Leu Ile Phe His Lys Thr Asn
            980                 985                 990

Thr Phe Val Lys Gln Asp Gly Thr  Ile Ile Asn Tyr Glu Met Lys Gly
        995                 1000                 1005

Ser Leu  Asn Ala Leu Ile Ser  Gly Tyr Leu Gly Val  Trp Val Pro
        1010                1015                1020
```

-continued

```
Val Gly Ala Ser Asp Ser Gln Asp Ala Arg Thr Val Ala Thr Glu
1025                1030                1035

Ser Ser Ser Ser Asn Asp Gly Ser Val Phe His Ser Asn Ala Ala
1040                1045                1050

Leu Asp Ser Asn Val Ile Tyr Glu Gly Phe Ser Asn Phe Gln Ala
1055                1060                1065

Met Pro Thr Ser Pro Glu Gln Ser Thr Asn Val Val Ile Ala Thr
1070                1075                1080

Lys Ala Asn Leu Phe Lys Glu Leu Gly Ile Thr Ser Phe Glu Leu
1085                1090                1095

Ala Pro Gln Tyr Arg Ser Ser Gly Asp Thr Asn Tyr Gly Gly Met
1100                1105                1110

Ser Phe Leu Asp Ser Phe Leu Asn Asn Gly Tyr Ala Phe Thr Asp
1115                1120                1125

Arg Tyr Asp Leu Gly Phe Asn Lys Ala Asp Gly Asn Pro Asn Pro
1130                1135                1140

Thr Lys Tyr Gly Thr Asp Gln Asp Leu Arg Asn Ala Ile Glu Ala
1145                1150                1155

Leu His Lys Asn Gly Met Gln Ala Ile Ala Asp Trp Val Pro Asp
1160                1165                1170

Gln Ile Tyr Ala Leu Pro Gly Lys Glu Val Val Thr Ala Thr Arg
1175                1180                1185

Val Asp Glu Arg Gly Asn Gln Leu Lys Asp Thr Asp Phe Val Asn
1190                1195                1200

Leu Leu Tyr Val Ala Asn Thr Lys Ser Ser Gly Val Asp Tyr Gln
1205                1210                1215

Ala Lys Tyr Gly Gly Glu Phe Leu Asp Lys Leu Arg Glu Glu Tyr
1220                1225                1230

Pro Ser Leu Phe Lys Gln Asn Gln Val Ser Thr Gly Gln Pro Ile
1235                1240                1245

Asp Ala Ser Thr Lys Ile Lys Gln Trp Ser Ala Lys Tyr Met Asn
1250                1255                1260

Gly Thr Asn Ile Leu His Arg Gly Ala Tyr Tyr Val Leu Lys Asp
1265                1270                1275

Trp Ala Thr Asn Gln Tyr Phe Asn Ile Ala Lys Thr Asn Glu Val
1280                1285                1290

Phe Leu Pro Leu Gln Leu Gln Asn Lys Asp Ala Gln Thr Gly Phe
1295                1300                1305

Ile Ser Asp Ala Ser Gly Val Lys Tyr Tyr Ser Ile Ser Gly Tyr
1310                1315                1320

Gln Ala Lys Asp Thr Phe Ile Glu Asp Gly Asn Gly Asn Trp Tyr
1325                1330                1335

Tyr Phe Asp Lys Asp Gly Tyr Met Val Arg Ser Gln Gln Gly Glu
1340                1345                1350

Asn Pro Ile Arg Thr Val Glu Thr Ser Val Asn Thr Arg Asn Gly
1355                1360                1365

Asn Tyr Tyr Phe Met Pro Asn Gly Val Glu Leu Arg Lys Gly Phe
1370                1375                1380

Gly Thr Asp Asn Ser Gly Asn Val Tyr Tyr Phe Asp Asp Gln Gly
1385                1390                1395
```

```
Lys Met  Val Arg Asp Lys Tyr  Ile Asn Asp Asp Ala  Asn Asn Phe
    1400             1405                 1410

Tyr His  Leu Asn Val Asp Gly  Thr Met Ser Arg Gly
    1415             1420                 1425

<210> SEQ ID NO 28
<211> LENGTH: 1084
<212> TYPE: PRT
<213> ORGANISM: Artificial Sequence
<220> FEATURE:
<223> OTHER INFORMATION: Peptide - Truncated alternansucrase amino acid
      sequence - Full length amino acid sequence

<400> SEQUENCE: 28

Met Leu Thr  Gly Leu Gln Thr  Ile Ser Gly Lys  Thr Tyr Tyr Leu Asp
1            5                10               15

Glu Gln Gly  His Leu Arg Lys  Asn Tyr Ala Gly  Thr Phe Asn Asn Gln
             20               25               30

Phe Met Tyr  Phe Asp Ala Asp  Thr Gly Ala Gly  Lys Thr Ala Ile Glu
             35               40               45

Tyr Gln Phe  Asp Gln Gly Leu  Val Ser Gln Ser  Asn Glu Asn Thr Pro
50                55                           60

His Asn Ala  Ala Lys Ser Tyr  Asp Lys Ser Ser  Phe Glu Asn Val Asp
65           70                75                            80

Gly Tyr Leu  Thr Ala Asp Thr  Trp Tyr Arg Pro  Thr Asp Ile Leu Lys
             85                90                            95

Asn Gly Asp  Thr Trp Thr Ala  Ser Thr Glu Thr  Asp Met Arg Pro Leu
             100              105              110

Leu Met Thr  Trp Trp Pro Asp  Lys Gln Thr Gln  Ala Asn Tyr Leu Asn
             115              120              125

Phe Met Ser  Ser Lys Gly Leu  Gly Ile Thr Thr  Thr Tyr Thr Ala Ala
130                135                140

Thr Ser Gln  Lys Thr Leu Asn  Asp Ala Ala Phe  Val Ile Gln Thr Ala
145          150                155                           160

Ile Glu Gln  Gln Ile Ser Leu  Lys Lys Ser Thr  Glu Trp Leu Arg Asp
             165              170              175

Ala Ile Asp  Ser Phe Val Lys  Thr Gln Ala Asn  Trp Asn Lys Gln Thr
             180              185              190

Glu Asp Glu  Ala Phe Asp Gly  Leu Gln Trp Leu  Gln Gly Gly Phe Leu
             195              200              205

Ala Tyr Gln  Asp Asp Ser His  Arg Thr Pro Asn  Thr Asp Ser Gly Asn
             210              215              220

Asn Arg Lys  Leu Gly Arg Gln  Pro Ile Asn Ile  Asp Gly Ser Lys Asp
225                230                235                       240

Thr Thr Asp  Gly Lys Gly Ser  Glu Phe Leu Leu  Ala Asn Asp Ile Asp
             245              250              255

Asn Ser Asn  Pro Ile Val Gln  Ala Glu Gln Leu  Asn Trp Leu His Tyr
             260              265              270

Leu Met Asn  Phe Gly Ser Ile  Thr Gly Asn Asn  Asp Asn Ala Asn Phe
             275              280              285

Asp Gly Ile  Arg Val Asp Ala  Val Asp Asn Val  Asp Ala Asp Leu Leu
             290              295              300

Lys Ile Ala  Gly Asp Tyr Phe  Lys Ala Leu Tyr  Gly Thr Asp Lys Ser
305          310                315                           320

Asp Ala Asn  Ala Asn Lys His  Leu Ser Ile Leu  Glu Asp Trp Asn Gly
             325              330              335
```

-continued

```
Lys Asp Pro Gln Tyr Val Asn Gln Gly Asn Ala Gln Leu Thr Met
                340                 345                 350
Asp Tyr Thr Val Thr Ser Gln Phe Gly Asn Ser Leu Thr His Gly Ala
                355                 360                 365
Asn Asn Arg Ser Asn Met Trp Tyr Phe Leu Asp Thr Gly Tyr Tyr Leu
            370                 375                 380
Asn Gly Asp Leu Asn Lys Lys Ile Val Asp Lys Asn Arg Pro Asn Ser
385                 390                 395                 400
Gly Thr Leu Val Asn Arg Ile Ala Asn Ser Gly Asp Thr Lys Val Ile
                405                 410                 415
Pro Asn Tyr Ser Phe Val Arg Ala His Asp Tyr Asp Ala Gln Asp Pro
                420                 425                 430
Ile Arg Lys Ala Met Ile Asp His Gly Ile Ile Lys Asn Met Gln Asp
                435                 440                 445
Thr Phe Thr Phe Asp Gln Leu Ala Gln Gly Met Glu Phe Tyr Tyr Lys
            450                 455                 460
Asp Gln Glu Asn Pro Ser Gly Phe Lys Lys Tyr Asn Asp Tyr Asn Leu
465                 470                 475                 480
Pro Ser Ala Tyr Ala Met Leu Leu Thr Asn Lys Asp Thr Val Pro Arg
                485                 490                 495
Val Tyr Tyr Gly Asp Met Tyr Leu Glu Gly Gln Tyr Met Glu Lys
                500                 505                 510
Gly Thr Ile Tyr Asn Pro Val Ile Ser Ala Leu Leu Lys Ala Arg Ile
                515                 520                 525
Lys Tyr Val Ser Gly Gly Gln Thr Met Ala Thr Asp Ser Ser Gly Lys
                530                 535                 540
Asp Leu Lys Asp Gly Glu Thr Asp Leu Leu Thr Ser Val Arg Phe Gly
545                 550                 555                 560
Lys Gly Ile Met Thr Ser Asp Gln Thr Thr Gln Asp Asn Ser Gln
                565                 570                 575
Asp Tyr Lys Asn Gln Gly Ile Gly Val Ile Val Gly Asn Asn Pro Asp
            580                 585                 590
Leu Lys Leu Asn Asn Asp Lys Thr Ile Thr Leu His Met Gly Lys Ala
            595                 600                 605
His Lys Asn Gln Leu Tyr Arg Ala Leu Val Leu Ser Asn Asp Ser Gly
    610                 615                 620
Ile Asp Val Tyr Asp Ser Asp Lys Ala Pro Thr Leu Arg Thr Asn
625                 630                 635                 640
Asp Asn Gly Asp Leu Ile Phe His Lys Thr Asn Thr Phe Val Lys Gln
                645                 650                 655
Asp Gly Thr Ile Ile Asn Tyr Glu Met Lys Gly Ser Leu Asn Ala Leu
                660                 665                 670
Ile Ser Gly Tyr Leu Gly Val Trp Val Pro Val Gly Ala Ser Asp Ser
            675                 680                 685
Gln Asp Ala Arg Thr Val Ala Thr Glu Ser Ser Ser Asn Asp Gly
    690                 695                 700
Ser Val Phe His Ser Asn Ala Ala Leu Asp Ser Asn Val Ile Tyr Glu
705                 710                 715                 720
Gly Phe Ser Asn Phe Gln Ala Met Pro Thr Ser Pro Glu Gln Ser Thr
                725                 730                 735
Asn Val Val Ile Ala Thr Lys Ala Asn Leu Phe Lys Glu Leu Gly Ile
                740                 745                 750
```

```
Thr Ser Phe Glu Leu Ala Pro Gln Tyr Arg Ser Ser Gly Asp Thr Asn
        755                 760                 765

Tyr Gly Gly Met Ser Phe Leu Asp Ser Phe Leu Asn Asn Gly Tyr Ala
770                 775                 780

Phe Thr Asp Arg Tyr Asp Leu Gly Phe Asn Lys Ala Asp Gly Asn Pro
785                 790                 795                 800

Asn Pro Thr Lys Tyr Gly Thr Asp Gln Asp Leu Arg Asn Ala Ile Glu
            805                 810                 815

Ala Leu His Lys Asn Gly Met Gln Ala Ile Ala Asp Trp Val Pro Asp
        820                 825                 830

Gln Ile Tyr Ala Leu Pro Gly Lys Glu Val Val Thr Ala Thr Arg Val
        835                 840                 845

Asp Glu Arg Gly Asn Gln Leu Lys Asp Thr Asp Phe Val Asn Leu Leu
850                 855                 860

Tyr Val Ala Asn Thr Lys Ser Ser Gly Val Asp Tyr Gln Ala Lys Tyr
865                 870                 875                 880

Gly Gly Glu Phe Leu Asp Lys Leu Arg Glu Glu Tyr Pro Ser Leu Phe
            885                 890                 895

Lys Gln Asn Gln Val Ser Thr Gly Gln Pro Ile Asp Ala Ser Thr Lys
        900                 905                 910

Ile Lys Gln Trp Ser Ala Lys Tyr Met Asn Gly Thr Asn Ile Leu His
        915                 920                 925

Arg Gly Ala Tyr Tyr Val Leu Lys Asp Trp Ala Thr Asn Gln Tyr Phe
930                 935                 940

Asn Ile Ala Lys Thr Asn Glu Val Phe Leu Pro Leu Gln Leu Gln Asn
945                 950                 955                 960

Lys Asp Ala Gln Thr Gly Phe Ile Ser Asp Ala Ser Gly Val Lys Tyr
            965                 970                 975

Tyr Ser Ile Ser Gly Tyr Gln Ala Lys Asp Thr Phe Ile Glu Asp Gly
        980                 985                 990

Asn Gly Asn Trp Tyr Tyr Phe Asp  Lys Asp Gly Tyr Met  Val Arg Ser
        995                 1000                1005

Gln Gln  Gly Glu Asn Pro Ile  Arg Thr Val Glu Thr  Ser Val Asn
    1010                1015                1020

Thr Arg  Asn Gly Asn Tyr Tyr  Phe Met Pro Asn Gly  Val Glu Leu
    1025                1030                1035

Arg Lys  Gly Phe Gly Thr Asp  Asn Ser Gly Asn Val  Tyr Tyr Phe
    1040                1045                1050

Asp Asp  Gln Gly Lys Met Val  Arg Asp Lys Tyr Ile  Asn Asp Asp
    1055                1060                1065

Ala Asn  Asn Phe Tyr His Leu  Asn Val Asp Gly Thr  Met Ser Arg
    1070                1075                1080

Gly
```

```
<210> SEQ ID NO 29
<211> LENGTH: 2057
<212> TYPE: PRT
<213> ORGANISM: Artificial Sequence
<220> FEATURE:
<223> OTHER INFORMATION: Mutant alternansucrases amino acid sequence
<220> FEATURE:
<221> NAME/KEY: Mutation
<222> LOCATION: (676)..(678)
<223> OTHER INFORMATION: Xaa - Asn, Lys at positions 676, 678 are
      replaced with Ser, Asn
```

<400> SEQUENCE: 29

```
Met Lys Gln Gln Glu Thr Val Thr Arg Lys Lys Leu Tyr Lys Ser Gly
1               5                   10                  15
Lys Val Trp Val Ala Ala Thr Ala Phe Ala Val Leu Gly Val Ser
            20                  25                  30
Thr Val Thr Thr Val His Ala Asp Thr Asn Ser Asn Val Ala Val Lys
                35                  40                  45
Gln Ile Asn Asn Thr Gly Thr Asn Asp Ser Gly Glu Lys Lys Val Pro
    50                  55                  60
Val Pro Ser Thr Asn Asn Asp Ser Leu Lys Gln Gly Thr Asp Gly Phe
65                  70                  75                  80
Trp Tyr Asp Ser Asp Gly Asn Arg Val Asp Gln Lys Thr Asn Gln Ile
                85                  90                  95
Leu Leu Thr Ala Glu Gln Leu Lys Lys Asn Asn Glu Lys Asn Leu Ser
                100                 105                 110
Val Ile Ser Asp Asp Thr Ser Lys Lys Asp Asp Glu Asn Ile Ser Lys
                115                 120                 125
Gln Thr Lys Ile Ala Asn Gln Gln Thr Val Asp Thr Ala Lys Gly Leu
    130                 135                 140
Thr Thr Ser Asn Leu Ser Asp Pro Ile Thr Gly Gly His Tyr Glu Asn
145                 150                 155                 160
His Asn Gly Tyr Phe Val Tyr Ile Asp Ala Ser Gly Lys Gln Val Thr
                165                 170                 175
Gly Leu Gln Asn Ile Asp Gly Asn Leu Gln Tyr Phe Asp Asp Asn Gly
            180                 185                 190
Tyr Gln Val Lys Gly Ser Phe Arg Asp Val Asn Gly Lys His Ile Tyr
                195                 200                 205
Phe Asp Ser Val Thr Gly Lys Ala Ser Ser Asn Val Asp Ile Val Asn
    210                 215                 220
Gly Lys Ala Gln Gly Tyr Asp Ala Gln Gly Asn Gln Leu Lys Lys Ser
225                 230                 235                 240
Tyr Val Ala Asp Ser Ser Gly Gln Thr Tyr Tyr Phe Asp Gly Asn Gly
                245                 250                 255
Gln Pro Leu Ile Gly Leu Gln Thr Ile Asp Gly Asn Leu Gln Tyr Phe
            260                 265                 270
Asn Gln Gln Gly Val Gln Ile Lys Gly Gly Phe Gln Asp Val Asn Asn
        275                 280                 285
Lys Arg Ile Tyr Phe Ala Pro Asn Thr Gly Asn Ala Val Ala Asn Thr
290                 295                 300
Glu Ile Ile Asn Gly Lys Leu Gln Gly Arg Asp Ala Asn Gly Asn Gln
305                 310                 315                 320
Val Lys Asn Ala Phe Ser Lys Asp Val Ala Gly Asn Thr Phe Tyr Phe
                325                 330                 335
Asp Ala Asn Gly Val Met Leu Thr Gly Leu Gln Thr Ile Ser Gly Lys
                340                 345                 350
Thr Tyr Tyr Leu Asp Glu Gln Gly His Leu Arg Lys Asn Tyr Ala Gly
            355                 360                 365
Thr Phe Asn Asn Gln Phe Met Tyr Phe Asp Ala Asp Thr Gly Ala Gly
        370                 375                 380
Lys Thr Ala Ile Glu Tyr Gln Phe Asp Gln Gly Leu Val Ser Gln Ser
385                 390                 395                 400
Asn Glu Asn Thr Pro His Asn Ala Ala Lys Ser Tyr Asp Lys Ser Ser
                405                 410                 415
```

```
Phe Glu Asn Val Asp Gly Tyr Leu Thr Ala Asp Thr Trp Tyr Arg Pro
            420                 425                 430

Thr Asp Ile Leu Lys Asn Gly Asp Thr Trp Thr Ala Ser Thr Glu Thr
            435                 440                 445

Asp Met Arg Pro Leu Leu Met Thr Trp Trp Pro Asp Lys Gln Thr Gln
    450                 455                 460

Ala Asn Tyr Leu Asn Phe Met Ser Ser Lys Gly Leu Gly Ile Thr Thr
465                 470                 475                 480

Thr Tyr Thr Ala Ala Thr Ser Gln Lys Thr Leu Asn Asp Ala Ala Phe
                485                 490                 495

Val Ile Gln Thr Ala Ile Glu Gln Gln Ile Ser Leu Lys Lys Ser Thr
            500                 505                 510

Glu Trp Leu Arg Asp Ala Ile Asp Ser Phe Val Lys Thr Gln Ala Asn
            515                 520                 525

Trp Asn Lys Gln Thr Glu Asp Glu Ala Phe Asp Gly Leu Gln Trp Leu
    530                 535                 540

Gln Gly Gly Phe Leu Ala Tyr Gln Asp Asp Ser His Arg Thr Pro Asn
545                 550                 555                 560

Thr Asp Ser Gly Asn Asn Arg Lys Leu Gly Arg Gln Pro Ile Asn Ile
                565                 570                 575

Asp Gly Ser Lys Asp Thr Thr Asp Gly Lys Gly Ser Glu Phe Leu Leu
            580                 585                 590

Ala Asn Asp Ile Asp Asn Ser Asn Pro Ile Val Gln Ala Glu Gln Leu
            595                 600                 605

Asn Trp Leu His Tyr Leu Met Asn Phe Gly Ser Ile Thr Gly Asn Asn
    610                 615                 620

Asp Asn Ala Asn Phe Asp Gly Ile Arg Val Asp Ala Val Asp Asn Val
625                 630                 635                 640

Asp Ala Asp Leu Leu Lys Ile Ala Gly Asp Tyr Phe Lys Ala Leu Tyr
                645                 650                 655

Gly Thr Asp Lys Ser Asp Ala Asn Ala Asn Lys His Leu Ser Ile Leu
            660                 665                 670

Glu Asp Trp Ser Gly Asn Asp Pro Gln Tyr Val Asn Gln Gln Gly Asn
            675                 680                 685

Ala Gln Leu Thr Met Asp Tyr Thr Val Thr Ser Gln Phe Gly Asn Ser
    690                 695                 700

Leu Thr His Gly Ala Asn Asn Arg Ser Asn Met Trp Tyr Phe Leu Asp
705                 710                 715                 720

Thr Gly Tyr Tyr Leu Asn Gly Asp Leu Asn Lys Lys Ile Val Asp Lys
                725                 730                 735

Asn Arg Pro Asn Ser Gly Thr Leu Val Asn Arg Ile Ala Asn Ser Gly
            740                 745                 750

Asp Thr Lys Val Ile Pro Asn Tyr Ser Phe Val Arg Ala His Asp Tyr
            755                 760                 765

Asp Ala Gln Asp Pro Ile Arg Lys Ala Met Ile Asp His Gly Ile Ile
    770                 775                 780

Lys Asn Met Gln Asp Thr Phe Thr Phe Asp Gln Leu Ala Gln Gly Met
785                 790                 795                 800

Glu Phe Tyr Tyr Lys Asp Gln Glu Asn Pro Ser Gly Phe Lys Lys Tyr
                805                 810                 815

Asn Asp Tyr Asn Leu Pro Ser Ala Tyr Ala Met Leu Leu Thr Asn Lys
            820                 825                 830
```

-continued

```
Asp Thr Val Pro Arg Val Tyr Tyr Gly Asp Met Tyr Leu Glu Gly Gly
        835                 840                 845

Gln Tyr Met Glu Lys Gly Thr Ile Tyr Asn Pro Val Ile Ser Ala Leu
    850                 855                 860

Leu Lys Ala Arg Ile Lys Tyr Val Ser Gly Gly Gln Thr Met Ala Thr
865                 870                 875                 880

Asp Ser Ser Gly Lys Asp Leu Lys Asp Gly Glu Thr Asp Leu Leu Thr
                885                 890                 895

Ser Val Arg Phe Gly Lys Gly Ile Met Thr Ser Asp Gln Thr Thr Thr
            900                 905                 910

Gln Asp Asn Ser Gln Asp Tyr Lys Asn Gln Gly Ile Gly Val Ile Val
        915                 920                 925

Gly Asn Asn Pro Asp Leu Lys Leu Asn Asn Asp Lys Thr Ile Thr Leu
    930                 935                 940

His Met Gly Lys Ala His Lys Asn Gln Leu Tyr Arg Ala Leu Val Leu
945                 950                 955                 960

Ser Asn Asp Ser Gly Ile Asp Val Tyr Asp Ser Asp Lys Ala Pro
                965                 970                 975

Thr Leu Arg Thr Asn Asp Asn Gly Asp Leu Ile Phe His Lys Thr Asn
            980                 985                 990

Thr Phe Val Lys Gln Asp Gly Thr Ile Ile Asn Tyr Glu Met Lys Gly
        995                 1000                1005

Ser Leu Asn Ala Leu Ile Ser Gly Tyr Leu Gly Val Trp Val Pro
    1010                1015                1020

Val Gly Ala Ser Asp Ser Gln Asp Ala Arg Thr Val Ala Thr Glu
    1025                1030                1035

Ser Ser Ser Ser Asn Asp Gly Ser Val Phe His Ser Asn Ala Ala
    1040                1045                1050

Leu Asp Ser Asn Val Ile Tyr Glu Gly Phe Ser Asn Phe Gln Ala
    1055                1060                1065

Met Pro Thr Ser Pro Glu Gln Ser Thr Asn Val Val Ile Ala Thr
    1070                1075                1080

Lys Ala Asn Leu Phe Lys Glu Leu Gly Ile Thr Ser Phe Glu Leu
    1085                1090                1095

Ala Pro Gln Tyr Arg Ser Ser Gly Asp Thr Asn Tyr Gly Gly Met
    1100                1105                1110

Ser Phe Leu Asp Ser Phe Leu Asn Asn Gly Tyr Ala Phe Thr Asp
    1115                1120                1125

Arg Tyr Asp Leu Gly Phe Asn Lys Ala Asp Gly Asn Pro Asn Pro
    1130                1135                1140

Thr Lys Tyr Gly Thr Asp Gln Asp Leu Arg Asn Ala Ile Glu Ala
    1145                1150                1155

Leu His Lys Asn Gly Met Gln Ala Ile Ala Asp Trp Val Pro Asp
    1160                1165                1170

Gln Ile Tyr Ala Leu Pro Gly Lys Glu Val Val Thr Ala Thr Arg
    1175                1180                1185

Val Asp Glu Arg Gly Asn Gln Leu Lys Asp Thr Asp Phe Val Asn
    1190                1195                1200

Leu Leu Tyr Val Ala Asn Thr Lys Ser Ser Gly Val Asp Tyr Gln
    1205                1210                1215

Ala Lys Tyr Gly Gly Glu Phe Leu Asp Lys Leu Arg Glu Glu Tyr
    1220                1225                1230
```

-continued

```
Pro Ser Leu Phe Lys Gln Asn Gln Val Ser Thr Gly Gln Pro Ile
1235                1240                1245

Asp Ala Ser Thr Lys Ile Lys Gln Trp Ser Ala Lys Tyr Met Asn
    1250                1255                1260

Gly Thr Asn Ile Leu His Arg Gly Ala Tyr Tyr Val Leu Lys Asp
1265                1270                1275

Trp Ala Thr Asn Gln Tyr Phe Asn Ile Ala Lys Thr Asn Glu Val
    1280                1285                1290

Phe Leu Pro Leu Gln Leu Gln Asn Lys Asp Ala Gln Thr Gly Phe
1295                1300                1305

Ile Ser Asp Ala Ser Gly Val Lys Tyr Tyr Ser Ile Ser Gly Tyr
    1310                1315                1320

Gln Ala Lys Asp Thr Phe Ile Glu Asp Gly Asn Gly Asn Trp Tyr
1325                1330                1335

Tyr Phe Asp Lys Asp Gly Tyr Met Val Arg Ser Gln Gln Gly Glu
    1340                1345                1350

Asn Pro Ile Arg Thr Val Glu Thr Ser Val Asn Thr Arg Asn Gly
1355                1360                1365

Asn Tyr Tyr Phe Met Pro Asn Gly Val Glu Leu Arg Lys Gly Phe
    1370                1375                1380

Gly Thr Asp Asn Ser Gly Asn Val Tyr Tyr Phe Asp Asp Gln Gly
1385                1390                1395

Lys Met Val Arg Asp Lys Tyr Ile Asn Asp Asp Ala Asn Asn Phe
1400                1405                1410

Tyr His Leu Asn Val Asp Gly Thr Met Ser Arg Gly Leu Phe Lys
    1415                1420                1425

Phe Asp Ser Asp Thr Leu Gln Tyr Phe Ala Ser Asn Gly Val Gln
1430                1435                1440

Ile Lys Asp Ser Tyr Ala Lys Asp Ser Lys Gly Asn Lys Tyr Tyr
    1445                1450                1455

Phe Asp Ser Ala Thr Gly Asn Asn Asp Thr Gly Lys Ala Gln Thr
1460                1465                1470

Trp Asp Gly Asn Gly Tyr Tyr Ile Thr Ile Asp Ser Asp Ala Asn
    1475                1480                1485

Asn Thr Ile Gly Val Asn Thr Asp Tyr Thr Ala Tyr Ile Thr Ser
    1490                1495                1500

Ser Leu Arg Glu Asp Gly Leu Phe Ala Asn Ala Pro Tyr Gly Val
1505                1510                1515

Val Thr Lys Asp Gln Asn Gly Asn Asp Leu Lys Trp Gln Tyr Ile
1520                1525                1530

Asn His Thr Lys Gln Tyr Glu Gly Gln Gln Val Gln Val Thr Arg
    1535                1540                1545

Gln Tyr Thr Asp Ser Lys Gly Val Ser Trp Asn Leu Ile Thr Phe
1550                1555                1560

Ala Gly Gly Asp Leu Gln Gly Gln Arg Leu Trp Val Asp Ser Arg
1565                1570                1575

Ala Leu Thr Met Thr Pro Phe Lys Thr Met Asn Gln Ile Ser Phe
1580                1585                1590

Ile Ser Tyr Ala Asn Arg Asn Asp Gly Leu Phe Leu Asn Ala Pro
    1595                1600                1605

Tyr Gln Val Lys Gly Tyr Gln Leu Ala Gly Met Ser Asn Gln Tyr
1610                1615                1620
```

-continued

```
Lys Gly Gln Gln Val Thr Ile Ala Gly Val Ala Asn Val Ser Gly
1625                1630                1635

Lys Asp Trp Ser Leu Ile Ser Phe Asn Gly Thr Gln Tyr Trp Ile
1640                1645                1650

Asp Ser Gln Ala Leu Asn Thr Asn Phe Thr His Asp Met Asn Gln
1655                1660                1665

Lys Val Phe Val Asn Thr Thr Ser Asn Leu Asp Gly Leu Phe Leu
1670                1675                1680

Asn Ala Pro Tyr Arg Gln Pro Gly Tyr Lys Leu Ala Gly Leu Ala
1685                1690                1695

Lys Asn Tyr Asn Asn Gln Thr Val Thr Val Ser Gln Gln Tyr Phe
1700                1705                1710

Asp Asp Gln Gly Thr Val Trp Ser Gln Val Val Leu Gly Gly Gln
1715                1720                1725

Thr Val Trp Val Asp Asn His Ala Leu Ala Gln Met Gln Val Ser
1730                1735                1740

Asp Thr Asp Gln Gln Leu Tyr Val Asn Ser Asn Gly Arg Asn Asp
1745                1750                1755

Gly Leu Phe Leu Asn Ala Pro Tyr Arg Gly Gln Gly Ser Gln Leu
1760                1765                1770

Ile Gly Met Thr Ala Asp Tyr Asn Gly Gln His Val Gln Val Thr
1775                1780                1785

Lys Gln Gly Gln Asp Ala Tyr Gly Ala Gln Trp Arg Leu Ile Thr
1790                1795                1800

Leu Asn Asn Gln Gln Val Trp Val Asp Ser Arg Ala Leu Ser Thr
1805                1810                1815

Thr Ile Met Gln Ala Met Asn Asp Asn Met Tyr Val Asn Ser Ser
1820                1825                1830

Gln Arg Thr Asp Gly Leu Trp Leu Asn Ala Pro Tyr Thr Met Ser
1835                1840                1845

Gly Ala Lys Trp Ala Gly Asp Thr Arg Ser Ala Asn Gly Arg Tyr
1850                1855                1860

Val His Ile Ser Lys Ala Tyr Ser Asn Glu Val Gly Asn Thr Tyr
1865                1870                1875

Tyr Leu Thr Asn Leu Asn Gly Gln Ser Thr Trp Ile Asp Lys Arg
1880                1885                1890

Ala Phe Thr Val Thr Phe Asp Gln Val Val Ala Leu Asn Ala Thr
1895                1900                1905

Ile Val Ala Arg Gln Arg Pro Asp Gly Met Phe Lys Thr Ala Pro
1910                1915                1920

Tyr Gly Glu Ala Gly Ala Gln Phe Val Asp Tyr Val Thr Asn Tyr
1925                1930                1935

Asn Gln Gln Thr Val Pro Val Thr Lys Gln His Ser Asp Ala Gln
1940                1945                1950

Gly Asn Gln Trp Tyr Leu Ala Thr Val Asn Gly Thr Gln Tyr Trp
1955                1960                1965

Ile Asp Gln Arg Ser Phe Ser Pro Val Thr Lys Val Val Asp
1970                1975                1980

Tyr Gln Ala Lys Ile Val Pro Arg Thr Thr Arg Asp Gly Val Phe
1985                1990                1995

Ser Gly Ala Pro Tyr Gly Glu Val Asn Ala Lys Leu Val Asn Met
2000                2005                2010
```

-continued

```
Ala Thr Ala Tyr Gln Asn Gln Val Val His Ala Thr Gly Glu Tyr
    2015                2020                2025

Thr Asn Ala Ser Gly Ile Thr Trp Ser Gln Phe Ala Leu Ser Gly
    2030                2035                2040

Gln Glu Asp Lys Leu Trp Ile Asp Lys Arg Ala Leu Gln Ala
    2045                2050                2055

<210> SEQ ID NO 30
<211> LENGTH: 2057
<212> TYPE: PRT
<213> ORGANISM: Artificial Sequence
<220> FEATURE:
<223> OTHER INFORMATION: Mutant alternansucrase amino acid sequence
<220> FEATURE:
<221> NAME/KEY: Mutation
<222> LOCATION: (768)..(770)
<223> OTHER INFORMATION: Xaa - Tyr, Asp, and Ala at positions 768 to 770
      are replaced by Ser, Glu, and Val

<400> SEQUENCE: 30

Met Lys Gln Gln Glu Thr Val Thr Arg Lys Lys Leu Tyr Lys Ser Gly
1               5                   10                  15

Lys Val Trp Val Ala Ala Ala Thr Ala Phe Ala Val Leu Gly Val Ser
            20                  25                  30

Thr Val Thr Thr Val His Ala Asp Thr Asn Ser Asn Val Ala Val Lys
        35                  40                  45

Gln Ile Asn Asn Thr Gly Thr Asn Asp Ser Gly Glu Lys Lys Val Pro
    50                  55                  60

Val Pro Ser Thr Asn Asn Asp Ser Leu Lys Gln Gly Thr Asp Gly Phe
65                  70                  75                  80

Trp Tyr Asp Ser Asp Gly Asn Arg Val Asp Gln Lys Thr Asn Gln Ile
                85                  90                  95

Leu Leu Thr Ala Glu Gln Leu Lys Lys Asn Asn Glu Lys Asn Leu Ser
            100                 105                 110

Val Ile Ser Asp Asp Thr Ser Lys Lys Asp Asp Glu Asn Ile Ser Lys
        115                 120                 125

Gln Thr Lys Ile Ala Asn Gln Gln Thr Val Asp Thr Ala Lys Gly Leu
    130                 135                 140

Thr Thr Ser Asn Leu Ser Asp Pro Ile Thr Gly Gly His Tyr Glu Asn
145                 150                 155                 160

His Asn Gly Tyr Phe Val Tyr Ile Asp Ala Ser Gly Lys Gln Val Thr
                165                 170                 175

Gly Leu Gln Asn Ile Asp Gly Asn Leu Gln Tyr Phe Asp Asp Asn Gly
            180                 185                 190

Tyr Gln Val Lys Gly Ser Phe Arg Asp Val Asn Gly Lys His Ile Tyr
        195                 200                 205

Phe Asp Ser Val Thr Gly Lys Ala Ser Ser Asn Val Asp Ile Val Asn
    210                 215                 220

Gly Lys Ala Gln Gly Tyr Asp Ala Gln Gly Asn Gln Leu Lys Lys Ser
225                 230                 235                 240

Tyr Val Ala Asp Ser Ser Gly Gln Thr Tyr Tyr Phe Asp Gly Asn Gly
                245                 250                 255

Gln Pro Leu Ile Gly Leu Gln Thr Ile Asp Gly Asn Leu Gln Tyr Phe
            260                 265                 270

Asn Gln Gln Gly Val Gln Ile Lys Gly Gly Phe Gln Asp Val Asn Asn
        275                 280                 285
```

-continued

```
Lys Arg Ile Tyr Phe Ala Pro Asn Thr Gly Asn Ala Val Ala Asn Thr
290                 295                 300

Glu Ile Ile Asn Gly Lys Leu Gln Gly Arg Asp Ala Asn Gly Asn Gln
305                 310                 315                 320

Val Lys Asn Ala Phe Ser Lys Asp Val Ala Gly Asn Thr Phe Tyr Phe
                325                 330                 335

Asp Ala Asn Gly Val Met Leu Thr Gly Leu Gln Thr Ile Ser Gly Lys
            340                 345                 350

Thr Tyr Tyr Leu Asp Glu Gln Gly His Leu Arg Lys Asn Tyr Ala Gly
        355                 360                 365

Thr Phe Asn Asn Gln Phe Met Tyr Phe Asp Ala Asp Thr Gly Ala Gly
370                 375                 380

Lys Thr Ala Ile Glu Tyr Gln Phe Asp Gln Gly Leu Val Ser Gln Ser
385                 390                 395                 400

Asn Glu Asn Thr Pro His Asn Ala Ala Lys Ser Tyr Asp Lys Ser Ser
                405                 410                 415

Phe Glu Asn Val Asp Gly Tyr Leu Thr Ala Asp Thr Trp Tyr Arg Pro
            420                 425                 430

Thr Asp Ile Leu Lys Asn Gly Asp Thr Trp Thr Ala Ser Thr Glu Thr
        435                 440                 445

Asp Met Arg Pro Leu Leu Met Thr Trp Trp Pro Asp Lys Gln Thr Gln
450                 455                 460

Ala Asn Tyr Leu Asn Phe Met Ser Ser Lys Gly Leu Gly Ile Thr Thr
465                 470                 475                 480

Thr Tyr Thr Ala Ala Thr Ser Gln Lys Thr Leu Asn Asp Ala Ala Phe
                485                 490                 495

Val Ile Gln Thr Ala Ile Glu Gln Ile Ser Leu Lys Lys Ser Thr
            500                 505                 510

Glu Trp Leu Arg Asp Ala Ile Asp Ser Phe Val Lys Thr Gln Ala Asn
        515                 520                 525

Trp Asn Lys Gln Thr Glu Asp Glu Ala Phe Asp Gly Leu Gln Trp Leu
530                 535                 540

Gln Gly Gly Phe Leu Ala Tyr Gln Asp Ser His Arg Thr Pro Asn
545                 550                 555                 560

Thr Asp Ser Gly Asn Asn Arg Lys Leu Gly Arg Gln Pro Ile Asn Ile
                565                 570                 575

Asp Gly Ser Lys Asp Thr Thr Asp Gly Lys Gly Ser Glu Phe Leu Leu
            580                 585                 590

Ala Asn Asp Ile Asp Asn Ser Asn Pro Ile Val Gln Ala Glu Gln Leu
        595                 600                 605

Asn Trp Leu His Tyr Leu Met Asn Phe Gly Ser Ile Thr Gly Asn Asn
610                 615                 620

Asp Asn Ala Asn Phe Asp Gly Ile Arg Val Asp Ala Val Asp Asn Val
625                 630                 635                 640

Asp Ala Asp Leu Leu Lys Ile Ala Gly Asp Tyr Phe Lys Ala Leu Tyr
                645                 650                 655

Gly Thr Asp Lys Ser Asp Ala Asn Ala Asn Lys His Leu Ser Ile Leu
            660                 665                 670

Glu Asp Trp Asn Gly Lys Asp Pro Gln Tyr Val Asn Gln Gln Gly Asn
        675                 680                 685

Ala Gln Leu Thr Met Asp Tyr Thr Val Thr Ser Gln Phe Gly Asn Ser
690                 695                 700
```

-continued

Leu Thr His Gly Ala Asn Asn Arg Ser Asn Met Trp Tyr Phe Leu Asp
705                 710                 715                 720

Thr Gly Tyr Tyr Leu Asn Gly Asp Leu Asn Lys Ile Val Asp Lys
            725                 730                 735

Asn Arg Pro Asn Ser Gly Thr Leu Val Asn Arg Ile Ala Asn Ser Gly
            740                 745                 750

Asp Thr Lys Val Ile Pro Asn Tyr Ser Phe Val Arg Ala His Asp Ser
            755                 760                 765

Glu Val Gln Asp Pro Ile Arg Lys Ala Met Ile Asp His Gly Ile Ile
        770                 775                 780

Lys Asn Met Gln Asp Thr Phe Thr Phe Asp Gln Leu Ala Gln Gly Met
785                 790                 795                 800

Glu Phe Tyr Tyr Lys Asp Gln Glu Asn Pro Ser Gly Phe Lys Lys Tyr
                805                 810                 815

Asn Asp Tyr Asn Leu Pro Ser Ala Tyr Ala Met Leu Leu Thr Asn Lys
            820                 825                 830

Asp Thr Val Pro Arg Val Tyr Tyr Gly Asp Met Tyr Leu Glu Gly Gly
            835                 840                 845

Gln Tyr Met Glu Lys Gly Thr Ile Tyr Asn Pro Val Ile Ser Ala Leu
    850                 855                 860

Leu Lys Ala Arg Ile Lys Tyr Val Ser Gly Gln Thr Met Ala Thr
865                 870                 875                 880

Asp Ser Ser Gly Lys Asp Leu Lys Asp Gly Glu Thr Asp Leu Leu Thr
                885                 890                 895

Ser Val Arg Phe Gly Lys Gly Ile Met Thr Ser Asp Gln Thr Thr Thr
            900                 905                 910

Gln Asp Asn Ser Gln Asp Tyr Lys Asn Gln Gly Ile Gly Val Ile Val
            915                 920                 925

Gly Asn Asn Pro Asp Leu Lys Leu Asn Asn Asp Lys Thr Ile Thr Leu
930                 935                 940

His Met Gly Lys Ala His Lys Asn Gln Leu Tyr Arg Ala Leu Val Leu
945                 950                 955                 960

Ser Asn Asp Ser Gly Ile Asp Val Tyr Asp Ser Asp Lys Ala Pro
            965                 970                 975

Thr Leu Arg Thr Asn Asp Asn Gly Asp Leu Ile Phe His Lys Thr Asn
            980                 985                 990

Thr Phe Val Lys Gln Asp Gly Thr Ile Ile Asn Tyr Glu Met Lys Gly
            995                 1000                1005

Ser Leu Asn Ala Leu Ile Ser Gly Tyr Leu Gly Val Trp Val Pro
    1010                1015                1020

Val Gly Ala Ser Asp Ser Gln Asp Ala Arg Thr Val Ala Thr Glu
    1025                1030                1035

Ser Ser Ser Ser Asn Asp Gly Ser Val Phe His Ser Asn Ala Ala
    1040                1045                1050

Leu Asp Ser Asn Val Ile Tyr Glu Gly Phe Ser Asn Phe Gln Ala
    1055                1060                1065

Met Pro Thr Ser Pro Glu Gln Ser Thr Asn Val Val Ile Ala Thr
    1070                1075                1080

Lys Ala Asn Leu Phe Lys Glu Leu Gly Ile Thr Ser Phe Glu Leu
    1085                1090                1095

Ala Pro Gln Tyr Arg Ser Ser Gly Asp Thr Asn Tyr Gly Gly Met
    1100                1105                1110

-continued

```
Ser Phe Leu Asp Ser Phe Leu Asn Asn Gly Tyr Ala Phe Thr Asp
1115                1120                1125

Arg Tyr Asp Leu Gly Phe Asn Lys Ala Asp Gly Asn Pro Asn Pro
1130                1135                1140

Thr Lys Tyr Gly Thr Asp Gln Asp Leu Arg Asn Ala Ile Glu Ala
1145                1150                1155

Leu His Lys Asn Gly Met Gln Ala Ile Ala Asp Trp Val Pro Asp
1160                1165                1170

Gln Ile Tyr Ala Leu Pro Gly Lys Glu Val Val Thr Ala Thr Arg
1175                1180                1185

Val Asp Glu Arg Gly Asn Gln Leu Lys Asp Thr Asp Phe Val Asn
1190                1195                1200

Leu Leu Tyr Val Ala Asn Thr Lys Ser Ser Gly Val Asp Tyr Gln
1205                1210                1215

Ala Lys Tyr Gly Gly Glu Phe Leu Asp Lys Leu Arg Glu Glu Tyr
1220                1225                1230

Pro Ser Leu Phe Lys Gln Asn Gln Val Ser Thr Gly Gln Pro Ile
1235                1240                1245

Asp Ala Ser Thr Lys Ile Lys Gln Trp Ser Ala Lys Tyr Met Asn
1250                1255                1260

Gly Thr Asn Ile Leu His Arg Gly Ala Tyr Tyr Val Leu Lys Asp
1265                1270                1275

Trp Ala Thr Asn Gln Tyr Phe Asn Ile Ala Lys Thr Asn Glu Val
1280                1285                1290

Phe Leu Pro Leu Gln Leu Gln Asn Lys Asp Ala Gln Thr Gly Phe
1295                1300                1305

Ile Ser Asp Ala Ser Gly Val Lys Tyr Tyr Ser Ile Ser Gly Tyr
1310                1315                1320

Gln Ala Lys Asp Thr Phe Ile Glu Asp Gly Asn Gly Asn Trp Tyr
1325                1330                1335

Tyr Phe Asp Lys Asp Gly Tyr Met Val Arg Ser Gln Gln Gly Glu
1340                1345                1350

Asn Pro Ile Arg Thr Val Glu Thr Ser Val Asn Thr Arg Asn Gly
1355                1360                1365

Asn Tyr Tyr Phe Met Pro Asn Gly Val Glu Leu Arg Lys Gly Phe
1370                1375                1380

Gly Thr Asp Asn Ser Gly Asn Val Tyr Tyr Phe Asp Asp Gln Gly
1385                1390                1395

Lys Met Val Arg Asp Lys Tyr Ile Asn Asp Asp Ala Asn Asn Phe
1400                1405                1410

Tyr His Leu Asn Val Asp Gly Thr Met Ser Arg Gly Leu Phe Lys
1415                1420                1425

Phe Asp Ser Asp Thr Leu Gln Tyr Phe Ala Ser Asn Gly Val Gln
1430                1435                1440

Ile Lys Asp Ser Tyr Ala Lys Asp Ser Lys Gly Asn Lys Tyr Tyr
1445                1450                1455

Phe Asp Ser Ala Thr Gly Asn Asn Asp Thr Gly Lys Ala Gln Thr
1460                1465                1470

Trp Asp Gly Asn Gly Tyr Tyr Ile Thr Ile Asp Ser Asp Ala Asn
1475                1480                1485

Asn Thr Ile Gly Val Asn Thr Asp Tyr Thr Ala Tyr Ile Thr Ser
1490                1495                1500
```

```
Ser Leu Arg Glu Asp Gly Leu Phe Ala Asn Ala Pro Tyr Gly Val
    1505                1510                1515

Val Thr Lys Asp Gln Asn Gly Asn Asp Leu Lys Trp Gln Tyr Ile
    1520                1525                1530

Asn His Thr Lys Gln Tyr Glu Gly Gln Gln Val Gln Val Thr Arg
    1535                1540                1545

Gln Tyr Thr Asp Ser Lys Gly Val Ser Trp Asn Leu Ile Thr Phe
    1550                1555                1560

Ala Gly Gly Asp Leu Gln Gly Gln Arg Leu Trp Val Asp Ser Arg
    1565                1570                1575

Ala Leu Thr Met Thr Pro Phe Lys Thr Met Asn Gln Ile Ser Phe
    1580                1585                1590

Ile Ser Tyr Ala Asn Arg Asn Asp Gly Leu Phe Leu Asn Ala Pro
    1595                1600                1605

Tyr Gln Val Lys Gly Tyr Gln Leu Ala Gly Met Ser Asn Gln Tyr
    1610                1615                1620

Lys Gly Gln Gln Val Thr Ile Ala Gly Val Ala Asn Val Ser Gly
    1625                1630                1635

Lys Asp Trp Ser Leu Ile Ser Phe Asn Gly Thr Gln Tyr Trp Ile
    1640                1645                1650

Asp Ser Gln Ala Leu Asn Thr Asn Phe Thr His Asp Met Asn Gln
    1655                1660                1665

Lys Val Phe Val Asn Thr Thr Ser Asn Leu Asp Gly Leu Phe Leu
    1670                1675                1680

Asn Ala Pro Tyr Arg Gln Pro Gly Tyr Lys Leu Ala Gly Leu Ala
    1685                1690                1695

Lys Asn Tyr Asn Asn Gln Thr Val Thr Val Ser Gln Gln Tyr Phe
    1700                1705                1710

Asp Asp Gln Gly Thr Val Trp Ser Gln Val Val Leu Gly Gly Gln
    1715                1720                1725

Thr Val Trp Val Asp Asn His Ala Leu Ala Gln Met Gln Val Ser
    1730                1735                1740

Asp Thr Asp Gln Gln Leu Tyr Val Asn Ser Asn Gly Arg Asn Asp
    1745                1750                1755

Gly Leu Phe Leu Asn Ala Pro Tyr Arg Gly Gln Gly Ser Gln Leu
    1760                1765                1770

Ile Gly Met Thr Ala Asp Tyr Asn Gly Gln His Val Gln Val Thr
    1775                1780                1785

Lys Gln Gly Gln Asp Ala Tyr Gly Ala Gln Trp Arg Leu Ile Thr
    1790                1795                1800

Leu Asn Asn Gln Gln Val Trp Val Asp Ser Arg Ala Leu Ser Thr
    1805                1810                1815

Thr Ile Met Gln Ala Met Asn Asp Asn Met Tyr Val Asn Ser Ser
    1820                1825                1830

Gln Arg Thr Asp Gly Leu Trp Leu Asn Ala Pro Tyr Thr Met Ser
    1835                1840                1845

Gly Ala Lys Trp Ala Gly Asp Thr Arg Ser Ala Asn Gly Arg Tyr
    1850                1855                1860

Val His Ile Ser Lys Ala Tyr Ser Asn Glu Val Gly Asn Thr Tyr
    1865                1870                1875

Tyr Leu Thr Asn Leu Asn Gly Gln Ser Thr Trp Ile Asp Lys Arg
    1880                1885                1890
```

| | | | | | | | | | | |
|---|---|---|---|---|---|---|---|---|---|---|
|Ala|Phe|Thr|Val|Thr|Phe|Asp|Gln|Val|Val|Ala|Leu|Asn|Ala|Thr|
| |1895| | | |1900| | | |1905| |

Ile Val Ala Arg Gln Arg Pro Asp Gly Met Phe Lys Thr Ala Pro
   1910                1915                1920

Tyr Gly Glu Ala Gly Ala Gln Phe Val Asp Tyr Val Thr Asn Tyr
   1925                1930                1935

Asn Gln Gln Thr Val Pro Val Thr Lys Gln His Ser Asp Ala Gln
   1940                1945                1950

Gly Asn Gln Trp Tyr Leu Ala Thr Val Asn Gly Thr Gln Tyr Trp
   1955                1960                1965

Ile Asp Gln Arg Ser Phe Ser Pro Val Val Thr Lys Val Val Asp
   1970                1975                1980

Tyr Gln Ala Lys Ile Val Pro Arg Thr Thr Arg Asp Gly Val Phe
   1985                1990                1995

Ser Gly Ala Pro Tyr Gly Glu Val Asn Ala Lys Leu Val Asn Met
   2000                2005                2010

Ala Thr Ala Tyr Gln Asn Gln Val Val His Ala Thr Gly Glu Tyr
   2015                2020                2025

Thr Asn Ala Ser Gly Ile Thr Trp Ser Gln Phe Ala Leu Ser Gly
   2030                2035                2040

Gln Glu Asp Lys Leu Trp Ile Asp Lys Arg Ala Leu Gln Ala
   2045                2050                2055

<210> SEQ ID NO 31
<211> LENGTH: 3870
<212> TYPE: DNA
<213> ORGANISM: Artificial Sequence
<220> FEATURE:
<223> OTHER INFORMATION: Gene - Inactive truncated alternansucrase
     Nucleotide sequence - Full Sequence

<400> SEQUENCE: 31

```
atgaaacaac aagaaacagt tacccgtaaa aaactttata atccggtaaa ggtttgggtt      60
gcagcagcta ctgcatttgc ggtattgggg gtttcaactg taacaacagt ccatgcggat     120
acaaattcga atgtcgctgt taagcaaata aataatacag gaaccaatga ttctggcgaa     180
aaaaaggtac cggttccatc aactaataat gatagtttga agcaaggaac agatggtttt     240
tggtatgatt cagacggcaa tcgtgtcgat cagaagacca atcagattct gcttactgcg     300
gaacaactta aaaaaataa cgaaaaaaat ttatcagtaa tcagtgatga tacatcaaaa     360
aaagatgatg aaaatatttc taagcagacc aaaattgcta atcaacaaac agtagatact     420
gctaaaggcc tgactaccag taatttatct gatcccatca ctgggggtca ctatgaaaat     480
cacaatggct actttgttta tatagatgct tcaggaaaac aagtaacagg tttgcaaaat     540
attgatggta atttacaata ttttgatgac aatggatatc aagtcaaggg atccttccga     600
gatgtcaacg gcaagcatat ctattttgat tcagtaacag ggaaagctag ttcaaatgtt     660
gatattgtta acggtaaagc tcaaggatat gatgcgcaag gcaaccaatt aagaaaagt     720 tatgtcgccg atagttctgg gcaaacttac tattttgatg gtaatggcca accgttaatc     780
ggcttgcaaa caattgatgg gaacctacaa tattttaacc aacaggggt tcaaataaag     840 ggtggtttcc aagatgttaa caataaacgt atttattttg caccaaacac aggtaatgcc     900
gttgccaata ctgaaataat taacggtaaa ttacaggggc gtgacgcaaa tggtaaccag     960
gtaaagaatg catttagtaa agatgttgca ggaaatacat ttatttttga cgcaaacggt    1020
gtgatgttaa cagggttgca aactatttca ggaaagacat attatcttga tgaacaagga    1080
```

```
cacctgagaa aaaattacgc gggaacattc aataatcagt ttatgtactt cgatgctgat   1140
acaggtgcgg gtaaaacagc gattgaatat caatttgatc aaggattggt atcacaaagt   1200
aatgaaaata ctcctcacaa tgccgcaaag tcttatgata aaagtagttt tgaaaatgtt   1260
gatggttact taacagcaga tacatggtat cgtccaaccg atattttaaa aaatggagat   1320
acttggacgg catctaccga aactgatatg cgtccgcttt taatgacatg gtggcctgac   1380
aaacaaacac aagcaaatta cttgaatttt atgtctagta aaggacttgg tataacgacc   1440
acttatacag cagctacgtc acaaaaaaca ctaaatgacg cagcctttgt tattcaaaca   1500
gcaattgaac aacaaatatc tttgaaaaaa agtactgagt ggttacgtga tgcaattgat   1560
agttttgtga agacgcaagc taattggaat aagcaaacag aagatgaagc tttcgatggt   1620
ttgcagtggc ttcaaggggg attcctagct tatcaagatg attcacatcg gacgccgaat   1680
actgattcag gaaataacag aaaactagga cgtcaaccaa ttaatatcga tggttcgaaa   1740
gatacaactg atggtaaagg ctctgaattc ttattagcta acgatattga caactcaaat   1800
ccgattgttc aagctgagca attaaactgg ctacactatt taatgaattt tggtagtatt   1860
acaggtaata atgacaatgc gaattttgat ggcattcgtg tagatgctgt tgataatgtt   1920
gatgctgatt tactaaaaat agctggcgat tattttaaag ctctatatgg tacagataaa   1980
agcgacgcca atgccaataa gcatttgtct attttagaag actggaacgg taaagatcct   2040
cagtatgtta atcaacaggg caatgcgcaa ttaacaatgg attacacagt tacttcacag   2100
tttggcaatt ctctaacaca tggcgccaac aacaggagta acatgtggta tttcttagat   2160
actggctatt atcttaatgg agatcttaat aagaagatag tagataagaa ccgtccaaat   2220
tctggcactt tggttaacag aattgctaat tcaggtgata caaagttat tccaaattat   2280 agttttgtta gagcacatga ttacgatgct caagatccaa ttagaaaagc catgattgat   2340
catggtatta ttaaaaacat gcaggatact ttcacttttg accaactggc tcagggaatg   2400
gaattctact ataaagatca agagaatccg tctggtttca aaaagtataa cgattataac   2460
ttacctagtg cttatgcaat gttgttgact aataaggata ctgtacctcg tgtctattat   2520
ggagatatgt acctcgaagg cgggcaatat atggaaaaag gacgagttta caatcctgtc   2580
atttcagcgt tgctcaaagc tagaataaaa tatgtttctg gtgggcaaac aatggctacc   2640
gatagttctg gaaaagacct taaagatggc gaaactgatt tgttaacaag tgttcgattt   2700
ggtaaaggaa ttatgacatc agatcaaacc acaacacaag acaatagcca agattataaa   2760
aatcaaggca tcggtgtcat tgttggtaat aaccctgacc ttaagttgaa caatgataag   2820
accattacct tgcatatggg aaaggcgcat aagaatcaac tttaccgtgc cttagtatta   2880
tcaaatgact caggaattga tgtttatgat agtgatgata agcaccaac tttgagaaca   2940 aatgacaacg gtgacttgat tttccataag acaaatacgt tgtgaagca agatggaact   3000 attataaatt acgaaatgaa gggatcatta atgctttaa tttcaggtta tttaggtgtc   3060
tgggtgccag ttggagctag tgattcacaa gatgctcgta cagtggcaac tgagtcatca   3120
tcaagtaatg atggttctgt attccattca aatgctgcat tagattctaa tgttatatat   3180
gaaggctttt caaactttca agcgatgccg acttctcctg agcaaagtac aaatgttgtt   3240
attgcaacaa aggctaactt attttaaagaa ttaggtatta ctagttttga gttagcacct   3300
caatataggt ctagtggtga cactaattac ggtggcatgt cattcttaga ttcttctta   3360 aataatggtt atgcatttac cgatagatat gatttaggct ttaacaaagc agacgggaat   3420
cctaacccaa caaagtatgg aacagatcaa gatttacgta atgcaataga ggcattacac   3480
```

```
aaaaacggca tgcaggctat agctgattgg gttcctgacc aaatatatgc tttaccagga    3540
aaggaagttg ttaccgctac tagagtagac gaacggggaa atcaactaaa agacacagat    3600
tttgtcaact tactctatgt tgctaatact aaaagtagtg gtgtggatta tcaggcaaag    3660
tatggcggcg aattttttaga taaattaaga gaagagtacc catcgttatt caaacagaac    3720
caagtatcga caggtcagcc aattgatgct tctacaaaaa ttaagcaatg gtcagctaaa    3780
tatatgaatg ggaccaatat tttacatcga ggtgcttatt atgttttgaa agactgggct    3840
actaaccagt attttaacat tgcaaaaacg                                      3870

<210> SEQ ID NO 32
<211> LENGTH: 1290
<212> TYPE: PRT
<213> ORGANISM: Artificial Sequence
<220> FEATURE:
<223> OTHER INFORMATION: Peptide - Inactive truncated alternansucrase
      amino acid sequence - Full length amino acid sequence

<400> SEQUENCE: 32

Met Lys Gln Gln Glu Thr Val Thr Arg Lys Lys Leu Tyr Lys Ser Gly
1               5                   10                  15

Lys Val Trp Val Ala Ala Ala Thr Ala Phe Ala Val Leu Gly Val Ser
            20                  25                  30

Thr Val Thr Thr Val His Ala Asp Thr Asn Ser Asn Val Ala Val Lys
        35                  40                  45

Gln Ile Asn Asn Thr Gly Thr Asn Asp Ser Gly Glu Lys Lys Val Pro
    50                  55                  60

Val Pro Ser Thr Asn Asn Asp Ser Leu Lys Gln Gly Thr Asp Gly Phe
65                  70                  75                  80

Trp Tyr Asp Ser Asp Gly Asn Arg Val Asp Gln Lys Thr Asn Gln Ile
                85                  90                  95

Leu Leu Thr Ala Glu Gln Leu Lys Lys Asn Asn Glu Lys Asn Leu Ser
            100                 105                 110

Val Ile Ser Asp Asp Thr Ser Lys Lys Asp Asp Glu Asn Ile Ser Lys
        115                 120                 125

Gln Thr Lys Ile Ala Asn Gln Gln Thr Val Asp Thr Ala Lys Gly Leu
    130                 135                 140

Thr Thr Ser Asn Leu Ser Asp Pro Ile Thr Gly Gly His Tyr Glu Asn
145                 150                 155                 160

His Asn Gly Tyr Phe Val Tyr Ile Asp Ala Ser Gly Lys Gln Val Thr
                165                 170                 175

Gly Leu Gln Asn Ile Asp Gly Asn Leu Gln Tyr Phe Asp Asp Asn Gly
            180                 185                 190

Tyr Gln Val Lys Gly Ser Phe Arg Asp Val Asn Gly Lys His Ile Tyr
        195                 200                 205

Phe Asp Ser Val Thr Gly Lys Ala Ser Ser Asn Val Asp Ile Val Asn
    210                 215                 220

Gly Lys Ala Gln Gly Tyr Asp Ala Gln Gly Asn Gln Leu Lys Lys Ser
225                 230                 235                 240

Tyr Val Ala Asp Ser Ser Gly Gln Thr Tyr Tyr Phe Asp Gly Asn Gly
                245                 250                 255

Gln Pro Leu Ile Gly Leu Gln Thr Ile Asp Gly Asn Leu Gln Tyr Phe
            260                 265                 270

Asn Gln Gln Gly Val Gln Ile Lys Gly Gly Phe Gln Asp Val Asn Asn
        275                 280                 285
```

-continued

```
Lys Arg Ile Tyr Phe Ala Pro Asn Thr Gly Asn Ala Val Ala Asn Thr
290                 295                 300
Glu Ile Ile Asn Gly Lys Leu Gln Gly Arg Asp Ala Asn Gly Asn Gln
305                 310                 315                 320
Val Lys Asn Ala Phe Ser Lys Asp Val Ala Gly Asn Thr Phe Tyr Phe
                325                 330                 335
Asp Ala Asn Gly Val Met Leu Thr Gly Leu Gln Thr Ile Ser Gly Lys
            340                 345                 350
Thr Tyr Tyr Leu Asp Glu Gln Gly His Leu Arg Lys Asn Tyr Ala Gly
        355                 360                 365
Thr Phe Asn Asn Gln Phe Met Tyr Phe Asp Ala Asp Thr Gly Ala Gly
370                 375                 380
Lys Thr Ala Ile Glu Tyr Gln Phe Asp Gln Gly Leu Val Ser Gln Ser
385                 390                 395                 400
Asn Glu Asn Thr Pro His Asn Ala Ala Lys Ser Tyr Asp Lys Ser Ser
                405                 410                 415
Phe Glu Asn Val Asp Gly Tyr Leu Thr Ala Asp Thr Trp Tyr Arg Pro
            420                 425                 430
Thr Asp Ile Leu Lys Asn Gly Asp Thr Trp Thr Ala Ser Thr Glu Thr
        435                 440                 445
Asp Met Arg Pro Leu Leu Met Thr Trp Trp Pro Asp Lys Gln Thr Gln
450                 455                 460
Ala Asn Tyr Leu Asn Phe Met Ser Ser Lys Gly Leu Gly Ile Thr Thr
465                 470                 475                 480
Thr Tyr Thr Ala Ala Thr Ser Gln Lys Thr Leu Asn Asp Ala Ala Phe
                485                 490                 495
Val Ile Gln Thr Ala Ile Glu Gln Ile Ser Leu Lys Lys Ser Thr
            500                 505                 510
Glu Trp Leu Arg Asp Ala Ile Asp Ser Phe Val Lys Thr Gln Ala Asn
        515                 520                 525
Trp Asn Lys Gln Thr Glu Asp Glu Ala Phe Asp Gly Leu Gln Trp Leu
530                 535                 540
Gln Gly Gly Phe Leu Ala Tyr Gln Asp Asp Ser His Arg Thr Pro Asn
545                 550                 555                 560
Thr Asp Ser Gly Asn Asn Arg Lys Leu Gly Arg Gln Pro Ile Asn Ile
                565                 570                 575
Asp Gly Ser Lys Asp Thr Thr Asp Gly Lys Gly Ser Glu Phe Leu Leu
            580                 585                 590
Ala Asn Asp Ile Asp Asn Ser Asn Pro Ile Val Gln Ala Glu Gln Leu
        595                 600                 605
Asn Trp Leu His Tyr Leu Met Asn Phe Gly Ser Ile Thr Gly Asn Asn
610                 615                 620
Asp Asn Ala Asn Phe Asp Gly Ile Arg Val Asp Ala Val Asp Asn Val
625                 630                 635                 640
Asp Ala Asp Leu Leu Lys Ile Ala Gly Asp Tyr Phe Lys Ala Leu Tyr
                645                 650                 655
Gly Thr Asp Lys Ser Asp Ala Asn Ala Asn Lys His Leu Ser Ile Leu
            660                 665                 670
Glu Asp Trp Asn Gly Lys Asp Pro Gln Tyr Val Asn Gln Gln Gly Asn
        675                 680                 685
Ala Gln Leu Thr Met Asp Tyr Val Thr Ser Gln Phe Gly Asn Ser
690                 695                 700
```

```
Leu Thr His Gly Ala Asn Asn Arg Ser Asn Met Trp Tyr Phe Leu Asp
705                 710                 715                 720

Thr Gly Tyr Tyr Leu Asn Gly Asp Leu Asn Lys Lys Ile Val Asp Lys
            725                 730                 735

Asn Arg Pro Asn Ser Gly Thr Leu Val Asn Arg Ile Ala Asn Ser Gly
        740                 745                 750

Asp Thr Lys Val Ile Pro Asn Tyr Ser Phe Val Arg Ala His Asp Tyr
    755                 760                 765

Asp Ala Gln Asp Pro Ile Arg Lys Ala Met Ile Asp His Gly Ile Ile
770                 775                 780

Lys Asn Met Gln Asp Thr Phe Thr Phe Asp Gln Leu Ala Gln Gly Met
785                 790                 795                 800

Glu Phe Tyr Tyr Lys Asp Gln Glu Asn Pro Ser Gly Phe Lys Lys Tyr
            805                 810                 815

Asn Asp Tyr Asn Leu Pro Ser Ala Tyr Ala Met Leu Leu Thr Asn Lys
        820                 825                 830

Asp Thr Val Pro Arg Val Tyr Tyr Gly Asp Met Tyr Leu Glu Gly Gly
    835                 840                 845

Gln Tyr Met Glu Lys Gly Thr Ile Tyr Asn Pro Val Ile Ser Ala Leu
850                 855                 860

Leu Lys Ala Arg Ile Lys Tyr Val Ser Gly Gly Gln Thr Met Ala Thr
865                 870                 875                 880

Asp Ser Ser Gly Lys Asp Leu Lys Asp Gly Glu Thr Asp Leu Leu Thr
            885                 890                 895

Ser Val Arg Phe Gly Lys Gly Ile Met Thr Ser Asp Gln Thr Thr Thr
        900                 905                 910

Gln Asp Asn Ser Gln Asp Tyr Lys Asn Gln Gly Ile Gly Val Ile Val
    915                 920                 925

Gly Asn Asn Pro Asp Leu Lys Leu Asn Asn Asp Lys Thr Ile Thr Leu
930                 935                 940

His Met Gly Lys Ala His Lys Asn Gln Leu Tyr Arg Ala Leu Val Leu
945                 950                 955                 960

Ser Asn Asp Ser Gly Ile Asp Val Tyr Asp Ser Asp Lys Ala Pro
            965                 970                 975

Thr Leu Arg Thr Asn Asp Asn Gly Asp Leu Ile Phe His Lys Thr Asn
        980                 985                 990

Thr Phe Val Lys Gln Asp Gly Thr Ile Ile Asn Tyr Glu Met Lys Gly
    995                 1000                1005

Ser Leu Asn Ala Leu Ile Ser Gly Tyr Leu Gly Val Trp Val Pro
    1010                1015                1020

Val Gly Ala Ser Asp Ser Gln Asp Ala Arg Thr Val Ala Thr Glu
    1025                1030                1035

Ser Ser Ser Ser Asn Asp Gly Ser Val Phe His Ser Asn Ala Ala
    1040                1045                1050

Leu Asp Ser Asn Val Ile Tyr Glu Gly Phe Ser Asn Phe Gln Ala
    1055                1060                1065

Met Pro Thr Ser Pro Glu Gln Ser Thr Asn Val Val Ile Ala Thr
    1070                1075                1080

Lys Ala Asn Leu Phe Lys Glu Leu Gly Ile Thr Ser Phe Glu Leu
    1085                1090                1095

Ala Pro Gln Tyr Arg Ser Ser Gly Asp Thr Asn Tyr Gly Gly Met
    1100                1105                1110
```

```
Ser Phe Leu Asp Ser Phe Leu Asn Asn Gly Tyr Ala Phe Thr Asp
    1115                1120                1125

Arg Tyr Asp Leu Gly Phe Asn Lys Ala Asp Gly Asn Pro Asn Pro
    1130                1135                1140

Thr Lys Tyr Gly Thr Asp Gln Asp Leu Arg Asn Ala Ile Glu Ala
    1145                1150                1155

Leu His Lys Asn Gly Met Gln Ala Ile Ala Asp Trp Val Pro Asp
    1160                1165                1170

Gln Ile Tyr Ala Leu Pro Gly Lys Glu Val Val Thr Ala Thr Arg
    1175                1180                1185

Val Asp Glu Arg Gly Asn Gln Leu Lys Asp Thr Asp Phe Val Asn
    1190                1195                1200

Leu Leu Tyr Val Ala Asn Thr Lys Ser Ser Gly Val Asp Tyr Gln
    1205                1210                1215

Ala Lys Tyr Gly Gly Glu Phe Leu Asp Lys Leu Arg Glu Glu Tyr
    1220                1225                1230

Pro Ser Leu Phe Lys Gln Asn Gln Val Ser Thr Gly Gln Pro Ile
    1235                1240                1245

Asp Ala Ser Thr Lys Ile Lys Gln Trp Ser Ala Lys Tyr Met Asn
    1250                1255                1260

Gly Thr Asn Ile Leu His Arg Gly Ala Tyr Tyr Val Leu Lys Asp
    1265                1270                1275

Trp Ala Thr Asn Gln Tyr Phe Asn Ile Ala Lys Thr
    1280                1285                1290

<210> SEQ ID NO 33
<211> LENGTH: 2847
<212> TYPE: DNA
<213> ORGANISM: Artificial Sequence
<220> FEATURE:
<223> OTHER INFORMATION: Gene - Inactive truncated alternansucrase
      nucleotide sequence - Full sequence

<400> SEQUENCE: 33
atgttaacag ggttgcaaac tatttcagga aagacatatt atcttgatga acaaggacac      60
ctgagaaaaa attacgcggg aacattcaat aatcagttta tgtacttcga tgctgataca     120
ggtgcgggta aaacagcgat tgaatatcaa tttgatcaag gattggtatc acaaagtaat     180
gaaaatactc ctcacaatgc cgcaaagtct tatgataaaa gtagttttga aaatgttgat     240
ggttacttaa cagcagatac atggtatcgt ccaaccgata ttttaaaaaa tggagatact     300
tggacggcat ctaccgaaac tgatatgcgt ccgcttttaa tgacatggtg gcctgacaaa     360
caaacacaag caaattactt gaatttttatg tctagtaaag gacttggtat aacgaccact     420
tatacagcag ctacgtcaca aaaaacacta atgacgcag cctttgttat tcaaacagca     480
attgaacaac aaatatcttt gaaaaaaagt actgagtggt acgtgatgc aattgatagt     540 tttgtgaaga cgcaagctaa ttggaataag caaacagaag atgaagcttt cgatggtttg     600
cagtggcttc aagggggatt cctagcttat caagatgatt cacatcggac gccgaatact     660
gattcaggaa ataacagaaa actaggacgt caaccaatta atatcgatgg ttcgaaagat     720
acaactgatg gtaaaggctc tgaattctta ttagctaacg atattgacaa ctcaaatccg     780
attgttcaag ctgagcaatt aaactggcta cactatttaa tgaattttgg tagtattaca     840
ggtaataatg acaatgcgaa ttttgatggc attcgtgtag atgctgttga taatgttgat     900
```

-continued

```
gctgatttac taaaaatagc tggcgattat tttaaagctc tatatggtac agataaaagc    960
gacgccaatg ccaataagca tttgtctatt ttagaagact ggaacggtaa agatcctcag   1020
tatgttaatc aacagggcaa tgcgcaatta acaatggatt acacagttac ttcacagttt   1080
ggcaattctc taacacatgg cgccaacaac aggagtaaca tgtggtattt cttagatact   1140
ggctattatc ttaatggaga tcttaataag aagatagtag ataagaaccg tccaaattct   1200
ggcactttgg ttaacagaat tgctaattca ggtgatacaa agttattcc aaattatagt    1260
tttgttagag cacatgatta cgatgctcaa gatccaatta aaaagccat gattgatcat    1320
ggtattatta aaacatgca ggatactttc acttttgacc aactggctca gggaatggaa    1380
ttctactata agatcaaga gaatccgtct ggtttcaaaa agtataacga ttataactta    1440
cctagtgctt atgcaatgtt gttgactaat aaggatactg tacctcgtgt ctattatgga   1500
gatatgtacc tcgaaggcgg gcaatatatg gaaaaaggga cgatttacaa tcctgtcatt   1560
tcagcgttgc tcaaagctag aataaaatat gtttctggtg gcaaacaat ggctaccgat    1620
agttctggaa aagaccttaa agatggcgaa actgatttgt taacaagtgt tcgatttggt   1680
aaaggaatta tgacatcaga tcaaaccaca acacaagaca atagccaaga ttataaaaat   1740
caaggcatcg gtgtcattgt tggtaataac cctgacctta gttgaacaa tgataagacc    1800
attaccttgc atatgggaaa ggcgcataag aatcaacttt accgtgcctt agtattatca   1860
aatgactcag gaattgatgt ttatgatagt gatgataaag caccaacttt gagaacaaat   1920
gacaacggtg acttgatttt ccataagaca aatacgtttg tgaagcaaga tggaactatt   1980
ataaattacg aaatgaaggg atcattaaat gctttaattt caggttattt aggtgtctgg   2040
gtgccagttg gagctagtga ttcacaagat gctcgtacag tggcaactga gtcatcatca   2100
agtaatgatg gttctgtatt ccattcaaat gctgcattag attctaatgt tatatatgaa   2160
ggcttttcaa actttcaagc gatgccgact tctcctgagc aaagtacaaa tgttgttatt   2220
gcaacaaagg ctaacttatt taagaatta ggtattacta gttttgagtt agcacctcaa    2280
tataggtcta gtggtgacac taattacggt ggcatgtcat tcttagattc tttcttaaat   2340
aatggttatg catttaccga tagatatgat ttaggctttta acaaagcaga cgggaatcct   2400
aacccaacaa agtatggaac agatcaagat ttacgtaatg caatagaggc attacacaaa   2460
aacggcatgc aggctatagc tgattgggtt cctgaccaaa tatatgcttt accaggaaag   2520
gaagttgtta ccgctactag agtagacgaa cggggaaatc aactaaaaga cacagattt    2580
gtcaacttac tctatgttgc taatactaaa agtagtggtg tggattatca ggcaaagtat   2640
ggcggcgaat tttagataa attaagagaa gagtacccat cgttattcaa acagaaccaa   2700
gtatcgacag gtcagccaat tgatgcttct acaaaaatta gcaatggtc agctaaatat   2760
atgaatggga ccaatatttt acatcgaggt gcttattatg ttttgaaaga ctgggctact   2820
aaccagtatt ttaacattgc aaaaacg                                       2847
```

<210> SEQ ID NO 34
<211> LENGTH: 949
<212> TYPE: PRT
<213> ORGANISM: Artificial Sequence
<220> FEATURE:
<223> OTHER INFORMATION: Peptide - Inactive truncated alternansucrase
    amino acid sequence - Full amino acid sequence -continued

```
<400> SEQUENCE: 34

Met Leu Thr Gly Leu Gln Thr Ile Ser Gly Lys Thr Tyr Tyr Leu Asp
1               5                   10                  15

Glu Gln Gly His Leu Arg Lys Asn Tyr Ala Gly Thr Phe Asn Asn Gln
            20                  25                  30

Phe Met Tyr Phe Asp Ala Asp Thr Gly Ala Gly Lys Thr Ala Ile Glu
        35                  40                  45

Tyr Gln Phe Asp Gln Gly Leu Val Ser Gln Ser Asn Glu Asn Thr Pro
    50                  55                  60

His Asn Ala Ala Lys Ser Tyr Asp Lys Ser Ser Phe Glu Asn Val Asp
65                  70                  75                  80

Gly Tyr Leu Thr Ala Asp Thr Trp Tyr Arg Pro Thr Asp Ile Leu Lys
                85                  90                  95

Asn Gly Asp Thr Trp Thr Ala Ser Thr Glu Thr Asp Met Arg Pro Leu
            100                 105                 110

Leu Met Thr Trp Trp Pro Asp Lys Gln Thr Gln Ala Asn Tyr Leu Asn
        115                 120                 125

Phe Met Ser Ser Lys Gly Leu Gly Ile Thr Thr Thr Tyr Thr Ala Ala
    130                 135                 140

Thr Ser Gln Lys Thr Leu Asn Asp Ala Ala Phe Val Ile Gln Thr Ala
145                 150                 155                 160

Ile Glu Gln Gln Ile Ser Leu Lys Lys Ser Thr Glu Trp Leu Arg Asp
                165                 170                 175

Ala Ile Asp Ser Phe Val Lys Thr Gln Ala Asn Trp Asn Lys Gln Thr
            180                 185                 190

Glu Asp Glu Ala Phe Asp Gly Leu Gln Trp Leu Gln Gly Gly Phe Leu
        195                 200                 205

Ala Tyr Gln Asp Asp Ser His Arg Thr Pro Asn Thr Asp Ser Gly Asn
    210                 215                 220

Asn Arg Lys Leu Gly Arg Gln Pro Ile Asn Ile Asp Gly Ser Lys Asp
225                 230                 235                 240

Thr Thr Asp Gly Lys Gly Ser Glu Phe Leu Leu Ala Asn Asp Ile Asp
                245                 250                 255

Asn Ser Asn Pro Ile Val Gln Ala Glu Gln Leu Asn Trp Leu His Tyr
            260                 265                 270

Leu Met Asn Phe Gly Ser Ile Thr Gly Asn Asn Asp Asn Ala Asn Phe
        275                 280                 285

Asp Gly Ile Arg Val Asp Ala Val Asp Asn Val Asp Ala Asp Leu Leu
    290                 295                 300

Lys Ile Ala Gly Asp Tyr Phe Lys Ala Leu Tyr Gly Thr Asp Lys Ser
305                 310                 315                 320

Asp Ala Asn Ala Asn Lys His Leu Ser Ile Leu Glu Asp Trp Asn Gly
                325                 330                 335

Lys Asp Pro Gln Tyr Val Asn Gln Gln Gly Asn Ala Gln Leu Thr Met
            340                 345                 350

Asp Tyr Thr Val Thr Ser Gln Phe Gly Asn Ser Leu Thr His Gly Ala
        355                 360                 365

Asn Asn Arg Ser Asn Met Trp Tyr Phe Leu Asp Thr Gly Tyr Tyr Leu
    370                 375                 380

Asn Gly Asp Leu Asn Lys Lys Ile Val Asp Lys Asn Arg Pro Asn Ser
385                 390                 395                 400

Gly Thr Leu Val Asn Arg Ile Ala Asn Ser Gly Asp Thr Lys Val Ile
                405                 410                 415
```

-continued

```
Pro Asn Tyr Ser Phe Val Arg Ala His Asp Tyr Asp Ala Gln Asp Pro
            420                 425                 430

Ile Arg Lys Ala Met Ile Asp His Gly Ile Ile Lys Asn Met Gln Asp
            435                 440                 445

Thr Phe Thr Phe Asp Gln Leu Ala Gln Gly Met Glu Phe Tyr Tyr Lys
        450                 455                 460

Asp Gln Glu Asn Pro Ser Gly Phe Lys Tyr Asn Asp Tyr Asn Leu
465                 470                 475                 480

Pro Ser Ala Tyr Ala Met Leu Leu Thr Asn Lys Asp Thr Val Pro Arg
                485                 490                 495

Val Tyr Tyr Gly Asp Met Tyr Leu Glu Gly Gln Tyr Met Glu Lys
            500                 505                 510

Gly Thr Ile Tyr Asn Pro Val Ile Ser Ala Leu Leu Lys Ala Arg Ile
            515                 520                 525

Lys Tyr Val Ser Gly Gln Thr Met Ala Thr Asp Ser Ser Gly Lys
            530                 535                 540

Asp Leu Lys Asp Gly Glu Thr Asp Leu Leu Thr Ser Val Arg Phe Gly
545                 550                 555                 560

Lys Gly Ile Met Thr Ser Asp Gln Thr Thr Gln Asp Asn Ser Gln
                565                 570                 575

Asp Tyr Lys Asn Gln Gly Ile Gly Val Ile Gly Asn Asn Pro Asp
            580                 585                 590

Leu Lys Leu Asn Asn Asp Lys Thr Ile Thr Leu His Met Gly Lys Ala
            595                 600                 605

His Lys Asn Gln Leu Tyr Arg Ala Leu Val Leu Ser Asn Asp Ser Gly
            610                 615                 620

Ile Asp Val Tyr Asp Ser Asp Lys Ala Pro Thr Leu Arg Thr Asn
625                 630                 635                 640

Asp Asn Gly Asp Leu Ile Phe His Lys Thr Asn Thr Phe Val Lys Gln
                645                 650                 655

Asp Gly Thr Ile Ile Asn Tyr Glu Met Lys Gly Ser Leu Asn Ala Leu
            660                 665                 670

Ile Ser Gly Tyr Leu Gly Val Trp Val Pro Val Gly Ala Ser Asp Ser
            675                 680                 685

Gln Asp Ala Arg Thr Val Ala Thr Glu Ser Ser Ser Asn Asp Gly
            690                 695                 700

Ser Val Phe His Ser Asn Ala Ala Leu Asp Ser Asn Val Ile Tyr Glu
705                 710                 715                 720

Gly Phe Ser Asn Phe Gln Ala Met Pro Thr Ser Pro Glu Gln Ser Thr
                725                 730                 735

Asn Val Val Ile Ala Thr Lys Ala Asn Leu Phe Lys Glu Leu Gly Ile
            740                 745                 750

Thr Ser Phe Glu Leu Ala Pro Gln Tyr Arg Ser Ser Gly Asp Thr Asn
            755                 760                 765

Tyr Gly Gly Met Ser Phe Leu Asp Ser Phe Leu Asn Asn Gly Tyr Ala
            770                 775                 780

Phe Thr Asp Arg Tyr Asp Leu Gly Phe Asn Lys Ala Asp Gly Asn Pro
785                 790                 795                 800

Asn Pro Thr Lys Tyr Gly Thr Asp Gln Asp Leu Arg Asn Ala Ile Glu
                805                 810                 815

Ala Leu His Lys Asn Gly Met Gln Ala Ile Ala Asp Trp Val Pro Asp
            820                 825                 830
```

-continued

```
Gln Ile Tyr Ala Leu Pro Gly Lys Glu Val Thr Ala Thr Arg Val
        835                 840                 845

Asp Glu Arg Gly Asn Gln Leu Lys Asp Thr Asp Phe Val Asn Leu Leu
850                 855                 860

Tyr Val Ala Asn Thr Lys Ser Ser Gly Val Asp Tyr Gln Ala Lys Tyr
865                 870                 875                 880

Gly Gly Glu Phe Leu Asp Lys Leu Arg Glu Glu Tyr Pro Ser Leu Phe
                885                 890                 895

Lys Gln Asn Gln Val Ser Thr Gly Gln Pro Ile Asp Ala Ser Thr Lys
                900                 905                 910

Ile Lys Gln Trp Ser Ala Lys Tyr Met Asn Gly Thr Asn Ile Leu His
        915                 920                 925

Arg Gly Ala Tyr Tyr Val Leu Lys Asp Trp Ala Thr Asn Gln Tyr Phe
930                 935                 940

Asn Ile Ala Lys Thr
945

<210> SEQ ID NO 35
<211> LENGTH: 30
<212> TYPE: DNA
<213> ORGANISM: Artificial Sequence
<220> FEATURE:
<223> OTHER INFORMATION: Primers

<400> SEQUENCE: 35
gccatggaac aacaagaaac agttacccgt                                       30

<210> SEQ ID NO 36
<211> LENGTH: 31
<212> TYPE: DNA
<213> ORGANISM: Artificial Sequence
<220> FEATURE:
<223> OTHER INFORMATION: Primers

<400> SEQUENCE: 36
agcttgcaaa gcacgcttat caatccatag c                                     31

<210> SEQ ID NO 37
<211> LENGTH: 33
<212> TYPE: DNA
<213> ORGANISM: Artificial Sequence
<220> FEATURE:
<223> OTHER INFORMATION: Primers

<400> SEQUENCE: 37
gccatggtaa cagggttgca aactatttca gga                                   33

<210> SEQ ID NO 38
<211> LENGTH: 36
<212> TYPE: DNA
<213> ORGANISM: Artificial Sequence
<220> FEATURE:
<223> OTHER INFORMATION: Primers

<400> SEQUENCE: 38 cgttttttgca atgttaaaat actggttagt agccca                               36

<210> SEQ ID NO 39
<211> LENGTH: 26
<212> TYPE: DNA
<213> ORGANISM: Artificial Sequence
<220> FEATURE:
<223> OTHER INFORMATION: Primers
```

```
<400> SEQUENCE: 39
atgaaacaac aagaaacagt tacccg                                              26

<210> SEQ ID NO 40
<211> LENGTH: 26
<212> TYPE: DNA
<213> ORGANISM: Artificial Sequence
<220> FEATURE:
<223> OTHER INFORMATION: Primers

<400> SEQUENCE: 40
cctcgagaca tagtcccatc aacatt                                              26

<210> SEQ ID NO 41
<211> LENGTH: 33
<212> TYPE: DNA
<213> ORGANISM: Artificial Sequence
<220> FEATURE:
<223> OTHER INFORMATION: Primers

<400> SEQUENCE: 41
ccctcgagac atagtcccat caacatttaa gtg                                      33

<210> SEQ ID NO 42
<211> LENGTH: 29
<212> TYPE: DNA
<213> ORGANISM: Artificial Sequence
<220> FEATURE:
<223> OTHER INFORMATION: Primers

<400> SEQUENCE: 42
ggaaataaca gaaaactagg acgtcaacc                                           29

<210> SEQ ID NO 43
<211> LENGTH: 31
<212> TYPE: DNA
<213> ORGANISM: Artificial Sequence
<220> FEATURE:
<223> OTHER INFORMATION: Primers

<400> SEQUENCE: 43
caaatttaaa tagtcctcga gacatagtcc c                                        31

<210> SEQ ID NO 44
<211> LENGTH: 27
<212> TYPE: DNA
<213> ORGANISM: Artificial Sequence
<220> FEATURE:
<223> OTHER INFORMATION: Primers

<400> SEQUENCE: 44
ctgaggatcg tttccggacc agtcttc                                             27

<210> SEQ ID NO 45
<211> LENGTH: 32
<212> TYPE: DNA
<213> ORGANISM: Artificial Sequence
<220> FEATURE:
<223> OTHER INFORMATION: Primers

<400> SEQUENCE: 45
ctaattggat cctgaacttc ggaatcatgt gc                                       32
```

```
<210> SEQ ID NO 46
<211> LENGTH: 37
<212> TYPE: DNA
<213> ORGANISM: Artificial Sequence
<220> FEATURE:
<223> OTHER INFORMATION: Primers

<400> SEQUENCE: 46
cactaattcc ggagacactt cattcttaga ttctttc                              37

<210> SEQ ID NO 47
<211> LENGTH: 37
<212> TYPE: DNA
<213> ORGANISM: Artificial Sequence
<220> FEATURE:
<223> OTHER INFORMATION: Primers

<400> SEQUENCE: 47
tagtgtctcc ggaagaccta tattgaggtg ctaactc                              37

<210> SEQ ID NO 48
<211> LENGTH: 37
<212> TYPE: DNA
<213> ORGANISM: Artificial Sequence
<220> FEATURE:
<223> OTHER INFORMATION: Primers

<400> SEQUENCE: 48
aatggttatg cggccgcttc ttcatggtat cgccta                               37

<210> SEQ ID NO 49
<211> LENGTH: 33
<212> TYPE: DNA
<213> ORGANISM: Artificial Sequence
<220> FEATURE:
<223> OTHER INFORMATION: Primers

<400> SEQUENCE: 49
ctttaatggc tcaaatactc gaggcaaagg ggc                                  33

<210> SEQ ID NO 50
<211> LENGTH: 37
<212> TYPE: DNA
<213> ORGANISM: Artificial Sequence
<220> FEATURE:
<223> OTHER INFORMATION: Primers

<400> SEQUENCE: 50
gatggttacg cggccgctaa cagttggtat cgtccta                              37

<210> SEQ ID NO 51
<211> LENGTH: 40
<212> TYPE: DNA
<213> ORGANISM: Artificial Sequence
<220> FEATURE:
<223> OTHER INFORMATION: Primers

<400> SEQUENCE: 51
aatggttcaa acactcgagg tcgtggcgct tggtatgtac                           40

<210> SEQ ID NO 52
<211> LENGTH: 36
<212> TYPE: DNA
<213> ORGANISM: Artificial Sequence
<220> FEATURE:
<223> OTHER INFORMATION: Primers
```

```
<400> SEQUENCE: 52
acggctatgc ggccgctagt tcatggtatc gtccaa                                    36

<210> SEQ ID NO 53
<211> LENGTH: 40
<212> TYPE: DNA
<213> ORGANISM: Artificial Sequence
<220> FEATURE:
<223> OTHER INFORMATION: Primers

<400> SEQUENCE: 53
tggctctaac actccaggta aggtgctgg atacgtattg                                 40

<210> SEQ ID NO 54
<211> LENGTH: 29
<212> TYPE: DNA
<213> ORGANISM: Artificial Sequence
<220> FEATURE:
<223> OTHER INFORMATION: Primers

<400> SEQUENCE: 54
ggaaataaca gaaaactagg acgtcaacc                                            29

<210> SEQ ID NO 55
<211> LENGTH: 31
<212> TYPE: DNA
<213> ORGANISM: Artificial Sequence
<220> FEATURE:
<223> OTHER INFORMATION: Primers

<400> SEQUENCE: 55
caaatttaaa tagtcctcga gacatagtcc c                                         31

<210> SEQ ID NO 56
<211> LENGTH: 21
<212> TYPE: PRT
<213> ORGANISM: Artificial Sequence
<220> FEATURE:
<223> OTHER INFORMATION: Peptide - CW repeats of alternansucrase amino
      acid sequence - Amino Acids 168 to 188

<400> SEQUENCE: 56

Ile Asp Ala Ser Gly Lys Gln Val Thr Gly Leu Gln Asn Ile Asp Gly
1               5                   10                  15

Asn Leu Gln Tyr Phe
            20

<210> SEQ ID NO 57
<211> LENGTH: 21
<212> TYPE: PRT
<213> ORGANISM: Artificial Sequence
<220> FEATURE:
<223> OTHER INFORMATION: Peptide - CW repeats of alternansucrase amino
      acid sequence - Amino Acids 189 to 209

<400> SEQUENCE: 57

Asp Asp Asn Gly Tyr Gln Val Lys Gly Ser Phe Arg Asp Val Asn Gly
1               5                   10                  15

Lys His Ile Tyr Phe
            20

<210> SEQ ID NO 58
<211> LENGTH: 21
<212> TYPE: PRT
<213> ORGANISM: Artificial Sequence
```

```
<220> FEATURE:
<223> OTHER INFORMATION: Peptide - CW repeats of alternansucrase amino
      acid sequence - Amino Acids 210 to 230

<400> SEQUENCE: 58

Asp Ser Val Thr Gly Lys Ala Ser Ser Asn Val Asp Ile Val Asn Gly
1               5                   10                  15

Lys Ala Gln Gly Tyr
            20

<210> SEQ ID NO 59
<211> LENGTH: 22
<212> TYPE: PRT
<213> ORGANISM: Artificial Sequence
<220> FEATURE:
<223> OTHER INFORMATION: Peptide - CW repeats of alternansucrase amino
      acid sequence - Amino Acids 231 to 252

<400> SEQUENCE: 59

Asp Ala Gln Gly Asn Gln Leu Lys Lys Ser Tyr Val Ala Asp Ser Ser
1               5                   10                  15

Gly Gln Thr Tyr Tyr Phe
            20

<210> SEQ ID NO 60
<211> LENGTH: 20
<212> TYPE: PRT
<213> ORGANISM: Artificial Sequence
<220> FEATURE:
<223> OTHER INFORMATION: Peptide - CW repeats of alternansucrase amino
      acid sequence - Amino Acids 253 to 272

<400> SEQUENCE: 60

Asp Gly Asn Gly Gln Pro Leu Ile Gly Leu Gln Thr Ile Asp Gly Asn
1               5                   10                  15

Leu Gln Tyr Phe
            20

<210> SEQ ID NO 61
<211> LENGTH: 21
<212> TYPE: PRT
<213> ORGANISM: Artificial Sequence
<220> FEATURE:
<223> OTHER INFORMATION: Peptide - CW repeats of alternansucrase amino
      acid sequence - Amino Acids 273 to 293

<400> SEQUENCE: 61

Asn Gln Gln Gly Val Gln Ile Lys Gly Gly Phe Gln Asp Val Asn Asn
1               5                   10                  15

Lys Arg Ile Tyr Phe
            20

<210> SEQ ID NO 62
<211> LENGTH: 21
<212> TYPE: PRT
<213> ORGANISM: Artificial Sequence
<220> FEATURE:
<223> OTHER INFORMATION: Peptide - CW repeats of alternansucrase amino
      acid sequence - Amino Acids 294 to 314

<400> SEQUENCE: 62

Ala Pro Asn Thr Gly Asn Ala Val Ala Asn Thr Glu Ile Ile Asn Gly
1               5                   10                  15

Lys Leu Gln Gly Arg
            20
```

```
<210> SEQ ID NO 63
<211> LENGTH: 22
<212> TYPE: PRT
<213> ORGANISM: Artificial Sequence
<220> FEATURE:
<223> OTHER INFORMATION: Peptide - CW repeats of alternansucrase amino
      acid sequence - Amino Acids 315 to 336

<400> SEQUENCE: 63

Asp Ala Asn Gly Asn Gln Val Lys Asn Ala Phe Ser Lys Asp Val Ala
1               5                   10                  15

Gly Asn Thr Phe Tyr Phe
            20

<210> SEQ ID NO 64
<211> LENGTH: 20
<212> TYPE: PRT
<213> ORGANISM: Artificial Sequence
<220> FEATURE:
<223> OTHER INFORMATION: Peptide - CW repeats of alternansucrase amino
      acid sequence - Amino Acids 337 to 356

<400> SEQUENCE: 64

Asp Ala Asn Gly Val Met Leu Thr Gly Leu Gln Thr Ile Ser Gly Lys
1               5                   10                  15

Thr Tyr Tyr Leu
            20

<210> SEQ ID NO 65
<211> LENGTH: 21
<212> TYPE: PRT
<213> ORGANISM: Artificial Sequence
<220> FEATURE:
<223> OTHER INFORMATION: Peptide - CW repeats of alternansucrase amino
      acid sequence - Amino Acids 357 to 377

<400> SEQUENCE: 65

Asp Glu Gln Gly His Leu Arg Lys Asn Tyr Ala Gly Thr Phe Asn Asn
1               5                   10                  15

Gln Phe Met Tyr Phe
            20

<210> SEQ ID NO 66
<211> LENGTH: 29
<212> TYPE: PRT
<213> ORGANISM: Artificial Sequence
<220> FEATURE:
<223> OTHER INFORMATION: Peptide - CW repeats of alternansucrase amino
      acid sequence - Amino Acids 1290 to 1318

<400> SEQUENCE: 66

Thr Asn Glu Val Phe Leu Pro Leu Gln Leu Gln Asn Lys Asp Ala Gln
1               5                   10                  15

Thr Gly Phe Ile Ser Asp Ala Ser Gly Val Lys Tyr Tyr
            20                  25

<210> SEQ ID NO 67
<211> LENGTH: 22
<212> TYPE: PRT
<213> ORGANISM: Artificial Sequence
<220> FEATURE:
<223> OTHER INFORMATION: Peptide - CW repeats of alternansucrase amino
      acid sequence - Amino Acids 1319 to 1340
```

```
<400> SEQUENCE: 67

Ser Ile Ser Gly Tyr Gln Ala Lys Asp Thr Phe Ile Glu Asp Gly Asn
1               5                   10                  15

Gly Asn Trp Tyr Tyr Phe
            20

<210> SEQ ID NO 68
<211> LENGTH: 32
<212> TYPE: PRT
<213> ORGANISM: Artificial Sequence
<220> FEATURE:
<223> OTHER INFORMATION: Peptide - CW repeats of alternansucrase amino
      acid sequence - Amino Acids 1341 to 1372

<400> SEQUENCE: 68

Asp Lys Asp Gly Tyr Met Val Arg Ser Gln Gln Gly Glu Asn Pro Ile
1               5                   10                  15

Arg Thr Val Glu Thr Ser Val Asn Thr Arg Asn Gly Asn Tyr Tyr Phe
            20                  25                  30

<210> SEQ ID NO 69
<211> LENGTH: 22
<212> TYPE: PRT
<213> ORGANISM: Artificial Sequence
<220> FEATURE:
<223> OTHER INFORMATION: Peptide - CW repeats of alternansucrase amino
      acid sequence - Amino Acids 1373 to 1394

<400> SEQUENCE: 69

Met Pro Asn Gly Val Glu Leu Arg Lys Gly Phe Gly Thr Asp Asn Ser
1               5                   10                  15

Gly Asn Val Tyr Tyr Phe
            20

<210> SEQ ID NO 70
<211> LENGTH: 22
<212> TYPE: PRT
<213> ORGANISM: Artificial Sequence
<220> FEATURE:
<223> OTHER INFORMATION: Peptide - CW repeats of alternansucrase amino
      acid sequence - Amino Acids 1395 to 1416

<400> SEQUENCE: 70

Asp Asp Gln Gly Lys Met Val Arg Asp Lys Tyr Ile Asn Asp Asp Ala
1               5                   10                  15

Asn Asn Phe Tyr His Leu
            20

<210> SEQ ID NO 71
<211> LENGTH: 21
<212> TYPE: PRT
<213> ORGANISM: Artificial Sequence
<220> FEATURE:
<223> OTHER INFORMATION: Peptide - CW repeats of alternansucrase amino
      acid sequence - Amino Acids 1417 to 1437

<400> SEQUENCE: 71

Asn Val Asp Gly Thr Met Ser Arg Gly Leu Phe Lys Phe Asp Ser Asp
1               5                   10                  15

Thr Leu Gln Tyr Phe
            20
```

```
<210> SEQ ID NO 72
<211> LENGTH: 22
<212> TYPE: PRT
<213> ORGANISM: Artificial Sequence
<220> FEATURE:
<223> OTHER INFORMATION: Peptide - CW repeats of alternansucrase amino
      acid sequence - Amino Acids 1438 to 1459

<400> SEQUENCE: 72

Ala Ser Asn Gly Val Gln Ile Lys Asp Ser Tyr Ala Lys Asp Ser Lys
1               5                   10                  15

Gly Asn Lys Tyr Tyr Phe
            20

<210> SEQ ID NO 73
<211> LENGTH: 22
<212> TYPE: PRT
<213> ORGANISM: Artificial Sequence
<220> FEATURE:
<223> OTHER INFORMATION: Peptide - CW repeats of alternansucrase amino
      acid sequence - Amino Acids 1460 to 1481

<400> SEQUENCE: 73

Asp Ser Ala Thr Gly Asn Asn Asp Thr Gly Lys Ala Gln Thr Trp Asp
1               5                   10                  15

Gly Asn Gly Tyr Tyr Ile
            20

<210> SEQ ID NO 74
<211> LENGTH: 25
<212> TYPE: PRT
<213> ORGANISM: Artificial Sequence
<220> FEATURE:
<223> OTHER INFORMATION: Peptide - CW repeats of alternansucrase amino
      acid sequence - Amino Acids 1482 to 1506

<400> SEQUENCE: 74

Thr Ile Asp Ser Asp Ala Asn Asn Thr Ile Gly Val Asn Thr Asp Tyr
1               5                   10                  15

Thr Ala Tyr Ile Thr Ser Ser Leu Arg
            20                  25

<210> SEQ ID NO 75
<211> LENGTH: 93
<212> TYPE: PRT
<213> ORGANISM: Artificial Sequence
<220> FEATURE:
<223> OTHER INFORMATION: Peptide - APY repeats of alternansucrase amino
      acid sequence - Amino Acids 1507 to 1599

<400> SEQUENCE: 75

Glu Asp Gly Leu Phe Ala Asn Ala Pro Tyr Gly Val Val Thr Lys Asp
1               5                   10                  15

Gln Asn Gly Asn Asp Leu Lys Trp Gln Tyr Ile Asn His Thr Lys Gln
            20                  25                  30

Tyr Glu Gly Gln Gln Val Gln Val Thr Arg Gln Tyr Thr Asp Ser Lys
        35                  40                  45

Gly Val Ser Trp Asn Leu Ile Thr Phe Ala Gly Gly Asp Leu Gln Gly
    50                  55                  60

Gln Arg Leu Trp Val Asp Ser Arg Ala Leu Thr Met Thr Pro Phe Lys
65                  70                  75                  80

Thr Met Asn Gln Ile Ser Phe Ile Ser Tyr Ala Asn Arg
                85                  90
```

```
<210> SEQ ID NO 76
<211> LENGTH: 78
<212> TYPE: PRT
<213> ORGANISM: Artificial Sequence
<220> FEATURE:
<223> OTHER INFORMATION: Peptide - APY repeats of alternansucrase amino
      acid sequence - Amino Acids 1600 to 1677

<400> SEQUENCE: 76

Asn Asp Gly Leu Phe Leu Asn Ala Pro Tyr Gln Val Lys Gly Tyr Gln
1               5                   10                  15

Leu Ala Gly Met Ser Asn Gln Tyr Lys Gly Gln Gln Val Thr Ile Ala
            20                  25                  30

Gly Val Ala Asn Val Ser Gly Lys Asp Trp Ser Leu Ile Ser Phe Asn
        35                  40                  45

Gly Thr Gln Tyr Trp Ile Asp Ser Gln Ala Leu Asn Thr Asn Phe Thr
    50                  55                  60

His Asp Met Asn Gln Lys Val Phe Val Asn Thr Thr Ser Asn
65                  70                  75

<210> SEQ ID NO 77
<211> LENGTH: 79
<212> TYPE: PRT
<213> ORGANISM: Artificial Sequence
<220> FEATURE:
<223> OTHER INFORMATION: Peptide - APY repeats of alternansucrase amino
      acid sequence - Amino Acids 1678 to 1756

<400> SEQUENCE: 77

Leu Asp Gly Leu Phe Leu Asn Ala Pro Tyr Arg Gln Pro Gly Tyr Lys
1               5                   10                  15

Leu Ala Gly Leu Ala Lys Asn Tyr Asn Asn Gln Thr Val Thr Val Ser
            20                  25                  30

Gln Gln Tyr Phe Asp Asp Gln Gly Thr Val Trp Ser Gln Val Val Leu
        35                  40                  45

Gly Gly Gln Thr Val Trp Val Asp Asn His Ala Leu Ala Gln Met Gln
    50                  55                  60

Val Ser Asp Thr Asp Gln Gln Leu Tyr Val Asn Ser Asn Gly Arg
65                  70                  75

<210> SEQ ID NO 78
<211> LENGTH: 79
<212> TYPE: PRT
<213> ORGANISM: Artificial Sequence
<220> FEATURE:
<223> OTHER INFORMATION: Peptide - APY repeats of alternansucrase amino
      acid sequence - Amino Acids 1757 to 1835

<400> SEQUENCE: 78

Asn Asp Gly Leu Phe Leu Asn Ala Pro Tyr Arg Gly Gln Gly Ser Gln
1               5                   10                  15

Leu Ile Gly Met Thr Ala Asp Tyr Asn Gly Gln His Val Gln Val Thr
            20                  25                  30

Lys Gln Gly Gln Asp Ala Tyr Gly Ala Gln Trp Arg Leu Ile Thr Leu
        35                  40                  45

Asn Asn Gln Gln Val Trp Val Asp Ser Arg Ala Leu Ser Thr Thr Ile
    50                  55                  60

Met Gln Ala Met Asn Asp Asn Met Tyr Val Asn Ser Ser Gln Arg
65                  70                  75
```

```
<210> SEQ ID NO 79
<211> LENGTH: 79
<212> TYPE: PRT
<213> ORGANISM: Artificial Sequence
<220> FEATURE:
<223> OTHER INFORMATION: Peptide - APY repeats of alternansucrase amino
      acid sequence - Amino Acids 1836 to 1914

<400> SEQUENCE: 79

Thr Asp Gly Leu Trp Leu Asn Ala Pro Tyr Thr Met Ser Gly Ala Lys
1               5                   10                  15

Trp Ala Gly Asp Thr Arg Ser Ala Asn Gly Arg Tyr Val His Ile Ser
                20                  25                  30

Lys Ala Tyr Ser Asn Glu Val Gly Asn Thr Tyr Tyr Leu Thr Asn Leu
            35                  40                  45

Asn Gly Gln Ser Thr Trp Ile Asp Lys Arg Ala Phe Thr Val Thr Phe
        50                  55                  60

Asp Gln Val Val Ala Leu Asn Ala Thr Ile Val Ala Arg Gln Arg
65                  70                  75

<210> SEQ ID NO 80
<211> LENGTH: 79
<212> TYPE: PRT
<213> ORGANISM: Artificial Sequence
<220> FEATURE:
<223> OTHER INFORMATION: Peptide - APY repeats of alternansucrase amino
      acid sequence - Amino Acids 1915 to 1993

<400> SEQUENCE: 80

Pro Asp Gly Met Phe Lys Thr Ala Pro Tyr Gly Glu Ala Gly Ala Gln
1               5                   10                  15

Phe Val Asp Tyr Val Thr Asn Tyr Asn Gln Gln Thr Val Pro Val Thr
                20                  25                  30

Lys Gln His Ser Asp Ala Gln Gly Asn Gln Trp Tyr Leu Ala Thr Val
            35                  40                  45

Asn Gly Thr Gln Tyr Trp Ile Asp Gln Arg Ser Phe Ser Pro Val Val
        50                  55                  60

Thr Lys Val Val Asp Tyr Gln Ala Lys Ile Val Pro Arg Thr Thr
65                  70                  75

<210> SEQ ID NO 81
<211> LENGTH: 64
<212> TYPE: PRT
<213> ORGANISM: Artificial Sequence
<220> FEATURE:
<223> OTHER INFORMATION: Peptide - APY repeats of alternansucrase amino
      acid sequence - Amino Acids 1994 to 2057

<400> SEQUENCE: 81

Arg Asp Gly Val Phe Ser Gly Ala Pro Tyr Gly Glu Val Asn Ala Lys
1               5                   10                  15

Leu Val Asn Met Ala Thr Ala Tyr Gln Asn Gln Val Val His Ala Thr
                20                  25                  30

Gly Glu Tyr Thr Asn Ala Ser Gly Ile Thr Trp Ser Gln Phe Ala Leu
            35                  40                  45

Ser Gly Gln Glu Asp Lys Leu Trp Ile Asp Lys Arg Ala Leu Gln Ala
        50                  55                  60

<210> SEQ ID NO 82
<211> LENGTH: 42
<212> TYPE: PRT
<213> ORGANISM: Artificial Sequence
```

```
<220> FEATURE:
<223> OTHER INFORMATION: Peptide - Catalytic domain of glucansucrase
      amino acid sequence - Nucleotides 281 to 433

<400> SEQUENCE: 82

Asp Ile Leu Arg Met Asp Ala Val Ala Phe Ile Trp Lys Gln Val Phe
1               5                   10                  15

Phe Lys Ser Glu Ala Ile Val His Pro Asp Trp Val Asn Tyr Val Arg
            20                  25                  30

Ser His Asp Asp Ile Gly Trp Thr Phe Ala
        35                  40

<210> SEQ ID NO 83
<211> LENGTH: 42
<212> TYPE: PRT
<213> ORGANISM: Artificial Sequence
<220> FEATURE:
<223> OTHER INFORMATION: Peptide - Catalytic domain of glucansucrase
      amino acid sequence - Nucleotides 1019 to 1173

<400> SEQUENCE: 83

Asp Ser Val Arg Val Asp Ala Pro Asp Asn Ile Asp Ala Asp His Ile
1               5                   10                  15

Asn Ile Leu Glu Asp Trp Asn His Ala Asp Asn Tyr Ser Phe Val Arg
            20                  25                  30

Ala His Asp Asn Asn Ser Gln Asp Gln Ile
        35                  40

<210> SEQ ID NO 84
<211> LENGTH: 42
<212> TYPE: PRT
<213> ORGANISM: Artificial Sequence
<220> FEATURE:
<223> OTHER INFORMATION: Peptide - Catalytic domain of glucansucrase
      amino acid sequence - Nucleotides 522 to 678

<400> SEQUENCE: 84

Asp Gly Tyr Arg Val Asp Ala Val Asp Asn Val Asp Ala Asp His Ile
1               5                   10                  15

Ser Ile Leu Glu Asp Trp Asp Asn Asn Asp Asn Tyr Ala Phe Ile Arg
            20                  25                  30

Ala His Asp Ser Glu Val Gln Thr Val Ile
        35                  40

<210> SEQ ID NO 85
<211> LENGTH: 42
<212> TYPE: PRT
<213> ORGANISM: Artificial Sequence
<220> FEATURE:
<223> OTHER INFORMATION: Peptide - Catalytic domain of glucansucrase
      amino acid sequence - Nucleotides 2212 to 2369

<400> SEQUENCE: 85

Asp Ser Ile Arg Ile Asp Ala Val Asp Phe Ile His Asn Asp His Ile
1               5                   10                  15

Ser Leu Val Glu Ala Gly Leu Asp Ala Gly Asn Tyr Ser Ile Ile His
            20                  25                  30

Ala His Asp Lys Gly Val Gln Glu Lys Val
        35                  40
```

-continued

```
<210> SEQ ID NO 86
<211> LENGTH: 42
<212> TYPE: PRT
<213> ORGANISM: Artificial Sequence
<220> FEATURE:
<223> OTHER INFORMATION: Peptide - Catalytic domain of glucansucrase
      amino acid sequence - Nucleotides 448 to 604

<400> SEQUENCE: 86

Asp Ser Ile Arg Val Asp Ala Val Asp Asn Val Asp Ala Asp His Val
1               5                   10                  15

Ser Ile Val Glu Ala Trp Ser Asp Asn Asp Ser Tyr Ser Phe Ala Arg
            20                  25                  30

Ala His Asp Ser Glu Val Gln Asp Leu Ile
        35                  40

<210> SEQ ID NO 87
<211> LENGTH: 42
<212> TYPE: PRT
<213> ORGANISM: Artificial Sequence
<220> FEATURE:
<223> OTHER INFORMATION: Peptide - Catalytic domain of glucansucrase
      amino acid sequence - Nucleotides 472 to 628

<400> SEQUENCE: 87

Asp Ser Ile Arg Val Asp Ala Val Asp Asn Val Asp Ala Asp His Leu
1               5                   10                  15

Ser Ile Leu Glu Ala Trp Ser Tyr Asn Asp Ser Tyr Ser Phe Ile Arg
            20                  25                  30

Ala His Asp Ser Glu Val Gln Asp Leu Ile
        35                  40

<210> SEQ ID NO 88
<211> LENGTH: 42
<212> TYPE: PRT
<213> ORGANISM: Artificial Sequence
<220> FEATURE:
<223> OTHER INFORMATION: Peptide - Catalytic domain of glucansucrase
      amino acid sequence - Nucleotides 501 to 657

<400> SEQUENCE: 88

Asp Gly Val Arg Val Asp Ala Val Asp Asn Val Asn Ala Asp His Leu
1               5                   10                  15

Ser Ile Leu Glu Ala Trp Ser His Asn Asp Asn Tyr Ala Phe Val Arg
            20                  25                  30

Ala His Asp Ser Glu Val Gln Ser Ile Ile
        35                  40

<210> SEQ ID NO 89
<211> LENGTH: 42
<212> TYPE: PRT
<213> ORGANISM: Artificial Sequence
<220> FEATURE:
<223> OTHER INFORMATION: Peptide - Catalytic domain of glucansucrase
      amino acid sequence - Nucleotides 460 to 624

<400> SEQUENCE: 89

Asp Gly Val Arg Val Asp Ala Val Asp Asn Val Asn Ala Asp His Leu
1               5                   10                  15

Ser Ile Leu Glu Ala Trp Ser Asp Asn Asp Asn Tyr Ile Phe Ile Arg
            20                  25                  30

Ala His Asp Ser Glu Val Gln Thr Val Ile
        35                  40
```

```
<210> SEQ ID NO 90
<211> LENGTH: 42
<212> TYPE: PRT
<213> ORGANISM: Artificial Sequence
<220> FEATURE:
<223> OTHER INFORMATION: Peptide - Catalytic domain of glucansucrase
      amino acid sequence - Nucleotides 546 to 702

<400> SEQUENCE: 90

Asp Gly Ile Arg Val Asp Ala Val Asp Asn Val Asp Ala Asp His Leu
1               5                   10                  15

Ser Ile Leu Glu Asp Trp Ser His Asn Asp Asn Tyr Ser Phe Val Arg
            20                  25                  30

Ala His Asp Ser Glu Val Gln Thr Val Ile
        35                  40

<210> SEQ ID NO 91
<211> LENGTH: 42
<212> TYPE: PRT
<213> ORGANISM: Artificial Sequence
<220> FEATURE:
<223> OTHER INFORMATION: Peptide - Catalytic domain of glucansucrase
      amino acid sequence - Nucleotides 497 to 653

<400> SEQUENCE: 91

Asp Gly Ile Arg Val Asp Ala Val Asp Asn Val Asp Ala Asp His Leu
1               5                   10                  15

Ser Ile Leu Glu Asp Trp Ser His Asn Asp Asn Tyr Ser Phe Val Arg
            20                  25                  30

Ala His Asp Ser Glu Val Gln Thr Val Ile
        35                  40

<210> SEQ ID NO 92
<211> LENGTH: 42
<212> TYPE: PRT
<213> ORGANISM: Artificial Sequence
<220> FEATURE:
<223> OTHER INFORMATION: Peptide - Catalytic domain of glucansucrase
      amino acid sequence - Nucleotides 630 to 807

<400> SEQUENCE: 92

Asp Gly Ile Arg Val Asp Ala Val Asp Asn Val Asp Ala Asp His Leu
1               5                   10                  15

Ser Ile Leu Glu Asp Trp Asn Gly Lys Asp Asn Tyr Ser Phe Val Arg
            20                  25                  30

Ala His Asp Tyr Asp Ala Gln Asp Pro Ile
        35                  40
```

FULLY ACTIVE ALTERNANSUCRASES PARTIALLY DELETED IN ITS CARBOXY-TERMINAL AND AMINO-TERMINAL DOMAINS AND MUTANTS THEREOF

FIELD OF THE INVENTION

The present invention relates to the recombinant production of truncated or mutated alternansucrases which maintain their enzymatic activity. More specifically, the present invention relates to nucleic acid sequences of truncated or mutated alternansucrases, vectors containing these nucleic acids sequences, host cells transformed with the nucleic acid sequences encoding truncated or mutated alternansucrases. In another aspect, the present invention provides a process to recombinantly produce alternansucrase with a high level of expression, while retaining the enzymatic activity.

Submission On Compact Disc

The contents of the following submission on compact discs are incorporated herein by reference in its entirety: A compact disc copy of the Sequence Listing (COPY 1), (file name: 11011702-Amended, date recorded: Jan. 17, 2007, size: 248 KB ); a duplicate compact disc copy of the Sequence Listing (COPY 2), (file name: 11011702-Amended, date recorded: Jan. 17, 2007, size: 248 KB ); a computer readable form copy of the Sequence Listing (CRF COPY) (file name: 11011702-Amended, date recorded: Jan. 17, 2007, size: 248 KB ).

BACKGROUND OF THE INVENTION

Glucansucrases, commonly known as glucosyltransferases, found in lactic acid bacteria (*Streptococci, Leuconostoc* sp., *Lactococcus* sp., and *Lactobacillus* sp.), are enzymes belonging to the glycosidase and transglycosidase of glycoside-hydrolase family 70 that catalyze the transfer of glucosyl units from the cleavage of sucrose to a growing α-glucan chain (Henrissat, B. *Biochem. Soc. Trans.* 26, 153-156 (1998)). The nature of the linkages between glucosyl units determines the water solubility and properties of the glucan. Thus, a higher content of an α-1,3 linkage results in greater insolubility (Monchois et al *FEMS Microbiol. Rev.* 23, 131-151 (1999)). In the presence of acceptor molecules, such as maltose, glucansucrases can catalyze the synthesis of low molecular weight oligosaccharides.

Glucansucrases have industrial value because of the production of glucans and oligosaccharides of biologically importance. They play a key role in cariogenic processes and thus can be used in the development of vaccines against caries. More specifically, glucansucrases synthesize glucans, which are of central importance in adhesive interactions in plaque, where they mediate attachment of bacteria to the tooth surface and to other bacteria, thus stabilizing the plaque biofilm, serve as energy stores aiding the survival of plaque bacteria and modulating the permeability of plaque and hence the acid level at the enamel surface (Colby et al *Soc. J. Appl. Microbiol. Symp.* Suppl., 83, 80S-88S (1991)).

Alternansucrase is a large glucansucrase having 2,057 amino acids that, in the absence of external acceptors and starting from sucrose, catalyzes the formation of fructose and an unusual polymer consisting of glucopyranosyl residues alternatively linked by α-1,6 and α1,3 osidic bonds, called alternan. The polysacharide alternan was first described by Jeanes et al *J. Am. Chem Soc,* 76, 5041-5052 (1954) as one of two extracellular α-D glucans, referred to as fraction S, produced by *Leuconostoc mesenteroides* NRRL B-1355. Since the α-1,3-linkages are part of the linear chain of the S fraction and there are not any conservative α-1,6 linkages, this fraction was not considered a true dextran, but was named alternan by Côté and Robyt (*Carbohydrate Res.* 101, 57-74 (1982)).

In the presence of external acceptors, such as for instance, maltose, isomaltose, isomaltriose and methyl-α-D-glucan and cellobiose, alternansucrase catalyzes at the acceptors the synthesis of α-D-glucan chains, in which the glucose moieties are predominantly alternating linked by α-1,6 and α1,3 glycosidic bonds and release of fructose. Depending on the acceptor used, the resulting products have different structures and molecular weights that are lower than high molecular weight alternan. They have a polymerization degree of less than 15. Because of the polymerization degree, these products are often referred to as oligoalternans (Pelenc et al, *Sciences Des Aliments* 11, 465-476 (1991)). In the preparation of oligoalternans using alternansucrase, maltose is an acceptor producing high oligoalternan yields, while panose is the first acceptor product which is formed starting from maltose through the formation of α-1,6 glycosidic bonds (Lopez-Mungia et al *Enzyme Microb. Technol.* 15, 77-85 (1993)).

Because of its physico-chemical properties (high solubility and low viscosity) alternan has valuable use in the pharmaceutical industry, for instance, as a carrier of pharmaceutically active ingredients or as blood plasma extenders. Also alternans have been suggested as additives in the textile, cosmetics and food industry and in particular as prebiotics. (Lopez-Munguia et al *Enzyme Microb, Technol.* 15 (1993). Besides acting as an additive, alternan can be used as a substitute for gum Arabic (Côté, *Carbohydrate Polymers* 19, 249-252 (1992)).

Alternan is generally prepared in a cell-free system using partially purified proteins or by fermentation using alternansucrase-producing strains of *Leuconostic mesenteroides.* Various purification methods for alternansucrases have been previously described (Lopez-Mungia et al, *Enzyme Microb, Technol.* 15, 77-85 (1993) Côté and Robyt, *Carbohydrate Research* 101, 57-74 (1982)). These methods are however complex, relatively costly and lead to very low protein yields.

Moreover, since the alternansucrase produced in the fermentation methods is not highly pure, dextran impurities are generally present in the alternan produced. Moreover, the enzyme production is induced by sucrose and the protein extracts are contaminated by the co-synthesized enzymes. To separate the dextran and other impurities from the alternan is relatively time-consuming and costly.

Alternative methods have been suggested such as the production of alternansucrase by recombinant means. In fact the alternansucrase gene was in fact cloned in *E. coli*, but the level of expression was extremely low, 160 U.1$^{-1}$ compared to the native 1,730 U.1$^{-1}$. Moreover, no information about the quality of the expressed product was reported (Arguello-Morales et al; *FEMS Microbiol. Lett.* 182, 81-85 (2000)). Furthermore, the expressed enzyme was highly degraded due to its expression in *E. coli.*

U.S. Pat. No. 6,570,065 describes methods for preparing transgenic plants which synthesize alternan due to the insertion of nucleic acid molecules encoding an alternansucrase. Also described in this patent application is the production of alternansucrase in *E. coli*. However, the full length DNA sequence coding for alternansucrase was used and hence the yields produced were low.

In view of the above, there is a need in this art to produce a highly purified and enzymatically active alternansucrase, which can be used to produce alternans and oligoalternans.

Thus, it is an object of the present invention to overcome the problems associated with the prior art.

It is another object of the present invention to provide a recombinantly produced alternansucrase that retains its enzyme activity, which has practically neither dextran nor dextransucrase impurities.

Another object of the present invention is to provide nucleic acid sequences of truncated and mutated alternansucrases, vectors and host cells transformed by the vectors.

Yet another object of the present invention is to provide amino acid sequences of truncated and mutated alternansucrases.

In another object, the present invention provides truncated variants of alternansucrase, which are better expressed and less degraded compared to the full length alternansucrase.

In yet another object, the present invention provides mutated alternansucrases which, when subject to an external acceptor synthesizes a large quantity of specific oligosaccharides such as oligodextrans and oligoalternans.

In still another object, the present invention provides a process for producing highly purified alternansucrases, which retain their catalytic activity.

In still another object, the present invention provides a composition comprising truncated or mutated alternansucrases and a pharmaceutically acceptable vehicle.

These and other objects are achieved by the present invention as evidenced by the summary of the invention, description of the preferred embodiments and the claims.

SUMMARY OF THE INVENTION

The present invention nucleotide sequences consisting essentially of a nucleotide sequence in FIG. 1 (SEQ ID NO. 1), starting from a nucleotide at position 195 to the nucleotide at position 4241 (SEQ ID No. 2) or 4469 (SEQ ID No. 3) or a nucleotide sequence starting from a nucleotide at position 1218 to the nucleotide at position 4469 (SEQ ID No. 4), a sequence complementary to SEQ ID Nos. 2 or 3 or 4 or a sequence that hybridizes to SEQ ID Nos. 2 or 3 or 4 under stringent hybridization conditions, provided that alternansucrase enzyme activity is retained.

In another aspect nucleotide sequences having mutations in the truncated alternansucrases are provided.

In another embodiment vectors are provided containing the truncated or mutated nucleic acid sequence.

A truncated or a mutated alternansucrase, which retains enzymatic activity is yet another embodiment of the present invention.

In yet another aspect, a method for the preparation of a mutated or truncated alternansucrase, said method comprising:

(a) culturing host cells, which are transformed with the vectors of the present invention under conditions permitting the expression of an alternansucrase; and (b) isolating said alternansucrase from the culture medium.

A method to produce alternans or oligoalternans, said method comprising reacting the truncated or mutated alternansucrase with maltose thereby producing alternans or oligoalternans is also encompassed by the present invention, as well as a composition, said composition comprising a truncated or mutated alternansucrase and a pharmaceutically acceptable vehicle.

BRIEF DESCRIPTION OF THE DRAWINGS

FIGS. 1A-1F are the DNA (SEQ ID No. 1) and amino acid sequence of the full-length alternansucrase (SEQ ID No. 25).

FIG. 2 is an alignment of the cell wall binding repeats (CW) and the repetitive units of amino acids APY (APY) found in alternansucrase. Part (A) (SEQ ID Nos. 56-65) shows the CW repeats of the variable region, while part (B) illustrates the CW (SEQ ID Nos. 66-74) and APY (SEQ ID Nos. 75-81) repeats in the C-terminal domain.

FIG. 3(*b*) is a drawing representing the truncated alternansucrase in Examples 18, 19 and 20.

Figure 3A:
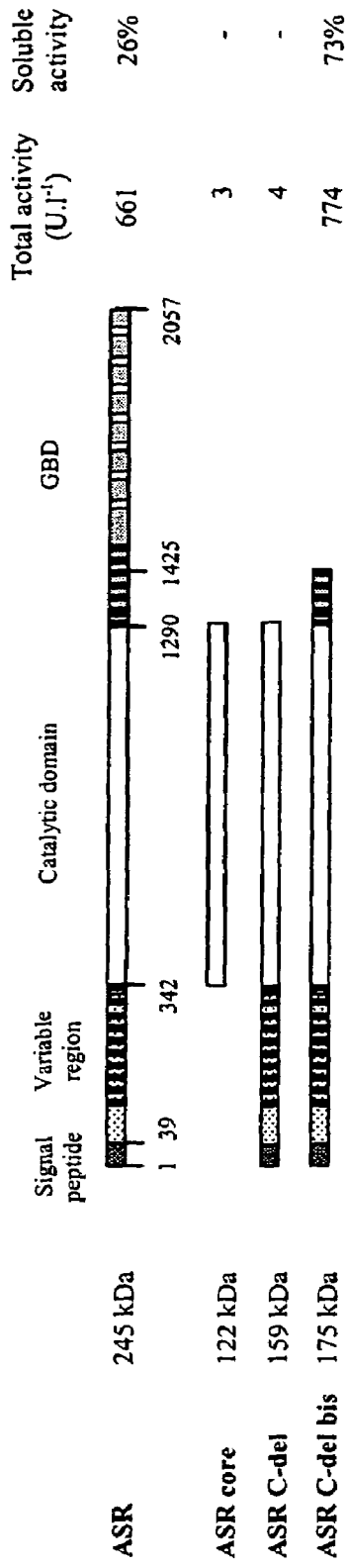
FIG. 3(*a*) is a drawing representing the truncated alternansucrase as exemplified in Examples 13 and 14
Figure 3B:
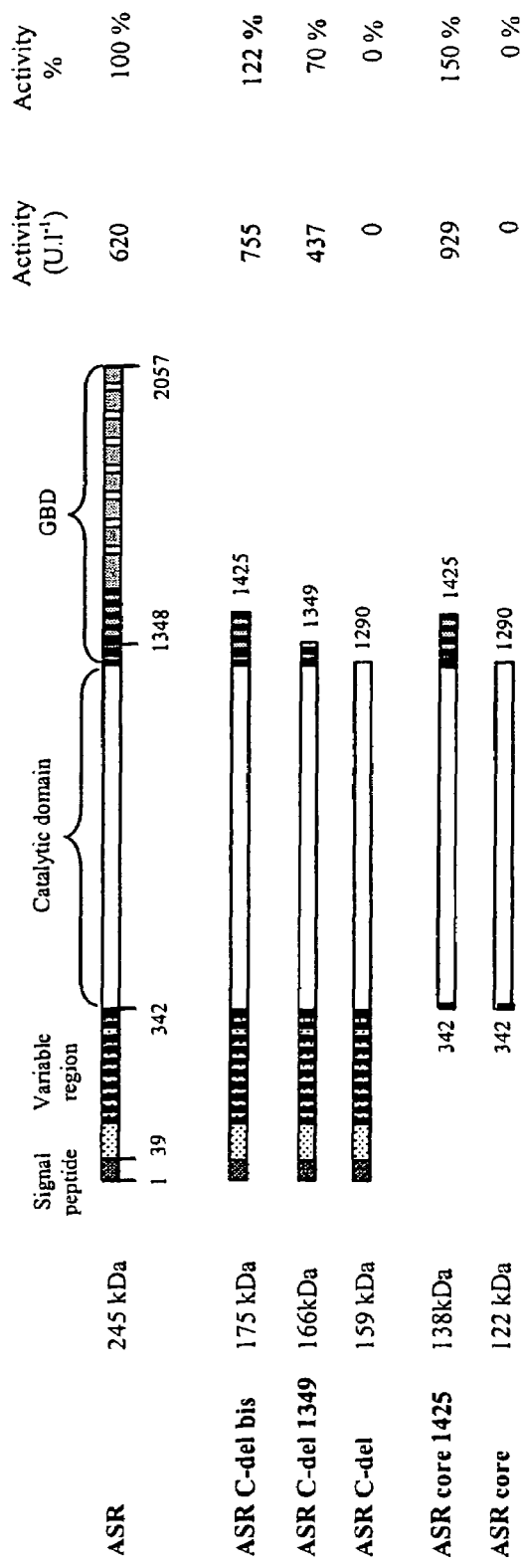

In both FIG. 3(*a*) and FIG. 3(*b*) the black stripes indicate the region having cell wall binding repeats (CW) and the white stripes indicate the region having APY repeats. Molecular weights were calculated with the thioredoxin and the 6×-His tag. The numbers represent the amino acid positions excluding the thioredoxin and the 6×-His tag.

Figure 4:
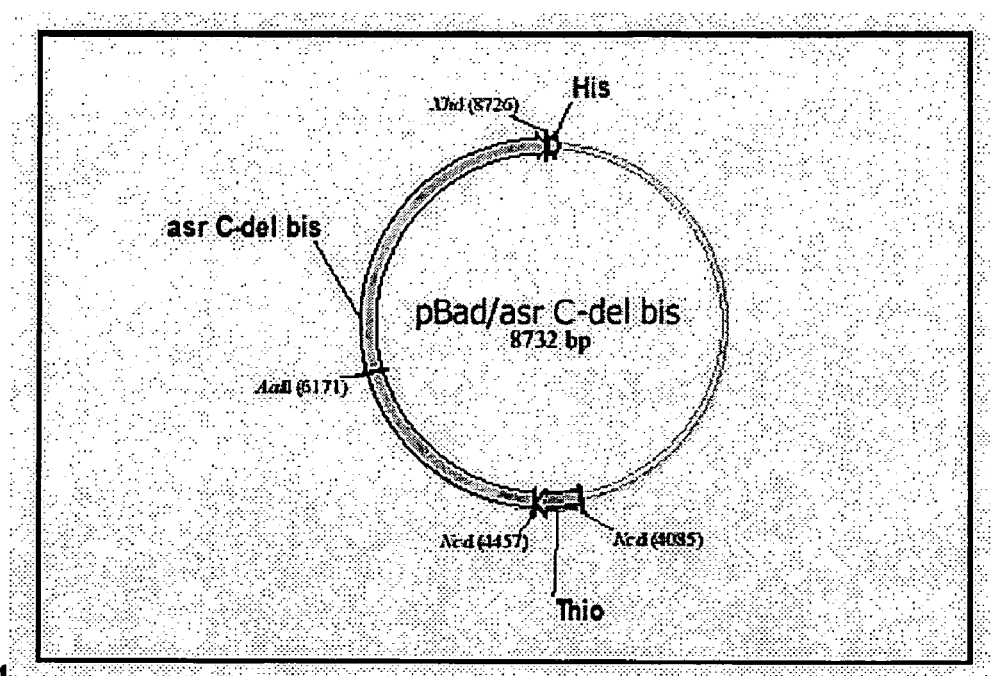

FIG. 4 is a representation of the plasmid [pBad asr C-del bis]. Thio indicates thioredoxin which is fused at the N-terminal. His represents the histidine tag which is fused at the C-terminal.

Figure 5:
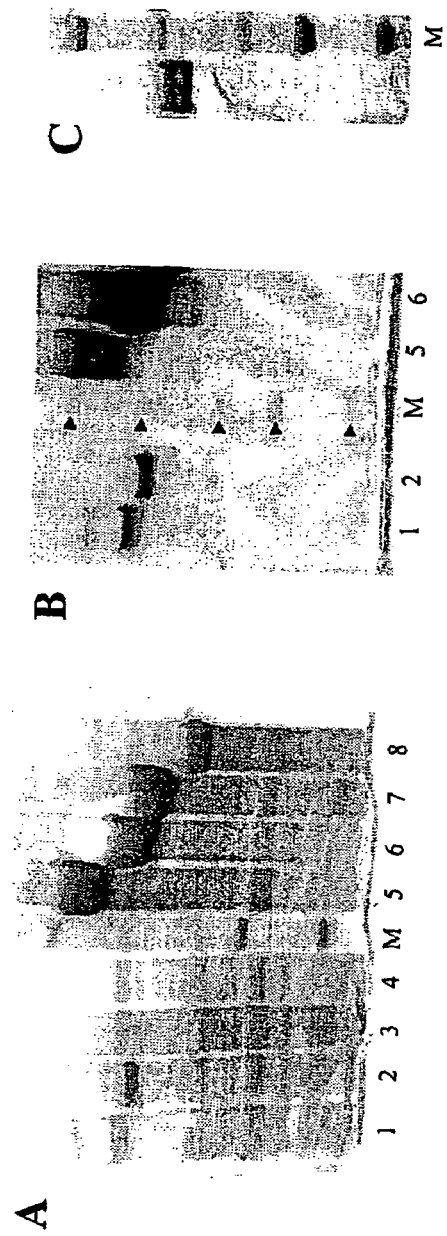

FIG. 5 are photographs of SDS-PAGE gels of the produced alternansucrase and the truncated variants. Photograph (A) is a colloidal blue stained gel. Photograph (B) is a zymogram detecting the polymer produced in situ. Photograph (C) is a silver stained gel with purified ASR C-bis del deleted of the thioredoxin. Loaded samples are ASR (lanes 1 and 5), ASR C-del bis (lanes 2 and 6), ASR C-del (lanes 3 and 7) and ASR core (lanes 4 and 8). Lanes 1 to 4 correspond to soluble protein extracts and lanes 5 to 8 correspond to insoluble protein extracts. M, molecular weight markers of 250, 150, 100, 75 and 50 kDa.

Figure 6:
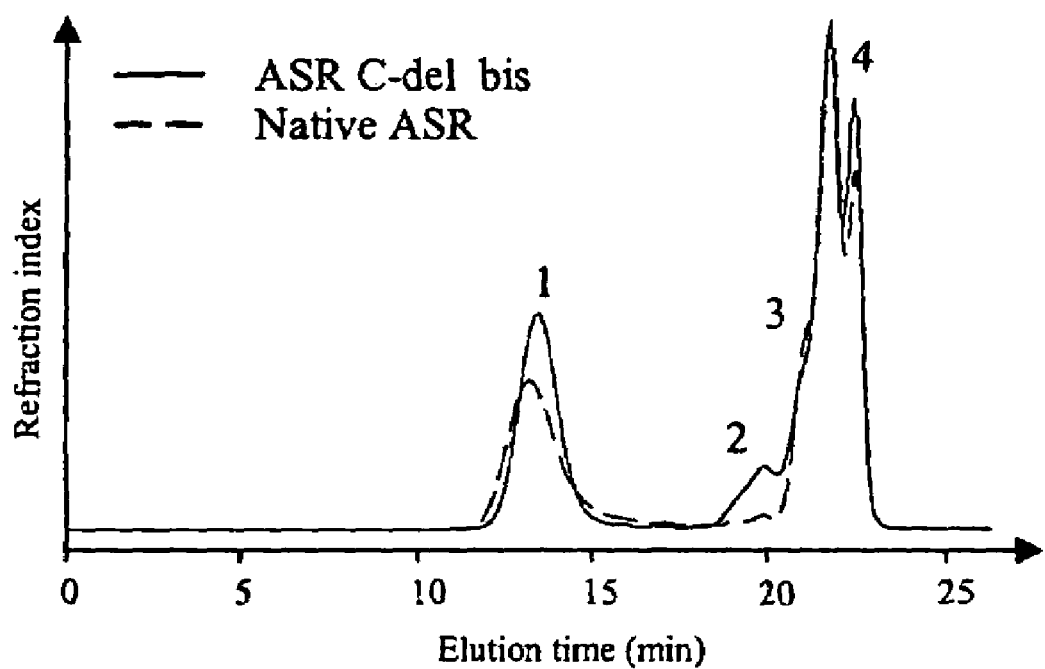

FIG. 6 is a drawing of the results from a gel permeation chromatography analysis of products synthesized by the native alternansucrase from *L. mesenteroides* NRRL B-23192 and ASR C-del bis. (1) indicates a polymer of 1,700 kDa. (2) indicates oligosaccharides of 1.3 kDa. (3) indicates disaccharides and (4) indicates monosaccharides.

Figure 7:
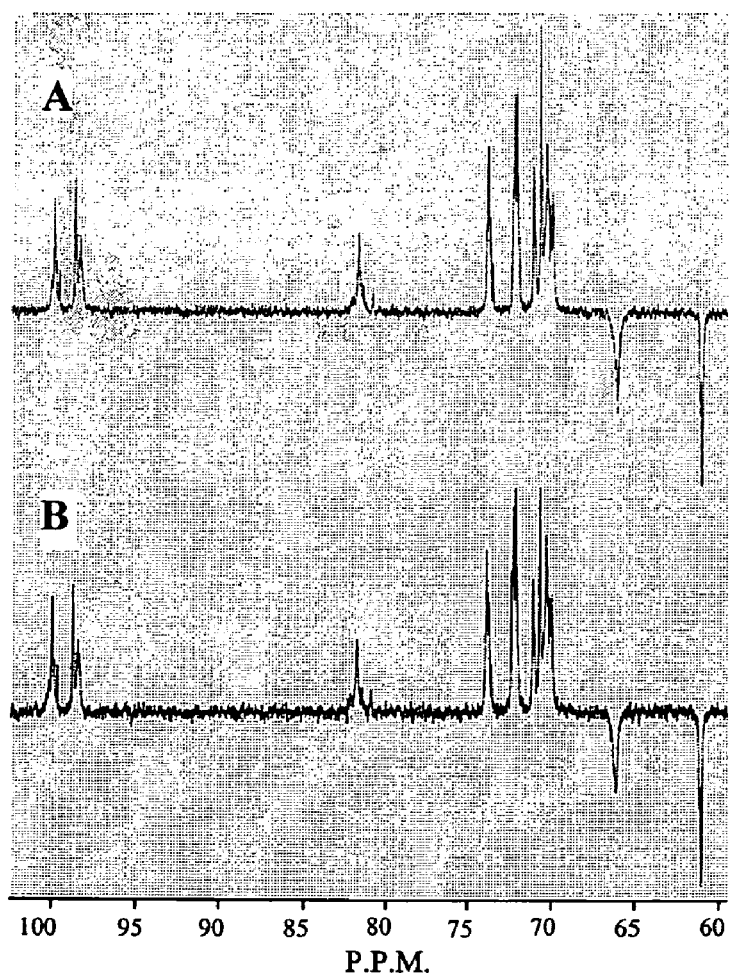

FIG. 7 are $^{13}$C NMR spectra of the polymers synthesized by (A) the native alternansucrase from *L. mesenteroides* NRRL B-23192 and (B) ASR C-del bis. The anomeric region shows two carbons of similar intensity corresponding to anomeric carbons involved in α-1,6 and α-1,3 linkages at 100.2 ppm and 98.5 ppm, respectively. The C6 and the C3 engaged in the glucosidic linkages were identified at 66.4 ppm and 82.5 ppm, respectively and the C6 not engaged in the linkage is located at 61.2 ppm.

FIG. 8 is a sequence alignment of the catalytic domain amino acids of glucansucrases from family 70 of glycoside-hydrolases and transglycosidases with various specificities. Solely AS (SEQ ID No. 82) is from the family 13 glycoside-hydrolases. AS and GTF-A (SEQ ID No. 83) produce α-1,4 linkages, GTF-I, (SEQ ID No. 86), GTF-C (SEQ ID No. 87) and GTF-L (SEQ ID No. 88) are specific for α-1,3 linkages, GTF-D (SEQ ID No. 89), DSR-S (SEQ ID No. 90) and DSR-C (SEQ ID No. 91) are specific for α-1,6 linkages, ASR (SEQ ID No. 92) is specific for alternating α-1,6 and α-1,3 linkages. AS, *N. polysaccharea*; GTF-A, *Lactobaccillus reuteri*; DSR-E1, SEQ ID No. 84), 2 SEQ ID No. 85) first and second catalytic domains, *L. mesenteroides* NRRL B-1229; GTF-I, *S. downei*; GTF-C, *S. mutans*; GTF-L, *S. S. salivarius*; GTF-D, *S. mutans*; DSR-S, *L. mesenteroides* NRRL B-512F; DSR-C, *L. mesenteroides* NRRL B-1335; ASR, alternansucrase from *L. mesenteroides* NRRL B-1335. β, β strands from the putative (β/α) 8 barrel. AAA: catalytic amino acids. AAA: specific amino acids of the alternansucrase that were mutated.

Where AS stands for amylosucrase; GTF stands for glucosyl transferase; DSR stands for dextransucrase; and ASR stands for alternansucrase.

Figure 9:
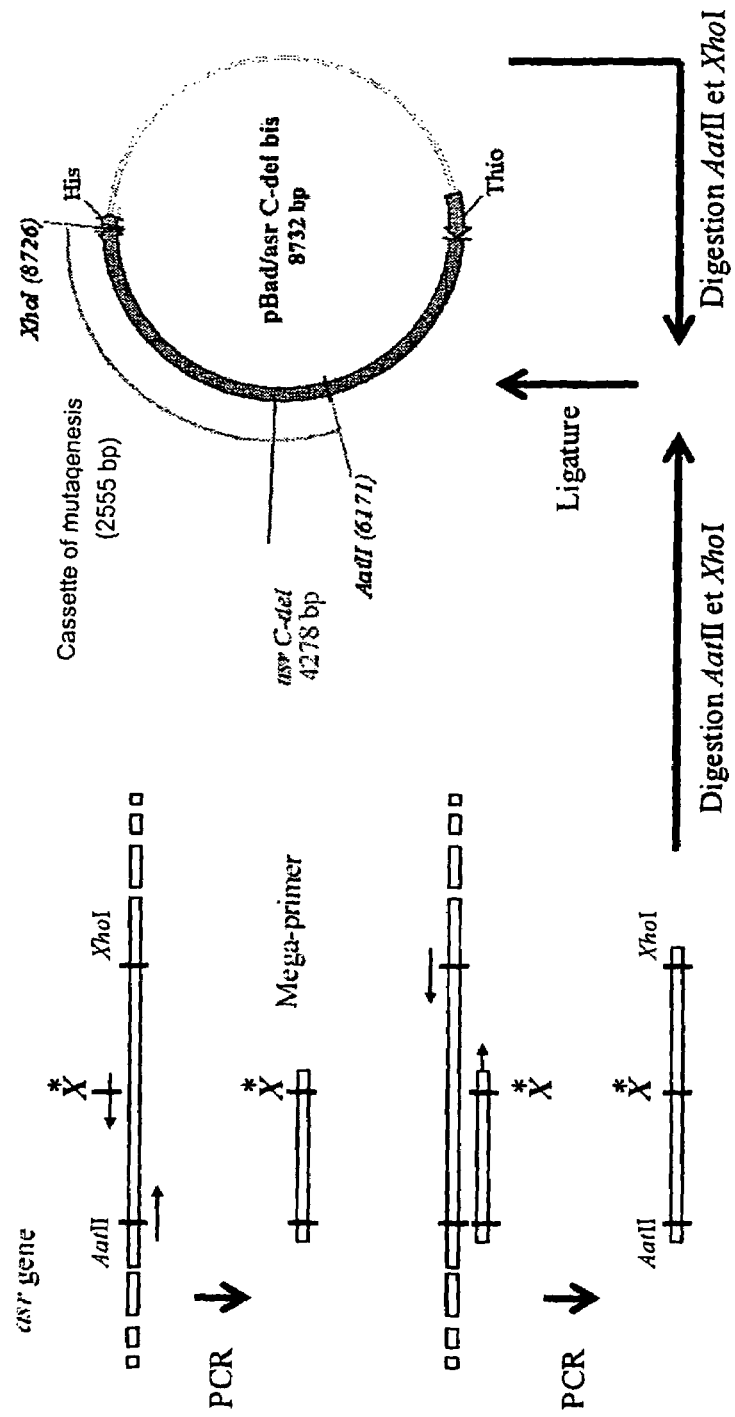

FIG. 9 is an illustration showing the construction of mutants by the method of mega-primers.

Figure 10:
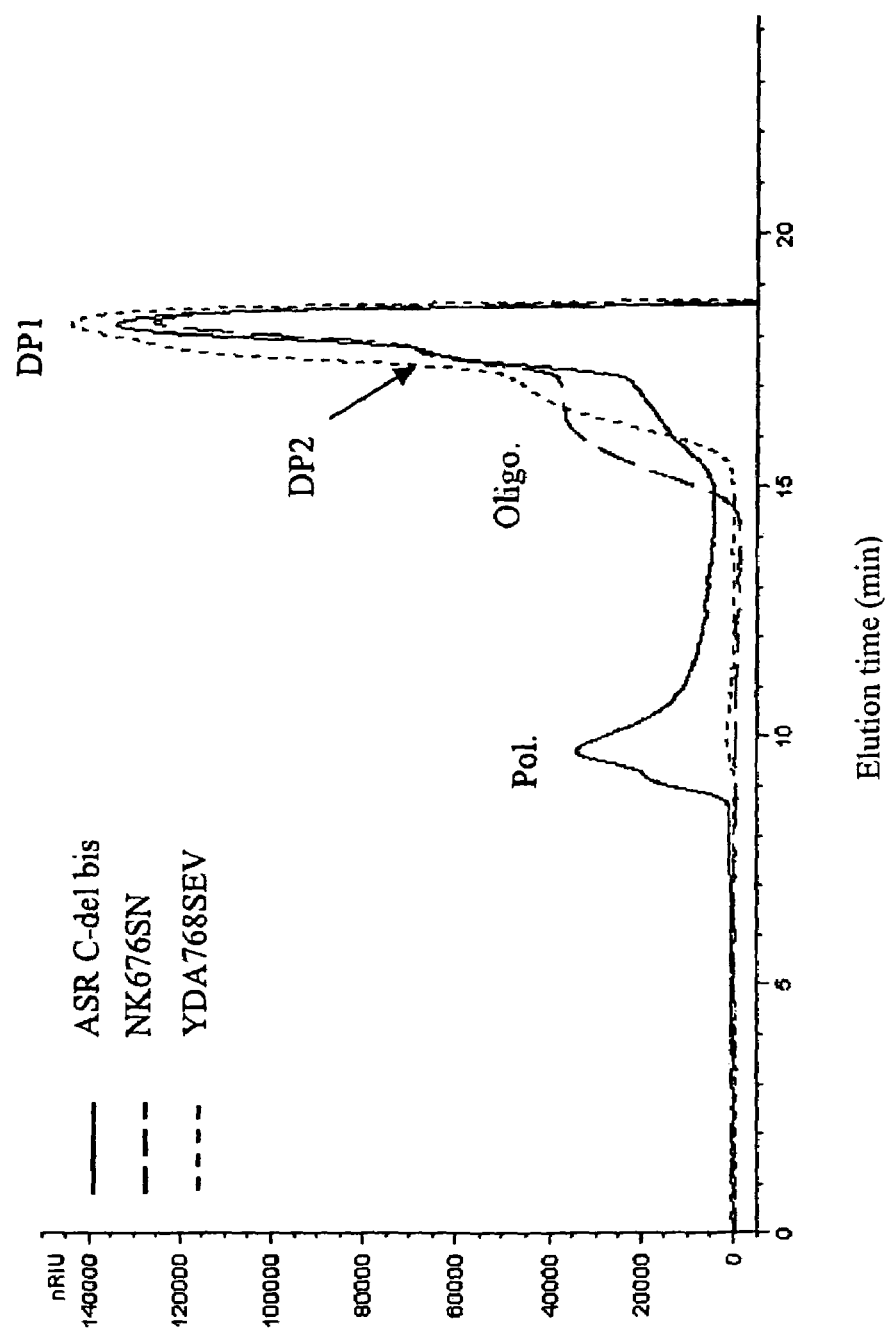

FIG. 10 is a drawing of a gel permeation analysis of the synthesized products in the polymerization conditions by ASR C-del bis, NK676SN and YDA768SEV mutants. The synthesis conditions were 30° C., 20 mM sodium acetate buffer pH 5.4, sucrose 100 g.l$^{-1}$, enzyme 0.5 U.ml$^{-1}$. Product identification: Pol., polymer of about 1.7 million Da MW (i.e., degree of polymerization (DP) of 10,500); Oligo., oligosaccharides of about 1.3 kDa MW (i.e., DP of 8); DP2, disaccharides; DP1 monosaccharides.

Figure 11:
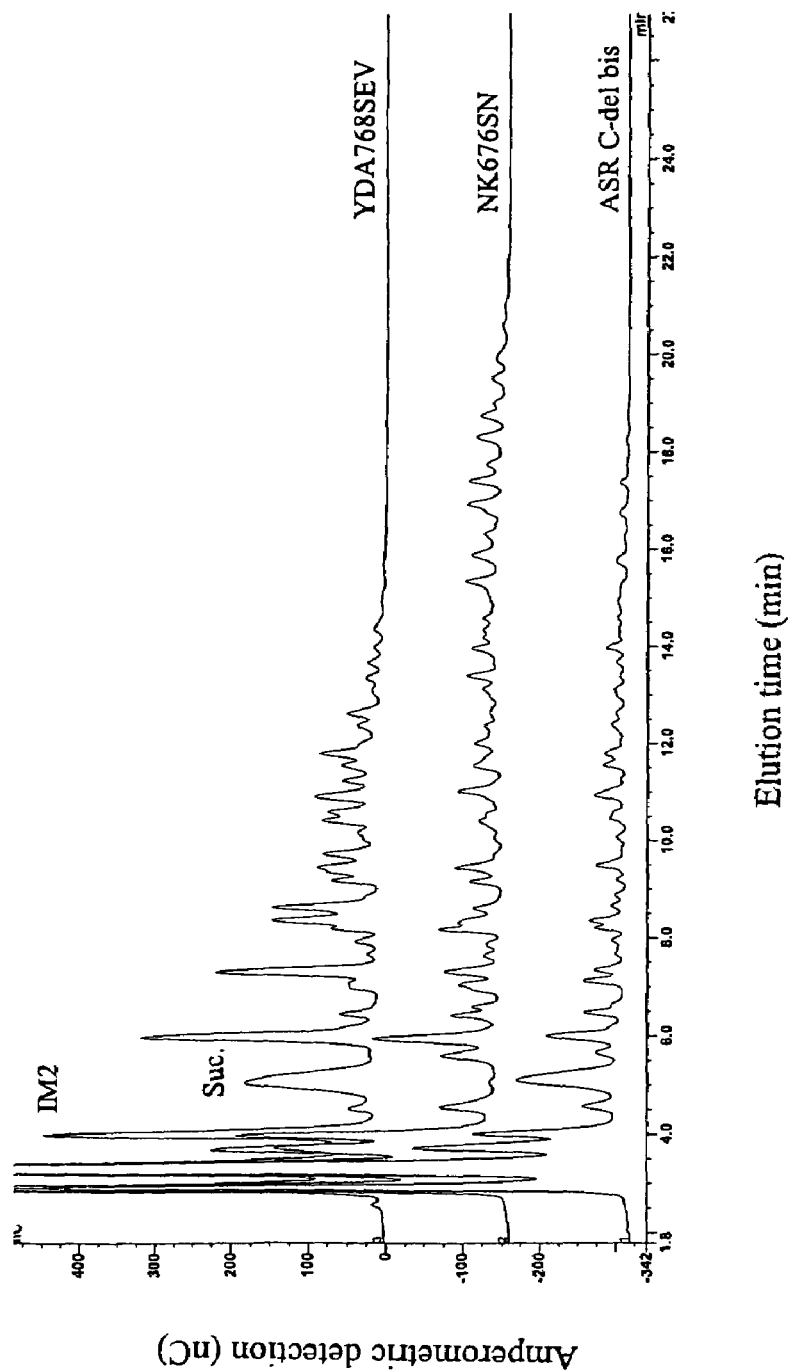

FIG. 11 is an HPAEC analysis of oligosaccharide population synthesized in the polymerization conditions by the ASR C-del bis, NK676SN, and YDA768SEV mutants. The synthesis conditions are the same as set forth in FIG. 10, Product identification: IM2, isomaltose; Suc., sucrose.

Figure 12:
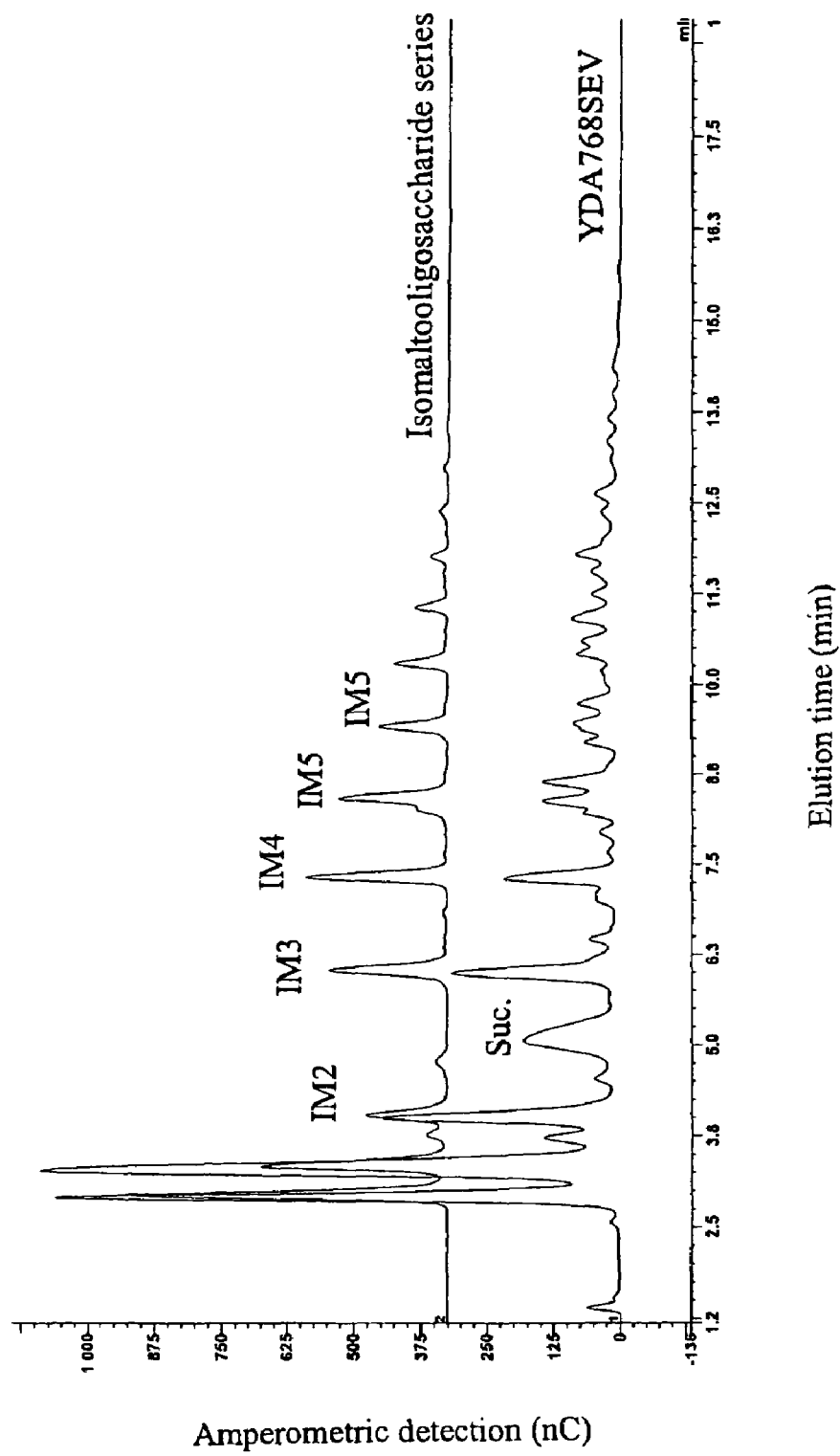

FIG. 12 is a graph showing the comparison of HPAEC analysis of oligosaccharide population synthesized by the YDA768SEV mutant (in polymerization conditions and a series of isomalooligosaccharides. The synthesis conditions were 30° C., 20 mM sodium acetate buffer pH 5.4, sucrose 100 g.l$^{-1}$, enzyme 0.5 U.ml$^{-1}$. Product identification: Suc., sucrose; IM2, isomaltose; IM3, isomaltotriose; IM4, isomaltotetraose; IM5, isomaltopentaose.

Figures 13A, 13B:
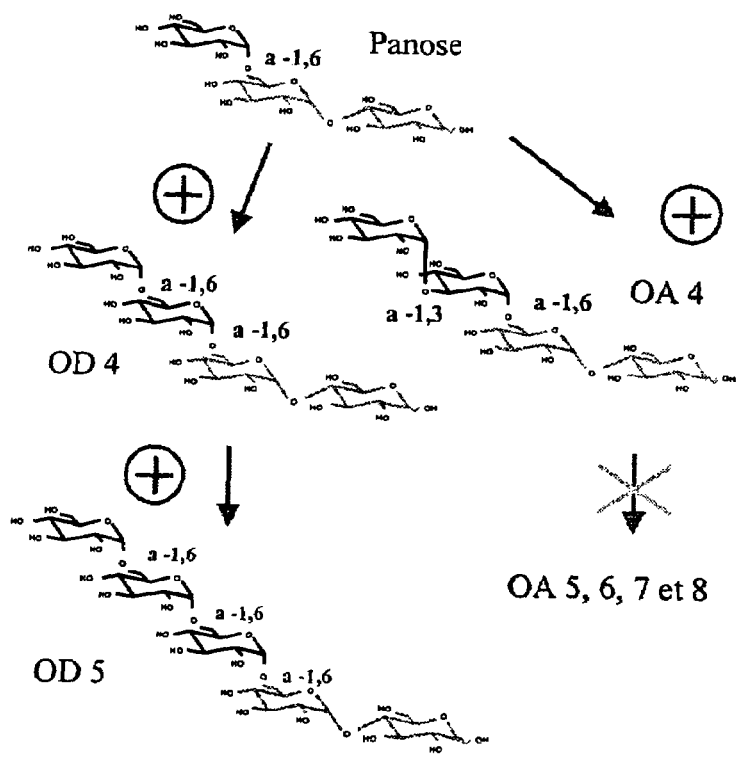

FIG. 13(A) is a table showing the yields of synthesized oligosaccharides analyzed by HPLC on a $C_{18}$ column.

FIG. 13(B) is a schematic representation of synthesized oligosaccharides. OD represents the oligodextran series and OA the oligoalternan series. The synthesis conditions were 30° C., 20 mM sodium acetate buffer pH 5.4, sucrose 100 g.l$^{-1}$, maltose 50 g.l$^{-1}$, enzyme 0.5 U.ml$^{-1}$.

Figure 14:
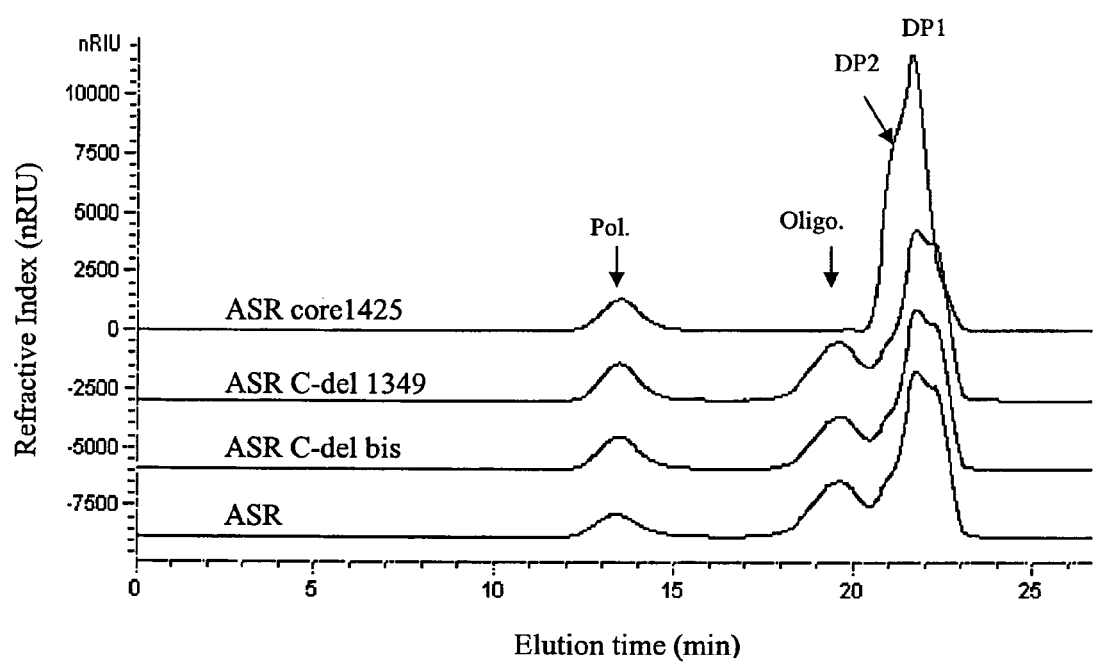

FIG. 14 is a gel permeation analysis of polymer synthesized products by ASR, ASR C-del bis, ASR C-del 1349 and ASR core 1425. The synthesis conditions were 20 mM sodium acetate buffer, pH 5.4, sucrose 100 g.l$^{-1}$, enzyme 0.5 U.ml$^{-1}$ at 30° C. Product identification: Pol., polymer of about 1.7 million Da MW (i.e., DP of 10,500); Oligo., oligosaccharides of about 1.3 kDa MW (i.e., DP of 8); DP2, disaccharides; DP1, monosaccharides.

Figure 15:
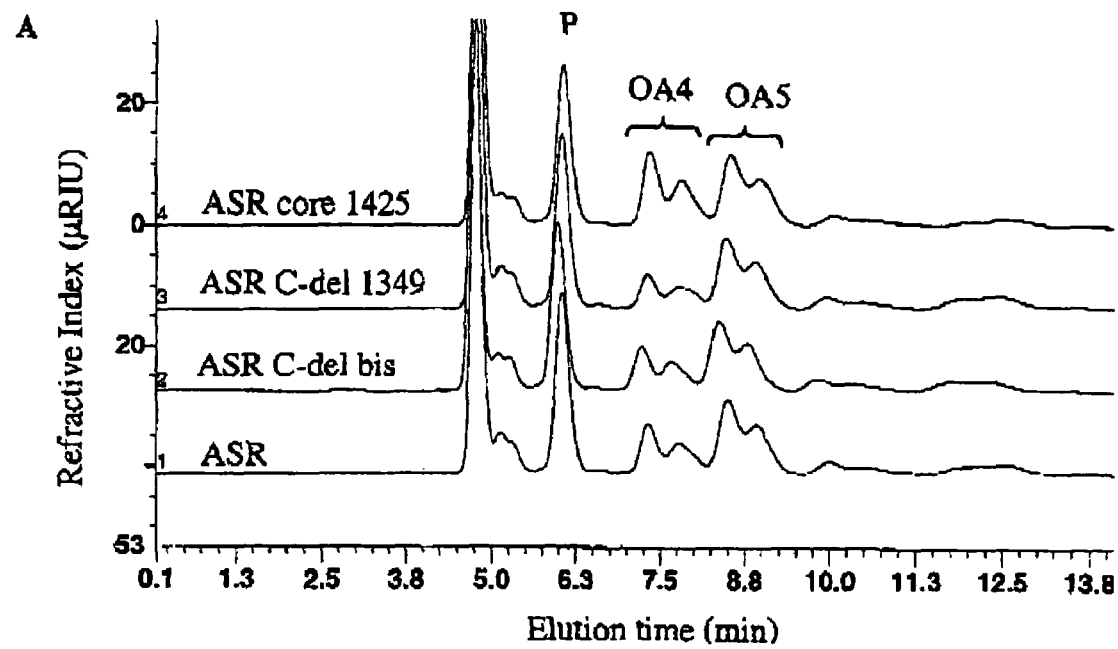

FIG. 15 is an HPLC chromatograph of the medium after an acceptor reaction. The synthesis conditions were 20 mM sodium acetate buffer, pH 5.4, sucrose 100 g.l$^{-1}$, enzyme 0.5 U.ml$^{-1}$, maltose 50 g.l$^{-1}$ at 30° C. The analysis conditions of HPLC were as follows: C18 column, 0.5 ml min-1, deionized water at 30° C., RI detection.

DETAILED DESCRIPTION OF PREFERRED EMBODIMENTS

By an enzyme possessing the enzymatic activity of alternansucrase is meant to mean an enzyme that catalyzes the conversion of saccharide into alternan or oligoalternans and fructose. This conversion may occur in the presence or absence of external acceptors such as maltose, isomalatose or isomaltotriose. In the absence of external acceptors, alternansucrases starting from sucrose catalyze the release of fructose and high molecular alternan, a polysaccharide composed of glucose units, the backbone of which consists of glucose units predominantly connected to each other by alternating α-1,3 and α-1,6 glycosidic bonds. The enzyme activity of the alternansucrases of the present invention can be measured as described in the Materials and Methods section and in the Examples.

As used herein, the terms "nucleotides", "polynucleotides", "nucleic acids" and oligonucleotides" are used interchangeably and include, but are not limited to RNA, DNA, DNA/RNA sequences of more than one nucleotide in either single chain or duplex form. The polynucleotide sequences of the present invention may be prepared from any known method including, but not limited to, any synthetic method, any recombinant method, any ex vivo generation method and the like, as well as combinations thereof.

The term "truncated" means to shorten either at the N' or C'-terminal of the amino acid or nucleic acid sequence. This shortening can be performed by using restriction enzymes, proteolytic enzymes, by synthetic synthesis and the like.

As used herein, the term "purified alternansucrase" means an alternansucrase possessing a degree of purity of at least 70% or 85% or 95%.

As used herein "ASR" stands for alternansucrase; "DP" stands for degree of polymerization; "CW" stands for cell wall binding-like repeats, "APY" stands for repetitive units of APY amino acids; "DSR" stands for dextransucrase; "GBD" stands for a glucan binding domain; "OA" stands for oligoalternan; "del" stands for delete and "OD" stands for oligodextran.

By "mammals" is meant any warm-blooded animal that has hair or fur, produces milk and bears live young.

By the term "consisting essentially of" when referring to nucleic acids or amino acids means that other minor ingredients or molecules can be present with the nucleic acids or amino acids sequences.

More specifically, the present invention relates to nucleic acids which encode a truncated alternansucrase or a mutated alternansucrase, a sequence complementary to whole or part of the above sequences or a sequence which hybridizes to the above sequences under stringent conditions, provided that the alternansucrase enzyme activity is maintained.

The stringent hybridization conditions are those as described By Sambrook et al, A Molecular Cloning Manual, $3^{rd}$ edition (2001) and occur under the following conditions:

Hybridization buffer: 2×SSC, 10× Denhardts solution (Ficoll 400 & PEG & BSA, ratio 1:1:1), 0.1% SDS, 5 mM EDTA, 50 mM Na$_2$HPO$_4$ 250 μg/ml herring sperm DNA, 50 μg/ml of tRNA or 0.25 M of sodium phosphate buffer, pH 7.2; 1 mM EDTA, 7% SDS;

Hybridization temperature T=60° C.

Washing Buffer: 2×SSC, 0.1% SDS

Washing temperature T=60° C.

Nucleic acid molecules which hybridize under stringent conditions with the nucleic acids of the present invention can, in principle encode alternansucrases from any microorganism such as from bacteria, gram-positive bacteria and in one aspect bacteria belonging to the genus *Leuconostoc*.

In a particular aspect the present invention relates to the nucleotide sequence in FIG. 1 (SEQ ID NO. 1) starting from a nucleotide at position 195 to the nucleotide at position 4241 (SEQ ID No. 2) or 4469 (SEQ ID No. 3) or a nucleotide sequence starting from a nucleotide at position 1218 to the nucleotide at position 4469 (SEQ ID No. 4) of SEQ ID No.1, a sequence complementary to SEQ ID Nos. 2 or 3 or 4 or a sequence that hybridizes to SEQ ID Nos. 2 or 3 or 4 under stringent hybridization conditions, provided that alternansucrase enzyme activity is retained.

In another aspect, the present invention provides a nucleic acid sequence in FIG. 1 (SEQ ID NO. 1), starting from a nucleotide at position 195 to the nucleotide at position 4241 (SEQ ID No. 2) or 4469 (SEQ ID No. 3) or a nucleotide sequence starting from a nucleotide at position 1218 to the nucleotide at position 4469 (SEQ ID No. 4) of SEQ ID No.1, wherein the nucleotides at positions 2220 to 2222 can be selected from AGT (SEQ ID No. 5), AGC (SEQ ID No. 6), TCT (SEQ ID No. 7), TCC (SEQ ID No. 8), TCA (SEQ ID No. 9), TCG (SEQ ID No. 10) and the nucleotides at positions 2226 to 2228 can be selected from AAT (SEQ ID No. 11) or AAC (SEQ ID No. 12) wherein T can be replaced by U, a sequence complementary to SEQ ID Nos. 5 to 12 or a sequence that hybridizes to SEQ ID Nos. 5 to 12 under stringent hybridization conditions provided that alternansucrase enzyme activity is retained.

In yet another aspect, the present invention provides a nucleic acid sequence in FIG. 1 (SEQ ID NO. 1), starting from a nucleotide at position 195 to the nucleotide at position 4241 (SEQ ID No. 2) or 4469 (SEQ ID No. 3) or a nucleotide sequence starting from a nucleotide at position 1218 to the nucleotide at position 4469 (SEQ ID No. 4) of SEQ ID No.1, wherein the nucleotides at positions 2496 to 2498 are selected from AGT (SEQ ID No. 13), AGC (SEQ ID No. 14), TCT (SEQ ID No. 15), TCC (SEQ ID No. 16), TCA (SEQ ID No. 17) or TCG (SEQ ID No. 18) and the nucleotides at positions 2499 to 2501 are selected from GAA (SEQ ID No. 19) or GAG (SEQ ID No. 20) and the nucleotides at positions 2502 to 2504 are selected from GTT (SEQ ID No. 21), GTC (SEQ ID No. 22), GTA (SEQ ID No. 23) and GTG (SEQ ID No. 24) wherein T can be replaced by U, a sequence complementary to SEQ ID Nos. 13 to 24 or a sequence that hybridizes to SEQ ID Nos. 13 to 24 under stringent hybridization conditions provided that alternansucrase enzyme activity is retained.

The present invention also relates to nucleic acids which encode an alternansucrase protein having at least 70%, or 80% or 90% sequence identity to that of SEQ ID No. 2 or SEQ ID No. 3 or SEQ ID No. 4, provided that the protein encoded by these sequences possesses alternansucrase enzymatic activity. Deviations from the basic nucleotide sequence of SEQ ID No. 2 or SEQ ID No. 3 or SEQ ID No. 4 can be produced by deletions, substitutions, insertions and recombinations, all of these methods are well known in the art and described by Sambrook et al, supra.

In another aspect the present invention relates to nucleic acids which encode a protein having at least 70%, or 80% or 90% sequence identity to that of SEQ ID No. 2 or SEQ ID No. 3 or SEQ ID No. 4 provided that the protein encoded by these sequences possesses alternansucrase enzymatic activity, wherein the nucleotides at positions 2220 to 2222 can be selected from AGT (SEQ ID No. 5), AGC (SEQ ID No. 6), TCT (SEQ ID No. 7), TCC (SEQ ID No. 8), TCA (SEQ ID No. 9), TCG (SEQ ID No. 10) and the nucleotides at positions 2226 to 2228 can be selected from AAT (SEQ ID No. 11) or AAC (SEQ ID No. 12) wherein T can be replaced by U.

In another aspect the present invention relates to nucleic acids which encode a protein having at least 70%, or 80% or 90% sequence identity to that of SEQ ID No. 2 or SEQ ID No. 3 or SEQ ID No. 4, provided that the protein encoded by these sequences possesses enzymatic activity, wherein the nucleotides at positions 2496 to 2498 are selected from AGT (SEQ ID No. 13), AGC (SEQ ID No. 14), TCT (SEQ ID No. 15), TCC (SEQ ID No. 16), TCA (SEQ ID No. 17) or TCG (SEQ ID No. 18) and the nucleotides at positions 2499 to 2501 selected from GAA (SEQ ID No. 19) or GAG (SEQ ID No. 20) and the nucleotides at position 2502 to 2504 are selected from GTT (SEQ ID No. 21), GTC (SEQ ID No. 22), GTA (SEQ ID No. 23) and GTG (SEQ ID No. 24) wherein T can be replaced by U.

The alternansucrase enzyme activity can be measured as set forth in the methods and examples section in the present application.

Oligonucleotides which can be used as, for example, as probes comprising SEQ ID Nos. 2 to 24 also form part of the present invention. Thus SEQ ID Nos. 2 to 24 can be labeled with radioactivity, enzymes, fluorescent markers and the like.

For genetic engineering in prokaryotic cells, the nucleic acids of the present invention or parts of these nucleic acids can by introduced into plasmids which permit mutagenesis or sequence modification by recombination of the nucleotide sequences. Standard methods to use these techniques are known in the art such as those described by Sambrook et al supra. The DNA fragments can also be connected to each other by adaptors or linkers and suitable restriction enzymes can be used to remove unwanted DNA sequences. Methods such as mutagenesis, primer repair restriction or ligation can be carried out to obtain the desired sequence with the appropriate insertions, deletions or substitutions.

Furthermore, the nucleic acid sequences of the present invention can also have attached thereto at the N- or the C-terminal nucleic acids encoding well-defined tags such as peptides of Poly-His, c-myc epitope or an HA-tag or small proteins such as bacterial GST, MBP, Thioredoxin, β-Galactosidase, VSV-Glycoprotein and the like. Nucleic acids encoding other protein tags include His-tag, T7-tag, S-tag, FLAG™ peptide, trpE, avidin/streptavidin, staphylococcal protein A or G, dihydrofolate reductase, cellulose binding domains, polycystein, polyphenylalanine and the like, an also be used in the present invention.

In one aspect, a nucleic acid encoding a thioredoxin is fused to the N-terminal nucleic acid sequences of the present invention and a His-x6 tag to the C-terminal nucleic acid sequences.

The nucleic acids of the present invention can be operably linked to a transcriptional unit comprising (1) elements having a regulatory role in gene expression such as promoters or enhancers (2) a structural or coding sequence which is transcribed into mRNA and translated into the protein and (3) appropriate initiation and termination signals.

Many suitable expression control sequences are known in the art. General methods of expressing recombinant proteins are also known and are exemplified in R. Kaufman, *Methods in Enzymology* 185, 537-566 (1990).

Promoter regions that can be used in the vectors of the present invention include lacL, lacZ, T3, T7, gpt, lambda PR, trc and arabinose.

The present invention further relates to vectors, in particular plasmids, cosmids, viruses, bacteriophages and other vectors commonly known in the gene technology art, which contain the nucleic acid sequences of the present invention. In one aspect of the present invention, the vectors are plasmids and can be selected from [pCR2.1-TOPO], [pUni/V5-His-TOPO], [pCRT7-E], [pGEX-6P-3], [pYes2.1-E], [pGEM-T] and [pBad/Thio TOPO]. In another aspect the present invention provides the plasmid vectors [pBad asr C-del bis], [pBad asr C-del bis ΔThio], [pBad asr core 1425] and [pBad asr C-del 1349].

The expression of the nucleic acids of the present invention can be in prokaryotic or eukaryotic cells. Examples of suitable cells include, but are not limited to VERO cells, HELA cells such as ATCC No. CCL3, CHO cell lines such as ATCC CCL61, COS cells such as COS-7 cells and ATCC No. CR: 1650 cells, W138, BHK, HepG2, 3T3 such as ATCC No. CRL6361, A549, PC12, K562 cells, 293 cells, Sf9 cells such as ATCC No. CRL1711, Cv1 cells such as ATCC No. CCL70 and JRKAT cells such as ATCC Tib152.

Other suitable cells that can be used in the present invention include, but are not limited to, prokaryotic host cell strains such as *Escherichia coli, Bacillus subtilis, Salmonella typhimurium*, or strains from the genera of *Pseudomonas, Streptomyces* and *Staphylococcus*, parasites such as *Apicomplexan* parasites (*Plasmodia, Toxoplasma, Cryptosporidia*) *Leishmania* or *Trypanosoma*.

Further suitable cells that can be used in the present invention include yeast cells such as those of *Saccharomyces* such as *Saccharomyces cerevisiae* or *Pombe, Pichia pastoris* and eukaryotic cells (plant cells, CHO cells and the like).

In yet another aspect the cells used for expression of the nucleic acids of the present invention are from *Escherichia coli* and the strains are selected from JM109, BL21(DE3) pLysS, Top 10 or Pir1. In another aspect the cells are from *Saccharomyces cerevisiae* and the strain is INVsc.

The present invention provides host cells transformed with the above-described nucleic acid sequences or with the vector described above and to cells descended from these transformed cells and containing the vector or nucleic acid sequences described herein. An example of the host cells provided by the present invention are *Escherichia coli* host cells in which the truncated or mutated alternansucrase can be secreted. The preparation of these host cells is well known to those of skill in this art.

The transformation of the host cells containing the DNA encoding the truncated or mutated alternansucrase can be carried out by culturing in nutrient media meeting the requirements of the particular host cell that is used such as pH, temperature, salt concentration, antibiotics, vitamins trace elements and the like.

Proteins, biologically active fragments thereof, as well as mutated proteins which are encoded by the nucleic acid molecules of the present invention and their methods for preparation are also encompassed by the present invention. Thus, the present invention provides a method for the preparation of a mutated or truncated alternansucrase, said method comprising:

(a) culturing a host cell comprising a truncated or mutated nucleic acid sequence described in the present invention under conditions permitting the expression of an alternansucrase; and (b) isolating said alternansucrase from the culture medium.

More specifically, the nucleic acid sequence can be selected from SEQ ID Nos. 2 to 24.

In addition to their isolation the alternansucrases of the present invention can be further purified after isolation. In this respect, conventional purification methods can be used such as precipitation, ion exchange chromatography, affinity chromatography, gel filtration, HPLC Reverse phase chromatography and the like. In one aspect, the truncated or mutated aternansucrase described in the present invention can be purified using a resin that is charged with nickel, due to the His tag.

If the isolated alternansucrase is insoluble, the protein can be treated with urea and the protein can be renatured by dialysis in a specific buffer.

Yet another aspect of the present invention is the provision of alternansucrase proteins consisting essentially of the amino acid sequence of FIG. 1 (SEQ ID NO. 25) from amino acid at position 1 to amino acid at position number 1349 (SEQ ID No. 26) or 1425 (SEQ ID No. 27) or from amino acid at position 342 to amino acid at position 1425 (SEQ ID No. 28). Homologous amino acid sequences, i.e., the degree of sequence similarity between amino acid sequences are also encompassed by the present invention. More specifically the present invention encompasses amino acid sequences that have 90% or 95% or 98% sequence similarity to SEQ ID Nos. 26 to 28, provided that these proteins retain alternansucrase enzyme activity.

In another aspect, the protein can be synthesized using the method of Merrifield, R. B. 1963, since the amino acid sequences are set forth herein. Therefore, synthetically synthesized alternansucrase proteins are another aspect of the present invention.

The present invention also provides mutant alternansucrases called NK676SN and YDA768SEV, in which the Asn and Lys amino acids at position 676, 678 are replaced with Ser and Asn respectively (SEQ ID No. 29) and the amino acids Tyr, Asp and Ala at position numbers 768 to 770 are replaced by Ser Glu and Val (SEQ ID No. 30).

These mutant alternansucrases can be used to synthesize specific oligosaccharides with different degrees of polymerization. For instance, the NK676SN mutant, when subjected to an acceptor reaction in which maltose is added to the reaction medium containing the enzyme and an appropriate buffer, oligodextrans and oligoalternans are produced. The yields of both of these compounds are similar to that using the truncated alternansucrase of the present invention. However, the oligosaccharides that are synthesized by the NK676SN mutant have identical structure to the truncated alternansucrase, this mutant synthesizes 140% more oligosaccharides than the truncated alternansucrase under polymerization conditions (sucrose only).

Moreover, the YDA768SEV mutant in the acceptor reaction produces less oligoalternans ($\alpha$-1,6 and $\alpha$-1,3 alternate glucosyls, more oligodextrans ($\alpha$-1,6 glucosyls) are synthesized than by a control dextransucrase, with the exception for an oligoalternan having a degree of polymerization of 4 (OA4). In this instance the YDA768SEV mutant produced a yield of 46% of OA4 compared to 22% for the truncated alternansucrase. This mutant also produces low polymer amounts and principally oligosaccharides, which are produced in an amount 50% greater when compared to the truncated alternansucrase.

It should be noted that specific truncations of the alternansucrase, which are truncated too short in the ASR (carboxy terminal) such as a truncation from nucleic acids of SEQ ID NO. 1 starting from nucleotides at position 195 to the nucleotide at position 4064 (SEQ ID NO. 31) and the protein counterpart from amino acid at position 1 of SEQ ID NO. 25 to amino acid at position 1290 (SEQ ID NO. 32) or nucleic acid 1218 to 4064 (SEQ ID No. 33) and amino acid 342 to 1290 (SEQ ID No. 34) are inactive forms of the enzyme. However, the examples and the content of the present application as a whole provides the skilled artisan with sufficient information to provide a multitude of activated truncated alternansucrases.

Fusion proteins having a protein tag, as described above, are also encompassed by the present invention. In this regard, the mutated or truncated proteins of the invention can be fused to at least one protein tag.

The preparation of alternan and/or fructose using the truncated or mutated alternansucrase of the present invention is yet another aspect of this invention. More specifically, alternansucrase-secreting microorganisms can be cultured in sucrose-containing medium leading to the synthesis of alternan or oligoalternans and fructose in the culture medium. The alternan and the fructose can then be further isolated from the culture medium by conventional methods such as ultrafiltration, nanofiltration, liquid chromatography and the like.

Alternatively, the truncated or mutated alternansucrase described herein can be subjected to purification and then used in a method to produce alternan, oligoalternans and/or fructose.

The fructose produced in the enzymatic reaction can be used, for example, to isolate fructose-containing syrups. The alternan can be used as a carrier of pharmaceutically active ingredients, blood plasma extenders, additives in the textile, cosmetics and food industry and/or as a substitute for gum Arabic.

An important application for hydrolysed alternan or synthesized oligoalternans is potential prebiotic properties and osteoporosis prevention:

Oligosaccharides have been traditionally used in food, animal feed, pharmaceutical and cosmetic industries as sweeteners, stabilizers or bulking agents (Monsan, P., Paul, F., *FEMS Microbiology Reviews*, 16, 187-192, (1995)). For the past 15 years, a new field of application based on the prebiotic properties of some such non-digestible molecules has developed (Gibson, G. R., Roberfroid, M. B., *J. Nutr.*, 125, 1401-

1412, (1995)). Indeed, oligosaccharides as prebiotics retained attention for their ability to resist the attack of digestive enzymes and to enhance the growth of "health promoting" bacteria (mainly *Bifidobacteria* and *Lactobacilli*) in the intestinal tract. This concept greatly stimulated the emergence of a prebiotics industry, which has grown rapidly to provide oligomers such as fructo-oligosaccharides, lactulose, galacto-oligosaccharides, xylo-oligosaccharides, soybean oligosaccharides or isomalto-oligosaccharides, almost always obtained via biological processes or plant extraction. Today, the research effort in this field is focused on the production of new oligosaccharide structures, the so-called "second generation of prebiotics", with new physical-chemical properties and possible different and more specific bioactivities (Tannock, W. G. *Probiotics and Prebiotics: Where are we going?*, Caister Academic Press, Wymondham, UK 2002.)

In this context, glucansucrases from lactic acid bacteria are very attractive tools. These transglycosidases are classified from sequence similarities in the family 70 of glycoside hydrolases (Coutinho, P. M. and Henrissat, B., available via the worldwide web at HTTP address afmb.cnrs-mrs.fr/CAZY/, 1999); (Monchois, V., Remaud-Simeon, M., Russell, R. R., Monsan, P., Willemot, R. M., *Appl. Microbiol. Biotechnol.,* 48, 465-472 (1997)); (Arguello-Morales, M. R., Remaud-Simeon, M., Pizzut, S., Sarcabal, P., Willemot, R., Monsan, P., *FEMS Microbiol. Lett.,* 182, 81-85 (2000)); (Bozonnet, S., Dols-Laffargue, M. Fabre, E., Pizzut, S., Remaud-Simeon, M., Monsan, P., Willemot, R. M., *J. Bacteriol.,* 184, 5753-5761 (2002)).

Thus, the present invention provides a method to produce alternans or oligoalternans, said method comprising; reacting the truncated or mutated alternansucrase of the present invention with maltose thereby producing alternans or oligoalternans.

In another aspect, the present invention provides a composition comprising any one of SEQ ID NOS. 26 to 30 and an acceptable vehicle. This acceptable vehicle can, for example, be selected from saline, adjuvants and the like. Examples of adjuvants include muramyl peptides, alum, montanide and the like.

The truncated or mutated alternansucrase can either be the purified protein, a recombinantly produced protein or a synthetically produced protein.

A number of embodiments of the invention have been described. Nevertheless, it will be understood that various modifications may be made without departing from the spirit and scope of the invention.

Materials and Methods

1. MICROORGANISM CULTURE 1.1. Strains: The following strains were used in the examples:

| Strain | Characteristics | Reference |
|---|---|---|
| *E. coli* JM109 | endA1, recA1, gyrA96, thi, hsdRZ17, ($r^-_k$, $m^+_k$), relA1, supE44, Δ(lac-proAB), [F', traD36, proAB, lacI$^q$Z ΔM15] | Promega |
| *E. coli* BL21(DE3)pLysS | F$^-$, ompT, hsdS$_B$, ($r_B^- m_B^-$), gal, dcm, (DE3), pLysS | Invitrogen |
| *E. coli* TOP10 | F$^-$, mcrA, Δ(mrr-hsdRMS-mcrBC), φ80lacZ ΔM15, ΔlacX74, recA1, deoR, araD139, Δ(ara-leu)7697, galU, galK, rpsL, (Str$^R$), endA1, nupG | Invitrogen |
| *E. coli* PIR1 | F$^-$, Δlac169, rpoS(Am), robA1, creC510, hsdR514, endA, recA1, uidA(AMluI), ?plr-116 | Invitrogen |
| *S. cerevisiae* INVSc | MATα, his3 Δl, leu2 trpl-289 ura3-52<br>MATα, his3 Δl, leu2 trpl-289 ura3-52 | Invitrogen |

The *E. coli* BL21(DE3)pLysS, *E. coli* TOP10 and *E. coli* JM109 strains were used for expression of the asr gene. Plasmid pLysS has a p15A origin of replication and confers chloramphenicol resistance. This plasmid encodes T7 lysozyme which can eliminate basal expression of the gene placed under the control of the T7 promoter by inhibiting the low level of T7 RNA polymerase present.

The *E. coli* TOP 10 strain was used in "TOPO TA cloning" and "TOPO XL" kits, allowing α-complementation and thus blue-white test screening of the clones.

The *E. coli* PIRI strain was used in the "Echo Cloning System"; it allows replication of the plasmid containing the R6Kγ origin of replication.

The *S. cerevisiae* strain was used for expression of the asr gene in the yeast.

1.2 Vectors: The following vectors were used:

| Plasmid | Size (kbp) | Characteristics | Reference |
|---|---|---|---|
| [pCR 2.1-TOPO] | 3.9 | resistance to ampicillin and to kanamycin α-complementation | Invitrogen TOPO TA cloning |
| [pUni/V5-His-TOPO] | 2.3 | resistance to kanamycin; R6kγ Epitope V5 origin of replication; His tag in fusion | Invitrogen Echo Cloning System |
| [pCRT7-E] | 2.6 | resistance to ampicillin and to zeomycin T7 promoter and terminator | Invitrogen Echo Cloning System |
| [pGEX-6P-3] | 4.9 | resistance to ampicillin; lactose promoter glutathione S-transferase (GST, in fusion | Amersham Pharmacia |
| [pYes2.1-E] | 5.8 | uracil auxotrophy; resistance to ampicillin 2μ origin of replication; inducible GAL1 promoter | Invitrogen |

-continued

| Plasmid | Size (kbp) | Characteristics | Reference |
|---|---|---|---|
| [pASR] | 9.4 | pGEM-T (Promega) + asr of *L. mesenteroides* NRRL B-1355 cloned under own promoter resistance to ampicillin | Arguello-Morales, Supra |
| [pBad/Thio TOPO] | 4.5 | resistance to ampicillin; arabinose promoter; thioredoxin in 5' fusion; V5 epitope and polyhistidine marker in 3' fusion | Invitrogen |
| [pUni/pCRT7 asr C-del] | 9.1 | asr gene deleted at 3' inserted into pUni and recombined with pCRT7; T7 promoter | This study |
| [pUni/pGex asr] | 13.4 | asr gene inserted in pUni and insertion of pGEX to place gene under the lactose promoter and in fusion to (GST) | This study |
| [pUni/pYes-asr 8bp] | 14.2 | asr gene inserted into pUni and recombined with pYes; galactose promoter | This study |
| [pBad asr] | 10.6 | whole asr gene cloned into [pBad/Thio TOPO] vector | This study |
| [pBad asr var-del] | 9.6 | asr gene deleted at 5' cloned into [pBad/Thio TOPO] vector | This study |
| [pBad asr C-del] | 8.3 | asr gene deleted at 3' cloned into [pBad/Thio TOPO] vector | This study |
| [pBad asr core] | 7.3 | asr gene deleted at 5' and 3' cloned into [pBad/Thio TOPO] vector | This study |
| [pBad asr C-del bis] | 8.7 | asr gene deleted at 3' cloned into [pBad/Thio TOPO] vector. Identical deletion to [pUni/pCRT7 asr C-del] | This study |
| [pBad asr C-del bis ΔThio] | 8.4 | identical to [pBad asr C-del bis] with the gene encoding thiorexoxin eliminated | This study |

1.3 Culture Conditions

1.3.1 Liquid Medium

The *E. coli* strains were essentially cultivated on Luria Bertani (LB) medium in some cases buffered (LBT) with Tris HCl 100 mM pH 6.4, or richer 2XYT medium.

They had the following composition:

|  | LB | 2XYT |
|---|---|---|
| Bactotryptone | 10 g/l | 16 g/l |
| Yeast extract | 5 g/l | 10 g/l |
| NaCl | 10 g/l | 5 g/l |
| Agar (for solid medium) | 15 to 20 g/l | |

*E. coli* was also cultured on a mineral medium:

Mineral Culture Medium (in g/l)

| salts A | | Salts B (1000x) | | Oligo-elements (1000x) | |
|---|---|---|---|---|---|
| $K_2HPO_4$ | 8.00 | $MgSO_4$ 7 $H_2O$ | 1.00 | (500x) $MnSO_4$, $H_2O$ | 0.020 |
| $Na_2HPO_4$ | 2.00 | $CaCl_2$, 2 $H_2O$ | 0.04 | $CoCl_2$, 6 $H_2O$ | 0.008 |
| $NH_4SO_4$ | 0.75 | $FeSO_4$, 7 $H_2O$ | 0.04 | $ZnSO_4$, 7 $H_2O$ | 0.004 |
| $(NH_4)_2HPO_4$ | 8.0 | (sterilized | | $AlCl_3$ | 0.002 |
| $NH_4Cl$ | 0.13 | by filtration after acidification, HCl pH2) | | $Na_2MoO_4$, 2 $H_2O$ | 0.004 |
| | | Thiamine | 0.01 | $CuCl_2$, 2 $H_2O$ | 0.002 |
| | | | | $H_3BO_4$ | 0.001 |

The oligo-elements then salts B in the above order were added to 60 ml of a 100 g/l citric acid solution (non metabolizable). 50 ml of distilled water, then salts A were added and diluted to 1 liter. The pH was adjusted to 6.5 with ammonia. The culture was autoclaved at 120° C., for 20 min. After sterilization, glucose (10 g/l final) was added from a 700 g/l stock solution sterilized separately by autoclaving. The saccharose was added next (50 g/l final) from a 500 g/l solution sterilized separately by filtration, 0.22 μm.

Media used for yeast strain *S. cerevisiae* INVSc:

| YPD medium | | Minimal SC medium | |
|---|---|---|---|
| Yeast extract | 1% | YNB (Yeast Nitrogen Base) | 0.67% |
| Peptone | 2% | Glucose or raffinose | 2% |

-continued

| YPD medium | | Minimal SC medium | |
|---|---|---|---|
| Glucose | 2% | Adenine, arginine, cysteine, leucine, lysine, threonine, tryptophan, uracil | 0.01% |
| agar (for solid medium) | 2% | Aspartic acid, histidine, isoleucine, methionine, phenylalanine, proline, serine, tyrosine, valine | 0.005% |
| | | Agar (for solid medium) | 2% |

The minimal medium was prepared without uracil to select yeasts transformed by the pYES2.1 vector. The carbon source was added after sterilization. During galactose induction of the gene, the carbon source was 1% raffinose and 2% galactose.

If necessary, the media was enriched by the following antibiotics:
Ampicillin, 100 μg/ml final;
Kanamycin, 50 μg/ml final;
Chloramphenicol, 34 μg/ml final.

1.3.2 Solid Medium

The colonies can be cultivated on solid type LB medium to visualize polymer production. For this, the growth and induction conditions were as follows:
Solid LB
Sucrose, 50 g/l
Arabinose, 0.002% (w/v)
Growth at 30° C., polymer bubbles appear after 48 h.

1.4. Storage of Strains

The strains of *E. coli* were stored at 4° C. on solid media or at −80° C. in liquid LB medium containing 15% (v/v) of glycerol.

1.5. Preparation of competent cells

The strains of *E. coli* JM109 and Top 10 were rendered competent by treatment with DMSO using the protocol established by Inoue et al (Inoue H., Nojima H., Okayama H., High efficiency transformation of *Escherichia coli* with plasmids, *Gene*, 96, 23-28, 1990)).

The cells to be treated were cultivated at 18° C. in 50 ml of SOC medium, until the absorbance at 600 nm reached 0.6. The cells were then kept on ice for 10 min, and centrifuged (5000 g, 10 min, 4° C.). The residue was taken up in 14 ml of iced TB buffer, then incubated on ice for 15 min. The cells were then centrifuged (5000 g, 10 min, 4° C.) and the residue was resuspended in 4 ml of iced TB buffer to which 280 μl of DMSO had been added. The solution of competent cells was stored on ice for 10 minutes before being divided into 50 μl aliquots and stored at −80° C.

This protocol could produce transformation efficiencies of the order of $10^7$ to $10^8$ transformants per μg of plasmid.

| SOC medium: | | TB buffer: | |
|---|---|---|---|
| Tryptone | 20 g/l | Pipes | 10 mM |
| Yeast extract | 5.5 g/l | $CaCl_2$ | 15 mM |
| NaCl | 10 mM | KCl | 250 mM |
| KCl | 10 mM | $MnCl_2$ | 55 mM |
| $Mg^{2+}$ | 10 mM | added extemporaneously | |
| Glucose | 20 mM | | |

2. MOLECULAR BIOLOGY TECHNIQUES 2.1. Extraction of Plasmidic DNA

Plasmid was extracted and purified using the "QIAprep" kit sold by Qiagen, which is based on the alkaline lysis method (Sambrook et al, 1989).

2 ml cultures were carried out over 15 hours in LB medium supplemented with ampicillin (100 μg/ml). The cells were centrifuged for 5 min at 10,000×g. They were then resuspended in an isotonic solution and lysedwith a sodium hydroxide/SDS solution (NaOH 0.2N, SDS 1%). The lysate was neutralized then was brought to high saline concentrations. The precipitate was settled by centrifuging (10 min at 10,000×g). The supernatant was then deposited on a micro-column which contained a silica membrane on which the plasmidic DNA was retained. DNA fixing was followed by a step for washing with a solution containing ethanol. The plasmid was eluted with 50 μl of water or TE buffer.

TE 1× Buffer:

| Tris HCl, pH 7.5 | 10 mM |
|---|---|
| EDTA pH 8.0 | 1 mM |

2.2. Primers

| Name | Sequence | Restriction site (bold) |
|---|---|---|
| Bad dir | GCCATGGAACAACAAGAAACAGTTACCCGT | NcoI |
| Bad inv | AGCTTGCAAAGCACGCTTATCAATCCATAGC | — |
| Bad var del | GCCATGGTAACAGGGTTGCAAACTATTTCAGGA | NcoI |
| Bad C-del | CGTTTTTGCAATGTTAAAATACTGGTTAGTAGCCCA | — |
| Echo dir[b] | ATGAAACAACAAGAAACAGTTACCCG | — |

-continued

| Name | Sequence | Restriction site (bold) |
|---|---|---|
| Echo inv C-del | CCTCGAGACATAGTCCCATCAACATT | — |
| Bad C-del 2 | CCCTCGAGACATAGTCCCATCAACATTTAAGG | — |
| For AsrCat | GGAAATAACAGAAAACTAGGACGTCAACC | AalII |
| Rev AsrCat | CAAATTTAAATAGTCCTCGAGACATAGTCCC | XhoI |
| Rev Asr NK676SN | CTGAGGATCGTTTCCGGACCAGTCTTC | BspEI |
| Rev Asr YDA768SEV | CTAATTGGATCCTGAACTTCGGAATCATGTGC | BamHI |
| ForDelLoop | CACTAATTCCGGAGACACTTCATTCTTAGATTCTTTC | BspEI |
| RevDelLoop | TAGTGTCTCCGGAAGACCTATATTGAGGTGCTAACTC | BspEI |
| CD dsrC dir | AATGGTTATGCGGCCGCTTCTTCATGGTATCGCCCTA | NotI |
| CD dsrC inv | CTTTAATGGCTCAAATACTCGAGGCAAAGGGGC | XhoI |
| CD dsrE dir | GATGGTTACGCGGCCGCTAACAGTTGGTATCGTCCTA | NotI |
| CD dsrE inv | AATGGTTCAAACACTCGAGGTCGTGGCGCTTGGTATGTAC | XhoI |
| CD dsrS dir | ACGGCTATGCGGCCGCTAGTTCATGGTATCGTCCAA | NotI |
| CD dsrS inv | TGGCTCTAACACTCCAGGTAAAGGTGCTGGATACGTATTG | XhoI |

SEQ ID NOS. 35 to 53 respectively.

2.3. PCR Conditions

2.3.1. Conventional PCR

Conventionally, for a final volume of 50 µl, the mixture for the PCR reaction was as follows:

| | |
|---|---|
| DNA (plasmidic extraction, diluted 1/10) | 1 µl |
| Direct and reverse primers (10 µM) | 1 µl each |
| dNTP (2.5 mM) | 4 µl |
| "High fidelity Expand buffer" (10X) | 5 µl |
| "high fidelity" enzyme mixture (3.5 U/µl) | 0.75 µl |
| milliQ water | to 50 µl |

The cycles for amplifying the asr gene (6 kb) were as follows:

| Initiation cycles: ×10 | 94° C. | 2 min | |
|---|---|---|---|
| | 94° C. | 10 s | |
| | 55° C. | 30 s | |
| | 68° C. | 6 min | |
| Cycles: ×15 | 94° C. | 10 s | |
| | 55° C. | 30 s | |
| | 68° C. | 6 min* | * in each cycle, the polymerization period was increased by 20 s |
| Termination | 68° C. | 15 min | |
| | 4° C. | ∞ | |

2.3.2. PCR with a Mega-Primer

The technique for inserting a mutation using the mega-primer technique initially necessitates amplification of the mega-primer (between 500 and 1000 bp). The reaction mixture was as follows:

| | |
|---|---|
| [pBad asr] (plasmidic extraction, diluted 1/10) | 1 µl |
| ForAsrCat or RevAsrCat depending on mutagenic primer (10 µM) | 1 µl |
| Primer (direct or reverse) containing the mutation (10 µM) | 1 µl |
| dNTP (2.5 mM) | 4 µl |
| pfU buffer (10X) | 5 µl |
| Turbo pfU polymerase | 0.5 µl |
| milliQ water | to 50 µl |

The conditions for amplifying the mega-primer with a size of less than 2.5 kb were as follows:

| Initiation cycles: ×30 | 94° C. | 5 min | |
|---|---|---|---|
| | 94° C. | 15 s | dehybridization of 2 DNA strands |
| | 52° C. | 30 s | hybridization of primers |
| | 72° C. | 2 min 30 | polymerization (knowing that $v_{pol}$ = 1 min/kb and that the gene to be amplified is less than 2.5 kb) |
| Termination | 72° C. | 7 min | |
| | 4° C. | ∞ | |

The mega primer, which contains the mutations to be introduced, was then purified on gel to properly eliminate the primers. The purified products were eluted in 30 µl of EB buffer (Qiagen). The mega primer was then used to amplify the whole cassette:

| | |
|---|---|
| [pBad asr] (plasmidic extraction, diluted 1/10) | 1 µl |
| ForAsrCat or RevAsrCat (10 µM) | 1 µl |
| Mega primer from preceding PCR | 8 µl |
| dNTP (2.5 mM) | 4 µl |
| "High Fidelity" Expand Mg$_2$Cl$_2$ buffer (10X) | 5 µl |

-continued

| "High Fidelity" enzyme mixture (3.5 U/µl) | 0.75 µl |
| milliQ water | to 50 µl |

The amplification cycles include a staged temperature drop to allow the mega primer to hybridize:

| Initiation | 94° C. | 5 min | |
| cycles: x30 | 94° C. | 15 s | dehybridisation of 2 DNA strands |
| | 70° C. | 5 s | hybridization of primers and mega primers |
| | 63° C. | 5 s | |
| | 52° C. | 30 s | |
| | 72° C. | 2 min 30 | polymerization (knowing that $v_{pol}$ = 1 min/kb and that the gene to be amplified is less than 2.5 kb) |
| Termination | 72° C. | 7 min | |
| | 4° C. | ∞ | |

2.4. Digestion of DNA

Digestion with the pair of enzymes Aat II and XhoI, was performed, which corresponds to an important step in ASR engineering protocols. XhoI was thus added first, and placed at 37° C. Thirty minutes later, the Aat II was added, and the reaction was continued for 30 minutes at 37° C.

2.5. Visualization of DNA

The DNA fragments (or plasmids) were analyzed by agarose gel electrophoresis (0.8% w/v) of agarose in TAE buffer (0.5×). The samples, deposited with 1× charge buffer into the wells, were migrated for 30 minutes in an electric field of 135 V. The size of the DNA fragments of the samples was determined using size markers of 1 to 10 kb ("1 kb step ladder", Promega). The gel was stained in an ethidium bromide solution (0.5 µg/ml) for 20 minutes, to visualize the DNA under a UV lamp ($\lambda$=254 nm).

| TAE buffer (50X) | | charge buffer 10X | |
| Tris | 24.2% (w/v) | glycerol | 50% (v/v) |
| glacial acetic acid | 5.71% (w/v) | bromophenol blue | 0.2% (w/v) |
| EDTA, 0.5 M, pH 8.0 | 10% (v/v) | xylene cyanol | 0.2% (w/v) |

2.6. Gel Purification of Digested DNA Fragments

The entire digestion solution was deposited on an agarose gel (0.8% (w/v), to separate the DNA fragments. To avoid ruining the DNA to be purified, the gel was cut to expose only a portion of the gel containing one track with the size markers to BET and UV, and one end of the well containing the separated fragments. After having verified that the DNA separation/digestion was correct, a notch in the gel exposed to UV allowed the corresponding fragment to be purified on the gel that was not exposed to UV to be located. The band, cut out blind, was then treated with a column purification kit, the QIA quick gel extraction kit sold by Qiagen.

2.7. Ligations

The procedure adopted used DNA ligase T4 (New England Biolabs) in very concentrated form (200 U). The ligase buffer was aliquoted.

Regarding the inserts, if the PCR amplification generated a major band, they were purified directly on the column following the supplier's protocol (Qiagen), to eliminate polymerase. They were then digested and purified again on the column to eliminate the restriction enzymes.

The typical reaction medium was as follows, for a 2.5 kb insert and a 6.2 vector for a final volume of 10 µl:

| purified vector (approx 45 ng/µl) | 4 µl |
| insert (approx 15 ng/µl) | 1 µl |
| ligase buffer (10X) | 1 µl |
| DNA T4 ligase (400 U/µl) | 0.5 µl |
| milliQ water | 3.5 µl |

The tubes were placed in a bath at 16° C. for 30 minutes, then at 4° C. until transformation.

2.8. Cell Transformation

Cell transformation was carried out by thermal shock or by electroporation, following the supplier's protocol (Invitrogen). The cells used were rendered chemocompetent by a conventional $CaCl_2$ and DMSO protocol or purchased competent, to have a higher transformation efficacy. The commercial competent cells used were *E. coli* TOP 10 electrocompetent One shot® from Invitrogen. Electroporation was carried out with a Pulse Controller II and a Gene Pulser II from Biorad in a 0.2 cm electroporation tank, and the electric shock was carried out at 2500 V, 200 Ω and 25 µF.

The yeasts were transformed during their growth phase using a conventional thermal shock protocol in the presence of lithium acetate.

3. PRODUCTION OF RECOMBINANT PROTEIN

3.1. Preparation of Soluble and Insoluble Protein Fractions

The bacteria were cultivated in LB medium (or MM medium) supplemented with the suitable antibiotic. The cultures were generally 10% inoculated from a preculture that had reached an $A_{600\ nm}$ of 2. The cultures were grown in baffled Erlenmeyer tubes filled to a maximum of ⅕ of their total volume. They were placed at 30° C. or 23° C., with agitation. In the case of culture in MM medium, the carbon source was 1% glucose (w/v).

At the end of culture, the medium was centrifuged (10 min, 4,500×g, 4° C.). The cell residue was taken up in the breaking buffer to obtain an $A_{600\ nm}$ of 80. The cells were then broken by treatment with ultrasound, in the cold, using an ultrasound probe. The operation was carried out in 4 cycles, each constituted by 15 seconds of pulse, 30 seconds stop, 15 seconds pulse and 5 minutes stop on ice. The sonicate was centrifuged (20 min, 27,000×g, 4° C.) and the supernatant then corresponded to the "soluble protein fraction" containing almost all of the ASR. This protein extract conventionally contains 10 to 20 g/l of total proteins (Bradford assay with a BSA calibration curve). The sonicate residue was resuspended in the same volume as the soluble protein fraction. This was the "insoluble protein fraction."

| breaking buffer | |
| Sodium acetate buffer, pH 5.4 | 20 Mm |
| 100% Triton | 1% |

4. ANALYSES OF PROTEINS BY ELECTROPHORESIS

The proteins were separated on a polyacrylamide gel constituted by a gel with a concentration of 4% and a separation gel at 6, 8 or 12% (w/v). The samples were incubated for 5 min at 95° C. in the presence of a denaturing solution (1×). The prestained marker comprised proteins of 250, 150, 100, 75, 50, 37, 15 and 10 kDa (Prestained Protein standard, Precision BioRad). The well volumes were 20 µl. Migration was effected under a constant tension of 100V.

Composition of gels and buffers:

| Concentration gel | | separation gel | |
|---|---|---|---|
| acrylamide/bis-acrylamide (37.5:1) | 4% (v/v) | | 8% (v/v) |
| Tris HC,l pH 6.8 | 125 mM | Tris HCl pH 8.8 | 375 mM |
| SDS | 0.1% (w/v) | | 0.1% 9 w/v) |
| TEMED | 0.2% (w/v) | | 0.2% (w/v) |
| Ammonium persulfate | 0.1% (w/v) | | 0.1% (w/v) |
| Denaturing solution (5×) | | migration buffer (5×) | |
| Tris HCl, pH 8.8 | 40 mM | basic Tris | 15.1 g/l |
| Glycerol | 50% (v/v) | Glycine | 72 g/l |
| SDS | 10% (w/v) | SDS | 5 g/l |
| Bromophenol blue | 0.04% V/v) | adjusted to pH 8.3 with HCl | |
| EDTA | 4 mM | | |
| β-mercaptoethanol | 20% (v/v) | | |

4.1. Staining Total Proteins

4.1.1. Staining with Coomassie Blue

The gel was placed in a solution composed of acetic acid (10%, v/v), methanol (30%, v/v) and Coomassie blue (0.2%, v/v). Staining was carried out over a minimum of 1 hour. Decoloration was then carried out by washing the gel several times in a solution of acetic acid (10%, v/v) and ethanol (30%, v/v).

Staining with Silver Nitrate by PhastGel

Silver nitrate stained gels were produced on a system of specific gels (PhastGel, Pharmacia). The acrylamide concentration was a gradient of 8-25%.

4.2. Zymogram

The detection level for this method was 0.01 ASR units per milliliter of sample deposited on the gel (20 µl deposit).

The gel was placed for 3 times 20 minutes in a solution containing sodium acetate (20 mM, pH 5.4), Triton (0.1%, v/v) and CaCl$_2$ (0.05 g/l), at ambient temperature. This step allowed the buffer to be changed to avoid the denaturing conditions of migration. The gel was then incubated overnight at ambient temperature in the same solution supplemented with sucrose (100 g/l) so that the glucansucrases synthesized polymer. The glucans were then fixed for 30 minutes in a solution of ethanol (75%, v/v) then the gel was incubated for 1 hour in a solution of periodic acid (0.7%, w/v) and acetic acid (5%, v/v). Non specific stains were avoided by washing three times in succession for 20 minutes in a solution of sodium metabisulfate (0.2%, w/v) and acetic acid (5%, v/v). Finally, the gel was brought into contact with Schiff's reagent until the desired color (pink) appeared. The staining reaction was stopped by washing the gel successively in a solution of sodium metabisulfite (0.5%, w/v) and acetic acid (5%, v/v). To prevent the staining from being too rapid and the band from becoming more visible, the Schiff's reagent was diluted (by 1/2) with the last washing solution.

4.3. Western Blot

4.3.1. Transfer

The proteins from the acrylamide gel were transferred to a nitrocellulose or PVDF membrane immersed in transfer buffer under a tension of 50 V for 2 h.

| Transfer buffer: | |
|---|---|
| Tris | 25 mM |
| Glycine | 192 mM |
| Methanol | 20% (v/v) |
| adjusted to pH 8.3 with HCl | |

4.3.2. Detection of Anti-6×His and Anti-Thio

The detection protocol was as follows:

| | | |
|---|---|---|
| membrane saturation | PBS + BSA 3% | 1 h minimum |
| Washing | PBS + 0.05% Tween 20 | 3 × 15 min |
| incubation with primary antibody | 1/5000 in PBS + 0.2% BSA | 1 h |
| Washing | PBS + 0.05% Tween 20 | 3 × 15 min |
| incubation with secondary antibody coupled to AP (sigma) | dilution 1/5000 in PBS + 0.2% BSA | 1 h |
| Washing | PBS + 0.05% Tween 20 | 3 × 15 min |
| Revealing | BCIP/NBT (Sigma) to desired staining, then stop by adding EDTA | |

PBS corresponds to 20 mM PBS, pH 7.3. The primary mouse antibody was either anti-6×His or anti-Thio (Invitrogen) and the secondary antibody was anti-mouse antibody coupled to alkaline phosphatase.

5. Characterization of Activity

5.1. Assay of Activity: DNS Method

One ASR unit represents the quantity of enzyme which liberates one µmole of fructose at 30° C. under the following conditions:

| | |
|---|---|
| Saccharose | 100 g/l |
| sodium acetate buffer, pH 5.4 | 20 mM |

The enzymatic activity was measured by the liberation of fructose using the 3,5-dinitrosalicylic acid (DNS) method, which can assay reducing sugars (Sumner and Howell, *J. Biol. Chem* 108 51-54 (1935)). One volume of sample was mixed with one volume of reagent. After 5 min at 95° C., the tubes were placed on ice. After adding 10 volumes of water, the absorbance was read at 540 nm. The fructose calibration range was in the range 0 to 2 g/l.

| DNS assay reagent (store away from light): | |
|---|---|
| 3,5-dinitrosalicylic acid | 10 g/l |
| double sodium and potassium tartrate | 300 g/l |
| NaOH | 16 g/l |

5.2. Calculation of Glucooligosaccharide Production Yields

The apparent yield of glucooligosaccharides (GOS) does not take into account the concentration of the residual acceptor. The remaining substrates at the end of the reaction were considered to be non-recoverable.

$$\text{Apparent yield of total } GOS = \frac{GOS - \text{final}}{0.474 \times \text{sucrose} - \text{initial} + \text{acceptor} - \text{initial}}$$

6. ANALYTICAL METHODS

6.1. Turbidity

The concentration of biomass was determined by measuring the absorbance of the culture medium at 600 nm using a Safas (Monaco) spectrophotometer. The absorbance is in linear relationship with the concentration of biomass for values in the range 0.1 to 0.6 absorbance units. Dilutions of the reaction medium were thus carried out if necessary to fall into this region of linearity.

6.2. Protein Assay

The proteins were assayed by Bradford's method (*Anal Biochem* 72, 248-254 (1976)) based on displacement of the absorption maximum of an acidic solution of Coomassie blue G250c from 465 nm to 595 nm caused by the presence of proteins. The micro-Bradford technique was preferentially used because of the small quantities of extracted proteins. The calibration curve was produced using a bovine serum albumin (BSA) solution.

6.3. High Performance Liquid Chromatography (HPLC) Analysis

6.3.1. C18 Column

The apparatus used was a Hewlett Packard Series 1050 chromatograph which was connected to a Hewlett Packard Series 1047A refractomer. The injection volume was fixed at 20 µl. Data acquisition and integration was handled by HPChem software (Hewlett Packard).

The acceptor reaction products were analyzed (up to 5 g/l) on a C18 Ultrasep column, 4×250 mm (Bischoff Chromatography) under the following conditions:
Temperature: 22° C.
Eluent: ultrapure water
Flow rate: 0.5 ml/min Solutions of maltose, sucrose and fructose at concentrations in the range 1 to 5 g/l were used as standards. Since the sugar response factors were similar, they were extrapolated to oligosaccharides for which there were no standards.

6.3.2 Dionex Column

HPLC analyses was carried out on a Dionex CarboPac PA 100 column to identify the oligosaccharides synthesized by the polymerization reaction up to sizes of about DP30. They were separated on a 4×250 mm column preceded by an identical support pre-column. Automatic injection (20 µl) was carried out with an ICS 758 injector. Detection was of the three-pulse type using a pulsed amperometric detector (Electrochemical Detector ED40). Data acquisition and integration was handled by HPChem software (Hewlett Packard).

Solutions of fructose, glucose, sucrose, leucrose, turanose, trehalulose, maltulose, isomaltulose (or palatinose), maltose, nigerose, isomaltose, isomaltotriose and isomaltotetraose (5 to 100 mg/l) were used as standards. The samples were diluted in ultrapure water in a maximum total sugar concentration of 2000 mg/l.

The separation conditions were as follows:
Temperature: 22° C.;
Mobile phase (NaOH 150 mM): 1 ml/min;
Gradient: sodium acetate
6 mM to 600 mM in 60 min.

6.3.3. Permeation Columns on Jordi and Shodex Gel

The apparatus used was identical to that used for HPLC analyses on a C18 column.

The gel permeation columns allowed analysis of populations of polymers and oligosaccharides. The products were diluted to a maximum of 10 g/l in 50 mM of NaCl, and analyzed on two Shodex columns in series, OH PAK SB-804 and KB-803 (with the coarsest porosity column at the head) under the following conditions:
Temperature: 50° C.
Mobile phase (NaCl 50 mM): 1 ml/min.

The calibration curve was produced with 2000, 503, 70 and 10 kDa dextran and fructose.

Analyses on the Jordi 1000 and Jordi 100000 (Altech) columns were carried out independently on each 8×300 column with a Jordi 100000 type pre-column. The samples were diluted to 10 g/l in mQ water. The analysis conditions were as follows:
Temperature: 50° C.
Mobile phase water/DMSO (80/20): 0.6 ml/min.

The calibration curve was produced with 2000, 500, 162, 70 and 10 kDa dextran, maltoheptaose, maltotetraose, isomaltotetraose, sucrose and fructose. The Jordi 1000 column was adapted to determine the size of molecules with a molar mass in the range 180 to 10000 Da while the Jordi 100000 was more suitable for determining the size of molecules with a molar mass in the range 10000 to 2000000 Da.

6.4. Capillary Electrophoresis

6.4.1. Partial Polymer Acetolysis

Partial polymer acetolysis was carried out under the following conditions:

| | | |
|---|---|---|
| selective acetolysis: | 2 mg of polymer + 200 µl of solution A | 3 h at 40° C. |
| extraction with chloroform: | samples dried in nitrogen +100 µl of mQ water +100 µl of chloroform, and agitate to emulsify recover upper phase | ×3 |
| deacylation: | +300 µl of solution B overnight at 37° C. vacuum dry samples | |

| solution A: | solution B: |
|---|---|
| 400 µl of acetic acid | 500 µl of methanol |
| 400 µl acetic anhydride | 500 µl ammonium |
| 40 µl sulfuric acid | |

6.4.2. Derivatization

The samples were derivatized with APTS (Interchim) under the following conditions:

| | |
|---|---|
| 20 nmol of dehydrated sugar +0.6 µl of APTS, 0.2 M (i.e. 120 mol, viz. an excess with respect to sugar) +0.6 µl of sodium cyanoborohydride, 1 M | 1 h at 75° C. or 1 h 30 at 55° C. |

The samples were taken up in 50 µl of water then diluted to 1/20 prior to analysis.

The analyses were carried out on a P/ACE 5000 (Beckman Coulter) capillary electrophoresis system equipped with a 4 mW laser. Detection was carried out by laser induced fluorescence (excitation at 488 nm and emission at 520 nm). Separation was carried out on a silica capillary (47 cm×50 µm internal diameter). Injections were carried out by applying 3.45 kPa of pressure for 5 ms. The analysis conditions were as follows:

| | |
|---|---|
| temperature: | 25° C. |
| buffer: | acetic acid (1%, v/v), triethylamine 15 mM, pH 3.7 (electrophoretic mode) or lithium tetraborate, 20 mM at pH 9.15 (electroendosmotic mode) |
| applied tension: | 20 kV (electrophoretic mode or electroendosmotic mode) |

EXAMPLES

Example 1

Bacterial Strains and Growth Conditions

Native alternansucrase was obtained from *Leuconostoc mesenteroides* NRRL B-23192, a mutant strain of NRRL B-1355 which is enriched in alternansucrase (Smith et al *Journal of Industrial Microbiology & Biotechnology* 21, 37-45 (1998)). This strain was grown at 27° C. on standard medium as previously described by Dols et al *Carbohydr. Res.* 305, 549-559 (1997). Cells and other insolubles were recovered by centrifugation and used as a native alternansucrase source. Genomic DNA was extracted from *L. Mesenteroides* NRRL B-1355. The strains were provided by the NCAUR stock culture collection in Peoria, Ill., USA. *E. coli* One Shot TOP10 (Invitrogen) was used for transformation of constructed plasmids and for expression of truncated asr genes. Bacterial cells were grown on LB medium with 100 µg.ml$^{-1}$ of ampicillin. The induction was performed using 0.02% arabinose (w/v). Cells were harvested after 19 hr by centrifugation (4,500×g), 10 min. 4° C.) and resuspended to Abs $_{600\ nm}$ of 80 in lysis buffer before sonication (20 mM sodium acetate buffer pH 5.4, Triton X-100 1%, lysozyme 1 mg. ml$^{-1}$, DNAsel 5 mg.ml$^{-1}$). The protein extracts obtained were centrifuged at 27,000×g for 30 minutes at 4° C.). The supernatant corresponds to the soluble fraction and the pellet was resuspended in the same volume of lysis buffer to yield the insoluble fraction.

A. DNA Manipulations.

Restriction enzymes were purchased from New England Biolabs and used according to the manufacturer's instructions. DNA purification was performed using QIAquick (PCR purification and gel extraction) and QIAprep (plasmid purification) from Qiagen. Genomic DNA of *Leconostoc mesenteroides* NRLL B-1355 strain was extracted with a Blood and Cell Culture Kit from Qiagen. DNA sequencing was carried out by Genome Express (Grenoble, France). PCR reactions were set up using the Expand Long Template PCR System (Roche Diagnosis Corporation).

Example 2

Cloning and Expression of the asr Truncated Genes

Different genes were deleted at the 5' and 3' end (FIG. 3) were generated by PCR amplification with the aid of the primer "Bad dir" for the constructions [pBad asr] and [pBad asr C-del] and the primer "Bad var del" for the constructions [pBad asr var del] and [pBad asr core]. The reverse primers used were "Bad inv" for the constructions [pBad asr] and [pBad asr core]. (See, Material and Methods for the primer sequences).

The forward primers were designed to place the alternansucrase gene (hereinafter asr gene) in the same reading frame as the gene coding for the thioredoxin in the vector. The forward primers contain a NcoI restriction site (CCATGG) (SEQ ID No. 49) including a start codon designed to remove the thioredoxin. The reverse primers were designed to eliminate the stop codon in the asr gene (if it was present) and to facilitate the same open reading frame of the polyhistidine tag. The PCR products obtained were directly inserted in the vector pBad/Thio TOPO in the extremities presented a topoisomerase I that facilitated their ligation. The clones were sequenced to confirm that no misincorporation had occurred.

The [pBad asr], [pBad asr core], [pBad asr C-del] and [pBad asr C-del bis] plasmids corresponding to the ASR, ASR core, ASR C-del and ASR C-del bis products were respectively constructed with the following primer couples: Bad dir/Bad inv, Bad var del/Bad C-del, Bad dir/Bad C-del and Bad dir/Bad C-del 2 (See, Materials and Methods). To express the asr C-del gene the vector pBad was placed under the control of the arabinose promoter.

The construction [pUni/pCRT7 asr C-del] was made by amplifying the asr gene with the primers "Echo direct" and "Echo inverse C-del" (See Materials and Methods). The PCR product was ligated in the vector pUni and the construction was obtained by recombining with the pCRT7 vector permitting the expression in *E. coli* (Echo system). In this case the protein is produced as a fusion protein with the polyhistidine C-terminal tag.

The PCR product was directly ligated into the vector pBad/Thio TOPO, The new construction that was obtained was called [pBad asr C-del bis] (FIG. 4). The gene was placed under the control of the arabinose promoter and was fused with two genes coding for thioredoxin at the N-terminal and for the polyhistidine tag at the C-terminal. The gene coding for the thioredoxin can be eliminated, due to the introduction of a NcoI site at the ATG codon in the primer "Bad dir." A sole NcoI site present upstream for the gene coding for thioredoxin, is sufficient to digest the construction with the restriction enzyme NcoI to eliminate the fragment of the gene coding for thioredoxin. This manipulation permits the conservation of the initiation codon and maintains the asr gene under the control of the arabinose promoter.

The different constructions were transformed in *E. coli* Top 10 using LB medium and 0.2% arabinose (w/v) was added. The truncated ASR protein in the variable zone starting with amino acid 342 produced an enzymatic activity of 27 U.1$^{-1}$ in culture, thus a 66% loss of catalytic activity with respect to the native, whole ASR protein under the same conditions (82 U.1$^{-1}$) The sequencing of this construct revealed the presence of 4 new mutations, thus 3 reflects a new protein. These mutations are Ile435Val. Ile498Val and Met843Val. The first two mutations are in the variable zone, thus a region non primordial for catalysis, but the third mutation is located in the catalytic domain at the extremity of the sheet β8.

Example 3

Resolubilization of the Insoluble Aggregates

Resolubilization of the insoluble aggregates expressed in [pBad asr C-del bis] was undertaken. The insoluble fractions with enzyme activities less than 5 U.1$^{-1}$ where the presence of aggregates was suspected were subjected to the following procedure. A protein fraction of the culture at 21 hours, 30° C.

and induction of 0.002% arabinose having a enzyme activity of 0.186 U.l$^{-1}$ was solubilized in a 20 mM phosphate buffer containing 8 M urea, pH 8.0 for a period of one hour. The proteins were renatured by dialysis in a 20 mM sodium acetate buffer pH 5.4. This step was performed at different dilutions of the solubilized extract of 1/120, 1/55. 1/21 and 1/6 to reduce protein precipitation where the proteins were too concentrated after renaturation. The enzyme activity was then measured and resulted in an activity of 50 U.l$^{-1}$ thus a gain of a factor of 263.

Another experiment was performed in which the [pBad asr C-delete bis] construct was expressed in a culture at 23° C. and with 0.02% arabinose. The cells were cultured for 22 hours. Under these conditions, the new enzyme activity was elevated to 5,000 U.l$^{-1}$, a value of 120 times the amount expressed by the whole asr gene under the control of its proper promoter.

Example 4

Purification of ASR C-del bis Without Thioredoxin in Native Conditions

To obtain the purification of ASR C-del bis in its native conditions, the thioredoxin was eliminated from the construct by digesting [pBad asr C-del bis] with NcoI, that permits the excision of the gene coding for thioredoxin. The plasmid obtained after deletion then was religated to itself to obtain the construction [pBad asr C-del bis ΔThio], in which the asr gene was placed under the control of the arabinose promoter and produces ASR C-del bis in fusion with the tag polyhistidine. The construct was then cultured at 23° C. and induced by 0.02% arabinose. The enzyme activity of the product was 1,200 U.l$^{-1}$, in the soluble fraction. Analysis by Western blot confirmed that the thioredoxin was no longer present in the [pBad asr C-del bis ΔThio] construct.

Example 5

Purification of ASR C-del Bis

The purification is performed using the resin Probond (Invitrogen) charged with nickel. The polyhistidine tag, by its intermediate imidazole groups has an affinity for nickel at ph 6.0. To elute the protein attached to the resin, the pH is diminished to 5.3, either to add protons to the histidines, or add them to the imidazole which enters into competition with the polyhistidine tag. The protocol for purification was carried out at 4° C. as follows:

5 ml of Probond resin charged with nickel is equilibrated with 20 volumes of PBS (20 mM phosphate, pH 7.3 500 mM NaCl) containing 20 mM imidazole. 7 ml of the soluble protein fraction (FS) obtained after expression was diluted in PBS containing 20 mM imidazole and added to the resin. 7 ml of the soluble protein fraction was mixed with 5 ml of the resin equilibrated with nickel and incubated for one hour. The affluent was recuperated and poured into a flask (EF). The resin was then washed with 4 volumes of resin of PBS containing 20 mM imidazole. Six times. Fractions called LAV1 and LAV2 were recuperated. The protein was eluted in batch for 10 minutes using 0.3 volumes of resin of PBS containing 100 mM imidazole, four times. The eluent was recuperated (EL). The protein was again eluted in batch for 10 minutes with 0.3 volumes of PBS resin containing 250 mM imidazole, five times. The eluent was recuperated (EL). The following Table I illustrates the results:

TABLE I

| Fraction | Volume | Activity U · ml$^{-1}$ | Efficiency |
| --- | --- | --- | --- |
| FS | 7 ml | 36 | 100% |
| EF | 7 ml | 3.6 | 27% |
| LAV1 | 20 ml | 1.8 | 27% |
| LAV2 | 20 ml | 0.4 | 27% |
| EL3 | 1.5 ml | 1 | 29% |
| EL4 | 1.5 ml | 1.7 | 29% |
| EL5 | 1.5 ml | 6.6 | 29% |
| EL6 | 1.5 ml | 2.1 | 29% |
| EL7 | 1.5 ml | 6.9 | 29% |
| EL8 | 1.5 ml | 9.2 | 29% |
| EL9 | 1.5 ml | 7.3 | 29% |

The purity of the ASR C-del bis was analyzed for purity for fractions 5, 7, 8 and 9 on SDS-PAGE colored with silver nitrate. A protein having a molecular weight of 160 kDa corresponded to ASR C-del bis.

The specific activity was then determined for the purified ASR C-del bis using a Bradford dosage with a standard range of BSA. The concentration was 48 mg.l$^{-1}$ equivalents of BSA. The enzymatic activity was determined by measuring the reduced sugar liberated by sucrose under the following conditions:

20 mM sodium acetate buffer, pH 5.4
sucrose 100 g.l$^{-1}$
30° C.

The activity of the extract was 7.7 U.ml$^{-1}$. This permitted the estimation of the specific activity of ASR C-del bis.

As=160. mg$^{-1}$

That corresponded, under the conditions utilized a catalytic rate of reaction of ASR C-del bis estimated as 25.760 min$^{-1}$=429 $^{s-1}$, corresponding to 429 moles of fructose liberated by one mole of ASR C-del bis per second.

Example 6

Expression of the Alternansucrase Having a Truncated Glucan Binding Domain

Expression of the alternansucrase having a truncated glucan binding domain, produced in the construct [pUni/pCRT7 asr C-del bis] was compared to the construction of the entire asr gene [pASR]. The results are set forth in the Table II below:

TABLE II

| Construction | E. coli strain | Medium | Inducer | Time of culture after induction | A600 final | New Activity | Acivity in the soluble fraction | Forms degraded |
| --- | --- | --- | --- | --- | --- | --- | --- | --- |
| [pASR] | JM109 | LB | none | 14 hours | 2.2 | 40 | 3% | 5 forms |
| [pUni/CRT7 asr C-del bis] | BL21 | MM | IPTG 1 mM | 9.5 hours | 4.6 | 391 | 90% | 1 form |

As can be seen from the above Table II, the level of production of asr C-del bis are superior to those obtained with the enzyme under control of their proper promoter. Moreover, 90% of ASR C-del is present in the soluble form after breaking of the cells as compared with only 3% of the production of the entire enzyme. Moreover the zymogram revealed that the ASR C-del bis has only one active form of 157 kDA, while the entire ASR construct produced a minimum of 5 degraded active forms ranging from 188 to 130 kDa.

Example 7

Construction of Mutants by the Mega-Primer Method

The three target sites selectionned for mutagenesis were present in the fragment of the gene asr C-del bis between the site AatII and XhoI that are unique in the plasmid. This fragment constitutes the cassette for mutagenesis. It was amplified to start with using the primers "ForAsrCat" and RevAsrCat, present, respectively in the restriction site AatII and XhoI. These primers have the following sequences:

```
ForAsrCat:  5' GGAAATAACAGAAAACTAGGACGTCAACC 3'    (SEQ ID No. 54)

RevAsrCat:  5' CAAATTTAAATAGTCCTCGAGACATAGTCCC 3'  (SEQ ID No. 55)
``` where the bolded sequence is indicative of the respective restriction sites.

For each mutation a supplementary primer was designed. This primer carries the mutation that was to be inserted, but also a silent mutation which introduced a restriction site (X). The presence of this additional restriction site permitted to confirm the insertion of the mutation with respect to the wild plasmid.

In a first instance, the mutagenic primer associated with a primer at the extremity of the cassette permitted to amplify a fragment of the cassette. The product amplified by PCR was used as a mega-primer with the opposite primer of the cassette to amplify the entire cassette.

The hybridization of the two primers having different sizes was effectuated with a decrease by increments of the hybridization temperature at the time of PCR amplification. The mutated cassette was then digested with the restriction enzymes AatII and XhoI and ligated in the vector [pBad asr C-del bis] after the wild cassette was removed by digestion with the same restriction enzymes of AatII and XhoI.

The mutagenized primer "RevAsr NK676SN" and "RevAsr YDA768SEV" were used to construct other mutants.

The above mutants were subjected to colored SDS-PAGE analysis using silver nitrate, which verified that the proteins expressed a protein having a molecular weight of 160 kDA. The effects of the mutations with respect to the enzyme activity and the production of polymer are set forth in the Table III below:

TABLE III

| Variants | Residual activity in comparison with the activity of the wild construct | Production of the polymer bubble on plate |
|---|---|---|
| NK676SN | 9 | Yes |
| YDA768SEV | 1.4 | No |

A. Mutant with Conserved Regiospecificity: NK676SN

1-Acceptor Reaction

Tested for acceptor reaction (see procedure below), the NK676SN mutant produces the same oligosaccharides (oligodextrans and oligoalternans) in similar yields compared to the ASR C-del bis.

2-Polymer Synthesis

The NK676SN mutant was strongly affected for the polymer synthesis. It only produces oligosaccharides that are similar to the ones synthesized by the ASR C-del bis when considering the molecular weight (average degree of polymerization DP of 8) as shown by gel permeation analysis (FIG. 10). As suggest by the similar profile on HPAEC analysis, the oligosaccharides produced by ASR C-del bis and NK676SN mutant also have identical structures (FIG. 11). The mutant synthesizes 140% more oligosaccharides compared to the ASR C-del bis (FIG. 10).

B. Mutant with Modified Regiospecificity: YDA768SEV

1-Acceptor Reaction

Tested for acceptor reaction (see procedure below), the YDA768SEV mutant shows a modification in oligoalternan synthesis compared to the control ASR C-del bis (FIG. 13A). In general, the mutant produces less oligoalternans (α-1,6 and α-1,3 alternated linked glucosyls) but more oligodextrans (α-1,6 linked glucosyls) that are synthesized by the control DSR-S dextransucrase. The exception is for the OA4 (DP4 oligoalternan) that is produced with a yield of 46% compared to 22% for the ASR C-del bis. The YDA768SEV mutant behaved like it was indifferently able to transfer glucose on panose through an α-1,6 or α-1,3 linkage formation, but α-1,3 linked glucose residue (i.e., OA4) was not recognized and cannot play the role of an acceptor. As a consequence, (i) the OA4 accumulates, (ii) almost no oligoalternans of higher DP are synthesized and (iii) more oligosaccharides of the oligodextran series are produced (FIG. 13A). Thus the YDA768SEV mutant, in term of acceptor reaction products, is in-between the ASR C-del bis and the DSR-S.

2-Polymer Synthesis

The YDA768SEV mutant is also strongly affected for polymer synthesis. It produces low polymer amount and principally oligosaccharides (FIG. 10). Compared to the ASR C-del bis, the produced oligosaccharides (in polymerization condition) are of lower molecular weight as depicted on the GPC chromatogram. This was corroborated by HPAEC analysis showing shorter oligosaccharides but in higher amounts (FIG. 11). The comparison with a series of isomaltooligosaccharides (solely composed of α-1,6 linked glucosyls) suggests the high content of isomaltose, isomaltotriose and isomaltotetraose (FIG. 12). This result indicates that the high content of α-1,6 linkages obtained by the acceptor reaction also occurs in the oligosaccharides produced in the polymer synthesis conditions. The mutant synthesizes about 50% more oligosaccharides compared to the ASR C-del bis (FIG. 10).

Example 8

Activity Assay

Activities were determined using the soluble fraction of *E. coli* extract as no other glucansucrase or sucrose acting enzyme is produced by the strain. One glucansucrase unit is defined as the enzyme quantity that releases 1 μmol of fructose per minute at 30° C. in sodium acetate buffer 20 mM pH 5.4 and 100 g.l$^{-1}$ of sucrose. Released reducing sugars were quantified by the DNS method Sumner, J. B., Howell, S. F., *J. Biol. Chem.*, 108, 51-54 (1935) using fructose as reference.

Example 9

SDS PAGE and Zymogram

SDS PAGE were performed using the Nu PAGE Novex 3-8% Tris-Acetate Gels (Invitrogen). Gels were stained with Colloidal Blue Staining Kit (Invitrogen). The Prestained Precision Protein Standard were purchased from Bio-Rad Laboratories. Zymogram to detect in-gel activity were performed by protein renaturation with activity buffer, incubation in 100 g.l$^{-1}$ sucrose and detection of the synthesized polymers with Schiff's reagent (Sigma-Aldrich) (Miller and Robyt, *Anal. Biochem*, 156, 357-363 (1986)). About 0.1 units were loaded per well.

Example 10

Glucan Structure Analysis

Glucans were produced from sucrose using 0.5 U.ml$^{-1}$ of soluble enzyme in the conditions of the activity assay. Sucrose depletion was monitored by HPLC using C18 column. The reaction was stopped by incubating for 5 min at 95° C. The mixture was then centrifuged 5 min at 5,000 g to remove precipitated proteins. The reaction mixture was then analyzed on GPC column. In order to purify the polymers from the produced fructose and the synthesized oligosaccharides, they were precipitated by addition of 1 volume of ethanol, recovered by centrifugation, washed three times with water and freeze-dried.

Glucans were produced from sucrose using 0.5 U.ml$^{-1}$ of soluble enzyme in the conditions of the activity assay. Sucrose depletion was monitored by HPLC using a C18 column. The reaction was stopped incubation at 95° C. (for 5 min). The mixture was then centrifuged 5 mn at 5,000 g to remove precipitated proteins. The reaction mixture was then analyzed on a GPC column. In order to purify the polymers from the produced fructose and the synthesized oligosaccharides, they were precipitated by addition of 1 volume of ethanol, recovered by centrifugation, washed three times with water and freeze-dried.

The $^{13}$C NMR (75.468 MHz) spectra of the glucans were recorded on a Brucker Avance 300 spectrometer. Samples were dissolved at 50 mg.ml$^{-1}$ in D$_2$O. Spectra were recorded at 333 K, 1.445 s acquisition time and 12,288 scans were accumulated.

Glycosidic linkage composition was determined after polymer methylation according to the modified prodecure from Ciucanu and Kerek (Oefner, P. J., Chiesa, C., *Glycobiology*, 4, 397-412 (1994)). The methylated polymers were hydrolyzed with 2 N trifluoroacetic acid at 110° C. for 2 h, reduced with NaBD$_4$ 10 mg.ml$^{-1}$ in 1 m NH$_4$/C$_2$H$_5$OH, 1:1, v/v freshly prepared and peracetylated with acetic anhydride 1 h at 110° C. The alditol acetates were solubilized in cyclohexane before injection into a gas chromatograph (GC) and gas chromatograph coupled to mass spectrometer (GC/MS). GC was performed on a Girdel series 30 equipped with an OVI capillary column (0.22 mm×25 m) using helium at a flow rate of 2.5 ml.min$^{-1}$ with a flame ionization detector at 310° C. The injector temperature was 260° C. and the temperature separation program ranged from 100 to 290° C. with 3° C.min$^{-1}$ speed. GC/MS analysis was performed on a Hewlett-Packard 5889X mass spectrometer (electron energy, 70 cV) working in electron impact coupled with Hewlett-Packard 5890 gas chromatograph series II fitted with a similar OV1 column (0.30 mm×12 m). Polymer acetolysis was performed as described elsewhere (Chen, F. T., Evangelista, R. A., *Anal. Biochem.*, 230, 273-280 (1995)). The reaction products were analyzed by capillary electrophoresis in electroosmotic mode with borate buffer in conditions that allow separation of disaccharide regioisomers as described by Joucla et al. (Evangelista, R. A., Liu, M. S., Chen, F. T. A., *Anal. Chem.*, 67, 2239-2245 (1995)).

Polymer acetolysis was performed as described elsewhere Lindberg et al., *Adv Carbohydr. Chem. Biochem*, 31, 182-240 (1975). The reaction products were analyzed by capillary electrophoresis in electroosmotic mode with borate buffer in conditions that allow separation of disaccharide regioisomers as described by Joucla et al., (*G. Electrophoresis*, 25, 861-869 (2004)).

Example 11

Acceptor Reaction

The reaction was performed with 100 g.l$^{-1}$ of sucrose and 50 g.l$^{-1}$ of maltose in the same conditions as the activity assay. The oligosaccharides produced were analyzed by HPLC on C18 column.

Example 12

High Pressure Liquid Chromatography Analysis

Completion of sucrose consumption and production of oligosaccharides by acceptor reaction were monitored by HPLC on C18 column (5 μm, 250×4 mm, Bishoff chromatography) with deionized water at a flow rate of 0.5 ml.min$^{-1}$. Glucan formation was analyzed by HPLC on successive Shodex SB-805 HQ and SB-8025 HQ gel permeation chromatography column at 50° C. with flow rate of 1 ml.min$^{-1}$ of NaCl 50 mM. The calibration standards used were dextrans of 2,000 kDa, 500 kDa, 70 kDa and 10 kDa, isomaltotriose, sucrose and fructose.

Example 13

Design of ASR Truncated Forms

Cloning of the full length ASR encoding gene was first performed in fusion with the thioredoxine and 6×His encoding genes at the 5' and 3' ends, respectively. To investigate the functions of the CW and APY repeats in alternansucrase activity and specificity, three truncated forms were constructed (FIG. 3(*a*)): the ASR core (from aa 342 to aa 1290) corresponding to the catalytic domain without any CW repeat, the ASR C-del (from aa 1 to aa 1290), which is deleted of the GBD and the ASR C-del bis (1-1425), which contains 4 CW repeats but no APY repeats.

Example 14

Expression and Activity Levels of the Truncated Forms

The genes were over expressed in *E. coli* with equivalent expression levels as attested on the colloidal blue stained SDS-PAGE (FIG. 5A). However, most of the ASR and truncated ASR proteins were concentrated in insoluble inclusion bodies. The full length alternansucrase was produced at a level of 661 U.l$^{-1}$ of culture, which is a 4-fold increase compared to our previous work (Arguello-Morales, M. A., et al., *FEMS Microbiol. Lett.*, 182, 81-85 (2000). 74% of the total activity was recovered in the insoluble extract (FIG. 3(*a*)). In addition, the zymograms of this insoluble fraction (FIG. 5B; lane 5) revealed a high degradation pattern with a major active form at 245 kDa corresponding to the expected size. The soluble fraction of ASR, which represents only 26% of the total activity produced (lane 1) was also very much degraded with a major active form of about 168 kDa. Using antibodies against thioredoxine or 6×His tag on western blot revealed that the degradation occurred from both protein extremities (data not shown). The expression by BL21 strains deficient in the La and OmpT proteases did not reduce the degradation.

ASR core and ASR C-del showed a very low activity corresponding to less than 1% of the full length ASR activity. On the contrary, ASR C-del bis was produced at 774 U.l$^{-1}$, an activity level similar to ASR. In this case, the activity recovered in the soluble fraction accounted for 73% of the total activity produced (FIG. 3(*a*)). ASR C-del bis was much less degraded than the entire ASR as revealed by colloidal blue stained SDS-PAGE and zymograms (FIG. 5).

Several conclusions can be drawn from these results. First, the ASR core that was designed here did not keep its activity showing that ASR is more sensitive to deletion than the GTF-I from *S. downei* for which an active catalytic core was obtained (Monchois, V., Arguello-Morales, M., Russell, R. R., *J. Bacteriol.* 181, 2290-2292 (1999)). The activity of ASR C-del bis also indicates that the APY repeats (removed in this construction) are not essential to maintain the activity.

Figure 2:
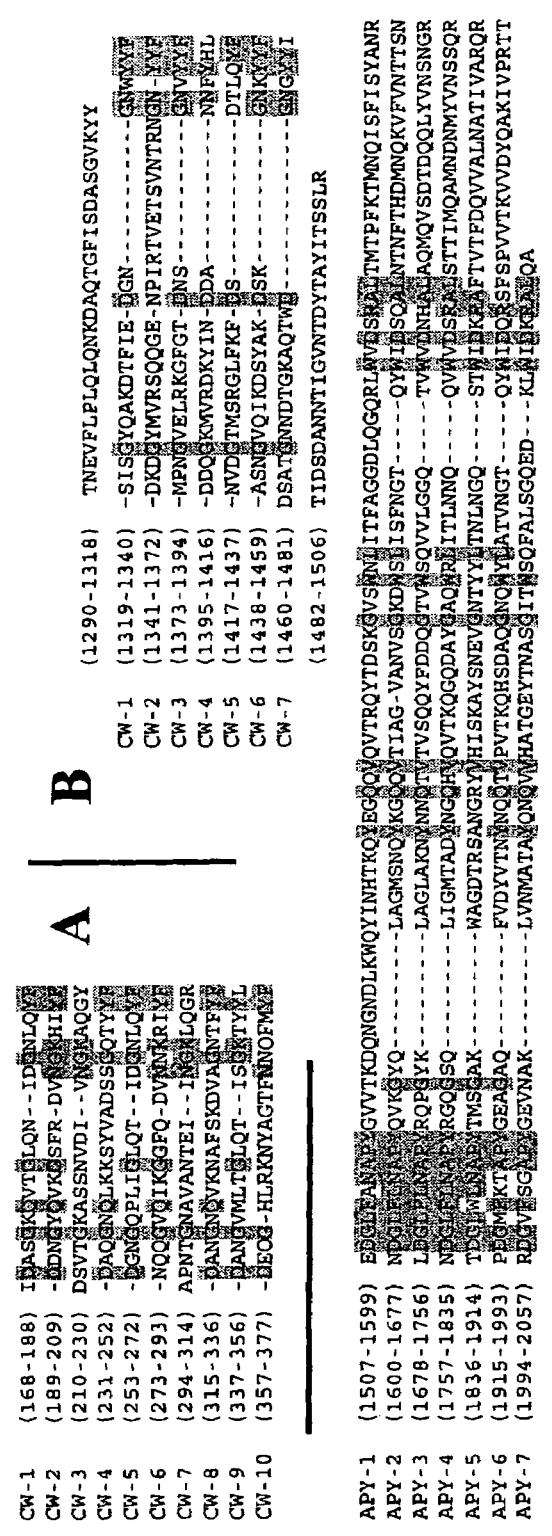

Opposed to this, the deletion of the 7 CW repeats (in ASR Cdel) provoked a high decrease of activity but the presence of four of them was sufficient to restore the activity at a level similar to that of the entire ASR (FIG. 2).

Furthermore, the multiple CW and APY repeats of the C-terminal end may be partly responsible for ASR degradation. Less degraded forms are produced in their absence. The sequence encoding these repeats contain numbers of codon clusters poorly represented in *E. coli*, which could induce an impediment to the translation process for the over-expressed gene.

Example 15

Purification of ASR C-del bis

ASR C-del bis deleted for the thioredoxin was purified by affinity chromatography on nickel-charged resin. This purification step enabled to eliminate all the contaminating proteins of *E. coli*. However, it also revealed the presence of two proteins of 147 and 134 kDa, which could not be separated (FIG. 5C). N-terminal amino acid sequencing of the two forms showed that the first form corresponds to the maturated ASR C-del bis devoid of the 39-residue signal sequence (theoretical MW calculated at 157 kDa) and the second form lacks the 102 next residues, starting at the amino acid 142 (theoretical MW calculated at 146 kDa). The cleavage site was located upstream of the N-terminal CW repeats between an alanine and a lysine (FIG. 2). Both bands cutted from electrophoresis gels catalyzed the formation of oligoalternans. The specific activity of the purified ASR C-del bis preparation was equal to 160 U.mg$^{-1}$. This corresponds to a turn-over of 404 s$^{-1}$ in the assay conditions, ranking ASR C-del bis in the most efficient glucose transferring enzymes compared to other glucansucrases. For example the *Streptococcus downei* MFe28 GTF-I has a kcat of 43 s$^{-1}$ Monchois et al *Appl. Environ. Microbiol.* 64, 1644-1649 (1998) and the *Neisseria polysaccharea* amylosucrase has a kcat of 1 s$^{-1}$ [(van der Veen, B. A. et al *FEBS Lett.*, 560, 91-97 (2004); Potocki, D. M., et al., *FEBS Lett.* 471, 219-223 (2000).

Example 16

Effect of the Deletion of the APY Motif on ASR Specificity

ASR is the only glucansucrase that possesses the APY motifs, which occurs successively seven times along the 550 last amino acids of the protein (FIG. 2B). This particularity among the glucansucrases reflects that APY repeats are a structural organization putatively involved in the alternating specificity of ASR. So, to examine the role of these repeats, the products formed by ASR C-del bis were compared to those synthesized by the native alternansucrase from *L. mesenteroides* NRRL B-23192, a strain that produces enzymatic extracts enriched in alternansucrase (Smith, M. R. et al, supra). First, gel permeation chromatography (GPC) chromatograms of the products obtained from 100 g.l$^{-1}$ sucrose showed that the both enzymes synthesize a polymer with an estimated molecular weight of 1,700 kDa corresponding to 10,500 glucosyl units (peak 1, FIG. 6). Both spectra also revealed the presence of oligosaccharides never described before with an estimated molecular weight of 1.3 kDa (peak 2, FIG. 6). These oligosaccharides are more concentrated in ASR C-del bis reaction medium. Obviously, the deletion of 3 of the last C-terminal CW repeats and APY repeats did not suppress polymerase activity showing that these repeats are not involved in polymer elongation. This was corroborated by the absence of any activating effect of the alternan when added from 0 to 1000 mg.l$^{-1}$ (data not shown) and by the absence of any detectable binding to dextran or alternan on western blot (Shah, D. S., Russell, R. R., *Microbiology*, 150, 1947-195616 (2004). The C-terminal part of glucansucrases was shown to play the role of glucan binding domain in streptococcal enzymes, which was also assumed for the *Leuconostoc* sp. glucansucrases. However, such evidence concerning the alternansucrase required revising the designation of GBD.

To figure out whether the APY motifs were involved in the ability to form α-1,6 and α-1,3 alternated linkages, the structure of the high molecular weight polymers separated from the oligosaccharides were analyzed. $^{13}$C NMR spectra were identical for both polymers and indicated the occurrence of α-1,6 linkages and of α-1,3 linkages (FIG. 7). These spectra are very similar to the spectrum of alternan synthesized by the native strain *L. mesenteroides* NRRL B-1355 (Seymour, F. K., Knapp, R. D., Chen, E. C. M., Bishop, S. H., Jeanes, A., *Carbohydrate Research*, 74, 41-1 (1979) described by Seymour et al. Quantification of glucosyl moieties was carried out by GC-MS after methylation and hydrolysis (Table IV) and the results are shown below.

TABLE IV

| | O-methyl-D-glucose | | | |
|---|---|---|---|---|
| | 2,3,4,6-tetra | 2,4,6-tri | 2,3,4-tri | 2,4-di |
| Native ASR | 13.9 | 28.7 | 47.4 | 10.1 |
| ASR | 14.1 | 30.2 | 45.8 | 9.9 |
| ASR C-del bis | 13.3 | 25.0 | 53.6 | 8.1 |

The results obtained are also very similar between polymers and are in accordance with the NMR spectra. About 50% of the residues are α-1,6 linked (2,3,4-tri-O-methylglucose) and 25% are α-1,3 linked glucosyls (2,4,6-tri-O-methylglucose). Considering the terminal glucosyl moiety (2,3,4,6-tetra-O-methylglucose) and branched 3,6-di-O-linked glucosyls (2,4-di-O-methylglucose), the unequal value attests that the polymers methylation was not complete. However the results are analogous to the structural analysis performed on alternan produced by *L. mesenteroides* NRRL B-1355 (Seymour et al supra) or by the heterologous alternansucrase (WO0047727). Indeed, the structure of the polymer produced by ASR C-del bis is consistent with the structure proposed by Seymour et al, composed of alternated α-1,6 and α-1,3 linkages in the backbone-chain and branches of consecutive α-1,6 linked glucosyl moiety to explain the "excess" of α-1,6 linked glucosyl residues. To check that the α-1,6 and α-1,3 linkages occur in an alternating pattern and not at random acetolysis of the polymers was performed. Since the α-1,6 linkages are 30 times more sensitive to acetolysis compared to the α-1,3 linkage (Lindberg, B., et al *Adv. Carbohydr. Chem. Biochem.*, 31, 185-240 (1975)), the reaction should essentially release glucose and nigerose Glcp-(α1→3)-Glc in the case of an alternated motif. The products of the reaction were analyzed by capillary electrophoresis in conditions that allow the separation of disaccharide regioisomers (Joucla, G., et al., *Electrophoresis*, 25, 861-869 (2004).

As expected the principal degradation products were glucose and nigerose. They were released in similar ratios for both the ASR C-del bis and ASR produced polymers (data not shown), thus probing the occurrence of α-1,6 and α-1,3 alternated motifs. According to the structure analysis, the polymer synthesized by the ASR C-del bis is identical to the one obtained with the native alternansucrase. It can be concluded that contrary to what was suspected, the APY motifs are not involved in the specific formation of alternating α-1,6 and α-1,3 linkage formation. However, the deletion of the repeats enabled to increase the solubility of the ASR C-del bis compared to ASR. Thus, these APY motifs are involved in the strong cell association previously pointed out for alternansucrase (Zahnley, J. C., Smith, M. R., *Appl. Biochem. Biotechnol.*, 87, 57-70 (2000).

In conclusion, the asr C-del bis construction shows several interesting features compared to the full length asr gene. First of all, the gene is well expressed by *E. coli*. In addition, the ASR C-del bis solubility is increased 3 fold compared to the full length ASR solubility. ASR C-del bis is also much less degraded compared to the full length ASR. It shows an incredibly high turnover compared to those of other glucansucrases. Moreover ASR C-del bis keeps its ability to synthesize alternan polymer showing that the APY motifs are not responsible for the alternating specificity. Therefore, ASR C-del bis is a very good candidate for further structure/function studies of ASR.

Example 17

Mutant Design and Construction

In absence of 3D structure of any glucansucrases from family 70 glycoside-hydrolases their primary sequences were compared in order to reveal sequence specificity of the alternansucrase that may be involved in the original catalytic process leading to alternated α-1,6 and α-1,3 linkages. Sequence comparison with the family 13 glycoside-hydrolases, the α-amylase family, led to propose a predicted catalytic domain putatively organized in a $(\beta/\alpha)_8$ barrel fold with a circular permutation. The putative catalytic residues D635, E673 and D767 of the alternansucrase are located in the barrel core at the extremity of β strands 4, 5 and 7 respectively (FIG. 8). It was assumed that the alternansucrase specificity may be engendered by distinctive amino acids located in this area which is in contact with substrates and products. The sequence comparison reveals 2 areas differing from the consensus usually found in the glucansucrases, downstream the catalytic amino acids E673 and D767 of strands β5 and β7 respectively (FIG. 8). In order to study their roles mutants were designated to recover the consensus: mutants NK676SN and YDA768SEV. The mutants were designed on the truncated alternansucrase variant ASR C-del bis. The activity of the mutants was respectively 9% and 1% of the ASR C-del bis activity. These mutants were analyzed according to their ability (i) to produce oligoalternans by acceptor reaction with maltose and sucrose and (ii) to synthesize oligosaccharides and polymer in presence of sucrose alone.

As demonstrated above, the NK676SN mutant has conserved regiospecificity, while the YDA768SEV mutant has modified regiospecificity.

Example 18

Further Truncated Alternansucrase Variants

The number of CW repeats required for maintaining alternansucrase specificity and efficiency were identified in this example.

Two new forms were constructed. One form had a truncation at amino acid 1349, which contains CW-0 and CW-1 (CW stands for cell wall binding repeats). Another form deleted of the variable region and containing the CW-0, CW-1, CW-2, CW-3 and CW-4. The results, as well as the particular truncations are set forth in FIG. 3(b).

An SDS PAGE analysis was then performed to ensure that the ASR truncated variants were produced to an equivalent protein level.

The ASR C-del bis contains 5 YY stretches of CW repeats and has a 22% higher activity compared to the full length ASR. The ASR C-del 1349 contains 2 YY stretches of CW repeats and shows a 30% decrease of activity compared to the full length ASR and also corresponds to an 42% decrease of activity compared to the ASR C-del bis construct.

The ASR core 1425 is truncated in the C-terminal part at amino acid 1425 like the ASR C-del bis, but is also truncated at amino acid 342 in the N-terminal part. The ASR core 1425 has a 23% higher activity compared to the ASR C-del bis or 50% higher compared to the full length ASR (see, results above).

The activity of variants was further investigated in the next Example 19.

Example 19

Polymer Synthesis by Variants

Sucrose was entirely consumed by all variants except for the ASR core 1425 that consumed 31% of sucrose.

ASR C-del 1349 synthesized polymer and oligosaccharides in similar amounts than the ASR and the ASR C-del bis do. (See, FIG. 14).

Concerning the ASR core 1425, no oligosaccharide was produced (FIG. 14); only polymer in equivalent amounts as the other variants. A previous kinetic study of product synthesized by the control ASR C-del bis revealed that at the stage of 30% sucrose consumption the amount of synthesized products are equally divided into polymer and oligosaccharides. Accordingly, the ASR core 1425 behavior is probably not related to the low sucrose consumption. This suggests that the variant is more adapted for polymer synthesis.

Example 20

Acceptor Reaction (Sucrose and Maltose)

The following results were obtained and are set forth in Table V.

TABLE V

| Oligosaccharides | Yield of Synthesized Oligosaccharides (%) | | | |
|---|---|---|---|---|
| | Entire ASR | ASR C-del bis | ASR C-del 1349 | ASR core 1425 |
| Panose | 31 | 27 | 30 | 27 |
| OA4 | 18 | 17 | 13 | 27 |
| OA5 | 31 | 28 | 30 | 30 |

All variants consumed 100% of sucrose. ASR C-del 1349 and ASR core 1425 synthesized the same products as the ASR and the ASR C-del bis controls: mainly panose and oligoalternans OA4 and OA % (See, FIG. 15).

However, the ASR C-del 1349 construct is less efficient for the synthesis of oligoalternans. The variant only produces 13% yield of OA4 compared to 18% yield produced by the ASR full length. The ASR core 1425 produces a high amount of OA4 corresponding to a 27% yield.

Conclusion

The construction ASR core 1425 is 50% more active compared to the ASR full length. That truncated variant shows a modified specificity on polymerization conditions with sucrose alone. Indeed, it strictly synthesizes polymer without any contaminating oligosaccharides. To the contrary, when maltose is added to the reaction medium the ASR core 1425 shows a 50% increase in yield synthesis of OA4 compared to the full length ASR. Thus, the ASR core 1425 is more efficient for production of the DP4 oligoalternans. This modified specificity is due to the deletion of the variable region since the ASR C-del variant is not affected.

Successive Truncations of CW Repeats

Considering both polymerization and acceptor reaction the truncated variant ASR C-del 1349 has a similar specificity compared to the full length ASR. However, the ASR C-del 1349 is 30% lower compared to the ASR full length.

The C-terminal CW repeats are essential to maintain any activity in the alternansucrase. The CW repeats are a part of the C-terminal domain of glucansucrases known as glucan binding domain. These CW repeats were neither previously identified by Arguello-Morales et al (2000) nor by Joucla et al (2001). This led in the past to an erroneous location of a position which defines the end of the catalytic domain and the beginning of the glucan binding domain (GBD). Indeed, the present results show that this position corresponds to amino acid 1290.

Moreover, the corresponding 1290 truncation of the ASR was tested in another glucansucrase, the GTF-I from *Streptococcus downei* Mfe28. That truncation in GTF-I gave an active glucansucrase (Monchois et al., 1999, Supra) whereas the truncation in ASR gives an inactive enzyme (ASR C-del).

Accordingly these results demonstrate that the glucan binding domain cannot completely be removed and this result is specific to alternansucrase. Moreover, the location of the truncation in the GBD is really essential since:

(1) when 0 YY is left in the construct, the enzyme is inactivated (truncation of the APY and 8 YY CW repeats: ASR C-del).

(2) when 2 YY are left in the construct a 30% decrease in activity is seen (Truncation of the APY and 6 YY CW repeats: ASR C-del 1349).

(3) when 5 YY repeats are left a 22% increase in activity is seen (truncation of the APY and 3 YY CW repeats: ASR C-del bis).

While the invention has been described in terms of various preferred embodiments, the skilled artisan will appreciate that various modifications, substitutions, omissions and changes may be made without departing from the scope thereof. Accordingly, it is intended that the scope of the present invention be limited by the scope of the following claims, including equivalents thereof.

What is claimed is:

1. An isolated polynucleotide sequence of SEQ ID NO: 2 consisting of the nucleotide residues starting from the nucleotide at position 195 to the nucleotide at position 4241 of SEQ ID NO: 1 or the full length complement of said polynucleotide.

* * * * *